US011713332B2

(12) United States Patent
Stoessel et al.

(10) Patent No.: US 11,713,332 B2
(45) Date of Patent: Aug. 1, 2023

(54) METAL COMPLEXES

(71) Applicant: Merck Patent GmbH, Darmstadt (DE)

(72) Inventors: Philipp Stoessel, Frankfurt am Main (DE); Christian Ehrenreich, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 869 days.

(21) Appl. No.: 16/317,304

(22) PCT Filed: Jul. 11, 2017

(86) PCT No.: PCT/EP2017/067359
§ 371 (c)(1),
(2) Date: Jan. 11, 2019

(87) PCT Pub. No.: WO2018/011186
PCT Pub. Date: Jan. 18, 2018

(65) Prior Publication Data
US 2019/0315787 A1    Oct. 17, 2019

(30) Foreign Application Priority Data
Jul. 14, 2016   (EP) ..................................... 16179378

(51) Int. Cl.
| C07F 15/00 | (2006.01) |
| H10K 85/30 | (2023.01) |
| H10K 50/11 | (2023.01) |
| H10K 50/15 | (2023.01) |
| H10K 50/16 | (2023.01) |
| H10K 101/10 | (2023.01) |

(52) U.S. Cl.
CPC ....... C07F 15/0033 (2013.01); H10K 50/156 (2023.02); H10K 50/16 (2023.02); H10K 85/342 (2023.02); H10K 50/11 (2023.02); H10K 2101/10 (2023.02)

(58) Field of Classification Search
CPC ........ C07F 15/0033; C07F 5/00; C07F 5/062; C07F 5/066; C07F 11/00; C07F 13/00; C07F 15/0006; C07F 15/002; C07F 15/0046; C07F 15/006; C07F 15/0073; C07F 15/0086; C07F 15/02; C07F 15/04; C07F 15/06; C07F 1/08–12; C07F 5/003; C07F 5/06–069; C07F 7/00; C07F 7/003; C07F 7/22–28; C07F 9/00; C07F 9/005; H01L 51/0085–0088; H01L 51/5064; H01L 51/5072; H01L 51/5016; H01L 51/0079; H01L 51/0081–0083; H01L 51/0091–0092; H01L 51/0077; H01L 51/0078; H01L 51/008; H01L 51/0084; H01L 51/0089; H01L 51/009; C09K 2211/183–188; C09K 11/06; C09K 2211/181; C09K 2211/182; C09K 2211/185; H10K 85/341; H10K 85/342; H10K 85/344; H10K 85/346; H10K 85/348; H10K 50/156; H10K 50/16; H10K 50/11; H10K 2101/10; Y02E 10/549; C07D 213/22; C07D 215/30; C07D 401/14
See application file for complete search history.

(56) References Cited

U.S. PATENT DOCUMENTS

| 7,332,232 | B2 | 2/2008 | Ma et al. | |
| 7,728,137 | B2 | 6/2010 | Stoessel et al. | |
| 2005/0170207 | A1 | 8/2005 | Ma et al. | |
| 2007/0176540 | A1* | 8/2007 | Watanabe | ........... H01L 51/0085 |
| | | | | 313/504 |
| 2008/0027220 | A1 | 1/2008 | Stossel et al. | |
| 2012/0286254 | A1* | 11/2012 | Stoessel | .............. H01L 51/0092 |
| | | | | 546/10 |
| 2015/0171348 | A1* | 6/2015 | Stoessel | .............. H01L 51/0085 |
| | | | | 252/301.16 |
| 2018/0026209 | A1 | 1/2018 | Stoessel et al. | |
| 2018/0254416 | A1 | 9/2018 | Stoessel et al. | |

FOREIGN PATENT DOCUMENTS

| DE | 4217588 A1 | 12/1993 |
| JP | 2007-524585 A | 8/2007 |
| JP | 2008-506652 A | 3/2008 |
| JP | 2012-195554 A | 10/2012 |
| JP | 2013-149812 A | 8/2013 |
| JP | 2013-235950 A | 11/2013 |
| JP | 2013-243234 A | 12/2013 |
| JP | 2018-510903 A | 4/2018 |
| JP | 2018-531896 A | 11/2018 |
| TW | 200540246 A | 12/2005 |
| WO | 2004081017 A1 | 9/2004 |
| WO | 2005/076380 A2 | 8/2005 |

(Continued)

OTHER PUBLICATIONS

Bera, Rati Kanta, et al. "Spectroscopic, potentiometric and theoretical studies of novel imino-phenolate chelators for Fe (III)." Spectrochimica Acta Part A: Molecular and Biomolecular Spectroscopy 134 (2015): 165-172. (Year: 2015).*

Grazina, Raquel, et al. "New tripodal hydroxypyridinone based chelating agents for Fe (III), Al (III) and Ga (III): Synthesis, physico-chemical properties and bioevaluation." Journal of inorganic biochemistry 103.2 (2009): 262-273. (Year: 2009).*

International Search Report for PCT/EP2017/067359, dated Sep. 19, 2017.

(Continued)

*Primary Examiner* — Jennifer A Boyd
*Assistant Examiner* — Braelyn R Watson
(74) *Attorney, Agent, or Firm* — Faegre Drinker Biddle & Reath LLP

(57) ABSTRACT

The present invention relates to metal complexes and to electronic devices, in particular organic electroluminescent devices, containing these metal complexes.

15 Claims, No Drawings

(56) References Cited

FOREIGN PATENT DOCUMENTS

| WO | 2007/086505 A1 | 8/2007 |
|---|---|---|
| WO | 2008/085064 A2 | 7/2008 |
| WO | 2009/021948 A1 | 2/2009 |
| WO | 2014/024668 A1 | 2/2014 |
| WO | 2015/117718 A1 | 8/2015 |
| WO | 2016124304 A1 | 8/2016 |
| WO | 2017032439 A1 | 3/2017 |

OTHER PUBLICATIONS

Baker et al., "Ruthenium cryptates with an unusual selectivity for nitrate", Dalton Trans., vol. 41, 2012, pp. 7005-7012.

Bera et al., "Spectroscopic, potentiometric and theoretical studies of novel imino-phenolate chelators for Fe(III)", Spectrochimica Acta Part A Molecular and Biomolecular Spectroscopy, vol. 134, 2015, pp. 165-172.

Kropf et al., "Biomimetic Models of the Photosynthetic Reaction Center Based on Ruthenium-Polypyridine Complexes", J. Phys. Chem. A, vol. 102, 1998, pp. 5499-5505.

Larsen et al., "Three-Dimensional Macrocyclic Encapsulation Reactions. III. Geometrical and Electronic Features of Tris(diimine) Complexes of Trigonal-Prismatic, Antiprismatic, and Intermediate Stereochemistry", Inorganic Chemistry, vol. 11, No. 11, 1972, pp. 2652-2668.

Stibrany et al., "A Tris(pyrazolyl) ?6-Arene Ligand That Selects Cu(I) over Cu(II)",Inorganic Chemistry, vol. 45, No. 24, 2006, pp. 9713-9720.

Tsubouchi et al., "Iron(III) complexation behavior of benzene-centered tripodal mono-,di- and tritopic ligands carrying a repeating-Ahe-(HO)Apr-sequence [Ahe=6-aminohexanoyl; (HO)Apr=3-(Nhydroxy)-aminopropanoyl]",New J. Chem., vol. 25, 2001, pp. 275-282.

\* cited by examiner

METAL COMPLEXES

RELATED APPLICATIONS

This application is a national stage entry, filed pursuant to 35 U.S.C. § 371, of PCT/EP2017/067359, filed Jul. 11, 2017, which claims the benefit of European Patent Application No. 16179378.1, filed. Jul. 14, 2016, which is incorporated herein by reference in its entirety.

The present invention relates to metal complexes which are suitable for use as emitters in organic electroluminescent devices.

In accordance with the prior art, the triplet emitters employed in phosphorescent organic electroluminescent devices (OLEDs) are above all iridium complexes, in particular, bis- and tris-ortho-metallated complexes containing aromatic ligands, where the ligands are bonded to the metal via a negatively charged carbon atom and a neutral nitrogen atom or via a negatively charged carbon atom and a neutral carbene carbon atom. Examples of such complexes are tris(phenylpyridyl)iridium(III) and derivatives thereof, such as, for example, complexes with 1- or 3-phenylisoquinoline ligands, with 2-phenylquinolines or with phenylcarbenes.

An improvement in the stability of the complexes has been achieved by the use of polypodal ligands, as described, for example, in WO 2004/081017 or U.S. Pat. No. 7,332,232. Even if these complexes containing polypodal ligands exhibit advantages compared with complexes which have the same ligand structure, but whose individual ligands are not polypodal, there is, however, still a need for improvement. This is due, in particular, to the more complex synthesis of the compounds, with, for example, very long reaction times and high reaction temperatures being required in the complexing reaction. Furthermore, even in the case of complexes having polypodal ligands, improvements are still desirable with respect to the properties, in particular in relation to efficiency, voltage and/or lifetime, on use in an organic electroluminescent device.

The object of the present invention is therefore the provision of novel metal complexes which are suitable as emitters for use in OLEDs. In particular, the object is to provide emitters which exhibit improved properties in relation to efficiency, operating voltage and/or lifetime. It is furthermore the object of the present invention to provide metal complexes whose synthesis can be carried out under milder synthesis conditions, in particular in relation to reaction duration and reaction temperature, in each case compared with complexes which contain structurally comparable ligands. It is furthermore the object of the present invention to provide metal complexes which do not exhibit facial-meridional isomerisation, which can represent a problem in the case of complexes in accordance with the prior art.

Surprisingly, it has been found that metal complexes containing a hexadentate tripodal ligand, where the bridge of the ligand which links the individual part-ligands has the structure described below, achieve this object and are very highly suitable for use in an organic electroluminescent device. The present invention therefore relates to these metal complexes and to organic electroluminescent devices which contain these complexes.

The invention thus relates to a monometallic metal complex containing a hexadentate tripodal ligand in which three bidentate part-ligands, which may be identical or different, are coordinated to a metal and the three bidentate part-ligands are linked via a bridge of the following formula (1):

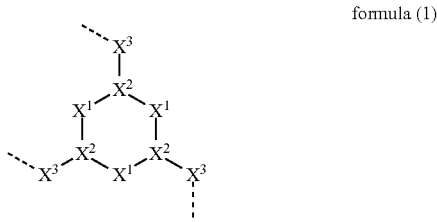

formula (1)

where the dashed bond represents the bond from the bidentate part-ligands to this structure, and the following applies to the symbols used:

$X^1$ is on each occurrence, identically or differently, $CR_2$ or O;

$X^2$ is on each occurrence, identically or differently, CR, P=O, B or Si, which is optionally substituted, with the proviso that, for $X^2$ equals P=O, B or Si, which is optionally substituted, $X^1$ stands for O; the substituents optionally present on $X^1$ and $X^2$ here may each, and also with one another, form an aliphatic or heteroaliphatic ring system;

$X^3$ is on each occurrence, identically or differently, —CR=CR—, —CR=N—, —CR—NR"—, —C(=O)—O—, —C(=O)—NR"—, —C(=O)—S—, —C(=S)—O—, —C(=S)—NR"—, —C(=S)—S—;

R is on each occurrence, identically or differently, H, D, F, Cl, Br, I, $N(R^1)_2$, CN, $NO_2$, $OR^1$, $SR^1$, COOH, C(=O)$N(R^1)_2$, $Si(R^1)_3$, $B(OR^1)_2$, C(=O)$R^1$, P(=O)$(R^1)_2$, S(=O)$R^1$, S(=O)$_2R^1$, $OSO_2R^1$, a straight-chain alkyl group having 1 to 20 C atoms or an alkenyl or alkynyl group having 2 to 20 C atoms or a branched or cyclic alkyl group having 3 to 20 C atoms, where the alkyl, alkenyl or alkynyl group may in each case be substituted by one or more radicals $R^1$, where one or more non-adjacent $CH_2$ groups may be replaced by $R^1C$=$CR^1$, C≡C, $Si(R^1)_2$, C=O, $NR^1$, O, S or $CONR^1$, or an aromatic or heteroaromatic ring system having 5 to 40 aromatic ring atoms, which may in each case be substituted by one or more radicals $R^1$; two or more radicals R which are bonded to $X^1$ and/or $X^2$ may also form an aliphatic or heteroaliphatic ring system with one another here; furthermore, two radicals R for $X^3$=—CR=CR— may also form an aliphatic, heteroaliphatic, aromatic or heteroaromatic ring system with one another; furthermore, the radicals R and R" for $X^3$=—CR—NR"— form a heteroaromatic ring system with one another;

R" is on each occurrence, identically or differently, H, D, a straight-chain alkyl group having 1 to 20 C atoms or a branched or cyclic alkyl group having 3 to 20 C atoms or an alkenyl group having 2 to 20 C atoms, where the alkyl group or alkenyl group may in each case be substituted by one or more radicals $R^1$ and where one or more non-adjacent $CH_2$ groups may be replaced by $Si(R^1)_2$, or an aromatic or heteroaromatic ring system having 5 to 40 aromatic ring atoms, which may in each case be substituted by one or more radicals $R^1$;

$R^1$ is on each occurrence, identically or differently, H, D, F, Cl, Br, I, $N(R^2)_2$, CN, $NO_2$, $OR^2$, $SR^2$, $Si(R^2)_3$, $B(OR^2)_2$, C(=O)$R^2$, P(=O)$(R^2)_2$, S(=O)$R^2$, S(=O)$_2R^2$, $OSO_2R^2$, a straight-chain alkyl group having 1 to 20 C atoms or an alkenyl or alkynyl group having 2 to 20 C atoms or a branched or cyclic alkyl group having 3 to 20 C atoms, where the alkyl, alkenyl or alkynyl group may in each case be substituted by one or more radicals $R^2$, where one or more non-adjacent $CH_2$ groups may be replaced by $R^2C=CR^2$, $C\equiv C$, $Si(R^2)_2$, $C=O$, $NR^2$, O, S or $CONR^2$, or an aromatic or heteroaromatic ring system having 5 to 40 aromatic ring atoms, which may in each case be substituted by one or more radicals $R^2$; a plurality of substituents $R^1$ here may also form an aliphatic, heteroaliphatic, aromatic or heteroaromatic ring system with one another;

$R^2$ is on each occurrence, identically or differently, H, D, F or an aliphatic, aromatic and/or heteroaromatic organic radical, in particular a hydrocarbon radical, having 1 to 20 C atoms, in which, in addition, one or more H atoms may be replaced by F;

the three bidentate ligands here may also be cyclised by a further bridge, in addition to the bridge of the formula (1), to form a cryptate.

If $X^1$ stands for C, this C atom then either carries a hydrogen atom and is substituted by a substituent other than hydrogen, or it carries two hydrogen atoms or two substituents other than hydrogen.

In accordance with the invention, the ligand is thus a hexadentate, tripodal ligand having three bidentate part-ligands. The structure of the hexadentate, tripodal ligand is represented schematically by the following formula (Lig):

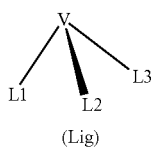

(Lig)

where V represents the bridge of the formula (1) and L1, L2 and L3 each, identically or differently on each occurrence, represent bidentate part-ligands. Bidentate here means that the respective part-ligand is coordinated or bonded to the metal in the complex via two coordination sites. Tripodal means that the ligand has three parts-ligands which are bonded to the bridge V or the bridge of the formula (1). Since the ligand has three bidentate part-ligands, this gives rise overall to a hexadentate ligand, i.e. a ligand which is coordinated or bonded to the metal via six coordination sites. The term "bidentate part-ligand" in the sense of this application means that this unit would be a bidentate ligand if the bridge of the formula (1) were not present. However, the formal abstraction of a hydrogen atom on this bidentate ligand and the linking to the bridge of the formula (1) means that this is no longer a separate ligand, but instead is part of the hexadentate ligand formed in this way, so that the term "part-ligand" is used for this.

The metal complex M(Lig) formed with this ligand of the formula (Lig) can thus be represented schematically by the following formula:

M(Lig)

where V represents the bridge of the formula (1), L1, L2 and L3 each, identically or differently on each occurrence, represent bidentate part-ligands, and M stands for a metal. As can be seen from the scheme drawing, all three bidentate part-ligands are coordinated to the metal via two coordination sites each in the compounds according to the invention.

Monometallic in the sense of the present invention means that the metal complex contains only a single metal atom, as also represented schematically by M(Lig). Metal complexes in which, for example, each of the three bidentate part-ligands is coordinated to a different metal atom are thus not covered by the invention.

The bonding of the ligand to the metal can be either a coordination bond or a covalent bond, or the covalent content of the bond can vary depending on the ligand and metal. If the present application refers to the ligand or part-ligand being coordinated or bonded to the metal, this, for the purposes of the present application, denotes any type of bonding of the ligand or part-ligand to the metal, irrespective of the covalent content of the bond.

The compounds according to the invention are preferably characterised in that they are uncharged, i.e. are electrically neutral. This is achieved in a simple manner by the charges of the three bidentate part-ligands and of the bridge of the formula (1) being selected so that they compensate for the charge of the complexed metal atom. Thus, if, for example, a metal atom in oxidation state +3 is used, charge neutrality can be achieved by each of the three bidentate part-ligands being monoanionic.

Preferred embodiments of the bridge of the formula (1) are shown below. The group $X^3$ can represent an alkenyl group, an imine group, an amide group, an ester group or the corresponding sulfur analogues of amide or ester groups. If $X^3$ stands for —CR=CR— and the radicals R form an aromatic or heteroaromatic ring system with one another, the group $X^3$, can also stand for an ortho-linked arylene or heteroarylene group. For $X^3$=—CR—NR"—, R and R" form a heteroaromatic ring system, so that the group stands for an ortho-linked heteroarylene group. In the case of asymmetrical groups $X^3$, any orientation of the groups is possible. This is explained diagrammatically below for the example of $X^3$=—C(=O)—O—. This gives rise to the following possible orientations of $X^3$, all of which are covered by the present invention:

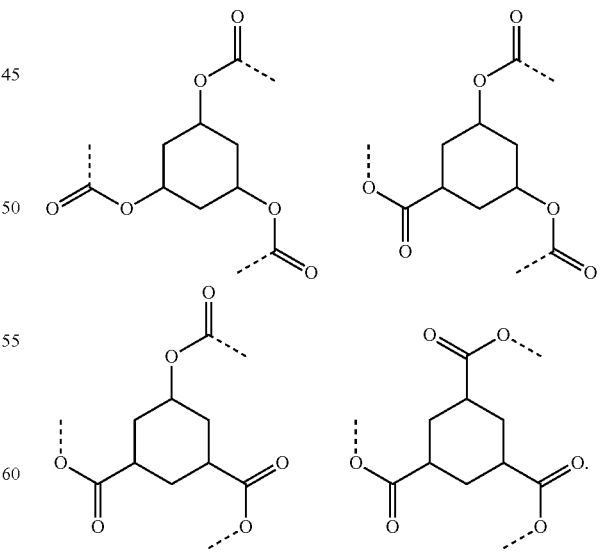

If $X^2$ stands for CR, in particular if all $X^2$ stand for CR, very particularly if additionally 0, 1, 2 or 3, in particular 3, of the $X^1$ stand for $CR_2$, the radicals R on $X^2$ can adopt different positions, depending on the configuration. Small radicals R, such as H or D, are preferred here. It is preferred that they are either all directed away from the metal (apical) or are all directed inwardly towards the metal (endohedral). This is illustrated below for the example of a complex with ester bridges. It applies in the same manner to ortho-arylene, ortho-heteroarylene, 1,2-olefin, imine and amide bridges, irrespective of how the bridge is oriented, i.e. whether the carbonyl group of the ester/amide bridge or the N atom of the imine bridge is bonded to the cyclohexane ring or to the aromatic group of the bidentate part-ligand.

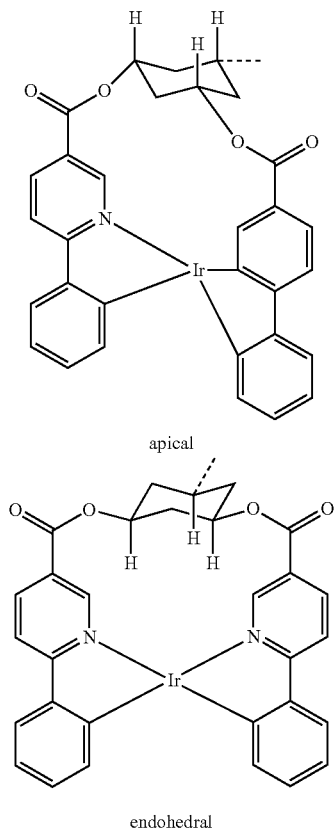

apical endohedral

The third part-ligand is not shown for reasons of clarity, but instead is only indicated by the dashed bond. Preference is therefore given to complexes which are able to adopt at least one of the two configurations. These are complexes in which all three groups $X^3$ are arranged equatorially on the central ring.

If $X^3$ stands for an alkenyl group or an imine group, these are cis-linked alkenyl or imine groups.

If $X^3$ stands for —CR=CR—, the group $X^3$ then represents an alkene group or, in the case of ring closure of the substituents optionally present, also an arylene or heteroarylene group. If $X^3$=—CR—NR"—, the group $X^3$ then represents a heteroaryl group through ring closure of R and R" to form a heteroaromatic system.

If $X^3$ stands for —C(=O)—NR"—, R" then preferably stands, identically or differently on each occurrence, for a straight-chain alkyl group having 1 to 10 C atoms or a branched or cyclic alkyl group having 3 to 10 C atoms or an aromatic or heteroaromatic ring system having 6 to 24 aromatic ring atoms, which may in each case be substituted by one or more radicals $R^1$. R" particularly preferably stands, identically or differently on each occurrence, for a straight-chain alkyl group having 1 to 5 C atoms or a branched or cyclic alkyl group having 3 to 6 C atoms or an aromatic or heteroaromatic ring system having 6 to 12 aromatic ring atoms, which may in each case be substituted by one or more radicals $R^1$, but is preferably unsubstituted.

The formulation that two or more radicals may form a ring with one another is, for the purposes of the present description, intended to be taken to mean, inter alia, that the two radicals are linked to one another by a chemical bond with formal abstraction of two hydrogen atoms. This is illustrated by the following scheme:

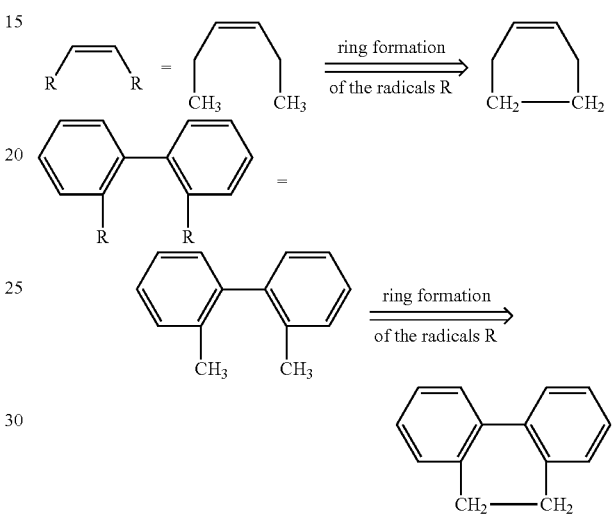

Correspondingly, the formation of bicyclic, tricyclic and oligocyclic ring systems is also possible. Furthermore, the above-mentioned formulation is also intended to be taken to mean that, in the case where one of the two radicals represents hydrogen, the second radical is bonded at the position to which the hydrogen atom was bonded, with formation of a ring. This will be illustrated by the following scheme:

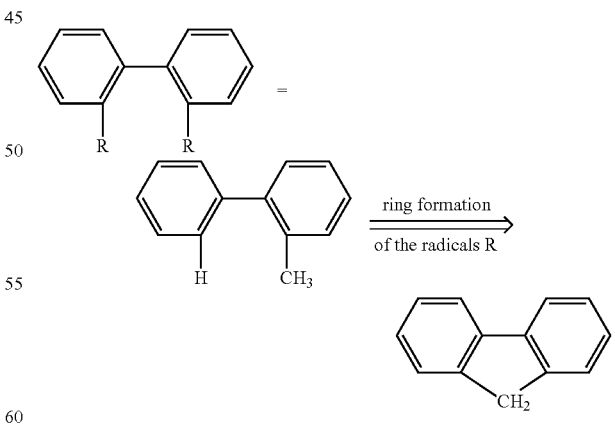

An aryl group in the sense of this invention contains 6 to 40 C atoms; a heteroaryl group in the sense of this invention contains 2 to 40 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, phenanthrene, quinoline, isoquinoline, etc.

An aromatic ring system in the sense of this invention contains 6 to 40 C atoms in the ring system. A heteroaromatic ring system in the sense of this invention contains 1 to 40 C atoms and at least one heteroatom in the ring system, with the proviso that the sum of C atoms and heteroatoms is at least 5. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be interrupted by a non-aromatic unit (preferably less than 10% of the atoms other than H), such as, for example, a C, N or O atom or a carbonyl group. Thus, for example, systems such as 9,9'-spirobifluorene, 9,9-diarylfluorene, triarylamine, diaryl ether, stilbene, etc., are also intended to be taken to be aromatic ring systems in the sense of this invention, as are systems in which two or more aryl groups are interrupted, for example, by a linear or cyclic alkyl group or by a silyl group. Furthermore, systems in which two or more aryl or heteroaryl groups are bonded directly to one another, such as, for example, biphenyl, terphenyl, quaterphenyl or bipyridine are likewise intended to be taken to be an aromatic or heteroaromatic ring system.

A cyclic alkyl, alkoxy or thioalkoxy group in the sense of this invention is taken to mean a monocyclic, bicyclic or polycyclic group.

For the purposes of the present invention, a $C_1$- to $C_{20}$-alkyl group, in which, in addition, individual H atoms or $CH_2$ groups may be substituted by the above-mentioned groups, is taken to mean, for example, the radicals methyl, ethyl, n-propyl, i-propyl, cyclopropyl, n-butyl, i-butyl, s-butyl, t-butyl, cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, adamantyl, trifluoromethyl, pentafluoroethyl, 2,2,2-trifluoroethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyl-n-hexadec-1-yl, 1,1-diethyl-n-octadec-1-yl, 1-(n-propyl)cyclohex-1-yl, 1-(n-butyl)cyclohex-1-yl, 1-(n-hexyl)cyclohex-1-yl, 1-(n-octyl)cyclohex-1-yl and 1-(n-decyl)cyclohex-1-yl. An alkenyl group is taken to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is taken to mean, for example, ethynyl, propynyl, butynyl, pentynyl, hexynyl, heptynyl or octynyl. A $C_1$- to $C_{40}$-alkoxy group is taken to mean, for example, methoxy, trifluoromethoxy, ethoxy, n-propoxy, i-propoxy, n-butoxy, i-butoxy, s-butoxy, t-butoxy or 2-methylbutoxy.

An aromatic or heteroaromatic ring system having 5-40 aromatic ring atoms, which may also in each case be substituted by the radicals mentioned above and which may be linked to the aromatic or heteroaromatic ring system via any desired positions, is taken to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, trans-monobenzoindenofluorene, cis- or trans-dibenzo-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

Suitable embodiments of the group of the formula (1) are the structures of the following formulae (2) to (6),

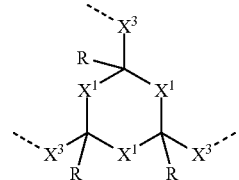

formula (2)

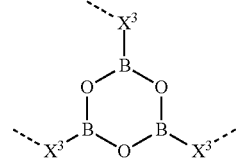

formula (3)

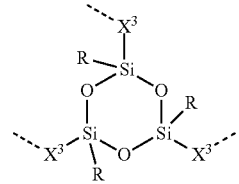

formula (4)

formula (5)

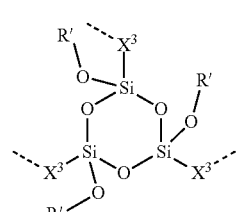

formula (6)

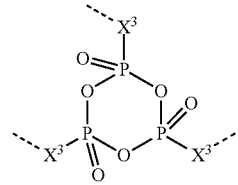

where the symbols used have the meanings given above, where the following additionally applies:
R' is on each occurrence, identically or differently, H, D, F, Cl, Br, I, $N(R^1)_2$, CN, $NO_2$, $OR^1$, $SR^1$, COOH, $C(=O)N(R^1)_2$, $C(=O)R^1$, $P(=O)(R^1)_2$, $S(=O)R^1$, $S(=O)_2R^1$, $OSO_2R^1$, a straight-chain alkyl group having 1 to 20 C atoms or an alkenyl or alkynyl group having 2 to 20 C atoms or a branched or cyclic alkyl group having 3 to 20 C atoms, where the alkyl, alkenyl or alkynyl group may in each case be substituted by one or more radicals $R^1$, where one or more non-adjacent $CH_2$ groups may be replaced by $R^1C=CR^1$, C≡C, C=O, $NR^1$, O, S or $CONR^1$, or an aromatic or heteroaromatic ring system having 5 to 40 aromatic ring atoms, which may in each case be substituted by one or more radicals $R^1$.

Preferred embodiments of the group of the formula (2) are the formulae (2a) or (2b), formula (2a)

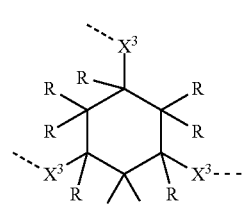

formula (2b)

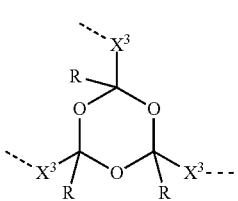

where the symbols used have the meanings given above.

In a preferred embodiment of the invention, all groups $X^1$ and $X^2$ in the group of the formula (1) stand for an optionally substituted carbon atom, where the substituent is preferably selected from the above-mentioned groups R, so that the central trivalent ring of the formula (1) represents a cyclohexane. A preferred embodiment of the formula (1) is thus the structure of the formula (2a).

Particularly preferably, all R of the groups $X^1$ and $X^2$ stand on each occurrence, identically or differently, for H or D, in particular for H.

Further preferred embodiments of the formula (2a) are the following formulae (2a-1) to (2a-4):

formula (2a-1)

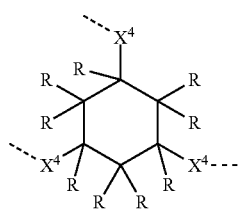

formula (2a-2)

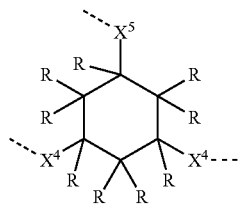

formula (2a-3)

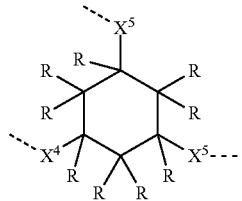

formula (2a-4)

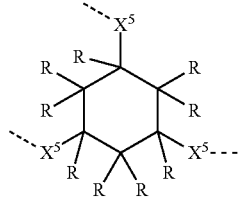

where the following additionally applies:
$X^4$ is on each occurrence, identically or differently, —CR=CR—, —CR=N—, —CR—NR"—, —C(=O)—O—, —C(=O)—NR"—, —C(=O)—S—, —C(=S)—O—, —C(=S)—NR"—, —C(=S)—S—;
$X^5$ is on each occurrence, identically or differently, —CR=CR—, —CR=N—, —CR—NR"—, —C(=O)—O—, —C(=O)—NR"—, —C(=O)—S—, —C(=S)—O—, —C(=S)—NR"—, —C(=S)—S—;
R is on each occurrence, identically or differently, H, D, F, Cl, Br, I, $N(R^1)_2$, CN, $NO_2$, $OR^1$, $SR^1$, COOH, $C(=O)N(R^1)_2$, $Si(R^1)_3$, $B(OR^1)_2$, $C(=O)R^1$, $P(=O)(R^1)_2$, $S(=O)R^1$, $S(=O)_2R^1$, $OSO_2R^1$, a straight-chain alkyl group having 1 to 20 C atoms or an alkenyl or alkynyl group having 2 to 20 C atoms or a branched or cyclic alkyl group having 3 to 20 C atoms, where the alkyl, alkenyl or alkynyl group may in each case be substituted by one or more radicals $R^1$, where one or more non-adjacent $CH_2$ groups may be replaced by $R^1C=CR^1$, C≡C, $Si(R^1)_2$, C=O, $NR^1$, O, S or $CONR^1$, or an aromatic or heteroaromatic ring system having 5 to 40 aromatic ring atoms, which may in each case be substituted by one or more radicals $R^1$; two or more radicals R which are bonded to the central cyclohexane ring may also form an aliphatic or heteroaliphatic ring system with one another here; furthermore, two radicals R for $X^4$=—CR=CR— may also form an aliphatic, heteroaliphatic, aromatic or heteroaromatic ring system, preferably an aromatic or heteroaromatic ring system, with one another; furthermore, R and R" for $X^4$ or $X^5$=—CR—NR"— form a heteroaromatic ring system; furthermore, two radicals R for $X^5$=—CR=CR— also do not form an aliphatic, heteroaliphatic, aromatic or heteroaromatic ring system with one another.

The following preferably applies to radicals R, in particular on the central cyclohexane ring of the formula (2) or the preferred embodiments:

R is on each occurrence, identically or differently, H, D, F, CN, $OR^1$, a straight-chain alkyl group having 1 to 10 C atoms or an alkenyl group having 2 to 10 C atoms or a branched or cyclic alkyl group having 3 to 10 C atoms, which may in each case be substituted by one or more radicals $R^1$, or an aromatic or heteroaromatic ring system having 5 to 24 aromatic ring atoms, which may in each case be substituted by one or more radicals $R^1$;

$R^1$ is on each occurrence, identically or differently, H, D, F, CN, $OR^2$, a straight-chain alkyl group having 1 to 10 C atoms or an alkenyl group having 2 to 10 C atoms or a branched or cyclic alkyl group having 3 to 10 C atoms, which may in each case be substituted by one or more radicals $R^2$, or an aromatic or heteroaromatic ring system having 5 to 24 aromatic ring atoms, which may in each case be substituted by one or more radicals $R^2$;

$R^2$ is on each occurrence, identically or differently, H, D, F or an aliphatic, aromatic and/or heteroaromatic organic radical having 1 to 20 C atoms, in which, in addition, one or more H atoms may be replaced by F.

The following particularly preferably applies to radicals R, in particular on the trivalent central cyclohexane ring of the formula (2) or the preferred embodiments:

R is on each occurrence, identically or differently, H, D, F, CN, a straight-chain alkyl group having 1 to 4 C atoms or a branched or cyclic alkyl group having 3 to 6 C atoms, which may in each case be substituted by one or more radicals $R^1$, or an aromatic or heteroaromatic ring system 6 to 12 aromatic ring atoms, which may in each case be substituted by one or more radicals $R^1$;

$R^1$ is on each occurrence, identically or differently, H, D, F, CN, a straight-chain alkyl group having 1 to 4 C atoms or a branched or cyclic alkyl group having 3 to 6 C atoms, which may in each case be substituted by one or more radicals $R^2$, or an aromatic or heteroaromatic ring system having 6 to 12 aromatic ring atoms, which may in each case be substituted by one or more radicals $R^2$;

$R^2$ is on each occurrence, identically or differently, H, D, F or an aliphatic or aromatic hydrocarbon radical having 1 to 12 C atoms.

Preferred divalent groups $X^3$ or the preferred embodiments $X^4$ or $X^5$, as occur in the structures of the formulae (1) to (6) or their preferred embodiments, are described below.

In a preferred embodiment of the invention, the symbol $X^3$ stands, identically or differently on each occurrence, for —CR=CR—, —CR=N—, —CR—NR"—, —C(=O)—O— or —C(=O)—NR"—. Preferred combinations for $X^3$ are:

| $X^3$ | $X^3$ | $X^3$ |
|---|---|---|
| —CR=CR— | —CR=CR— | —CR=CR— |
| —C(=O)—O— | —C(=O)—O— | —C(=O)—O— |
| —C(=O)—O— | —C(=O)—O— | —CR=CR— |
| —C(=O)—O— | —CR=CR— | —CR=CR— |
| —C(=O)—NR"— | —C(=O)—NR"— | —C(=O)—NR"— |
| —C(=O)—NR"— | —C(=O)—NR"— | —CR=CR— |
| —C(=O)—NR"— | —CR=CR— | —CR=CR— |
| —CR—NR"— | —CR=CR— | —CR=CR— |
| —CR—NR"— | —CR—NR"— | —CR=CR— |
| —CR—NR"— | —CR—NR"— | —CR—NR"— |
| —C(=O)—O— | —C(=O)—O— | —CR—NR"— |
| —C(=O)—O— | —CR=CR— | —CR—NR"— |
| —C(=O)—O— | —CR—NR"— | —CR—NR"— |
| —C(=O)—NR"— | —C(=O)—NR"— | —CR—NR"— |
| —C(=O)—NR"— | —CR—NR"— | —CR—NR"— |
| —CR=N— | —CR=N— | —CR=N— |
| —CR=CR— | —CR=CR— | —CR=N— |
| —CR=CR— | —CR=N— | —CR=N— |

The group of the formula (1) can preferably be represented by the following formulae (1a) to (1q):

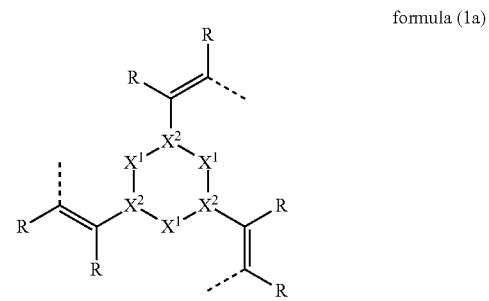

formula (1a)

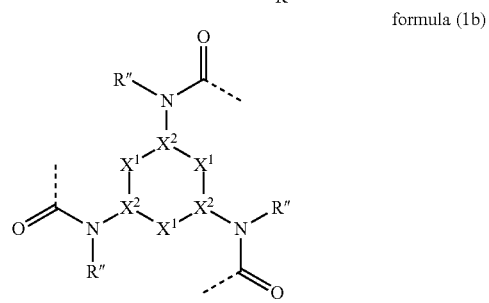

formula (1b)

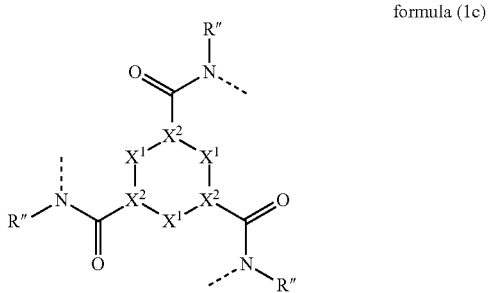

formula (1c)

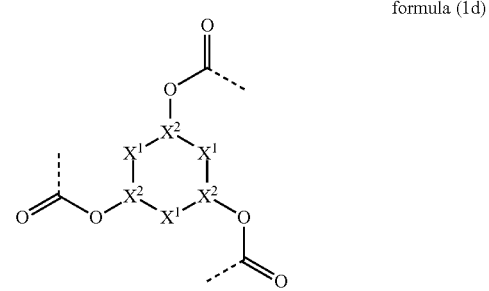

formula (1d)

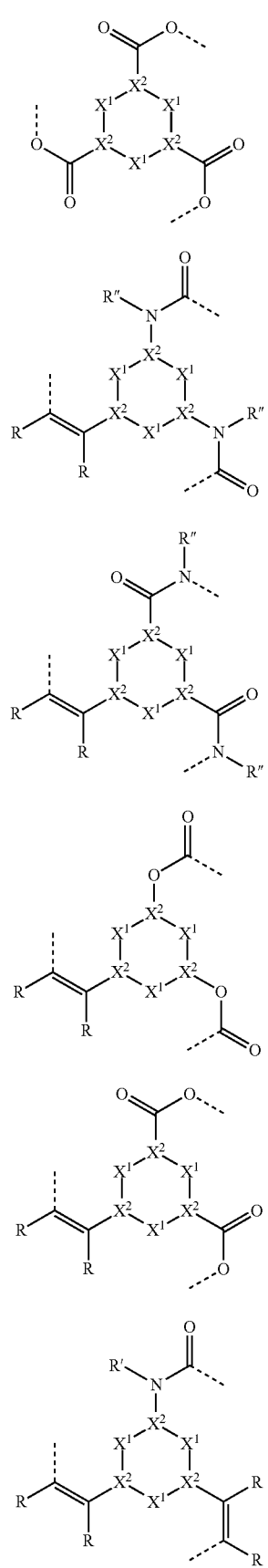
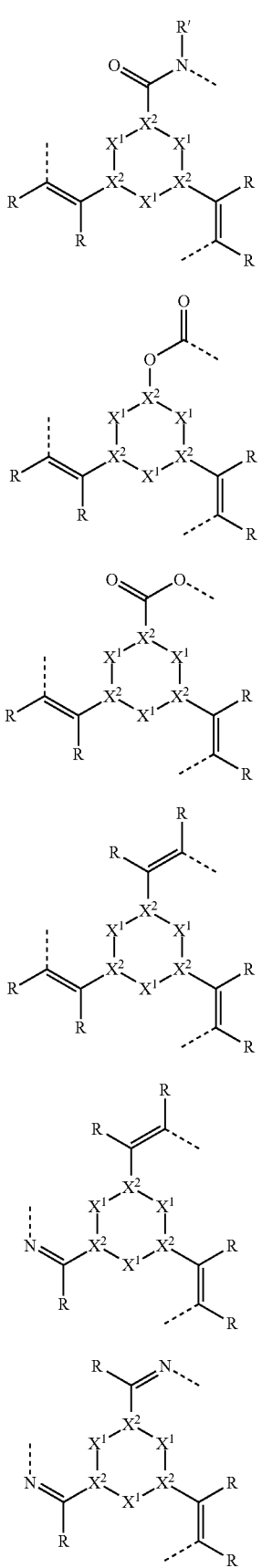

formula (1q)

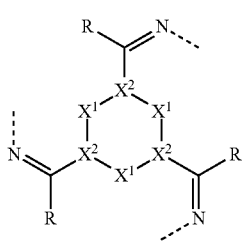

where the symbols have the meanings given above. The radicals R in the formulae (1a) and (1f) to (1p) preferably form an aromatic or heteroaromatic ring system with one another here.

In a preferred embodiment of the invention, the symbol $X^4$ stands, identically or differently on each occurrence, for —CR=CR—, —CR=N—, —C(=O)—O— or —C(=O)—NR"— and the symbol $X^5$ stands, identically or differently on each occurrence, for —CR=CR—, —CR=N—, —CR—NR"—, —C(=O)—O— or —C(=O)—NR"—.

As described above, the group $X^3$, or $X^4$ or $X^5$, in an embodiment of the invention is a cis-linked alkenyl group. In particular, it may be preferred if the radicals R in $X^3$, $X^4$ or $X^5$ form an aliphatic or heteroaliphatic ring system with one another. The way in which such ring formation of substituents looks is described in detail below.

If the substituents of the group $X^3$, $X^4$ or $X^5$ stand for a cis-linked alkenyl group or for —CR—NR"— and form an aromatic or heteroaromatic ring system with one another, this is preferably an arylene or heteroarylene group having 5 to 13 aromatic ring atoms, which preferably contains a maximum of two heteroatoms, particularly preferably a maximum of one heteroatom, where the heteroatoms are selected from N, O or S, preferably N or O, particularly preferably N. This does not exclude the possibility that any substituents bonded to this group may also contain heteroatoms.

Preferred embodiments of the group $X^3$, $X^4$ or $X^5$ which include an aromatic or heteroaromatic ring system of this type are the structures of the following formulae (7) to (23), formula (7)

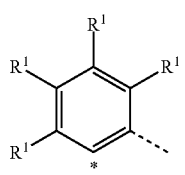

formula (8)

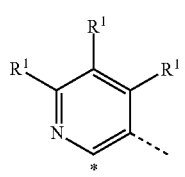

formula (9)

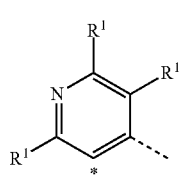

formula (10)

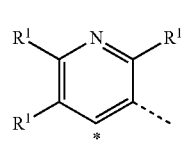

formula (11)

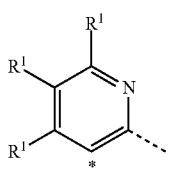

formula (12)

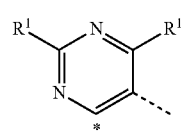

formula (13)

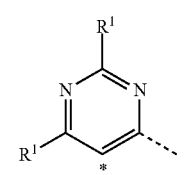

formula (14)

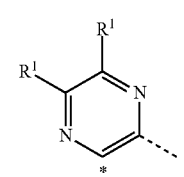

formula (15)

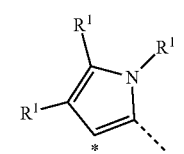

formula (16)

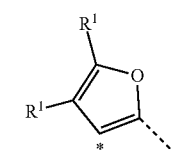

formula (17)

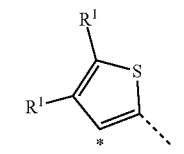

formula (18)

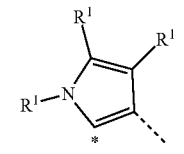

formula (19)
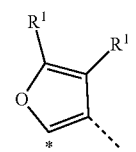

formula (20)
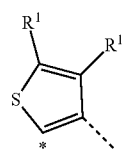

formula (21)
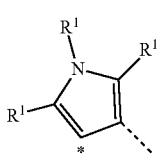

formula (22)
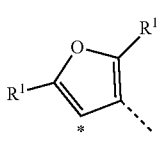

formula (23)
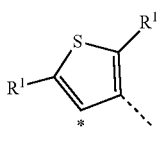

where the dashed bonds in each case represents the position of the bond from the bidentate part-ligands to this structure, * represents the position of the linking of the unit of the formulae (7) to (23) to the central trivalent cyclic group, and the other symbols used have the meanings given above.

In a preferred embodiment of the invention, in the case where $X^3$, $X^4$ or $X^5$ is equal to —CR—NR"—, the radicals R and R" form a heteroaromatic ring system having five ring atoms.

If the group $X^3$, $X^4$ or $X^5$ stands for —CR—NR"—, preferred embodiments of the group of the formula (1) are the structures of the following formulae (24) to (31), formula (24)
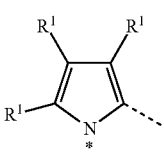

formula (25)
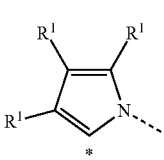

formula (26)
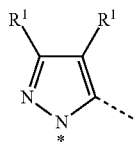

formula (27)
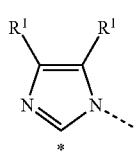

formula (28)
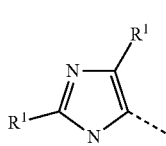

formula (29)
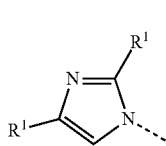

formula (30)
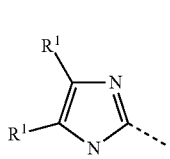

formula (31)
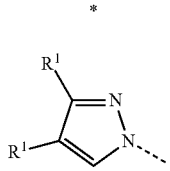

where the symbols used have the meanings given above.

Particular preference is given to the optionally substituted six-membered aromatic groups and six-membered heteroaromatic groups of the formulae (7) to (11) depicted above. Very particular preference is given to ortho-phenylene, i.e. a group of the formula (7) shown above.

Adjacent substituents may, as shown above, also form a ring system with one another here, so that condensed structures, also condensed arylene and heteroarylene groups, such as, for example, naphthalene, quinoline, benzimidazole, carbazole, dibenzofuran or dibenzothiophene, may form. Ring formation of this type is shown diagrammatically below for groups of the formula (7) shown above, which results in groups of the following formulae (7a) to (7j):

formula (7a)
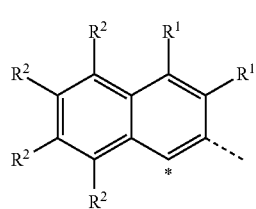

formula (7b)
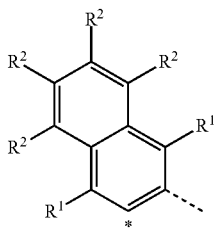

formula (7c)
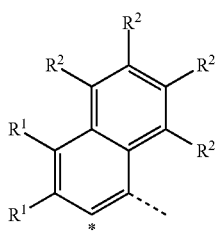

formula (7d)
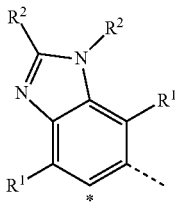

formula (7e)
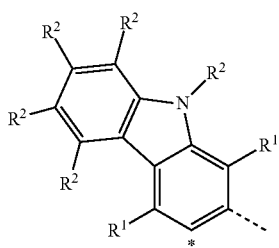

formula (7f)
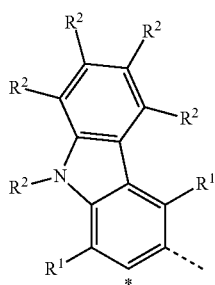

formula (7g)
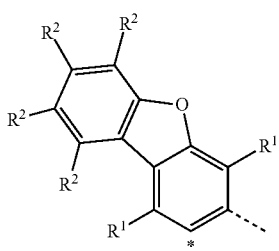

formula (7h)
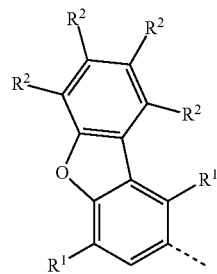

formula (7i)
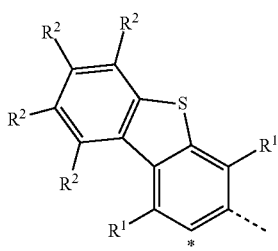

formula (7j)
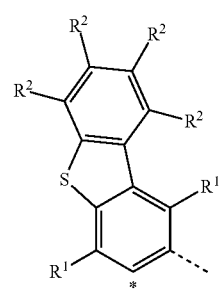

where the symbols used have the meanings given above.

In general, the three groups $X^3$, $X^4$ and $X^5$ which are present in the unit of the formulae (1) to (6) or preferred embodiments thereof may be identical or different. In a preferred embodiment of the invention, all three groups $X^3$ are identical and are also identically substituted. This preference is due to the better synthetic accessibility. In a further preferred embodiment of the invention, one group $X^3$ is different, where the two other groups $X^3$ may likewise be identical or different. This preference is due to better solubility and a generally lower sublimation temperature of the compounds.

The preferred metals of the metal complex according to the invention are described below. In a preferred embodiment of the invention, the metal is a transition metal, where transition metals in the sense of the present invention do not include the lanthanides and actinides, or is a main-group metal. If the metal stands for a main-group metal, it is then preferably selected from metals from the third or fourth main group, preferably Al(III), In(III), Ga(III) or Sn(IV), in particular Al(III). If the metal stands for a transition metal, it is then preferably selected from the group consisting of chromium, molybdenum, tungsten, rhenium, ruthenium, osmium, rhodium, iridium, iron, cobalt, nickel, palladium, platinum, copper, silver and gold, in particular molybdenum, tungsten, rhenium, ruthenium, osmium, iridium, copper, platinum and gold. Iridium is very particularly preferred. The metals can be in various oxidation states here. The above-mentioned metals are preferably in the oxidation states Cr(0), Cr(III), Cr(VI), Mo(0), Mo(III), Mo(VI), W(0), W(III), W(VI), Re(I), Re(III), Re(IV), Ru(II), Ru(III), Os(II), Os(III), Os(IV), Rh(III), Ir(III), Ir(IV), Fe(II), Fe(III), Co(II), Co(III), Ni(II), Ni(IV), Pt(IV), Cu(II), Cu(III), Au(III) and Au(V). Particular preference is given to Mo(0), W(0), Re(I), Ru(II), Os(II), Rh(III) and Ir(III). Very particular preference is given to Ir(III).

It is particularly preferred if the preferred embodiments of the part-ligands, as described in greater detail below, and of the bridge of the formula (1) are combined with the preferred embodiments of the metal. Particular preference is thus given to metal complexes in which the metal is Ir(III) and which contain a bridge of the formulae (1a) to (1d) or of the formulae (2) to (6) or (2a) or (2b) and which contain the preferred embodiments mentioned above as divalent alkenyl or arylene or heteroarylene group $X^3$ in the group of the formulae (1) to (6) or the preferred embodiments.

The bidentate part-ligands which are linked to the bridge of the formula (1) or the preferred embodiments mentioned above are described below. The preferred embodiments of the bidentate part-ligands depend, in particular, on the respective metal used. The three bidentate part-ligands may be identical or different. If all three bidentate part-ligands are selected identically, metal complexes having $C_3$ symmetry thereby form, even if the unit of the formula (1) has $C_3$ symmetry, which is advantageous with respect to the synthesis of the ligands. However, it may also be advantageous to select the three bidentate part-ligands differently or to select two part-ligands identically and the third part-ligand differently therefrom, so that metal complexes having $C_1$ symmetry form, since this allows greater variation latitude of the ligands, so that the desired properties of the complex, such as, for example, the position of the HOMO and LUMO or the emission colour, can be varied more easily. In addition, the solubility of the complexes can also be improved in this way, without having to use long aliphatic or aromatic, solubility-promoting groups. Furthermore, asymmetrical complexes frequently have a lower sublimation temperature than similar symmetrical complexes.

In a preferred embodiment of the invention, the three bidentate part-ligands are either selected identically or two of the bidentate part-ligands are selected identically and the third bidentate part-ligand is different from the first two bidentate part-ligands. "Identical part-ligands" here means that firstly the ligand structure itself is selected identically and secondly that these structures are also identically substituted.

In a preferred embodiment of the invention, each of the bidentate part-ligands is, identically or differently, either monoanionic or neutral. Particularly preferably, each of the bidentate part-ligands is monoanionic.

In a further preferred embodiment of the invention, the coordinating atoms of the bidentate part-ligands are selected, identically or differently on each occurrence, from C, N, P, O, S and/or B, particularly preferably C, N and/or O.

If the metal is selected from the main-group metals, the coordinating atoms of the bidentate part-ligands are then preferably selected, identically or differently on each occurrence, from N, O and/or S. The bidentate part-ligands particularly preferably contain two nitrogen atoms or two oxygen atoms or one nitrogen atom and one oxygen atom per part-ligand as coordinating atoms. The coordinating atoms of each of the three part-ligands may be identical here, or they may be different.

If the metal is selected from the transition metals, the coordinating atoms of the bidentate part-ligands are then preferably selected, identically or differently on each occurrence, from C, N, O and/or S, particularly preferably C, N and/or O and very particularly preferably C and/or N. The bidentate part-ligands here preferably contain one carbon atom and one nitrogen atom or two carbon atoms or two nitrogen atoms or two oxygen atoms or one oxygen atom and one nitrogen atom per part-ligand as coordinating atoms. The coordinating atoms of each of the three-part-ligands may be identical here, or they may be different. Particularly preferably, at least one of the bidentate part-ligands contains one carbon atom and one nitrogen atom or two carbon atoms as coordinating atoms, in particular one carbon atom and one nitrogen atom. Very particularly badly, at least two of the bidentate part-ligands and in particular all three bidentate part-ligands contain one carbon atom and one nitrogen atom or two carbon atoms as coordinating atoms, in particular one carbon atom and one nitrogen atom. This applies, in particular, if the metal is Ir(III). If the metal is Ru, Co, Fe, Os, Cu or Ag, the coordinating atoms of the bidentate part-ligands are also particularly preferably two nitrogen atoms.

In a particularly preferred embodiment of the invention, the metal is Ir(III) and two of the bidentate part-ligands are coordinated to the iridium via in each case one carbon atom and one nitrogen atom and the third of the bidentate part-ligands is coordinated to the iridium via one carbon atom and one nitrogen atom or via two nitrogen atoms or via one nitrogen atom and one oxygen atom or via two oxygen atoms, in particular via one carbon atom and one nitrogen atom. This is thus particularly preferably an iridium complex in which all three bidentate part-ligands are ortho-metallated, i.e. form with the iridium a metallacycle which contains a metal-carbon bond.

It is furthermore preferred if the metallacycle formed from the metal and the bidentate part-ligand is a five-membered ring, which is especially preferred if the coordinating atoms are C and N, N and N or N and O. If the coordinating atoms are O, a six-membered metallacycle may also be preferred. This is depicted diagrammatically below:

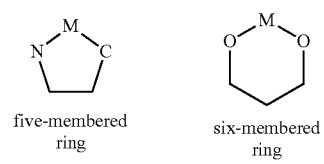

five-membered ring    six-membered ring where M represents the metal, N represents a coordinating nitrogen atom, C represents a coordinating carbon atom and O represent coordinating oxygen atoms and the carbon atoms drawn in represent atoms of the bidentate ligand.

The structures of the bidentate part-ligands which are preferred if the metal is a transition metal are described below.

In a preferred embodiment of the invention, at least one of the bidentate part-ligands, particularly preferably at least two of the bidentate part-ligands, very particularly preferably all three of the bidentate part-ligands stand, identically or differently on each occurrence, for a structure of the following formulae (L-1), (L-2), (L-3) or (L-4), formula (L-1)

formula (L-2)

formula (L-3)

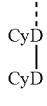

formula (L-4)

where the dashed bond represents the bond from the part-ligand to the bridge of the formulae (1) to (6) or the preferred embodiments, and the following applies to the other symbols used:

CyC is, identically or differently on each occurrence, an optionally substituted aryl or heteroaryl group having 5 to 14 aromatic ring atoms, which is in each case coordinated to the metal via a carbon atom and which is in each case connected to CyD via a covalent bond;

CyD is, identically or differently on each occurrence, an optionally substituted heteroaryl group having 5 to 14 aromatic ring atoms, which is coordinated to the metal via a nitrogen atom or via a carbene carbon atom and which is connected to CyC via a covalent bond;

a plurality of the optional substituents here may form a ring system with one another; furthermore, the optional radicals are preferably selected from the above-mentioned radicals R.

CyD in the part-ligands of the formulae (L-1) and (L-2) here is preferably coordinated via a neutral nitrogen atom or via a carbene carbon atom. Furthermore, one of the two groups CyD in the ligand of the formula (L-3) is preferably coordinated via a neutral nitrogen atom and the other of the two groups CyD via an anionic nitrogen atom. Furthermore, CyC in the part-ligands of the formulae (L-1), (L-2) and (L-4) is preferably coordinated via anionic carbon atoms.

Particular preference is given to the bidentate part-ligands (L-1) and (L-2).

If a plurality of the substituents, in particular a plurality of radicals R, form a ring system with one another, the formation of a ring system from substituents which are bonded to directly adjacent carbon atoms is possible. It is furthermore also possible that the substituents on CyC and CyD in the formulae (L-1) and (L-2) or the substituents on the two groups CyD in formula (L-3) or the substituents on the two groups CyC in formula (L-4) form a ring with one another, enabling CyC and CyD or the two groups CyD or the two groups CyC together also to form a single condensed aryl or heteroaryl group as bidentate ligands.

In a preferred embodiment of the present invention, CyC is an aryl or heteroaryl group having 6 to 13 aromatic ring atoms, particularly preferably having 6 to 10 aromatic ring atoms, very particularly preferably having 6 aromatic ring atoms, which is coordinated to the metal via a carbon atom, may be substituted by one or more radicals R and is bonded to CyD via a covalent bond.

Preferred embodiments of the group CyC are the structures of the following formulae (CyC-1) to (CyC-20),

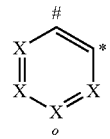
(CyC-1)

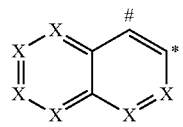
(CyC-2)

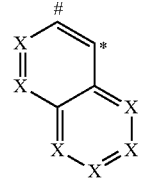
(CyC-3)

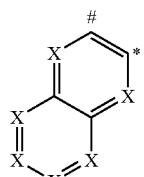
(CyC-4)

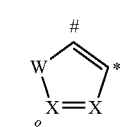
(CyC-5)

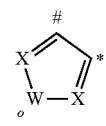
(CyC-6)

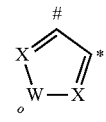
(CyC-7)

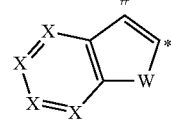
(CyC-8)

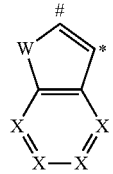
(CyC-9)

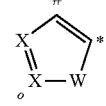

(CyC-10) 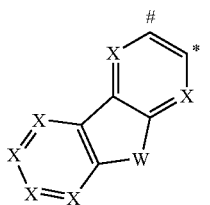

(CyC-11) 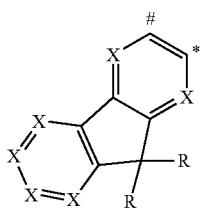

(CyC-12) 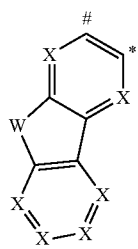

(CyC-13) 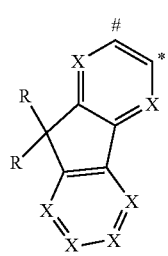

(CyC-14) 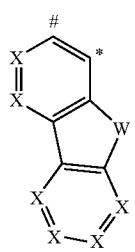

(CyC-15) 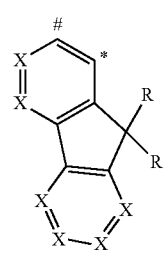

(CyC-16) 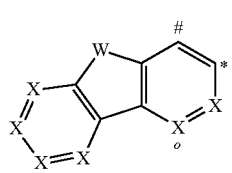

(CyC-17) 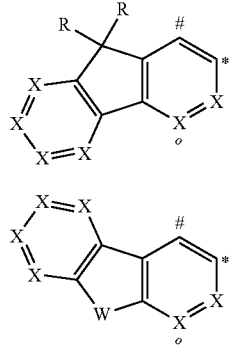

(CyC-18)

(CyC-19) 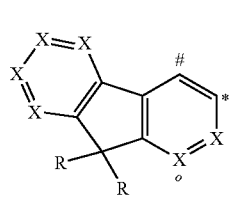

(CyC-20) 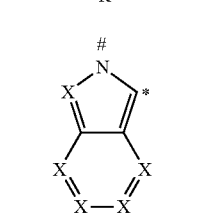

where the group is in each case bonded to CyD in (L-1) or (L-2) or to CyC in (L-4) at the position denoted by # and is coordinated to the metal at the position denoted by *, R has the meanings given above, and the following applies to the other symbols used:

X is on each occurrence, identically or differently, CR or N, with the proviso that a maximum of two symbols X per ring stand for N;

W is on each occurrence, identically or differently, CR or N;

with the proviso that, if the bridge of the formulae (1) to (6) or the preferred embodiments is bonded to CyC, one symbol X stands for C and the bridge of the formulae (1) to (6) or the preferred embodiments is bonded to this carbon atom. If the group CyC is bonded to the bridge of the formulae (1) to (6) or the preferred embodiments, the bonding preferably takes place via the position marked by "o" in the formulae depicted above, so that the symbol X marked by "o" then preferably stands for C. The structures depicted above which do not contain a symbol X marked by "o" are preferably not bonded directly to the bridge of the formulae (1) to (6) or the preferred embodiments, since this type of bonding to the bridge is disadvantageous for steric reasons. Groups CyC of this type are preferably only bonded in (L-1) or as the lower group in (L-4) gebunden.

Preferably, in total a maximum of two symbols X in CyC stand for N, particularly preferably a maximum of one symbol X in CyC stands for N, very particularly preferably all symbols X stand for CR, with the proviso that, if the bridge of the formulae (1) to (6) or the preferred embodiments is bonded to CyC, one symbol X stands for C and the bridge of the formulae (1) to (6) or the preferred embodiments is bonded to this carbon atom.

Particularly preferred groups CyC are the groups of the following formulae (CyC-1a) to (CyC-20a),
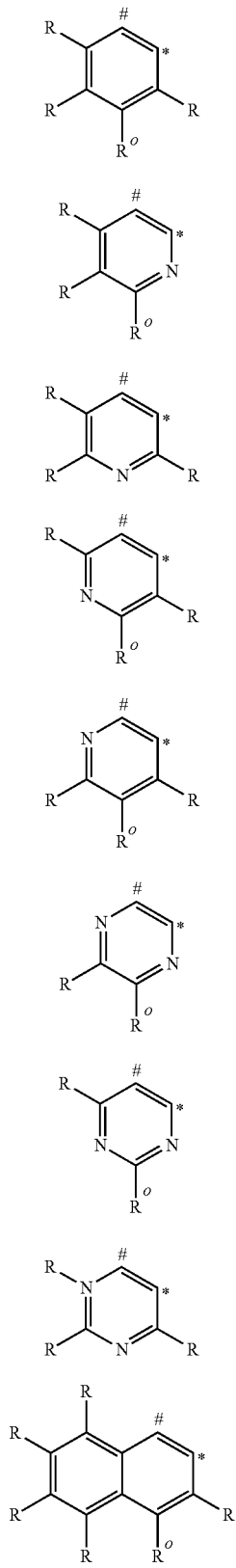
(CyC-1a)
(CyC-1b)
(CyC-1c)
(CyC-1d)
(CyC-1e)
(CyC-1f)
(CyC-1g)
(CyC-1h)
(CyC-2a)
-continued
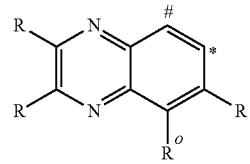
(CyC-2b)
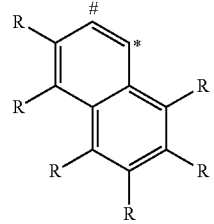
(CyC-3a)
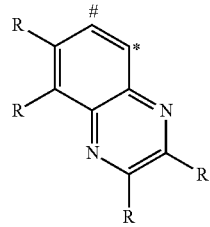
(CyC-3b)
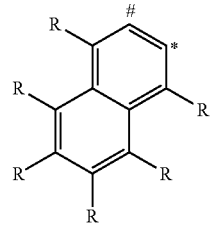
(CyC-4a)
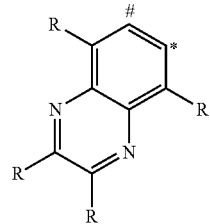
(CyC-4b)
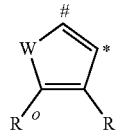
(CyC-5a)
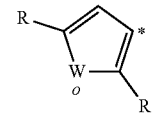
(CyC-6a)
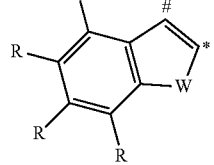
(CyC-7a)

(CyC-8a) 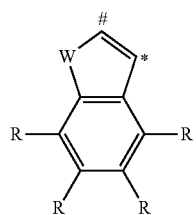
(CyC-9a) 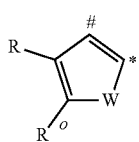
(CyC-10a) 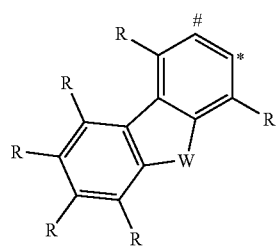
(CyC-11a) 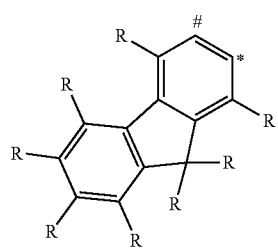
(CyC-12a) 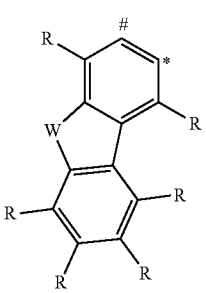
(CyC-13a) 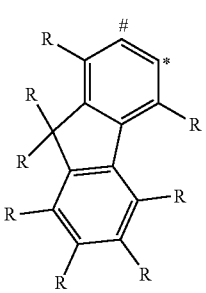
(CyC-14a) 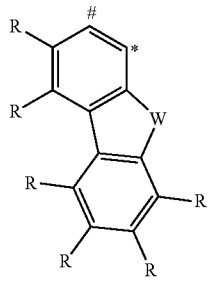
(CyC-15a) 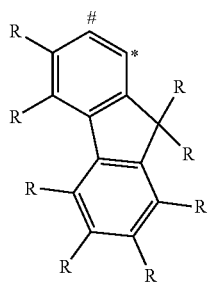
(CyC-16a) 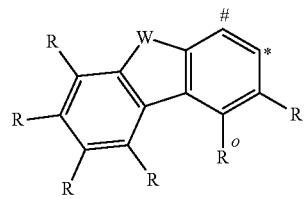
(CyC-17a) 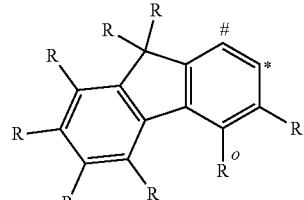
(CyC-18a) 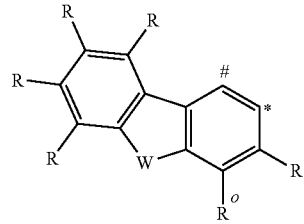
(CyC-19a) 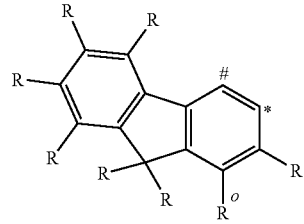

(CyC-20a)

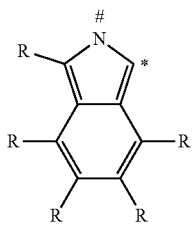

where the symbols used have the meanings given above and, if the bridge of the formulae (1) to (6) or the preferred embodiments is bonded to CyC, a radical R is not present and the bridge of the formulae (1) to (6) or the preferred embodiments is bonded to the corresponding carbon atom. If the group CyC is bonded to the bridge of the formulae (1) to (6) or the preferred embodiments, the bonding preferably takes place via the position marked by "o" in the formulae depicted above, so that the radical R is then preferably not present in this position. The structures depicted above which do not contain a carbon atom marked by "o" are preferably not bonded directly to the bridge of the formulae (1) to (6) or the preferred embodiments.

Preferred groups of the groups (CyC-1) to (CyC-19) are the groups (CyC-1), (CyC-3), (CyC-8), (CyC-10), (CyC-12), (CyC-13) and (CyC-16), and particular preference is given to the groups (CyC-1a), (CyC-3a), (CyC-8a), (CyC-10a), (CyC-12a), (CyC-13a) and (CyC-16a).

In a further preferred embodiment of the invention, CyD is a heteroaryl group having 5 to 13 aromatic ring atoms, particularly preferably having 6 to 10 aromatic ring atoms, which may be coordinated to the metal via a neutral nitrogen atom or via a carbene carbon atom and which may be substituted by one or more radicals R and which is bonded to CyC via a covalent bond.

Preferred embodiments of the group CyD are the structures of the following formulae (CyD-1) to (CyD-14), (CyD-1)

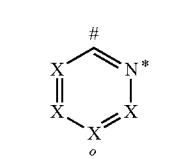

(CyD-2)

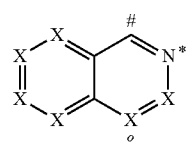

(CyD-3)

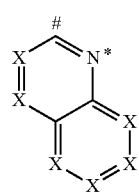

(CyD-4)

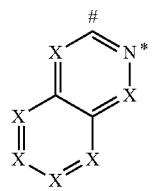

(CyD-5)

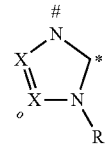

(CyD-6)

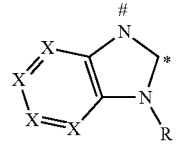

(CyD-7)

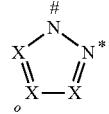

(CyD-8)

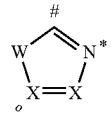

(CyD-9)

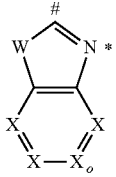

(CyD-10)

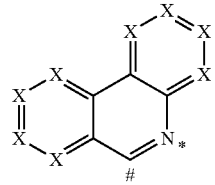

(CyD-11)

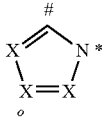

(CyD-12)

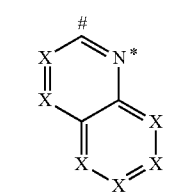

(CyD-13)

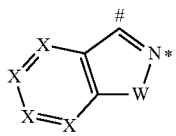

(CyD-14)

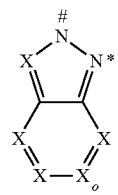

where the group is in each case bonded to CyC in (L-1) or (L-2) or to CyD in (L-3) at the position denoted by # and is coordinated to the metal at the position denoted by *, where X, W and R have the meanings given above, with the proviso that, if the bridge of the formulae (1) to (6) or the preferred embodiments is bonded to CyD, one symbol X stands for C and the bridge of the formulae (1) to (6) or the preferred embodiments is bonded to this carbon atom. If the group CyD is bonded to the bridge of the formulae (1) to (6) or the preferred embodiments, the bonding preferably takes place via the position marked by "o" in the formulae depicted above, so that the symbol X marked by "o" then preferably stands for C. The structures depicted above which do not contain a symbol X marked by "o" are preferably not bonded directly to the bridge of the formulae (1) to (6) or the preferred embodiments, since this type of bonding to the bridge is disadvantageous for steric reasons. Groups CyD of this type are preferably only bonded in (L-2) or as the lower group in (L-3).

The groups (CyD-1) to (CyD-4), (CyD-7) to (CyD-10), (CyD-13) and (CyD-14) are coordinated to the metal via a neutral nitrogen atom, (CyD-5) and (CyD-6) are coordinated to the metal via a carbene carbon atom and (CyD-1.1) and (CyD-12) are coordinated to the metal via an anionic nitrogen atom.

Preferably, in total a maximum of two symbols X in CyD stand for N, particularly preferably a maximum of one symbol X is CyD stands for N, especially preferably all symbols X stand for CR, with the proviso that, if the bridge of the formulae (1) to (6) or the preferred embodiments is bonded to CyD, one symbol X stands for C and the bridge of the formulae (1) to (6) or the preferred embodiments is bonded to this carbon atom.

Particularly preferred groups CyD are the groups of the following formulae (CyD-1a) to (CyD-14b), (CyD-1a)

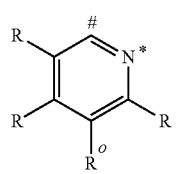

(CyD-2a)

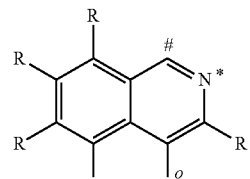

(CyD-3a)

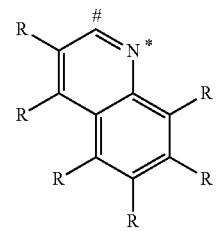

(CyD-3b)

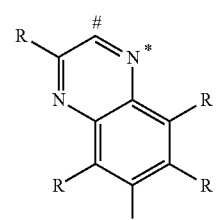

(CyD-4a)

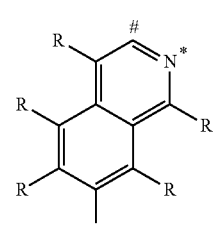

(CyD-5a)

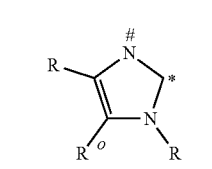

(CyD-6a)

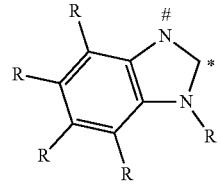

(CyD-7a)

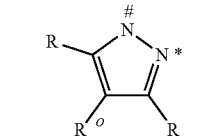

(CyD-8a)

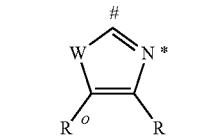

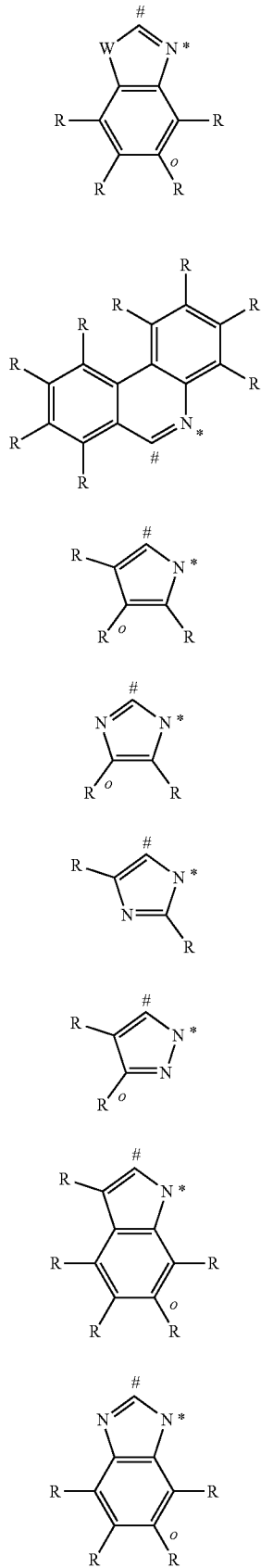
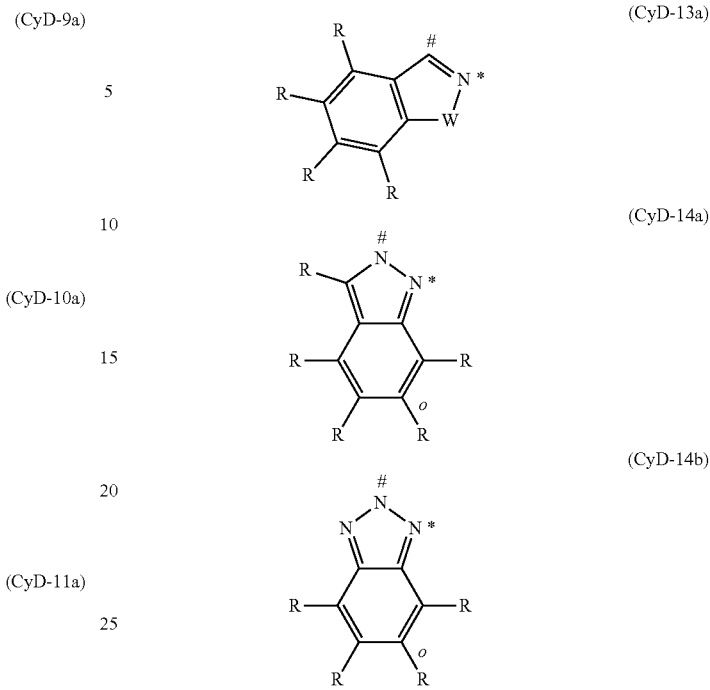

where the symbols used have the meanings given above and, if the bridge of the formulae (1) to (6) or the preferred embodiments is bonded to CyD, a radical R is not present and the bridge of the formulae (1) to (6) or the preferred embodiments is bonded to the corresponding carbon atom. If the group CyD is bonded to the bridge of the formulae (1) to (6) or the preferred embodiments, the bonding preferably takes place via the position marked by "o" in the formulae depicted above, so that the radical R is then preferably not present in this position. The structures depicted above which do not contain a carbon atom marked by "o" are preferably not bonded directly to the bridge of the formulae (1) to (6) or the preferred embodiments.

Preferred groups of the groups (CyD-1) to (CyD-10) are the groups (CyD-1), (CyD-2), (CyD-3), (CyD-4), (CyD-5) and (CyD-6), in particular (CyD-1), (CyD-2) and (CyD-3), and particular preference is given to the groups (CyD-1a), (CyD-2a), (CyD-3a), (CyD-4a), (CyD-5a) and (CyD-6a), in particular (CyD-1a), (CyD-2a) and (CyD-3a).

In a preferred embodiment of the present invention, CyC is an aryl or heteroaryl group having 6 to 13 aromatic ring atoms, and at the same time CyD is a heteroaryl group having 5 to 13 aromatic ring atoms. CyC is particularly preferably an aryl or heteroaryl group having 6 to 10 aromatic ring atoms, and at the same time CyD is a heteroaryl group having 5 to 10 aromatic ring atoms. CyC is very particularly preferably an aryl or heteroaryl group having 6 aromatic ring atoms, and CyD is a heteroaryl group having 6 to 10 aromatic ring atoms. CyC and CyD here may be substituted by one or more radicals R.

The preferred groups (CyC-1) to (CyC-20) and (CyD-1) to (CyD-14) mentioned above can be combined with one another as desired in the part-ligands of the formulae (L-1) and (L-2) so long as at least one of the groups CyC and CyD has a suitable linking site to the bridge of the formulae (1) to (6) or the preferred embodiments, where suitable linking sites in the above-mentioned formulae are denoted by "o".

It is especially preferred if the groups CyC and CyD mentioned above as particularly preferred, i.e. the groups of the formulae (CyC-1a) to (CyC-20a) and the groups of the formulae (CyD-1a) to (CyD-14b), are combined with one another, so long as at least one of these groups has a suitable linking site to the bridge of the formulae (1) to (6) or the preferred embodiments, where suitable linking sites in the above-mentioned formulae are denoted by "o". Combinations in which neither CyC nor CyD has such a suitable linking site to the bridge of the formulae (1) to (6) or the preferred embodiments are therefore not preferred.

It is very particularly preferred if one of the groups (CyC-1), (CyC-3), (CyC-8), (CyC-10), (CyC-12), (CyC-13) and (CyC-16), and in particular the groups (CyC-1a), (CyC-3a), (CyC-8a), (CyC-10a), (CyC-12a), (CyC-13a) and (CyC-16a), are combined with one of the groups (CyD-1), (CyD-2) and (CyD-3), and in particular with one of the groups (CyD-1a), (CyD-2a) and (CyD-3a).

Preferred part-ligands (L-1) are the structures of the following formulae (L-1-1) and (L-1-2), and preferred part-ligands (L-2) are the structures of the following formulae (L-2-1) to (L-2-3),

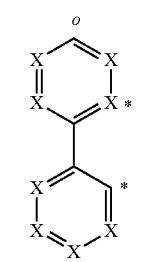
(L-1-1)

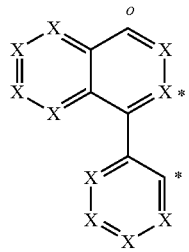
(L-1-2)

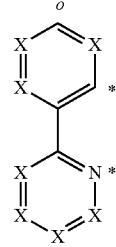
(L-2-1)

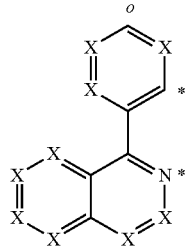
(L-2-2)

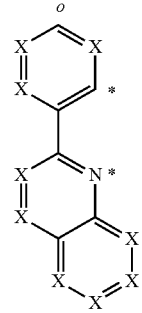
(L-2-3)

where the symbols used have the meanings given above and "o" represents the position of the bond to the bridge of the formulae (1) to (6) or the preferred embodiments.

Particularly preferred part-ligands (L-1) are the structures of the following formulae (L-1-1a) and (L-1-2b), and particularly preferred part-ligands (L-2) are the structures of the following formulae (L-2-1a) to (L-2-3a),

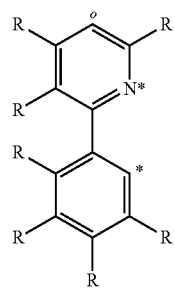
(L-1-1a)

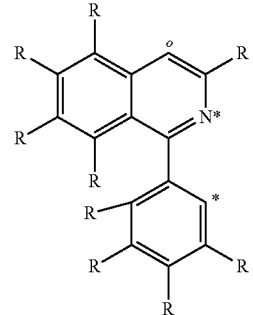
(L-1-2a)

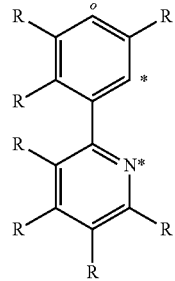
(L-2-1a)

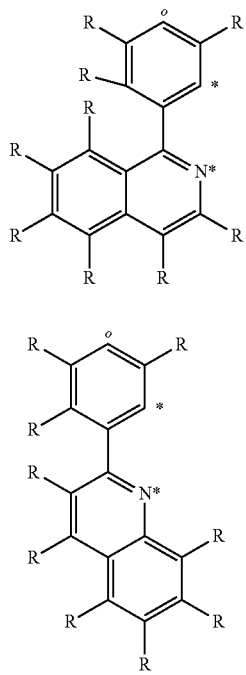

(L-2-2a)

(L-2-3a)

where the symbols used have the meanings given above and "o" represents the position of the bond to the bridge of the formulae (1) to (6) or the preferred embodiments.

The above-mentioned preferred groups CyD in the part-ligands of the formula (L-3) can likewise be combined with one another as desired, where it is preferred to combine a neutral group CyD, i.e. a group (CyD-1) to (CyD-10), (CyD-13) or (CyD-14), with an anionic group CyD, i.e. a group (CyD-11) or (CyD-12), so long as at least one of the preferred groups CyD has a suitable linking site to the bridge of the formulae (1) to (6) or the preferred embodiments, where suitable linking sites are denoted by "o" in the above-mentioned formulae.

The above-mentioned preferred groups CyC in the part-ligands of the formula (L-4) can likewise be combined with one another as desired, so long as at least one of the preferred groups CyC has a suitable linking site to the bridge of the formulae (1) to (6) or the preferred embodiments, where suitable linking sites in the above-mentioned formulae are denoted by "o".

If two radicals R, one of which is bonded to CyC and the other to CyD in the formulae (L-1) and (L-2) or one of which is bonded to one group CyD and the other is bonded to the other group CyD in formula (L-3), or one of which is bonded to one group CyC and the other is bonded to the other group CyC in formula (L-4), form a ring system with one another, bridged part-ligands and, for example, also part-ligands which overall represent a single larger heteroaryl group, such as, for example, benzo[h]quinoline, etc., may arise. The ring formation between the substituents on CyC and CyD in the formulae (L-1) and (L-2) or between the substituents on the two groups CyD in the formula (L-3) or between the substituents on the two groups (CyC) in formula (L-4) preferably takes place here by a group of one of the following formulae (24) to (33),

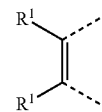
formula (32)

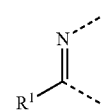
formula (33)

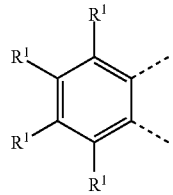
formula (34)

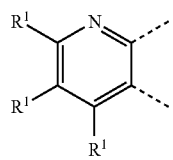
formula (35)

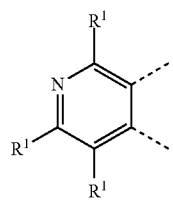
formula (36)

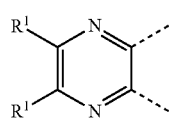
formula (37)

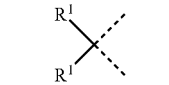
formula (38)

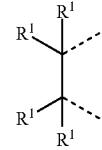
formula (39)

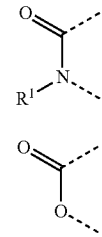
formula (40)

formula (41)

where $R^1$ has the meanings give above and the dashed bonds indicate the bonds to CyC or CyD. The asymmetrical groups of those mentioned above can be incorporated in each of the two possibilities, for example in the case of the group of the formula (41) the oxygen atom can be bonded to the group CyC and the carbonyl group to the group CyD, or the oxygen atom can be bonded to the group CyD and the carbonyl group to the group CyC.

The group of the formula (38) is particularly preferred if the ring formation thus gives rise to a six-membered ring, as depicted, for example, below by the formulae (L-23) and (L-24).

Preferred ligands which arise through ring formation of two radicals R on the different rings are the structures of the formulae (L-5) to (L-32) shown below,

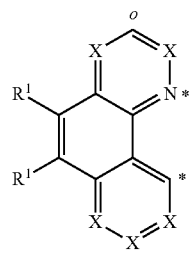
(L-5)

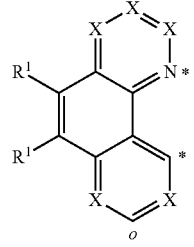
(L-6)

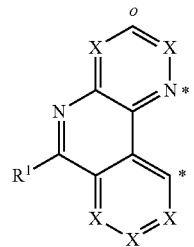
(L-7)

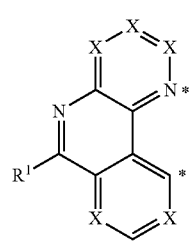
(L-8)

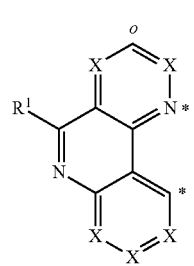
(L-9)

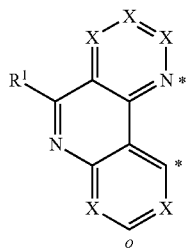
(L-10)

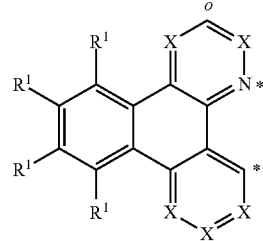
(L-11)

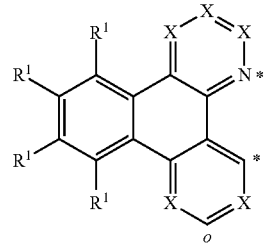
(L-12)

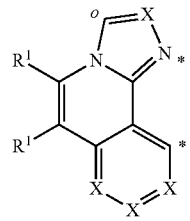
(L-13)

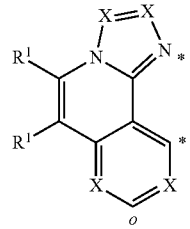
(L-14)

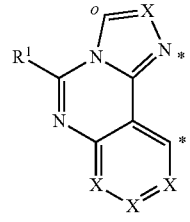
(L-15)

(L-16)
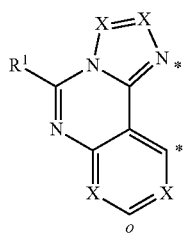
(L-17)
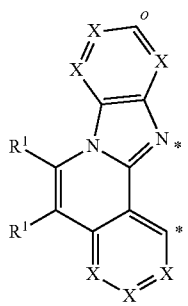
(L-18)
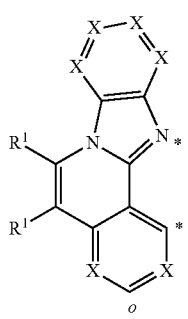
(L-19)
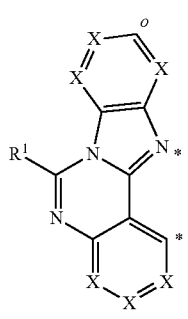
(L-20)
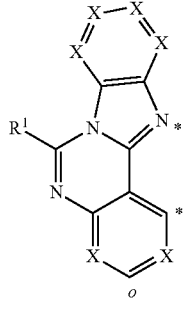
(L-21)
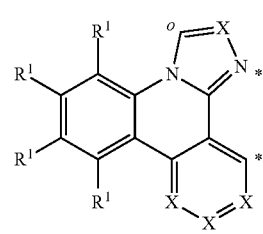
(L-22)
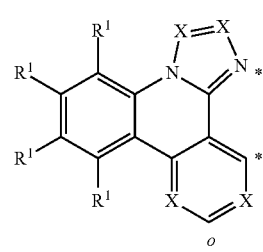
(L-23)
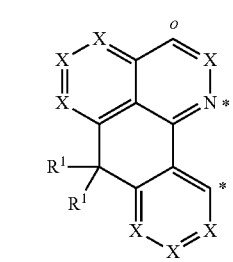
(L-24)
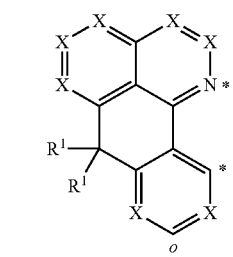
(L-25)
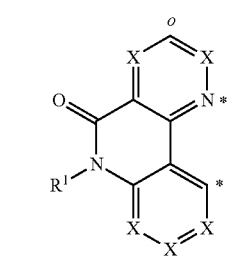
(L-26)
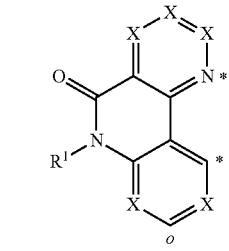

(L-27) 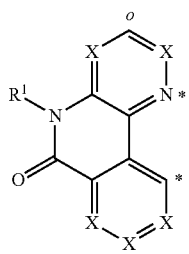

(L-28) 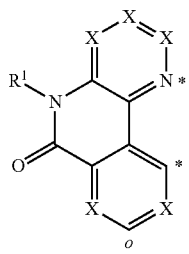

(L-29) 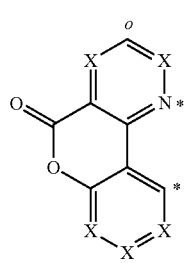

(L-30) 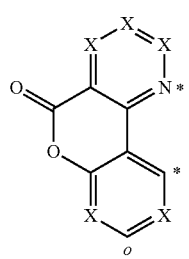

(L31) 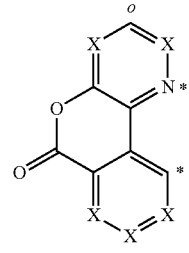

(L-32) 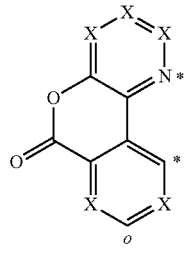

where the symbols used have the meanings given above and "o" indicates the position at which this part-ligand is linked to the bridge of the formulae (1) to (6) or the preferred embodiments.

In a preferred embodiment of the part-ligands of the formulae (L-5) to (L-32), in total one symbol X stands for N and the other symbols X stand for CR, or all symbols X stand for CR. Particularly preferably, all symbols X stand for CR.

In a further embodiment of the invention, it is preferred, in the case where one of the atoms X stands for N in the groups (CyC-1) to (CyC-20) or (CyD-1) to (CyD-14) or in the part-ligands (L-5) to (L-32), if a group R which is not equal to hydrogen or deuterium is bonded as substituent adjacent to this nitrogen atom. This applies analogously to the preferred structures (CyC-1a) to (CyC-20a) or (CyD-1a) to (CyD-14b) in which a group R which is not equal to hydrogen or deuterium is preferably bonded as substituent adjacent to a non-coordinating nitrogen atom.

This substituent R is preferably a group selected from $CF_3$, $OCF_3$, alkyl or alkoxy groups having 1 to 10 C atoms, in particular branched or cyclic alkyl or alkoxy groups having 3 to 10 C atoms, a dialkylamino group having 2 to 10 C atoms, aromatic or heteroaromatic ring systems or aralkyl or heteroaralkyl groups. These groups are sterically bulky groups. Furthermore preferably, this radical R may also form a ring with an adjacent radical R.

A further suitable bidentate part-ligand for metal complexes in which the metal is a transition metal is the part-ligand of the following formula (L-33) or (L-34), (L-33) 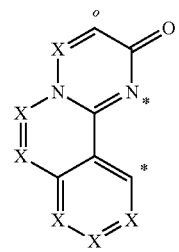

(L-34) 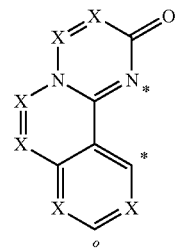

where R has the meanings given above, * represents the position of the coordination to the metal, "o" represents the position of the linking of the part-ligand to the group of the formulae (1) to (6) or the preferred embodiments, and the following applies to the other symbols used:

X is on each occurrence, identically or differently, CR or N, with the proviso that a maximum of one symbol of X per ring stands for N and furthermore with the proviso that one symbol X stands for C and the group of the formulae (1) to (6) or the preferred embodiments is bonded to this carbon atom.

If two radicals R which are bonded to adjacent carbon atoms in the part-ligands (L-33) and (L-34) form an aromatic ring with one another, this together with the two adjacent carbon atoms is preferably a structure of the following formula (42),

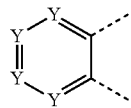

formula (42)

where the dashed bonds symbolise the linking of this group in the part-ligand and Y stands, identically or differently on each occurrence, for $CR^1$ or N and preferably a maximum of one symbol Y stands for N.

In a preferred embodiment of the part-ligand (L-33) or (L-34), a maximum of one group of the formula (42) is present. These are thus preferably part-ligands of the following formulae (L-35) to (L-40),

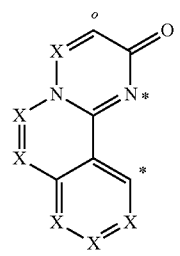

(L-35)

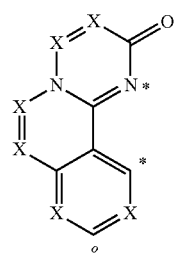

(L-36)

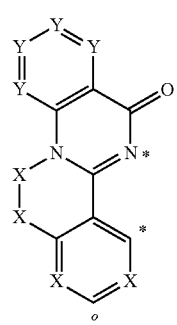

(L-37)

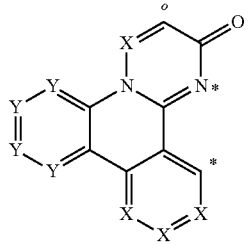

(L-38)

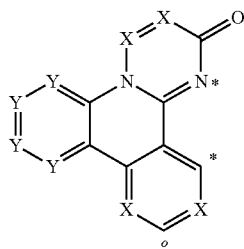

(L-39)

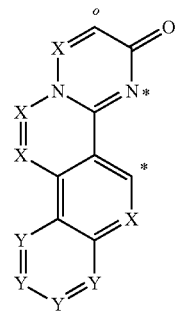

(L-40)

where X stands on each occurrence, identically or differently, for CR or N, but the radicals R do not form an aromatic or heteroaromatic ring system with one another and the other symbols have the meanings given above.

In a preferred embodiment of the invention, a total of 0, 1 or 2 of the symbols X and, if present, Y stand for N in the part-ligands of the formulae (L-33) to (L-40). Particularly preferably, a total of 0 or 1 of the symbols X and, if present, Y stand for N.

Preferred embodiments of the formulae (L-35) to (L-40) are the structures of the following formulae (L-35a) to (L-40f),

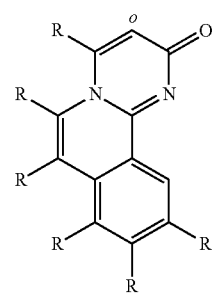

(L-35a)

-continued
(L-35b)
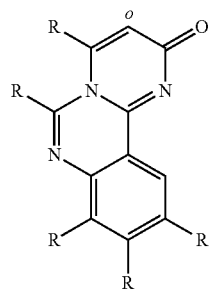
(L-35c)
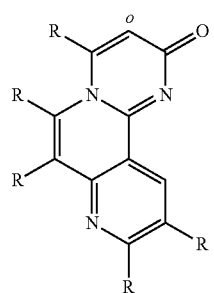
(L-35d)
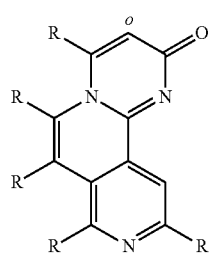
(L-36a)
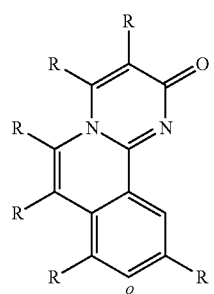
(L-36b)
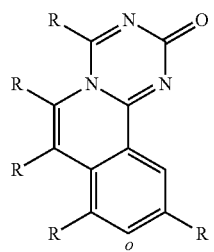
-continued
(L-36c)
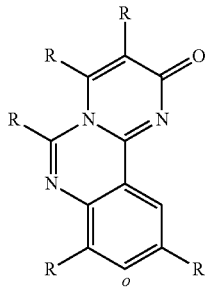
(L-36d)
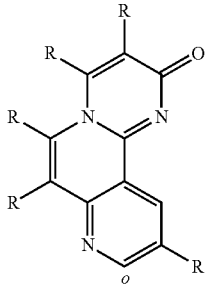
(L-37a)
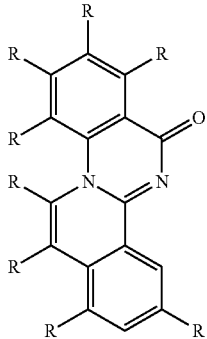
(L-37b)
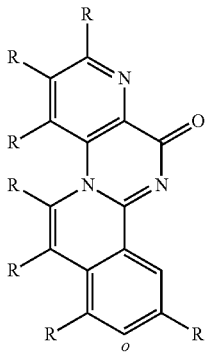
(L-37c)
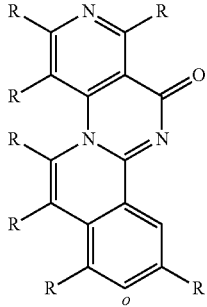

(L-37d)
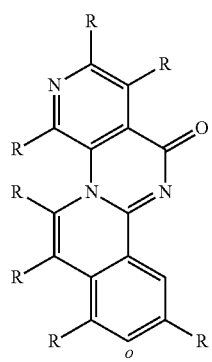
(L-37e)
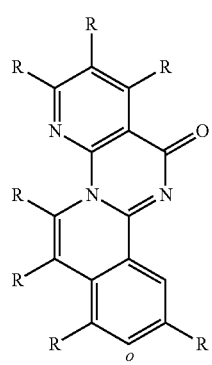
(L-37f)
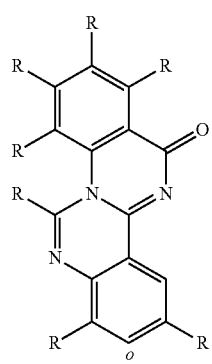
(L-37g)
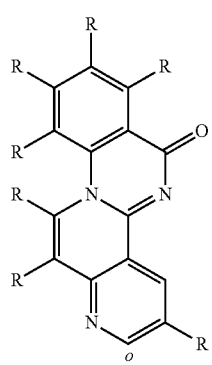
(L-38a)
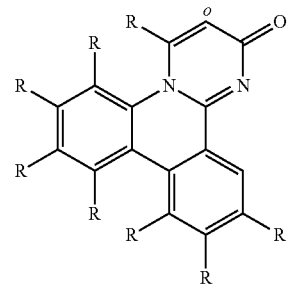
(L-38b)
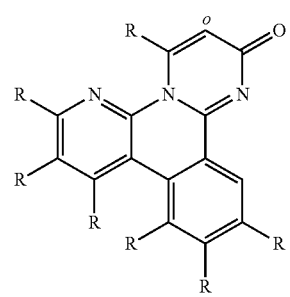
(L-38c)
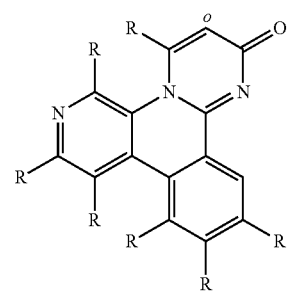
(L-38d)
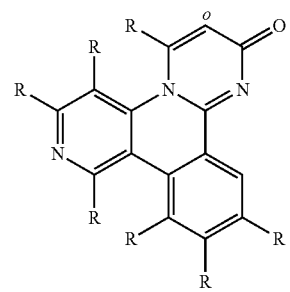
(L-38e)
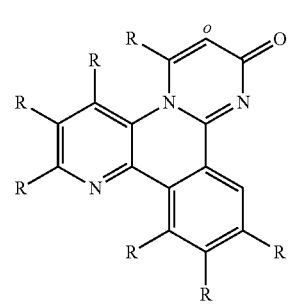

(L-38f)
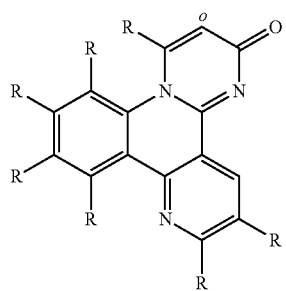
(L-38g)
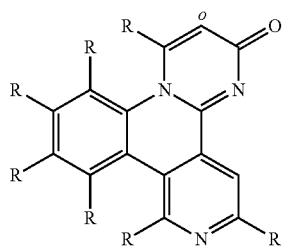
(L-39a)
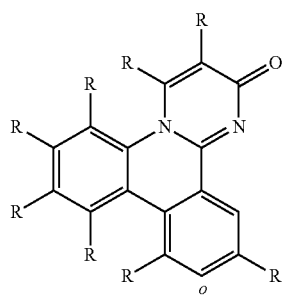
(L-39b)
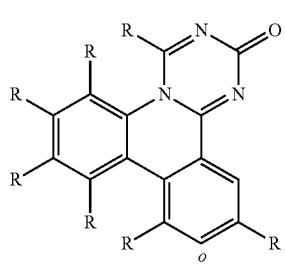
(L-39c)
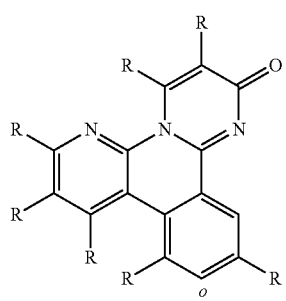
(L-39d)
(L-39e)
(L-39f)
(L-39g)
(L-40a)

-continued

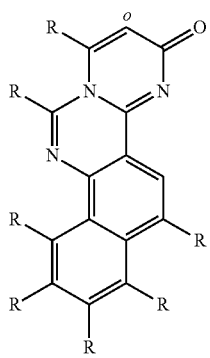
(L-40b)

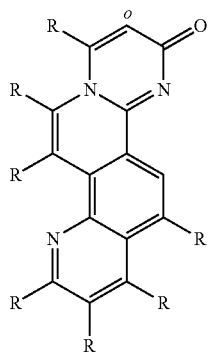
(L-40c)

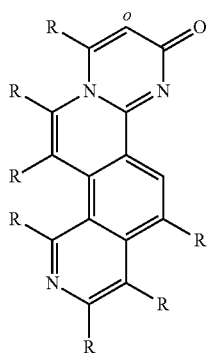
(L-40d)

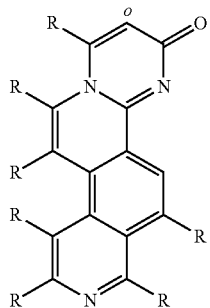
(L-40e)

-continued

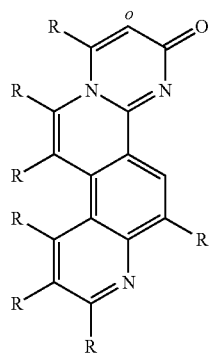
(L-40f)

where the symbols used have the meanings given above and "o" indicates the position of the linking to the group of the formulae (1) to (6) or the preferred embodiments.

In a preferred embodiment of the invention, the group X which is in the ortho position to the coordination to the metal stands for CR, in which R, which is bonded in the ortho position to the coordination to the metal, is preferably selected from the group consisting of H, D, F and methyl.

In a further embodiment of the invention, it is preferred, in the case where one of the atoms X or, if present, Y stands for N, if a group R which is not equal to hydrogen or deuterium is bonded as substituent adjacent to this nitrogen atom.

This substituent R is preferably a group selected from $CF_3$, $OCF_3$, alkyl or alkoxy groups having 1 to 10 C atoms, in particular branched or cyclic alkyl or alkoxy groups having 3 to 10 C atoms, a dialkylamino group having 2 to 10 C atoms, aromatic or heteroaromatic ring systems or aralkyl or heteroaralkyl groups. These groups are sterically bulky groups. This radical R may furthermore preferably also form a ring with an adjacent radical R.

If the metal of the complex according to the invention stands for a main-group metal, in particular for Al or Ga, at least one of the bidentate part-ligands, preferably at least two of the bidentate part-ligands, particularly preferably all three bidentate part-ligands, is (are) preferably selected on each occurrence, identically or differently, from the part-ligands of the following formulae (L-41) to (L-45),

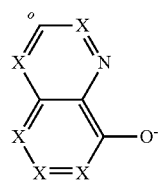
(L-41)

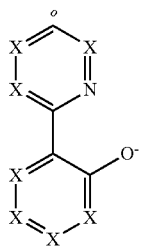
(L-42)

-continued (L-43)

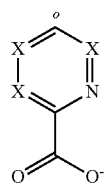

(L-44)

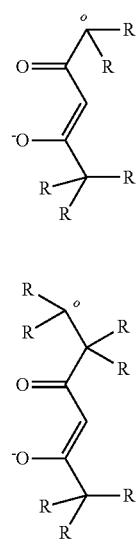

(L-45)

where the part-ligands (L-41) to (L-43) are each coordinated to the metal via the nitrogen atom explicitly drawn in and the negatively charged oxygen atom, and the part-ligand (L-44) is coordinated to the metal via the two oxygen atoms, X has the meanings given above, and "o" indicates the position via which the part-ligand is linked to the group of the formulae (1) to (6) or the preferred embodiments.

These part-ligands may also be preferred for transition metals in combination with two-part-ligands which are coordinated to the metal via one carbon atom and one nitrogen atom or via two carbon atoms, in particular the part-ligands (L-1) to (L-40).

In the part-ligands of the formulae (L-41) to (L-43), preferably a maximum of two symbols X stand for N, particularly preferably a maximum of one symbol X stands for N. Very particularly preferably, all symbols X stand for CR. Preferred part-ligands of the formulae (L-41) to (L-43) are therefore the part-ligands of the following formulae (L-41a) to (L-43a), (L-41a)

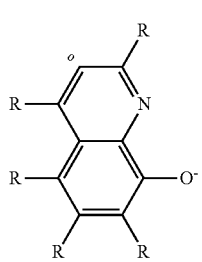

-continued (L-42a)

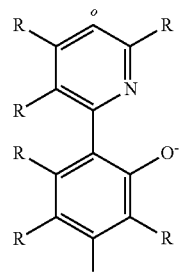

(L-43a)

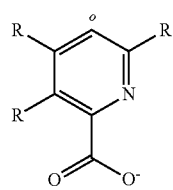

where the symbols used have the meanings given above and "o" indicates the position via which the part-ligand is linked to the group of the formulae (1) to (6) or the preferred embodiments.

In these formulae, R particularly preferably stands for hydrogen, where "o" indicates the position via which the part-ligand is linked to the group of the formulae (1) to (6) or the preferred embodiments, so that the structures are those of the following formulae (L-41b) to (L-43b), (L-34b)

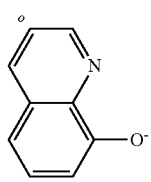

(L-34b)

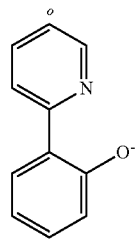

(L-34b)

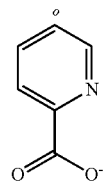

where the symbols used have the meanings given above.

Preferred substituents as may be present on the part-ligands described above are described below. These substituents may furthermore also be present as substituents on the group $X^3$. In particular, it is also preferred if the aliphatic or heteroaliphatic ring structures described below are present on the groups $X^3$.

In a preferred embodiment of the invention, the metal complexes according to the invention contain two substituents R which are bonded to adjacent carbon atoms and which form an aliphatic or heteroaliphatic ring of one of the formulae described below with one another. The two substituents R which form this aliphatic ring may be present here on one or more of the bidentate part-ligands. Likewise, the two substituents R may be present on one or more of the groups $X^3$. The aliphatic or heteroaliphatic ring which is formed by the ring formation of two substituents R with one another is preferably described by one of the following formulae (43) to (49),

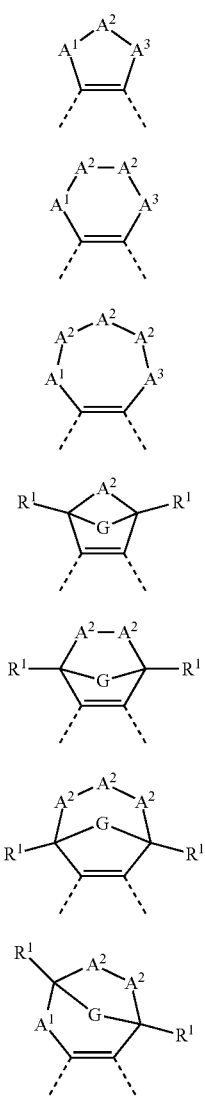

formula (43)

formula (44)

formula (45)

formula (46)

formula (47)

formula (48)

formula (49)

where $R^1$ and $R^2$ have the meanings given above, the dashed bonds indicate the linking of the two carbon atoms in the ligand, and furthermore:

$A^1$, $A^3$ are, identically or differently on each occurrence, $C(R^3)_2$, O, S, $NR^3$ or C(=O);

$A^2$ is $C(R^1)_2$, O, S, $NR^3$ or C(=O);

G is an alkylene group having 1, 2 or 3 C atoms, which may be substituted by one or more radicals $R^2$, or is —$CR^2$=$CR^2$— or an ortho-linked arylene or heteroarylene group having 5 to 14 aromatic ring atoms, which may be substituted by one or more radicals $R^2$;

$R^3$ is, identically or differently on each occurrence, H, D, F, a straight-chain alkyl or alkoxy group having 1 to 10 C atoms, a branched or cyclic alkyl or alkoxy group having 3 to 10 C atoms, where the alkyl or alkoxy group may in each case be substituted by one or more radicals $R^2$, where one or more non-adjacent $CH_2$ groups may be replaced by $R^2C$=$CR^2$, C≡C, $Si(R^2)_2$, C=O, $NR^2$, O, S or $CONR^2$, or an aromatic or heteroaromatic ring system having 5 to 24 aromatic ring atoms, which may in each case be substituted by one or more radicals $R^2$, or an aryloxy or heteroaryloxy group having 5 to 24 aromatic ring atoms, which may be substituted by one or more radicals $R^2$; two radicals $R^3$ which are bonded to the same carbon atom may form an aliphatic or aromatic ring system with one another here and thus form a spiro system; furthermore, $R^3$ may form an aliphatic ring system with an adjacent radical R or $R^1$;

with the proviso that no two heteroatoms are bonded directly to one another and no two groups C=O are bonded directly to one another in these groups.

In a preferred embodiment of the invention, $R^3$ is not equal to H or D.

In the structures of the formulae (43) to (49) depicted above and the further embodiments of these structures indicated as preferred, a double bond is formally formed between the two carbon atoms. This represents a simplification of the chemical structure if these two carbon atoms are bonded into an aromatic or heteroaromatic system and the bond between these two carbon atoms is thus formally between the bond order of a single bond and that of a double bond. The drawing—in of the formal double bond should thus not be interpreted as limiting for the structure, but instead it is apparent to the person skilled in the art that this is an aromatic bond.

If adjacent radicals in the structures according to the invention form an aliphatic ring system, it is then preferred if this contains no acidic benzylic protons. Benzylic protons are taken to mean protons which are bonded to a carbon atom which is bonded directly to the ligand. This can be achieved by the carbon atoms of the aliphatic ring system which are bonded directly to an aryl or heteroaryl group being fully substituted and containing no bonded hydrogen atoms. Thus, the absence of acidic benzylic protons in the formulae (43) to (45) is achieved by $A^1$ and $A^3$, if they stand for $C(R^3)_2$, being defined in such a way that $R^3$ is not equal to hydrogen. This can furthermore also be achieved by the carbon atoms of the aliphatic ring system which are bonded directly to an aryl or heteroaryl group being the bridgeheads of a bi- or polycyclic structure. The protons bonded to bridgehead carbon atoms are, owing to the spatial structure of the bi- or polycycle, significantly less acidic than benzylic protons on carbon atoms which are not bonded in a bi- or polycyclic structure, and are regarded as non-acidic protons in the sense of the present invention. Thus, the absence of acidic benzylic protons is achieved in formula (46) to (49) by it being a bicyclic structure, meaning that $R^1$, if it stands for H, is significantly less acidic than benzylic protons, since the corresponding anion of the bicyclic structure is not resonance-stabilised. Even if $R^1$ in formulae (46) to (49) stands for H, this is therefore a non-acidic proton in the sense of the present application.

In a preferred embodiment of the structure of the formulae (43) to (49), a maximum of one of the groups $A^1$, $A^2$ and $A^3$ stands for a heteroatom, in particular for O or $NR^3$, and the other groups stand for $C(R^3)_2$ or $C(R^1)_2$ or $A^1$ and $A^3$ stand, identically or differently on each occurrence, for O or NR³ and A² stands for C(R¹)₂. In a particularly preferred embodiment of the invention, A¹ and A³ stand, identically or differently on each occurrence, for C(R³)₂ and A² stands for C(R¹)₂ and particularly preferably for C(R³)₂ or CH₂.

Preferred embodiments of the formula (43) are thus the structures of the formulae (43-A), (43-B), (43-C) and (43-D), and a particularly preferred embodiment of the formula (43-A) are the structures of the formulae (43-E) and (43-F),

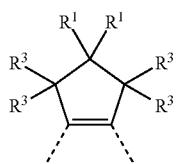

formula (43-A)

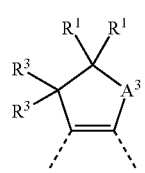

formula (43-B)

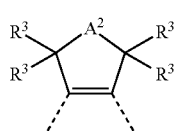

formula (43-C)

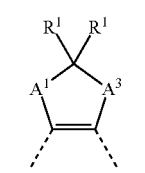

formula (43-D)

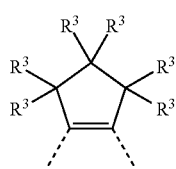

formula (43-E)

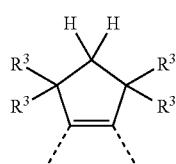

formula (43-F)

where R¹ and R³ have the meanings given above and A¹, A² and A³ stand, identically or differently on each occurrence, for O or NR³.

Preferred embodiments of the formula (44) are thus the structures of the formulae (44-A), (44-B), (44-C) and (44-D), and a particularly preferred embodiment of the formula (44-A) are the structures of the formulae (44-E) and (44-F),

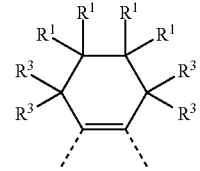

formula (44-A)

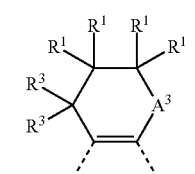

formula (44-B)

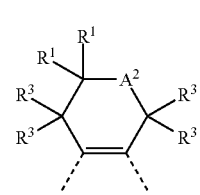

formula (44-C)

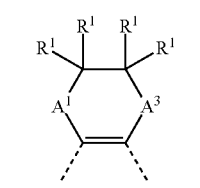

formula (44-D)

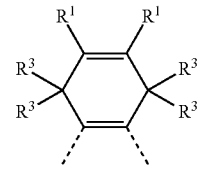

formula (44-E)

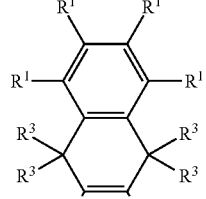

formula (44-F)

where R¹ and R³ have the meanings given above and A¹, A² and A³ stand, identically or differently on each occurrence, for O or NR³.

Preferred embodiments of the formula (45) are the structures of the following formulae (45-A) to (45-F),

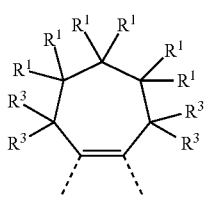

formula (45-A)

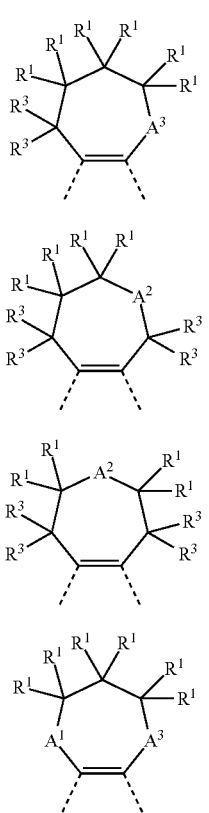

formula (45-B)

formula (45-C)

formula (44-D)

formula (44-E)

where $R^1$ and $R^3$ have the meanings given above and $Z^1$, $Z^2$ and $Z^3$ stand, identically or differently on each occurrence, for O or $NR^3$.

In a preferred embodiment of the structure of the formula (46), the radicals $R^1$ which are bonded to the bridgehead stand for H, D, F or $CH_3$. Furthermore preferably, $A^2$ stands for $C(R^1)_2$ or O, and particularly preferably for $C(R^3)_2$. Preferred embodiments of the formula (46) are thus structures of the formulae (46-A) and (46-B), and a particularly preferred embodiment of the formula (46) is a structure of the formula (46-C),

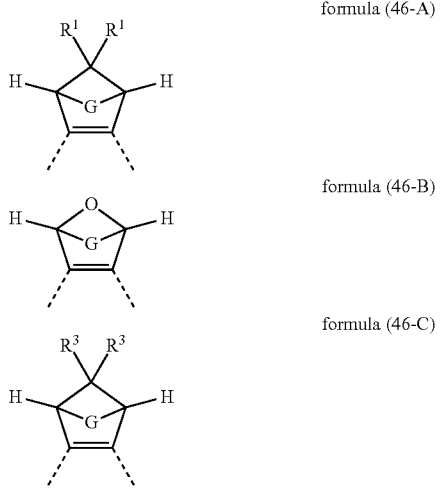

formula (46-A)

formula (46-B)

formula (46-C)

where the symbols used have the meanings given above.

In a preferred embodiment of the structures of the formulae (47), (48) and (49), the radicals $R^1$ which are bonded to the bridgehead stand for H, D, F or $CH_3$. Furthermore preferably, $A^2$ stands for $C(R^1)_2$. Preferred embodiments of the formulae (47), (48) and (49) are thus the structures of the formulae (47-A), (48-A) and (49-A),

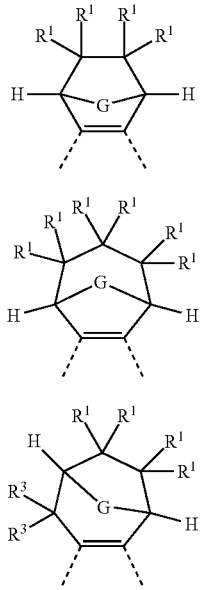

formula (47-A)

formula (48-A)

formula (49-A)

where the symbols used have the meanings given above.

The group G in the formulae (46), (46-A), (46-B), (46-C), (47), (47-A), (48), (48-A), (49) and (49-A) furthermore preferably stands for a 1,2-ethylene group, which may be substituted by one or more radicals $R^2$, where $R^2$ preferably stands, identically or differently on each occurrence, for H or an alkyl group having 1 to 4 C atoms, or an ortho-arylene group having 6 to 10 C atoms, which may be substituted by one or more radicals $R^2$, but is preferably unsubstituted, in particular an ortho-phenylene group, which may be substituted by one or more radicals $R^2$, but is preferably unsubstituted.

In a further preferred embodiment of the invention, $R^3$ in the groups of the formulae (43) to (49) and in the preferred embodiments stands, identically or differently on each occurrence, for F, a straight-chain alkyl group having 1 to 10 C atoms or a branched or cyclic alkyl group having 3 to 20 C atoms, where in each case one or more non-adjacent $CH_2$ groups may be replaced by $R^2C=CR^2$ and one or more H atoms may be replaced by D or F, or an aromatic or heteroaromatic ring system having 5 to 14 aromatic ring atoms, which may in each case be substituted by one or more radicals $R^2$; two radicals $R^3$ here which are bonded to the same carbon atom may form an aliphatic or aromatic ring system with one another and thus form a spiro system; furthermore, $R^3$ may form an aliphatic ring system with an adjacent radical R or $R^1$.

In a particularly preferred embodiment of the invention, $R^3$ in the groups of the formulae (43) to (49) and in the preferred embodiments stands, identically or differently on each occurrence, for F, a straight-chain alkyl group having 1 to 3 C atoms, in particular methyl, or an aromatic or heteroaromatic ring system having 5 to 12 aromatic ring atoms, which may in each case be substituted by one or more radicals $R^2$, but is preferably unsubstituted; two radicals $R^3$ here which are bonded to the same carbon atom may form an aliphatic or aromatic ring system with one another and thus form a spiro system; furthermore, $R^3$ may form an aliphatic ring system with an adjacent radical R or $R^1$.

Examples of particularly suitable groups of the formula (43) are the groups shown below:

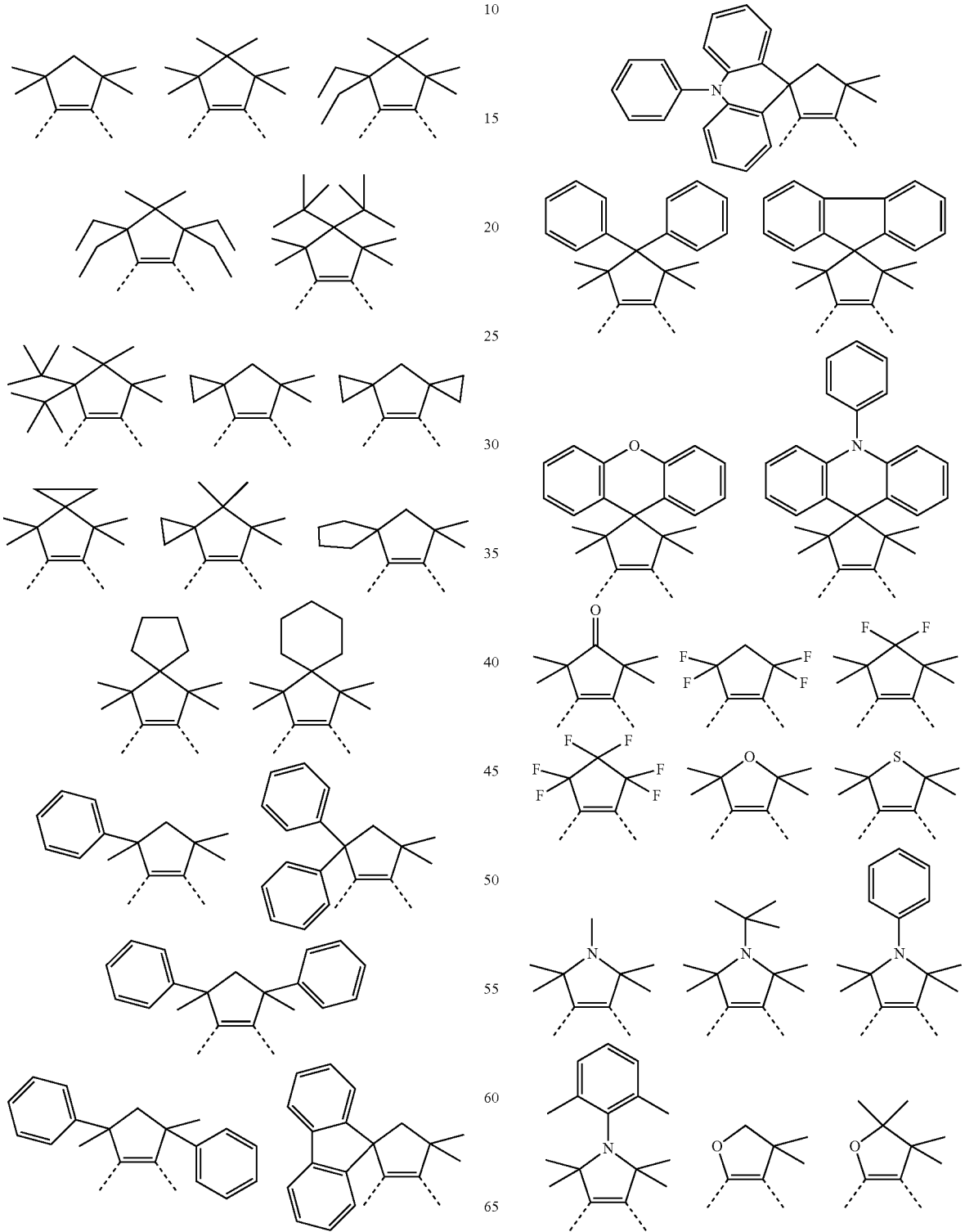

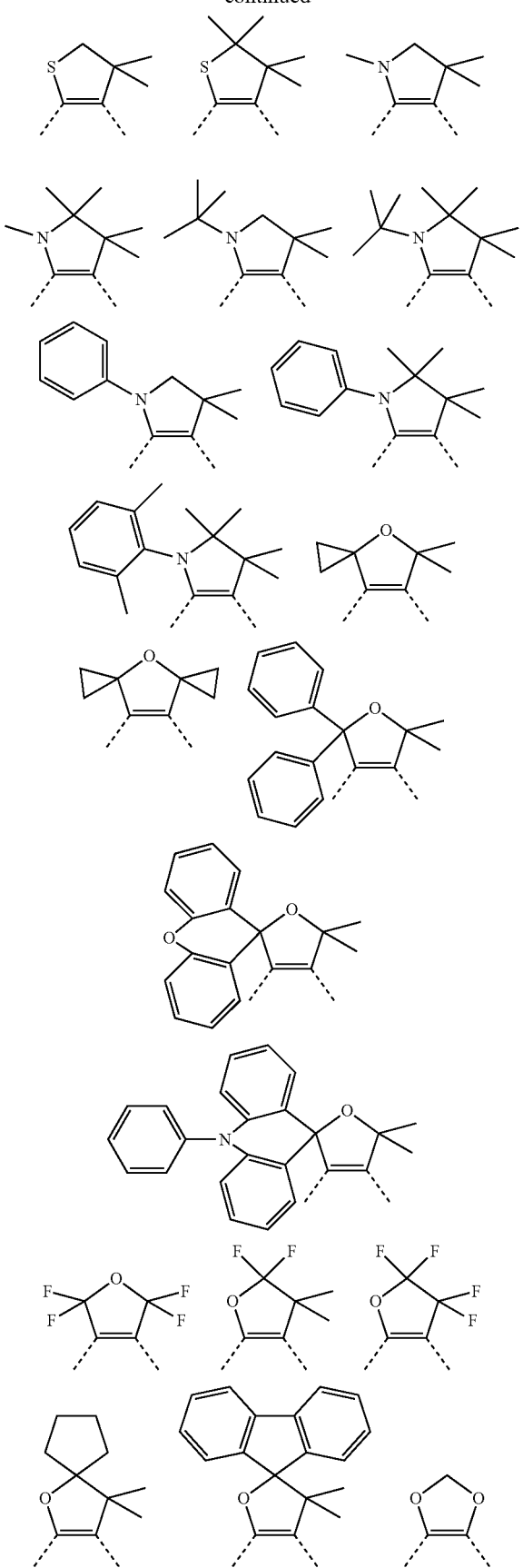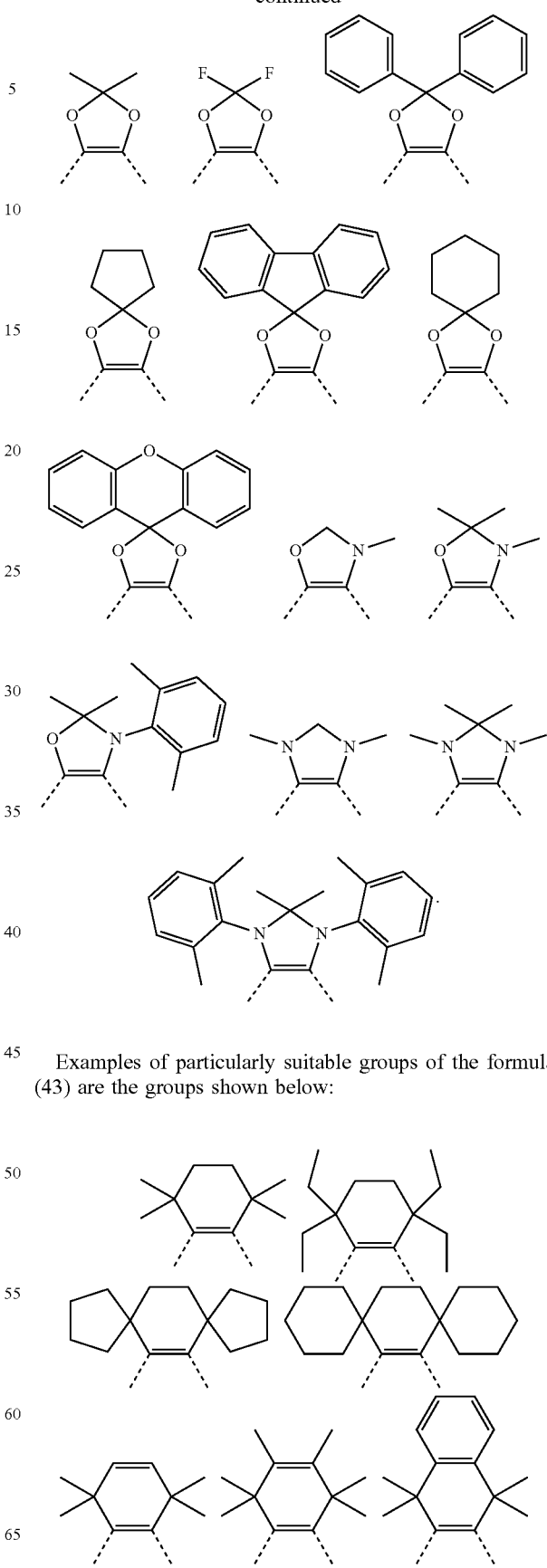
Examples of particularly suitable groups of the formula (43) are the groups shown below:

-continued

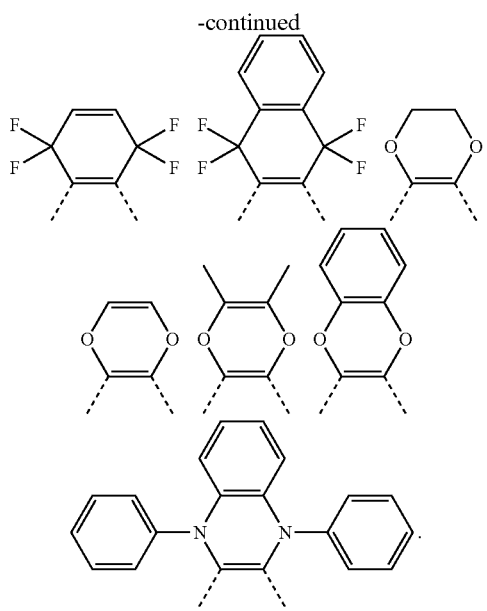

Examples of particularly suitable groups of the formulae (45), (48) and (49) are the groups shown below:

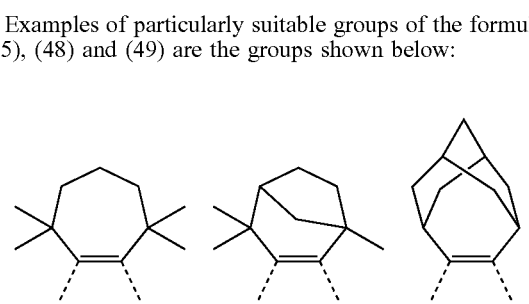

Examples of particularly suitable groups of the formula (46) are the groups depicted below:

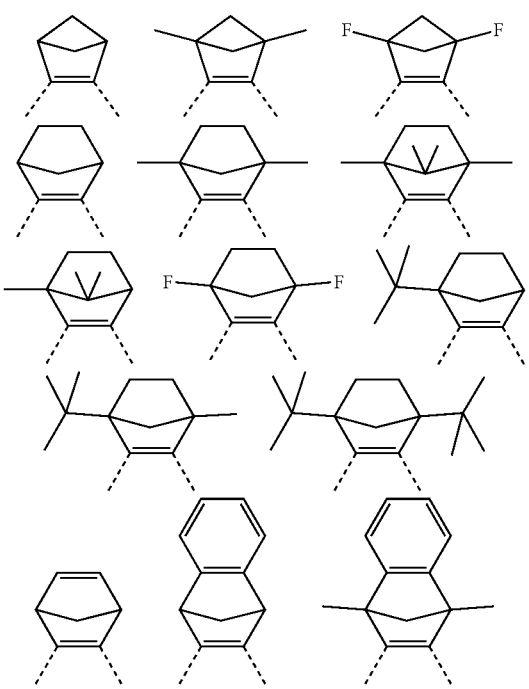

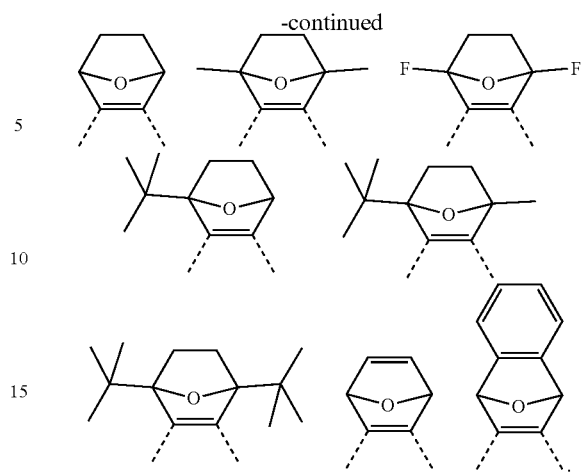

Examples of particularly suitable groups of the formula (47) are the groups shown below:

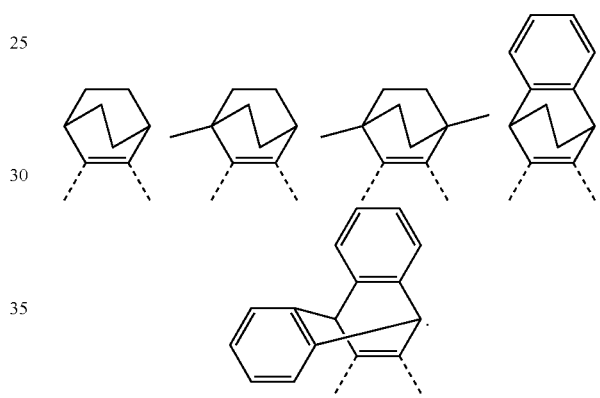

If radicals R are bonded in the bidentate part-ligands, these radicals R are preferably selected on each occurrence, identically or differently, from the group consisting of H, D, F, Br, I, $N(R^1)_2$, CN, $Si(R^1)_3$, $B(OR^1)_2$, $C(=O)R^1$, a straight-chain alkyl group having 1 to 10 C atoms or an alkenyl group having 2 to 10 C atoms or a branched or cyclic alkyl group having 3 to 10 C atoms, where the alkyl or alkenyl group may in each case be substituted by one or more radicals $R^1$, or an aromatic or heteroaromatic ring system having 5 to 30 aromatic ring atoms, which may in each case be substituted by one or more radicals $R^1$; two adjacent radical R here or R with $R^1$ may also form a mono- or polycyclic, aliphatic or aromatic ring system with one another. These radicals R are particularly preferably selected on each occurrence, identically or differently, from the group consisting of H, D, F, $N(R^1)_2$, a straight-chain alkyl group having 1 to 6 C atoms, in particular having 1 to 4 C atoms, or a branched or cyclic alkyl group having 3 to 10 C atoms, in particular having 3 to 6 C atoms, where one or more H atoms may be replaced by D or F, or an aromatic or heteroaromatic ring system having 5 to 24 aromatic ring atoms, in particular having 6 to 13 aromatic ring atoms, which may in each case be substituted by one or more radicals $R^1$; two adjacent radicals R here or R with $R^1$ may also form a mono- or polycyclic, aliphatic or aromatic ring system with one another.

Preferred radicals $R^1$ which are bonded to R are, identically or differently on each occurrence, H, D, F, $N(R^2)_2$, CN, a straight-chain alkyl group having 1 to 10 C atoms or an alkenyl group having 2 to 10 C atoms or a branched or cyclic alkyl group having 3 to 10 C atoms, where the alkyl group may in each case be substituted by one or more radicals $R^2$, or an aromatic or heteroaromatic ring system having 5 to 24 aromatic ring atoms, which may in each case be substituted by one or more radicals $R^2$; two or more adjacent radicals $R^1$ here may form a mono- or polycyclic, aliphatic ring system with one another. Particularly preferred radicals $R^1$ which are bonded to R are, identically or differently on each occurrence, H, F, CN, a straight-chain alkyl group having 1 to 5 C atoms or a branched or cyclic alkyl group having 3 to 5 C atoms, which may in each case be substituted by one or more radicals $R^2$, or an aromatic or heteroaromatic ring system having 5 to 13 aromatic ring atoms, which may in each case be substituted by one or more radicals $R^2$; two or more adjacent radicals $R^1$ here may form a mono- or polycyclic, aliphatic ring system with one another.

Preferred radicals $R^2$ are, identically or differently on each occurrence, H, F or an aliphatic hydrocarbon radical having 1 to 5 C atoms or an aromatic hydrocarbon radical having 6 to 12 C atoms; two or more substituents $R^2$ here may also form a mono- or polycyclic, aliphatic ring system with one another.

The metal complexes according to the invention can be chiral structures, depending on the configuration of the bridge. If, in addition, the tripodal ligand of the complexes is also chiral, the formation of diastereomers and a plurality of enantiomer pairs is possible. The complexes according to the invention then include both the mixtures of the various diastereomers or the corresponding racemates and also the individual isolated diastereomers or enantiomers.

If ligands having $C_3$ or $C_{3v}$ symmetry are employed in the ortho-metallation, a racemic mixture of the complexes having $C_3$ symmetry, i.e. of the Δ and Λ enantiomers, is usually formed. These can be separated by standard methods (chromatography on chiral materials/columns or racemate separation by crystallisation). This is shown in the following scheme for the example of a ligand having $C_3$ symmetry which carries three phenylpyridine part-ligands and also applies analogously to all other ligands having $C_3$ or $C_{3v}$ symmetry.

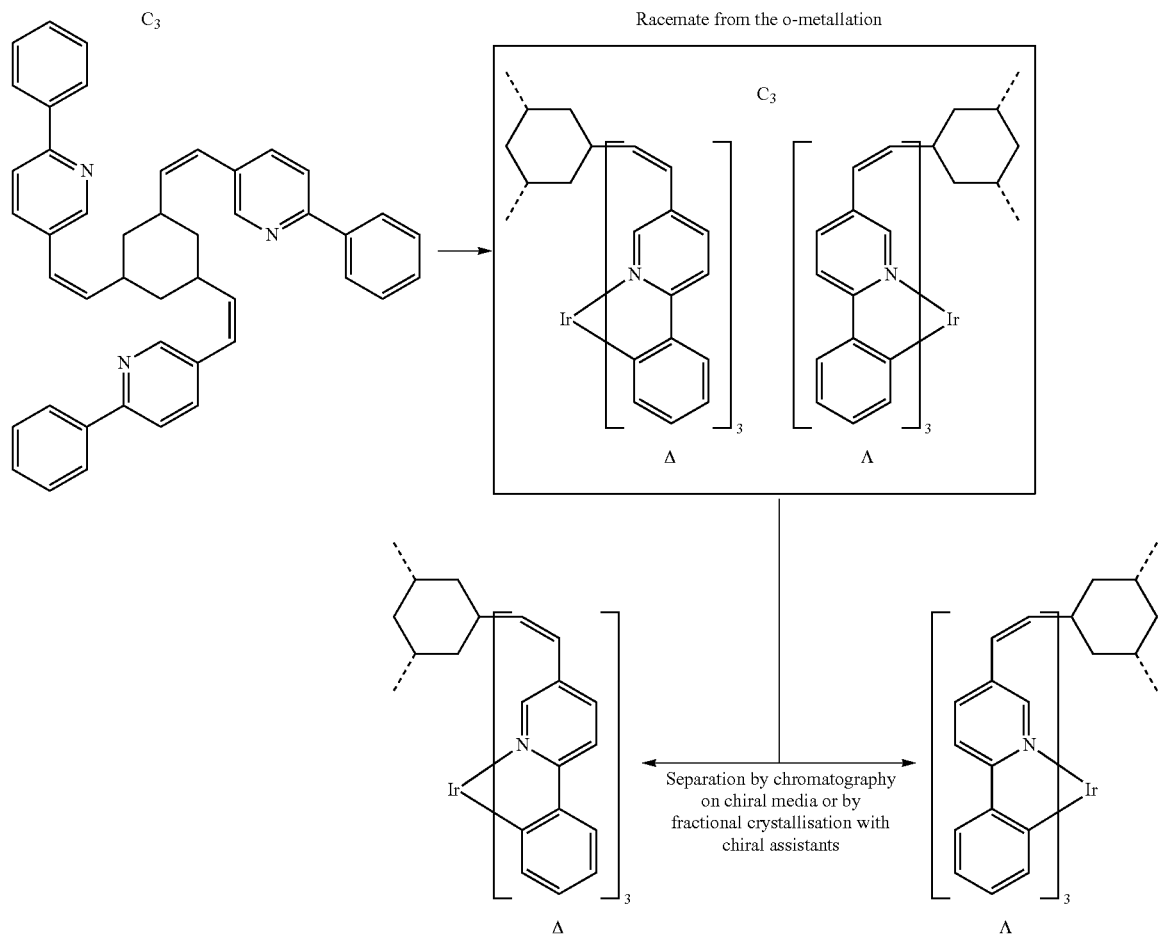

The racemate separation by fractional crystallisation of diastereomeric salt pairs can be carried out by conventional methods. To this end, the neutral Ir(III) complexes can be oxidised (for example using peroxides, $H_2O_2$ or electrochemically), the salt of an enantiomerically pure, monoanionic base (chiral base) can be added to the cationic Ir(IV) complexes produced in this way, the diastereomeric salts produced in this way can be separated by fractional crystallisation, and these can then be reduced to the enantiomerically pure neutral complex with the aid of a reducing agent (for example zinc, hydrazine hydrate, ascorbic acid, etc.), as shown diagrammatically below.

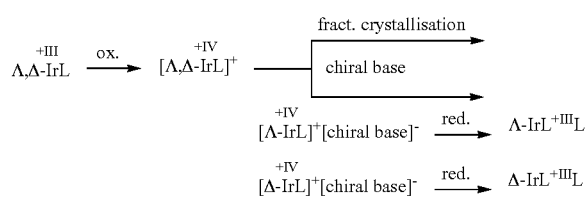

In addition, an enantiomerically pure or enantiomerically enriched synthesis is possible by complexation in a chiral medium (e.g. R- or S-1,1-binaphthol).

Analogous processes can also be carried out with complexes of ligands having $C_s$ symmetry.

If ligands having $C_1$ symmetry are employed in the complexation, a diastereomer mixture of the complexes is usually formed, which can be separated by standard methods (chromatography, crystallisation).

Enantiomerically pure complexes having $C_3$ symmetry can also be synthesised specifically. To this end, an enantiomerically pure ligand having $C_3$ symmetry is prepared, complexed, the diastereomer mixture obtained is separated, and the chiral group is subsequently cleaved off.

The preferred embodiments mentioned above can be combined with one another as desired. In a particularly preferred embodiment of the invention, the preferred embodiments mentioned above apply simultaneously.

The metal complexes according to the invention can in principle be prepared by various processes. To this end, a metal salt is generally reacted with the corresponding free ligand.

The present invention therefore furthermore relates to a process for the preparation of the metal complexes according to the invention by reaction of the corresponding free ligands with metal alkoxides of the formula (50), with metal ketoketonates of the formula (51), with metal halides of the formula (52) or with metal carboxylates of the formula (53),

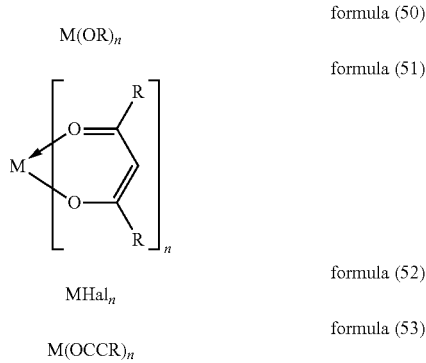

where M stands for the metal of the metal complex according to the invention that is being synthesised, n stands for the valency of the metal M, R has the meanings given above, Hal=F, Cl, Br or I, and the metal starting materials may also be in the form of the corresponding hydrates. R here preferably stands for groups as defined for $R^2$, particularly preferably for an alkyl group having 1 to 4 C atoms.

It is likewise possible to use metal compounds, in particular iridium compounds, which carry both alkoxide and/or halide and/or hydroxyl radicals as well as ketoketonate radicals. These compounds may also be charged. Corresponding iridium compounds which are particularly suitable as starting materials are disclosed in WO 2004/085449. [IrCl$_2$(acac)$_2$]-, for example Na[IrI$_2$(acac)$_2$], are particularly suitable. Metal complexes with acetylacetonate derivatives as ligand, for example Ir(acac)$_3$ or tris(2,2,6,6-tetramethylheptane-3,5-dionato)iridium, and IrCl$_3$.xH$_2$O, where x usually stands for a number between 2 and 4.

The synthesis of the complexes is preferably carried out as described in WO 2002/060910 and in WO 2004/085449. The synthesis here can also be activated, for example, thermally, photochemically and/or by microwave radiation. The synthesis can furthermore also be carried out in an autoclave under increased pressure and/or at elevated temperature.

The reactions can be carried out without addition of solvents or melting aids in a melt of the corresponding ligands to be o-metallated. If necessary, solvents or melting aids can be added. Suitable solvents are protic or aprotic solvents, such as aliphatic and/or aromatic alcohols (methanol, ethanol, isopropanol, t-butanol, etc.), oligo- and polyalcohols (ethylene glycol, 1,2-propanediol, glycerol, etc.), alcohol ethers (ethoxyethanol, diethylene glycol, triethylene glycol, polyethylene glycol, etc.), ethers (di- and triethylene glycol dimethyl ether, diphenyl ether, etc.), aromatic, heteroaromatic and/or aliphatic hydrocarbons (toluene, xylene, mesitylene, chlorobenzene, pyridine, lutidine, quinoline, isoquinoline, tridecane, hexadecane, etc.), amides (DMF, DMAC, etc.), lactams (NMP), sulfoxides (DMSO) or sulfones (dimethyl sulfone, sulfolane, etc.). Suitable melting aids are compounds which are in solid form at room temperature, but melt on warming of the reaction mixture and dissolve the reactants, so that a homogeneous melt forms. Particularly suitable are biphenyl, m-terphenyl, triphenylene, R- or S-binaphthol or the corresponding racemate, 1,2-, 1,3-, 1,4-bisphenoxybenzene, triphenylphosphine oxide, 18-crown-6, phenol, 1-naphthol, hydroquinone, etc. The use of hydroquinone is particularly preferred.

These processes, optionally followed by purification, such as, for example, recrystallisation or sublimation, enable the compounds of the formula (1) according to the invention to be obtained in high purity, preferably greater than 99% (determined by means of $^1$H-NMR and/or HPLC).

The metal complexes according to the invention can also be rendered soluble by suitable substitution, for example by relatively long alkyl groups (about 4 to 20 C atoms), in particular branched alkyl groups, or optionally substituted aryl groups, for example, xylyl, mesityl or branched terphenyl or quaterphenyl groups. In particular, the use of condensed-on aliphatic groups, as represented, for example, by the formulae (43) to (49) disclosed above, leads to a significant improvement in the solubility of the metal complexes. Compounds of this type are then soluble in common organic solvents, such as, for example, toluene or xylene, at room temperature in sufficient concentration to be able to process the complexes from solution. These soluble compounds are particularly suitable for processing from solution, for example by printing processes.

The metal complexes according to the invention can also be mixed with a polymer. It is likewise possible to incorporate these metal complexes into a polymer covalently. This is possible, in particular, with compounds which are substituted by reactive leaving groups, such as bromine, iodine, chlorine, boronic acid or boronic acid ester, or by reactive, polymerisable groups, such as olefins or oxetanes. These can be used as monomers for the generation of corresponding oligomers, dendrimers or polymers. The oligomerisation or polymerisation here preferably takes place via the halogen functionality or the boronic acid functionality or via the polymerisable group. It is furthermore possible to crosslink the polymers via groups of this type. The compounds and polymers according to invention can be employed as a crosslinked or uncrosslinked layer.

The invention therefore furthermore relates to oligomers, polymers or dendrimers containing one or more of the metal complexes according to the invention mentioned above, where one or more bonds are present from the metal complex according to invention to the polymer, oligomer or dendrimers instead of one or more hydrogen atoms and/or substituents. Depending on the linking of the metal complex according to the invention, this therefore forms a side chain of the oligomer or polymer or is linked in the main chain. The polymers, oligomers or dendrimers may be conjugated, partly conjugated or non-conjugated. The oligomers or polymers may be linear, branched or dendritic. The same preferences as described above apply to the recurring units of the metal complexes according to invention in oligomers, dendrimers and polymers.

For the preparation of the oligomers or polymers, the monomers according to invention are homopolymerised or copolymerised with further monomers. Preference is given to copolymers in which the metal complexes according to invention are present to the extent of 0.01 to 99.9 mol %, preferably 5 to 90 mol %, particularly preferably 5 to 50 mol %. Suitable and preferred comonomers which form the polymer backbone are selected from fluorenes (for example in accordance with EP 842208 or WO 2000/022026), spirobifluorenes (for example in accordance with EP 707020, EP 894107 or WO 2006/061181), para-phenylenes (for example in accordance with WO 92/18552), carbazoles (for example in accordance with WO 2004/070772 or WO 2004/113468), thiophenes (for example in accordance with EP 1028136), dihydrophenanthrenes (for example in accordance with WO 2005/014689), cis- and trans-indenofluorenes (for example in accordance with WO 2004/041901 or WO 2004/113412), ketones (for example in accordance with WO 2005/040302), phenanthrenes (for example in accordance with WO 2005/104264 or WO 2007/017066) or also a plurality of these units. The polymers, oligomers and dendrimers may also contain further units, for example hole-transport units, in particular those based on triarylamines, and/or electron-transport units.

The processing of the metal complexes according to the invention from the liquid phase, for example by spin coating or by printing processes, requires formulations of the metal complexes according to the invention. These formulations can be, for example, solutions, dispersions or emulsions. It may be preferred to use mixtures of two or more solvents for this purpose. Suitable and preferred solvents are, for example, toluene, anisole, o-, m- or p-xylene, methyl benzoate, mesitylene, tetralin, veratrol, THF, methyl-THF, THP, chlorobenzene, dioxane, phenoxytoluene, in particular 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane, hexamethylindane, 2-methylbiphenyl, 3-methylbiphenyl, 1-methylnaphthalene, 1-ethylnaphthalene, ethyl octanoate, diethyl sebacate, octyl octanoate, heptylbenzene, menthyl isovalerate, cyclohexyl hexanoate or mixtures of these solvents.

The present invention therefore furthermore relates to a formulation comprising at least one metal complex according to the invention or at least one polymer, oligomer or dendrimer according to the invention and at least one further compound. The further compound may be, for example, a solvent, in particular one of the above-mentioned solvents or a mixture of these solvents. However, the further compound may also be a further organic or inorganic compound which is likewise employed in the electronic device, for example a matrix material. This further compound may also be polymeric.

The metal complex according to the invention described above or the preferred embodiments indicated above can be used in the electronic device as active component or as oxygen sensitisers. The present invention thus furthermore relates to the use of a compound according to the invention in an electronic device or as oxygen sensitiser. The present invention still furthermore relates to an electronic device comprising at least one compound according to the invention.

An electronic device is taken to mean a device which comprises an anode, a cathode and at least one layer, where this layer comprises at least one organic or organometallic compound. The electronic device according to the invention thus comprises an anode, a cathode and at least one layer which comprises at least one metal complex according to the invention. Preferred electronic devices here are selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), which are taken to mean both purely organic solar cells and dye-sensitised solar cells, organic optical detectors, organic photoreceptors, organic field-quench devices (O-FQDs), light-emitting electrochemical cells (LECs), oxygen sensors or organic laser diodes (O-lasers), comprising at least one metal complex according to the invention in at least one layer. Particular preference is given to organic electroluminescent devices. This applies, in particular, if the metal is iridium or aluminium. Active components are generally the organic or inorganic materials which have been introduced between the anode and cathode, for example charge-injection, charge-transport or charge-blocking materials, but in particular emission materials and matrix materials. The compounds according to the invention exhibit particularly good properties as emission material in organic electroluminescent devices. Organic electroluminescent devices are therefore a preferred embodiment of the invention. Furthermore, the compounds according to the invention can be employed for the generation of singlet oxygen or in photocatalysis. In particular if the metal is ruthenium, the use as photosensitiser in a dye-sensitised solar cell ("Gratzel cell") is preferred.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers, charge-generation layers and/or organic or inorganic p/n junctions. It is possible here for one or more hole-transport layers to be p-doped, for example with metal oxides, such as $MoO_3$ or $WO_3$, or with (per)fluorinated electron-deficient aromatic compounds, and/or for one or more electron-transport layers to be n-doped. Interlayers which have, for example, an exciton-blocking function and/or control the charge balance in the electroluminescent device may likewise be introduced between two emitting layers. However, it should be pointed out that each of these layers does not necessarily have to be present.

The organic electroluminescent device here may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to three-layer systems, where the three layers exhibit blue, green and orange or red emission (for the basic structure see, for example, WO 2005/011013), or systems which have more than three emitting layers. It may also be a hybrid system, where one or more layers fluoresce and one or more other layers phosphoresce. A further embodiment for white-emitting OLEDs are tandem OLEDs. White-emitting organic electroluminescent devices can be used for lighting applications or, with colour filters, also for full-colour displays.

In a preferred embodiment of the invention, the organic electroluminescent device comprises the metal complex according to the invention as emitting compound in one or more emitting layers.

If the metal complex according to the invention is employed as emitting compound in an emitting layer, it is preferably employed in combination with one or more matrix materials. The mixture of the metal complex according to the invention and the matrix material comprises between 1 and 99% by vol., preferably between 1 and 90% by vol., particularly preferably between 3 and 40% by vol., in particular between 5 and 25% by vol., of the metal complex according to the invention, based on the mixture as a whole comprising emitter and matrix material. Correspondingly, the mixture comprises between 99.9 and 1% by vol., preferably between 99 and 10% by vol., particularly preferably between 97 and 60% by vol., in particular between 95 and 75% by vol., of the matrix material, based on the mixture as a whole comprising emitter and matrix material.

The matrix material employed can in general be all materials which are known for this purpose in accordance with the prior art. The triplet level of the matrix material is preferably higher than the triplet level of the emitter.

Suitable matrix materials for the compounds according to the invention are ketones, phosphine oxides, sulfoxides and sulfones, for example in accordance with WO 2004/013080, WO 2004/093207, WO 2006/005627 or WO 2010/006680, triarylamines, carbazole derivatives, for example CBP (N,N-biscarbazolylbiphenyl), m-CBP or the carbazole derivatives disclosed in WO 2005/039246, US 2005/0069729, JP 2004/288381, EP 1205527, WO 2008/086851 or US 2009/0134784, indolocarbazole derivatives, for example in accordance with WO 2007/063754 or WO 2008/056746, indenocarbazole derivatives, for example in accordance with WO 2010/136109 or WO 2011/000455, azacarbazoles, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, diazasilole derivatives, for example in accordance with WO 2010/054729, diazaphosphole derivatives, for example in accordance with WO 2010/054730, triazine derivatives, for example in accordance with WO 2010/015306, WO 2007/063754 or WO 2008/056746, zinc complexes, for example in accordance with EP 652273 or WO 2009/062578, dibenzofuran derivatives, for example in accordance with WO 2009/148015 or WO 2015/169412, or bridged carbazole derivatives, for example in accordance with US 2009/0136779, WO 2010/050778, WO 2011/042107 or WO 2011/088877.

It may also be preferred to employ a plurality of different matrix materials as a mixture, in particular at least one electron-conducting matrix material and at least one hole-conducting matrix material. A preferred combination is, for example, the use of an aromatic ketone, a triazine derivative or a phosphine oxide derivative with a triarylamine derivative or a carbazole derivative as mixed matrix for the metal complex according to the invention. Preference is likewise given to the use of a mixture of a charge-transporting matrix material and an electrically inert matrix material which is not involved or not involved to a significant extent in charge transport, as described, for example, in WO 2010/108579. Preference is likewise given to the use of two electron-transporting matrix materials, for example triazine derivatives and lactam derivatives, as described, for example, in WO 2014/094964.

It is furthermore preferred to employ a mixture of two or more triplet emitters together with a matrix. The triplet emitter having the shorter-wave emission spectrum serves here as co-matrix for the triplet emitter having the longer-wave emission spectrum. Thus, for example, the metal complexes according to the invention can be employed as co-matrix for triplet emitters emitting at longer wavelength, for example for green- or red-emitting triplet emitters. It may also be preferred here if both the metal complex emitting at shorter wavelength and also the metal complex emitting at longer wavelength is a compound according to the invention. The metal complexes according to the invention can also be employed in other functions in the electronic device, for example as hole-transport material or p-dopant in a hole-injection or -transport layer, as charge-generation material, as electron-blocking material, as hole-blocking material or as electron-transport material or n-dopant, for example in an electron-transport layer, depending on the choice of the metal and the precise structure of the ligand. If the metal complex according to the invention is an aluminium complex, this is preferably employed in an electron-transport layer or hole-blocking layer. The metal complexes according to the invention can likewise be employed as matrix material for other phosphorescent metal complexes in an emitting layer.

The cathode preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag, may also be used in addition to the said metals, in which case combinations of the metals, such as, for example, Mg/Ag, Ca/Ag or Ba/Ag, are generally used. It may also be preferred to introduce a thin interlayer of a material having a high dielectric constant between a metallic cathode and the organic semiconductor. Suitable for this purpose are, for example, alkali metal or alkaline-earth metal fluorides, but also the corresponding oxides or carbonates (for example LiF, $Li_2O$, $BaF_2$, MgO, NaF, CsF, $Cs_2CO_3$, etc.). Organic alkali-metal complexes, for example Liq (lithium quinolinate), are likewise suitable for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/NiOx, Al/PtOx) may also be preferred. For some applications, at least one of the electrodes must be transparent or partially transparent in order either to facilitate irradiation of the organic material (O-SCs) or the coupling-out of light (OLEDs/PLEDs, O-LASERs). Preferred anode materials here are conductive mixed metal oxides. Particular preference is given to indium tin oxide (ITO) or indium zinc oxide (IZO). Preference is furthermore given to conductive, doped organic materials, in particular conductive doped polymers, for example PEDOT, PANI or derivatives of these polymers. It is furthermore preferred for a p-doped hole-transport material to be applied to the anode as hole-injection layer, where suitable p-dopants are metal oxides, for example $MoO_3$ or $WO_3$, or (per)fluorinated electron-deficient aromatic compounds. Further suitable p-dopants are HAT-CN (hexacyanohexaazatriphenylene) or the compound NPD9 from Novaled. A layer of this type simplifies hole injection in materials having a low HOMO, i.e. a large value of the HOMO.

All materials as are used in accordance with the prior art for the layers can generally be used in the further layers, and the person skilled in the art will be able to combine each of these materials with the materials according to the invention in an electronic device without inventive step.

The device is correspondingly structured (depending on the application), provided with contacts and finally hermetically sealed, since the lifetime of such devices is drastically shortened in the presence of water and/or air.

Preference is furthermore given to an organic electroluminescent device, characterised in that one or more layers are applied by means of a sublimation process, in which the materials are vapour-deposited in vacuum sublimation units at an initial pressure of usually less than $10^{-5}$ mbar, preferably less than $10^{-6}$ mbar. It is also possible for the initial pressure to be even lower or even higher, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and thus structured.

Preference is furthermore given to an organic electroluminescent device, characterised in that one or more layers are produced from solution, such as, for example, by spin coating, or by means of any desired printing process, such as, for example, screen printing, flexographic printing, offset printing or nozzle printing, but particularly preferably LITI (light induced thermal imaging, thermal transfer printing) or ink-jet printing. Soluble compounds are necessary for this purpose, which are obtained, for example, through suitable substitution.

The organic electroluminescent device may also be produced as a hybrid system by applying one or more layers from solution and applying one or more other layers by vapour deposition. Thus, for example, it is possible to apply an emitting layer comprising a metal complex according to the invention and a matrix material from solution and to apply a hole-blocking layer and/or an electron-transport layer on top by vacuum vapour deposition.

These processes are generally known to the person skilled in the art and can be applied by him without problems to organic electroluminescent devices containing compounds of the formula (1) or the preferred embodiments indicated above.

The electronic devices according to the invention, in particular organic electroluminescent devices, are distinguished over the prior art by one or more of the following surprising advantages:

1. The metal complexes according to invention can be synthesised in very high yield and very high purity with extraordinarily short reaction times and at comparatively low reaction temperatures.
2. The metal complexes according to the invention have excellent thermal stability, which is also evident on sublimation of the complexes.
3. The metal complexes according to invention exhibit neither thermal nor photochemical fac/mer or mer/fac isomerisation, which results in advantages in the use of these complexes.
4. The metal complexes according to invention in some cases have a very narrow emission spectrum, which results in high colour purity of the emission, as is desirable, in particular, for display applications.
5. Organic electroluminescent devices containing the metal complexes according to the invention as emitting materials have a very long lifetime.
6. Organic electroluminescent devices containing the metal complexes according to the invention as emitting materials have excellent efficiency.

These above-mentioned advantages are not accompanied by impairment of the other electronic properties.

The invention is explained in greater detail by the following examples without wishing to restrict it thereby. The person skilled in the art will be able to use the descriptions to produce further electronic devices according to the invention without inventive step and thus carry out the invention throughout the range claimed.

EXAMPLES

The following syntheses are carried out, unless indicated otherwise, under a protective-gas atmosphere in dried solvents. The metal complexes are additionally handled with exclusion of light or under yellow light. The solvents and reagents can be purchased, for example, from Sigma-ALDRICH or ABCR. The respective numbers in square brackets or the numbers indicated for individual compounds refer to the CAS numbers of the compounds known from the literature. Ligands containing imine units are depicted pictorially below with respect to their conformation at the imine bond as they are present in the metal complex, irrespective of whether they are obtained from the synthesis as the cis form, trans form or as a mixture.

1. Preparation of the Organic Synthones:

Example S1

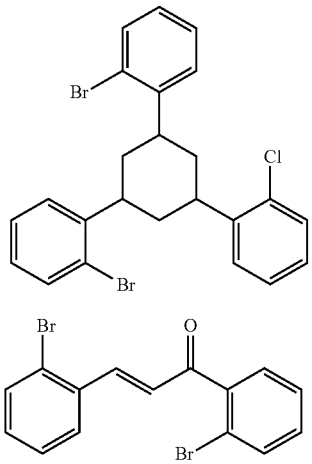
a)

Preparation in accordance with G. Markopoulos et al., Angew. Chem., Int. Ed., 2012, 51, 12884.

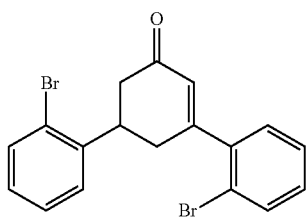
b)

Procedure in accordance with JP 2000-169400. 5.7 g (105 mmol) of sodium methoxide are added in portions to a solution of 36.6 g (100 mmol) of 1,3-bis(2-bromophenyl)-2-propen-1-one [126824-93-9], step a), in 300 ml of dry acetone, and the mixture is then stirred at 40° C. for 12 h. The solvent is removed in vacuo, the residue is taken up in ethyl acetate, washed three times with 200 ml of water each time, twice with 200 ml of sat. sodium chloride solution each time and dried over magnesium sulfate.

The oil obtained after removal of the solvent in vacuo is subjected to flash chromatography (Torrent CombiFlash, Axel Semrau). Yield: 17.9 g (44 mmol), 44%. Purity: about 97% according to $^1$H-NMR.

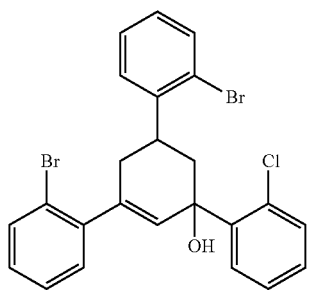
c)

2.4 g (2.4 mmol) of anhydrous copper(I) chloride [7758-89-6] are added at 0° C. to a solution of 2-chlorophenylmagnesium bromide (200 mmol) [36692-27-0] in 200 ml of di-n-butyl ether, and the mixture is stirred for a further 30 min. A solution of 40.6 g (100 mmol) of step b) in 200 ml of toluene is then added dropwise over the course of 30 min., and the mixture is stirred at 0° C. for a further 5 h. The reaction mixture is quenched by careful addition of 100 ml of water and then with 220 ml of 1N hydrochloric acid. The organic phase is separated off, washed twice with 200 ml of water each time, once with 200 ml of saturated sodium hydrogencarbonate solution, once with 200 ml of sat. sodium chloride solution and dried over magnesium sulfate. The oil obtained after removal of the solvent in vacuo is filtered through silica gel with toluene. The crude product obtained in this way is reacted further without further purification. Yield: 49.8 g (96 mmol), 96%. Purity: about 90-95% according to $^1$H-NMR.

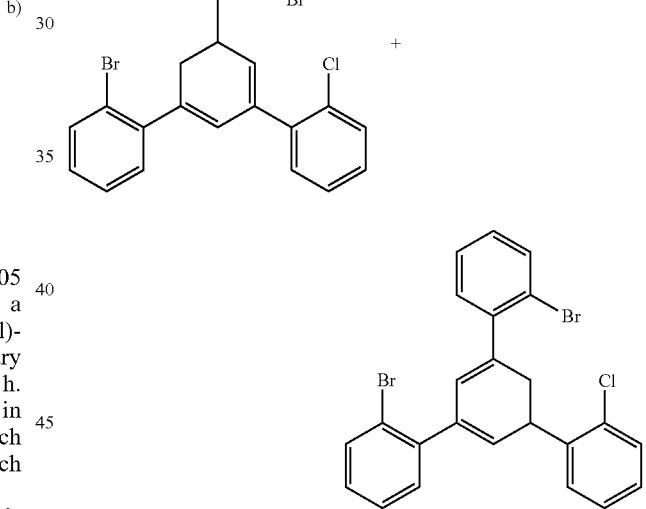
d)

1.0 ml of trifluoromethanesulfonic acid and then, in portions, 50 g of phosphorus pentoxide are added to a solution, cooled to 0° C., of 51.9 g (100 mmol) of step c) in 500 ml of dichloromethane (DCM). The mixture is allowed to warm to room temperature and is stirred for a further 2 h. The supernatant is decanted off from the phosphorus pentoxide, the latter is suspended in 200 ml of DCM, and the supernatant is again decanted off. The combined DCM phases are washed twice with water and once with sat. sodium chloride solution and dried over magnesium sulfate. The wax obtained after removal of the solvent in vacuo is subjected to flash chromatography (Torrent CombiFlash, Axel Semrau). Yield: 31.5 g (63 mmol), 63%, isomer mixture. Purity: about 90-95% according to $^1$H-NMR.

e) 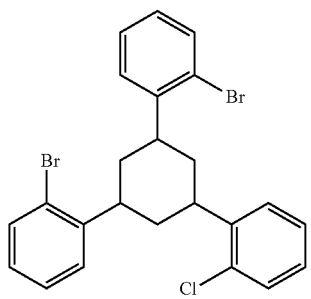

A mixture of 25.0 g (50 mmol) of step d), 2 g of Pd/C (10%), 200 ml of methanol and 300 ml of ethyl acetate is charged with 3 bar of hydrogen in a stirred autoclave and hydrogenated at 30° C. until the uptake of hydrogen is complete. The mixture is filtered through a Celite bed which has been pre-slurried with ethyl acetate, the filtrate is evaporated to dryness. The oil obtained in this way is subjected to flash chromatography (Torrent CombiFlash, Axel Semrau). Yield: 17.2 g (34 mmol), 68%. Purity: about 95% according to $^1$H-NMR, cis,cis isomer.

The following compounds can be prepared analogously.

| Ex. | Starting materials if different from S1 | Product | Yield a) to e) |
|---|---|---|---|
| S2 | 246-139-77-5 | ![product S2] | 21% |
| S3 | 246-139-77-5 147438-85-5 | ![product S3] | 19% |
| S4 | 246-139-77-5 147438-85-5 | ![product S4] | 14% |

Example S5

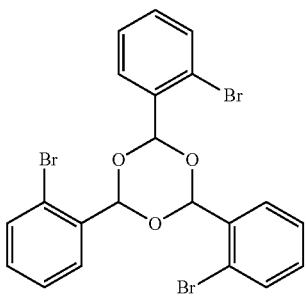 [SMILES: Brc1ccccc1C1OC(c2ccccc2Br)OC(c2ccccc2Br)O1]

801 mg (10 mmol) of nanoscale zinc oxide are added to a vigourously stirred melt, held at a temperature of 40° C., of 18.5 g (100 mmol) of 2-bromobenzaldehyde. After 16 h, 100 ml of toluene are added to the reaction mixture, the zinc oxide is filtered off through Celite, all the toluene is removed in vacuo, and the wax obtained in this way is recrystallised from acetone. Yield: 6.3 g (34 mmol), 34%. Purity: about 95% according to $^1$H-NMR, cis,cis isomer.

Example S6

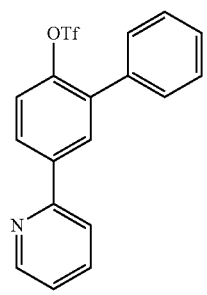

S6

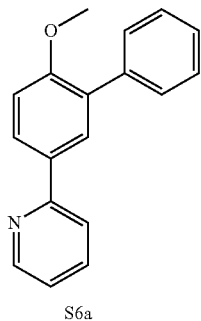

S6a a) A mixture of 22.6 g (100 mmol) of (6-methoxy-[1,1'-biphenyl]-3-yl)boronic acid [459423-16-6], 16.6 g (105 mmol) of 2-bromopyridine [109-04-6], 21.2 g (200 mmol) of sodium carbonate, 1.2 g (1 mmol) of tetrakis(triphenylphosphino)palladium [14221-01-3], 300 ml of toluene, 100 mol of ethanol and 300 ml of water is heated under reflux with vigourous stirring for 18 h. After cooling, the org. phase is separated off, washed twice with 300 ml of water each time and once with 300 ml of sat. NaCl solution and dried over magnesium sulfate. The oil obtained after evaporation of the org. phase is dried at 80° C. under an oil-pump vacuum and reacted without further purification. Yield: 25.6 g (98 mmol), 98%; purity: about 95% according to $^1$H-NMR.

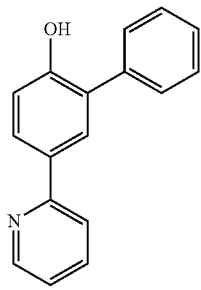

S6b b) A mixture of 26.1 g (100 mmol) of 5-(2-pyridyl)-[1,1'-biphenyl]-2-ol S6a and 81.9 g (700 mmol) of pyridinium hydrochloride are heated at 190° C. for 3 h. After cooling, the reaction mixture is poured into 500 ml of water, extracted five times with 200 ml of dichloromethane each time, the org. phase is washed twice with 200 ml of water and once with 200 ml of sat. NaCl solution, the solvent is removed in vacuo, 300 ml of toluene are added for azeotropic drying, and all of the latter is removed by distillation in vacuo. The viscous oil obtained in this way is reacted without further purification. Yield: 21.0 g (85 mmol) 85%; purity: about 95% according to $^1$H-NMR.

c) S6

34 ml (200 mmol) of trifluoromethanesulfonic anhydride [358-23-6] are added dropwise to a solution, cooled to 0° C., of 24.7 g (100 mmol) of S6b in a mixture of 300 ml of dichloromethane and 80 ml of pyridine with vigourous stirring. The reaction mixture is allowed to warm to RT, stirred for a further 16 h, poured into 1000 ml of ice-water with stirring and the latter is then extracted three times with 300 ml of dichloromethane. The combined org. phases are washed twice with 300 ml of ice-water each time and once with 500 ml of sat. NaCl solution and then dried over sodium sulfate. The wax remaining after removal of the dichloromethane in vacuo is recrystallised from acetonitrile. Yield: 32.6 g (86 mmol), 86%; purity: about 95% according to $^1$H-NMR.

S7 can be obtained analogously, replacing 2-bromopyridine with 2-bromo-4-tert-butylpyridine [50488-34-1]:

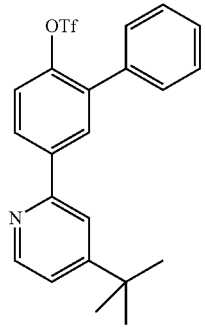 [SMILES: CC(C)(C)c1ccnc(-c2ccc(OS(=O)(=O)C(F)(F)F)c(-c3ccccc3)c2)c1]

Example S10: 5-Bromo-2-[1,1,2,2,3,3-hexamethyl-indan-5-yl]pyridine

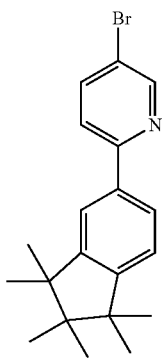 [SMILES: CC1(C)c2ccc(-c3ccc(Br)cn3)cc2C(C)(C)C1(C)C]

A mixture of 164.2 g (500 mmol) of 2-(1,1,2,2,3,3-hexamethylindan-5-yl)-4,4,5,5-tetramethyl-1,3,2-dioxaborolane [152418-16-9] (boronic acids can be employed analogously), 142.0 g (500 mmol) of 5-bromo-2-iodopyridine [223463-13-6], 159.0 g (1.5 mol) of sodium carbonate, 5.8 g (5 mmol) of tetrakis(triphenylphosphino)palladium(0), 700 ml of toluene, 300 ml of ethanol and 700 ml of water is heated under reflux with vigourous stirring for 16 h. After cooling, 1000 ml of toluene are added, the organic phase is separated off, and the aqueous phase is then extracted with 300 ml of toluene. The combined organic phases are washed once with 500 ml of saturated sodium chloride solution. After the organic phase has been dried over sodium sulfate and the solvent has been removed in vacuo, the crude product is recrystallised twice from about 300 ml of EtOH. Yield: 130.8 g (365 mmol), 73%. Purity: about 95% according to $^1$H-NMR.

The following compound can be prepared analogously:

Example S20

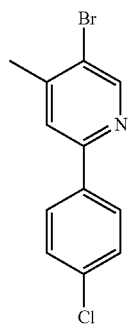

A mixture of 25.1 g (100 mmol) of 2,5-dibromo-4-methylpyridine [3430-26-0], 15.6 g (100 mmol) of 4-chlorophenylboronic acid [1679-18-1], 27.6 g (200 mmol) of potassium carbonate, 1.57 g (6 mmol) of triphenylphosphine [603-35-0], 676 mg (3 mmol) of palladium(II) acetate [3375-31-3], 200 g of glass beads (diameter 3 mm), 200 ml of acetonitrile and 100 ml of ethanol is heated under reflux for 48 h. After cooling, the solvents are removed in vacuo, 500 ml of toluene are added, the mixture is washed twice with 300 ml of water each time, once with 200 ml of sat. sodium chloride solution, dried over magnesium sulfate, filtered through a pre-slurried silica-gel bed, and the latter is rinsed with 300 ml of toluene. After removal of the toluene in vacuo, the product is recrystallised once from methanol/ethanol (1:1 vv) and once from n-heptane. Yield: 17.3 g (61 mmol), 61%. Purity: about 95% according to $^1$H-NMR.

Example S21

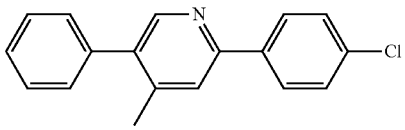 [SMILES: Cc1cc(-c2ccc(Cl)cc2)ncc1-c1ccccc1]

A mixture of 28.3 g (100 mmol) of S20, 12.8 g (105 mmol) of phenylboronic acid, 31.8 g (300 mmol) of sodium

| Ex. | Boronic acid/ester Pyridine | Product | Yield |
|---|---|---|---|
| S11 | HO-B-OH (phenyl) 98-80-6 / Br-pyridine-Br-phenyl 1381937-40-1 | Br-pyridine-phenyl, phenyl | 73% | carbonate, 787 mg (3 mmol) of triphenylphosphine, 225 mg (1 mmol) of palladium(II) acetate, 300 ml of toluene, 150 ml of ethanol and 300 ml of water is heated under reflux for 48 h. After cooling, the mixture is extended with 300 ml of toluene, die org. phase is separated off, washed once with 300 ml of water, once with 200 ml of sat. sodium chloride solution and dried over magnesium sulfate. After removal of the solvent, the residue is chromatographed on silica gel (toluene/ethyl acetate, 9:1 vv). Yield: 17.1 g (61 mmol), 61%. Purity: about 97% according to $^1$H-NMR.

The following compounds can be synthesised analogously:

| Ex. | Boronic ester | Product | Yield |
|---|---|---|---|
| S22 | 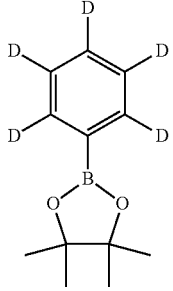 245043-33-8 | 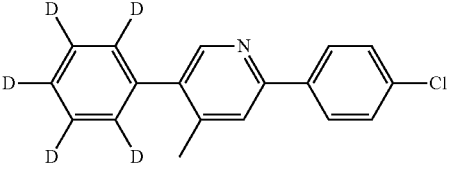 [SMILES: [2H]c1c([2H])c([2H])c(-c2cnc(-c3ccc(Cl)cc3)cc2C)c([2H])c1[2H]] | 56% |
| S23 | 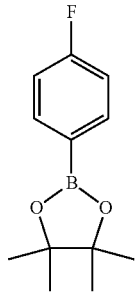 214360-58-4 | 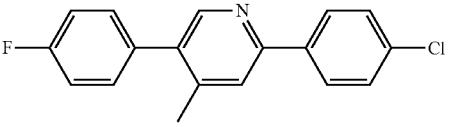 | 61% |
| S24 | 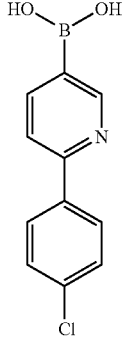 1264513-60-1 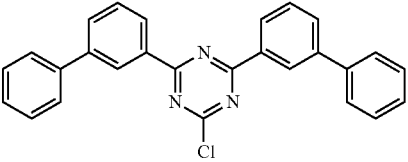 1205748-61-3 | 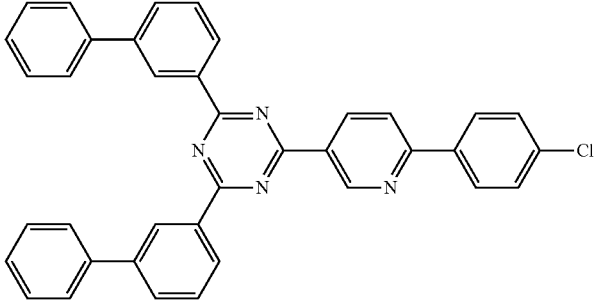 [SMILES: Clc1ccc(-c2ccc(-c3nc(-c4cccc(-c5ccccc5)c4)nc(-c4cccc(-c5ccccc5)c4)n3)cn2)cc1] | 70% |

Example S30: 2-[1,1,2,2,3,3-Hexamethylindan-5-yl]-5-(4,4,5,5-tetra-methyl-1,3,2-dioxaborolan-2-yl)pyridine Variant A:

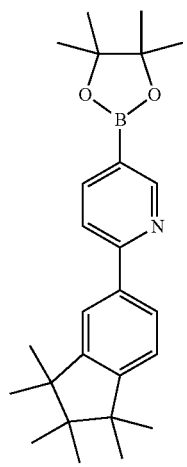

A mixture of 35.8 g (100 mmol) of S10, 25.4 g (100 mmol) of bis(pinacolato)diborane [73183-34-3], 49.1 g (500 mmol) of potassium acetate, 1.5 g (2 mmol) of 1,1-bis(diphenylphosphino)ferrocenepalladium(II) dichloride complex with DCM [95464-05-4], 200 g of glass beads (diameter 3 mm), 700 ml of 1,4-dioxane and 700 ml of toluene is heated under reflux for 16 h. After cooling, the suspension is filtered through a Celite bed, and the solvent is removed in vacuo. The black residue is digested with 1000 ml of hot cyclohexane, filtered through a Celite bed while still hot, then evaporated to about 200 ml, during which the product begins to crystallise. The crystallisation is completed overnight in the refrigerator, and the crystals are filtered off and washed with a little n-heptane. A second product fraction can be obtained from the mother liquor. Yield: 31.6 g (78 mmol), 78%. Purity: about 95% according to $^1$H-NMR.

Variant B: Reaction of Aryl Chlorides

As for variant A, but replacing 1,1-bis(diphenylphosphino)ferrocenepalladium(II) dichloride complex with DCM with 1.5 mmol of S-Phos [657408-07-6] and 1.0 mmol of palladium(II) acetate.

The following compounds can be prepared analogously, where cyclohexane, toluene, acetonitrile, ethyl acetate or mixtures of the said solvents can also be used instead of n-heptane for the purification:

| Ex. | Bromide/triflate - Variant A<br>Chloride - Variant B | Product | Yield |
|---|---|---|---|
| S31 | (1246851-70-6) | | 88% |
| S32 | S11 | | 70% |
| S33 | S21 | | 86% |
| S34 | S22 | | 79% |

-continued

| Ex. | Bromide/triflate - Variant A<br>Chloride - Variant B | Product | Yield |
|---|---|---|---|
| S35 | S23 | | 77% |
| S36 | S6 | | 64% |
| S37 | S7 | | 69% |
| S38 | S24 | | 74% |

| Ex. | Bromide/triflate - Variant A<br>Chloride - Variant B | Product | Yield |
|---|---|---|---|
| S39 | 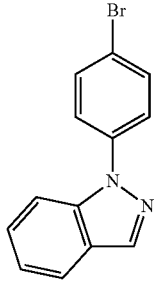<br>838820-83-0 | 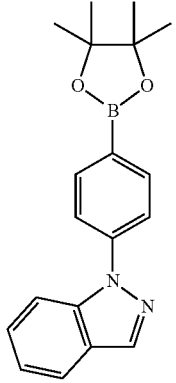 [SMILES: CC1(C)OB(c2ccc(-n3ncc4ccccc43)cc2)OC1(C)C] | 83% |
| S40 | 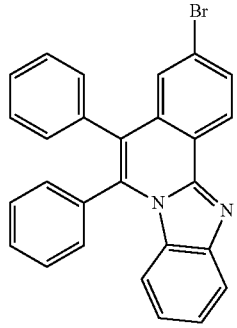<br>1447946-51-1 | 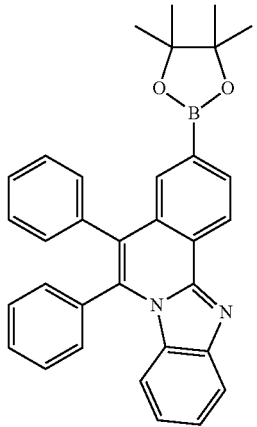 [SMILES: CC1(C)OB(c2ccc3c(c2)c(-c2ccccc2)c(-c2ccccc2)n2c4ccccc4nc32)OC1(C)C] | 80% |
| S41 | 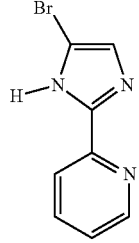<br>71048-48-1 | 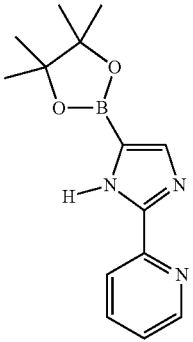 [SMILES: CC1(C)OB(c2cnc(-c3ccccn3)[nH]2)OC1(C)C] | 36% |
| S42 | 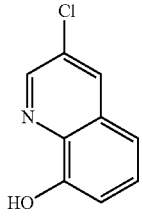<br>102878-83-1 | 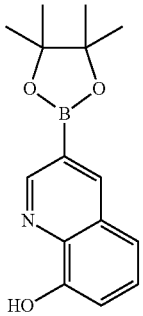 [SMILES: CC1(C)OB(c2cnc3c(O)cccc3c2)OC1(C)C] | 48% |

| Ex. | Bromide/triflate - Variant A<br>Chloride - Variant B | Product | Yield |
|---|---|---|---|
| S43 | 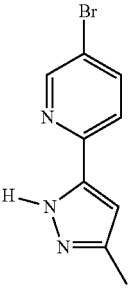<br>1239480-83-1 | 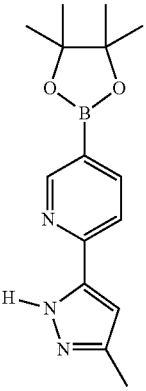 [SMILES: Cc1cc(-c2ccc(B3OC(C)(C)C(C)(C)O3)cn2)[nH]n1] | 46% |

Example S100

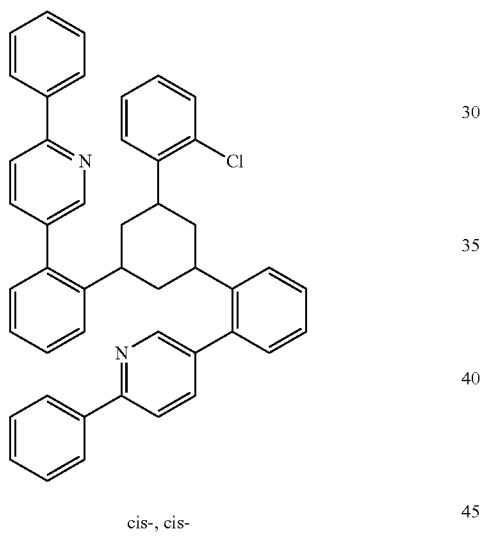

cis-, cis-

A mixture of 54.5 g (100 mmol) of S1, 59.0 g (210 mmol) of 2-phenyl-5-(4,4,5,5-tetramethyl-1,3,2-dioxaborolan-2-yl)pyridine [879291-27-7], 127.4 g (600 mmol) of tripotassium phosphate, 1.57 g (6 mmol) of triphenylphosphine and 449 mg (2 mmol) of palladium(II) acetate in 750 ml of toluene, 300 ml of dioxane and 500 ml of water is heated under reflux for 30 h. After cooling, the org. phase is separated off, washed twice with 300 ml of water each time, once with 300 ml of saturated sodium chloride solution and dried over magnesium sulfate. The magnesium sulfate is filtered off through a Celite bed which has been pre-slurried with toluene, the filtrate is evaporated to dryness in vacuo, and the foam which remains is recrystallised from acetonitrile/ethyl acetate. Yield: 41.8 g (64 mmol), 64%. Purity: about 95% according to $^1$H-NMR.

The following compounds can be prepared analogously:
| Ex. | Starting materials | Product | Yield |
|---|---|---|---|
| S101 | S1<br>S31 | 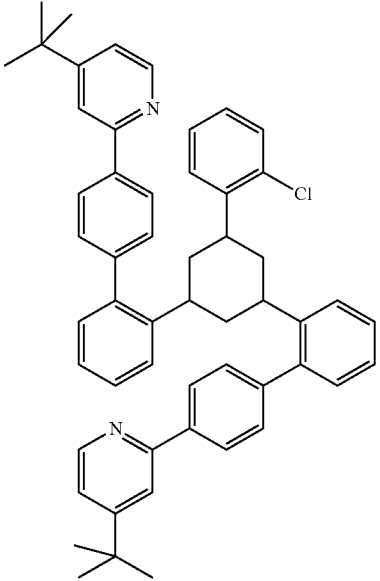 [SMILES: CC(C)(C)c1ccnc(-c2ccc(-c3ccccc3C3CC(c4ccccc4Cl)CC(c4ccccc4-c4ccc(-c5cc(C(C)(C)C)ccn5)cc4)C3)cc2)c1] | 68% |
| S102 | S3<br>S31 | 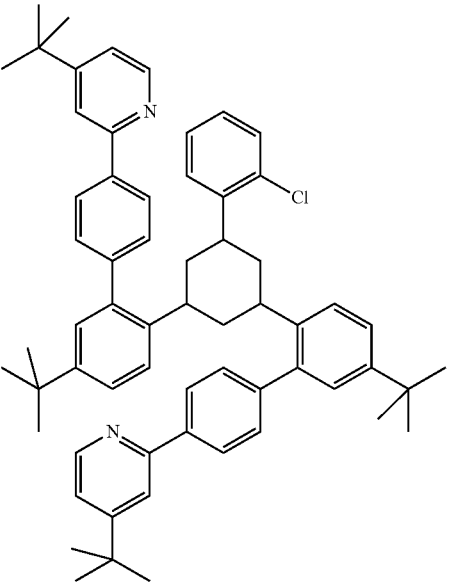 [SMILES: CC(C)(C)c1ccnc(-c2ccc(-c3cc(C(C)(C)C)ccc3C3CC(c4ccccc4Cl)CC(c4ccc(C(C)(C)C)cc4-c4ccc(-c5cc(C(C)(C)C)ccn5)cc4)C3)cc2)c1] | 60% |

-continued
| Ex. | Starting materials | Product | Yield |
|---|---|---|---|
| S103 | S3 S32 | 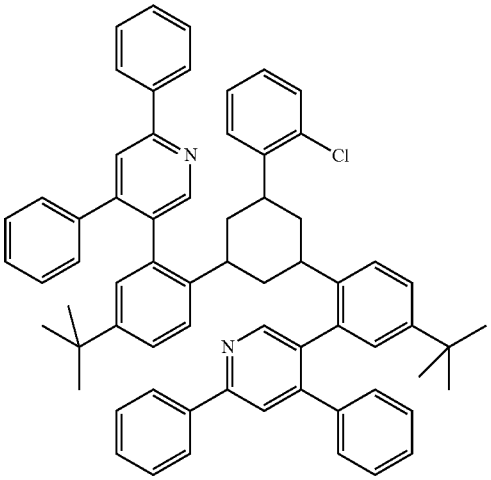 [SMILES: CC(C)(C)c1ccc(C2CC(c3ccccc3Cl)CC(c3ccc(C(C)(C)C)cc3-c3cnc(-c4ccccc4)cc3-c3ccccc3)C2)c(-c2cnc(-c3ccccc3)cc2-c2ccccc2)c1] | 60% |
| S104 | S3 S33 | 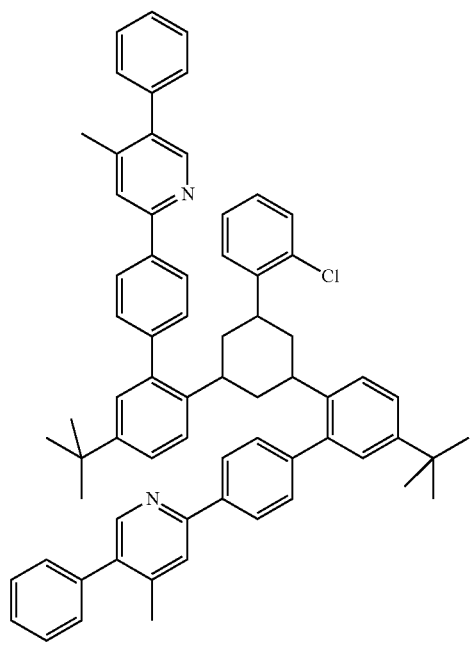 [SMILES: Cc1cc(-c2ccc(-c3cc(C(C)(C)C)ccc3C3CC(c4ccccc4Cl)CC(c4ccc(C(C)(C)C)cc4-c4ccc(-c5cc(C)c(-c6ccccc6)cn5)cc4)C3)cc2)ncc1-c1ccccc1] | 69% |

-continued

| Ex. | Starting materials | Product | Yield |
|---|---|---|---|
| S105 | S3 S34 | | 64% |
| S106 | S4 S35 | | 61% |

-continued
| Ex. | Starting materials | Product | Yield |
|---|---|---|---|
| S107 | S3<br>S36 | 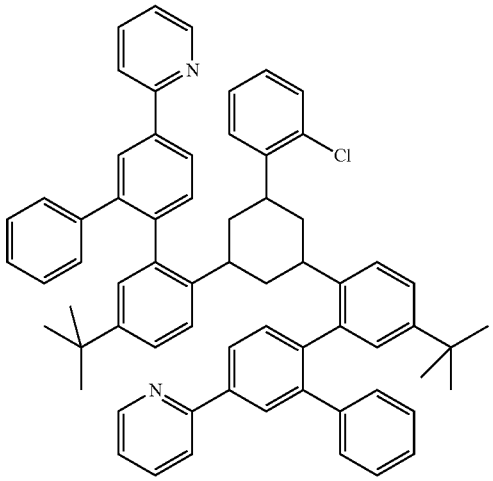 [SMILES: CC(C)(C)c1ccc(C2CC(c3ccccc3Cl)CC(c3ccc(C(C)(C)C)cc3-c3ccc(-c4ccccn4)cc3-c3ccccc3)C2)c(-c2ccc(-c3ccccn3)cc2-c2ccccc2)c1] | 63% |
| S108 | S3<br>S37 | 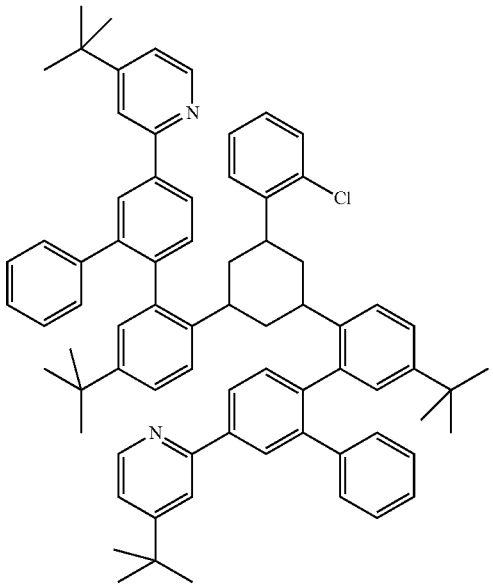 [SMILES: CC(C)(C)c1ccnc(-c2ccc(-c3cc(C(C)(C)C)ccc3C3CC(c4ccccc4Cl)CC(c4ccc(C(C)(C)C)cc4-c4ccc(-c5cc(C(C)(C)C)ccn5)cc4-c4ccccc4)C3)c(-c3ccccc3)c2)c1] | 60% |

| Ex. | Starting materials | Product | Yield |
|---|---|---|---|
| S109 | S3 S38 | 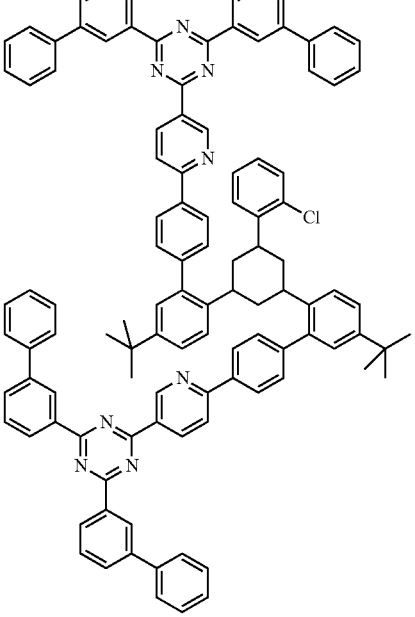 | 66% |

Example S200

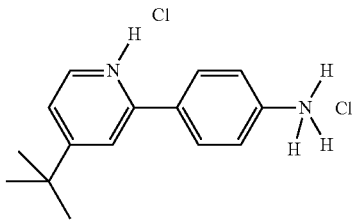

A mixture of 29.0 g (100 mmol) of S31, 20.2 g (200 mmol) of pivaloyl-amide, 97.8 g (300 mmol) of caesium carbonate, 1157 mg (2 mmol) of Xanthphos, 449 mg (2 mmol) of palladium(II) acetate, 500 ml of dioxane and 200 g of glass beads (diameter 3 mm) is stirred at 100° C. for 12 h. The dioxane is substantially removed in vacuo, the residue is taken up in 500 ml of water and 500 ml of ethyl acetate, the org. phase is washed twice with 300 ml of water and once with 300 ml of sat. sodium chloride solution and then dried over magnesium sulfate. The drying agent is filtered off through a Celite bed which has been pre-slurried with ethyl acetate, and the filtrate is evaporated to dryness. The oily residue is taken up in 200 ml of dioxane, 50 ml conc. HCl are added, and the solution is boiled under reflux for 12 h, the dioxane is then substantially distilled off, during which the product crystallises out. The product is filtered off with suction, washed with ice-cold water and dried in vacuo. Yield: 19.0 g (63 mmol), 63%. Purity: about 95% according to $^1$H-NMR.

The following compounds can be prepared analogously:

| Ex. | Starting material | Product | Yield |
|---|---|---|---|
| S201 | S33 | 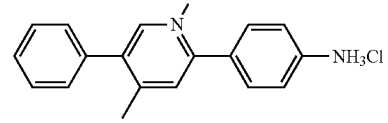 | 66% |
| S202 | S37 | 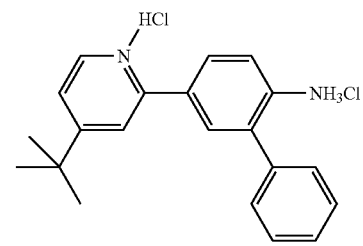 | 60% |

Example S300

A mixture of 24.9 g (100 mmol) of 2-(4-aminophenyl)-5-bromopyridine [1264652-77-8], 26.7 g (105 mmol) of bis(pinacolato)diborane [73183-34-3], 29.5 g (300 mmol) of potassium acetate, anhydrous, 561 mg (2 mmol) of tricyclohexylphosphine, 224 mg (1 mmol) of palladium(II) acetate and 500 ml of dioxane is stirred at 90° C. for 16 h. After removal of the solvent in vacuo, the residue is taken up in 500 ml of ethyl acetate, filtered through a Celite bed, the filtrate is evaporated in vacuo to incipient crystallisation, and finally about 100 ml of methanol are added dropwise in order to complete the crystallisation. Yield: 20.1 g (68 mmol), 68%; purity: about 95% according to $^1$H-NMR.

The following compounds can be synthesised analogously:

2. Preparation of Hexadentate Ligands L:

Example L1

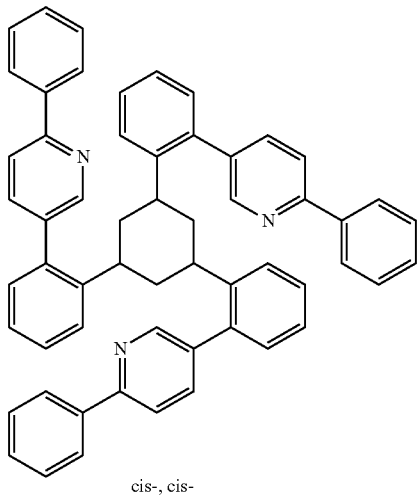 [SMILES: c1ccc(-c2ccc(-c3ccccc3C3CC(c4ccccc4-c4ccc(-c5ccccc5)nc4)CC(c4ccccc4-c4ccc(-c5ccccc5)nc4)C3)cn2)cc1]

cis-, cis-

A mixture of 50.5 g (100 mmol) of S1, 98.4 g (350 mmol) of 2-phenyl-5-(4,4,5,5-tetramethyl-1,3,2-dioxaborolan-2-yl) pyridine [879291-27-7], 106.0 g (1 mol) of sodium carbonate, 2.1 g (5 mmol) of S-Phos [657408-07-6], 674 mg (3 mmol) of palladium(II) acetate, 750 ml of toluene, 200 ml of dioxane and 500 ml of water is heated at 70° C. with very vigourous stirring for 24 h. The mixture is allowed to cool, the aqueous phase is separated off, and the organic phase is evaporated to dryness. After evaporation of the organic phase from the Suzuki coupling, the brown foam is taken up in 300 ml of dichloromethane:ethyl acetate (1:1, vv) and filtered through a silica-gel bed (diameter 15 cm, length 20 cm) which has been pre-slurried with dichloromethane:ethyl acetate (1:1, vv) in order to remove brown components. After evaporation, the foam which remains is recrystallised from 300 ml of ethyl acetate with addition of 300 ml of boiling methanol and then recrystallised a second time from 250 ml of pure ethyl acetate and subsequently sublimed in a bulb tube in a high vacuum (p about $10^{-5}$ mbar, T 260° C.). Yield: 45.6 g (59 mmol), 59%. Purity: about 99.7% according to $^1$H-NMR, cis,cis isomer.

The following compounds can be prepared analogously, where the purification can also be carried out by chromatography (e.g. Torrent CombiFlash from Axel Semrau):

| Ex. | Bromide Boronic ester | Product | Yield |
|---|---|---|---|
| L2 | S3 S30 | 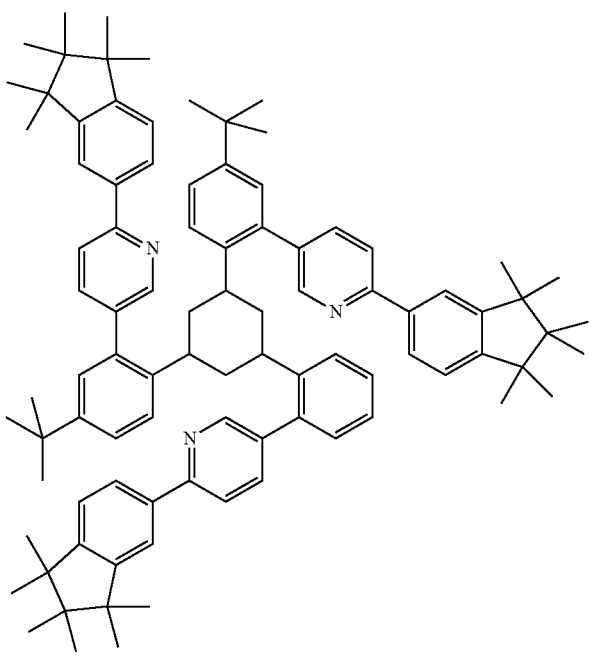 [SMILES: CC(C)(C)c1ccc(C2CC(c3ccccc3-c3ccc(-c4ccc5c(c4)C(C)(C)C(C)(C)C5(C)C)nc3)CC(c3ccc(C(C)(C)C)cc3-c3ccc(-c4ccc5c(c4)C(C)(C)C(C)(C)C5(C)C)nc3)C2)c(-c2ccc(-c3ccc4c(c3)C(C)(C)C(C)(C)C4(C)C)nc2)c1] | 59% |

-continued
| Ex. | Bromide Boronic ester | Product | Yield |
|---|---|---|---|
| L3 | S2 S31 | 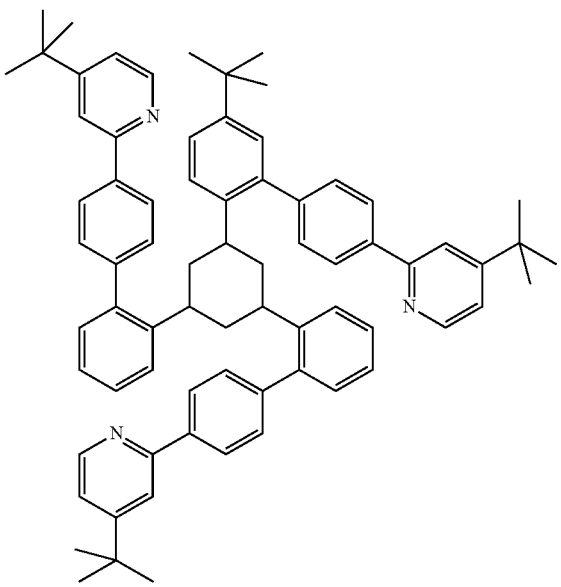 [SMILES: CC(C)(C)c1ccnc(-c2ccc(-c3ccccc3C3CC(c4ccccc4-c4ccc(-c5cc(C(C)(C)C)ccn5)cc4)CC(c4ccc(C(C)(C)C)cc4-c4ccc(-c5cc(C(C)(C)C)ccn5)cc4)C3)cc2)c1] | 65% |
| L4 | S4 S32 | 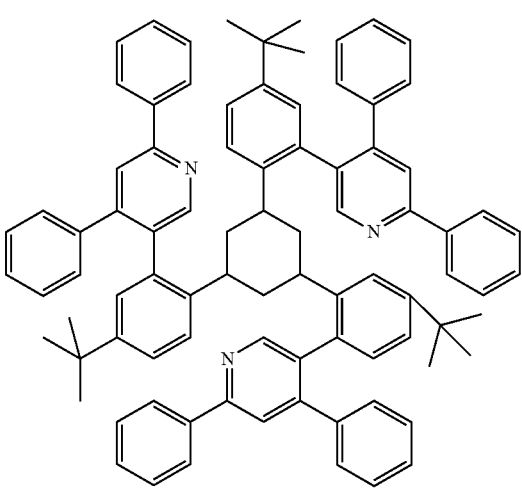 [SMILES: CC(C)(C)c1ccc(C2CC(c3ccc(C(C)(C)C)cc3-c3cnc(-c4ccccc4)cc3-c3ccccc3)CC(c3cc(C(C)(C)C)ccc3-c3cnc(-c4ccccc4)cc3-c3ccccc3)C2)c(-c2cnc(-c3ccccc3)cc2-c2ccccc2)c1] | 60% |

| Ex. | Bromide Boronic ester | Product | Yield |
|---|---|---|---|
| L5 | S3 S33 | 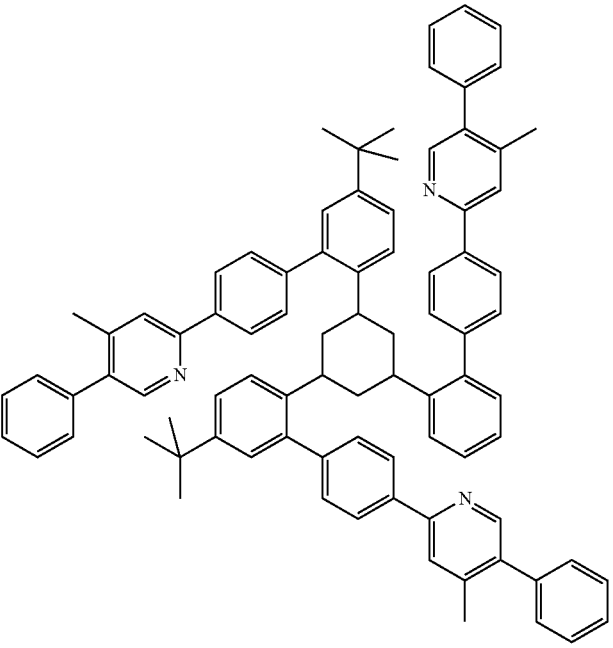 [SMILES: Cc1cc(-c2ccc(-c3ccccc3C3CC(c4ccc(C(C)(C)C)cc4-c4ccc(-c5cc(C)c(-c6ccccc6)cn5)cc4)CC(c4ccc(C(C)(C)C)cc4-c4ccc(-c5cc(C)c(-c6ccccc6)cn5)cc4)C3)cc2)ncc1-c1ccccc1] | 63% |
| L6 | S3 S37 | 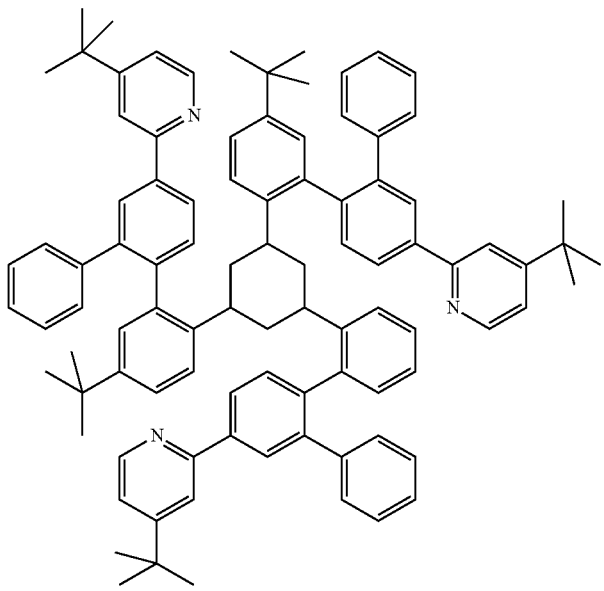 [SMILES: CC(C)(C)c1ccnc(-c2ccc(-c3ccccc3C3CC(c4ccc(C(C)(C)C)cc4-c4ccc(-c5cc(C(C)(C)C)ccn5)cc4-c4ccccc4)CC(c4ccc(C(C)(C)C)cc4-c4ccc(-c5cc(C(C)(C)C)ccn5)cc4-c4ccccc4)C3)c(-c3ccccc3)c2)c1] | 58% |

| Ex. | Bromide Boronic ester | Product | Yield |
|---|---|---|---|
| L7 | S3 S38 | 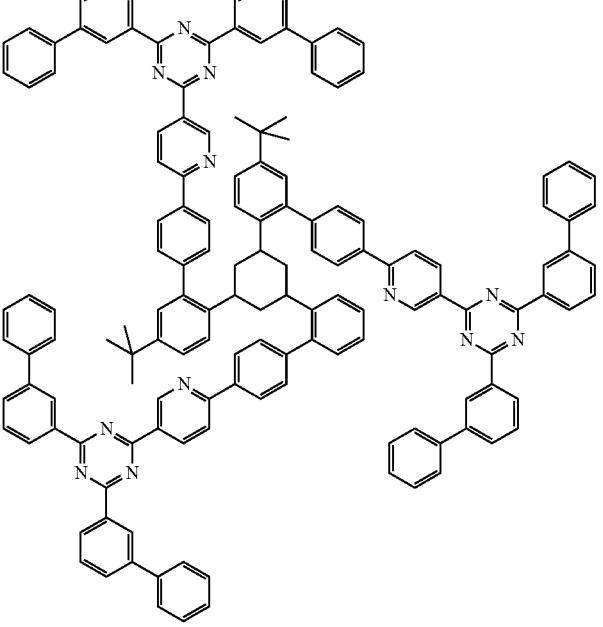 | 57% |
| L8 | S3 1383803-71-1 | 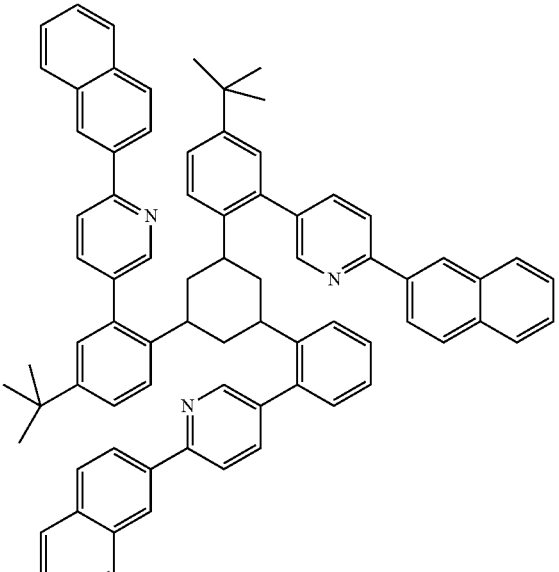 | 60% |

| Ex. | Bromide Boronic ester | Product | Yield |
|---|---|---|---|
| L9 | S1 1310383-27-7 | 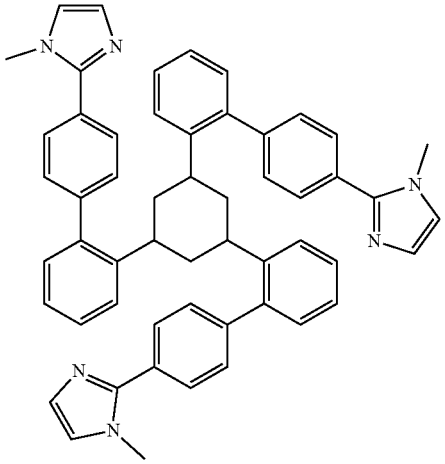 [SMILES: Cn1ccnc1-c1ccc(-c2ccccc2C2CC(c3ccccc3-c3ccc(-c4nccn4C)cc3)CC(c3ccccc3-c3ccc(-c4nccn4C)cc3)C2)cc1] | 55% |
| L10 | S3 1146340-38-6 | 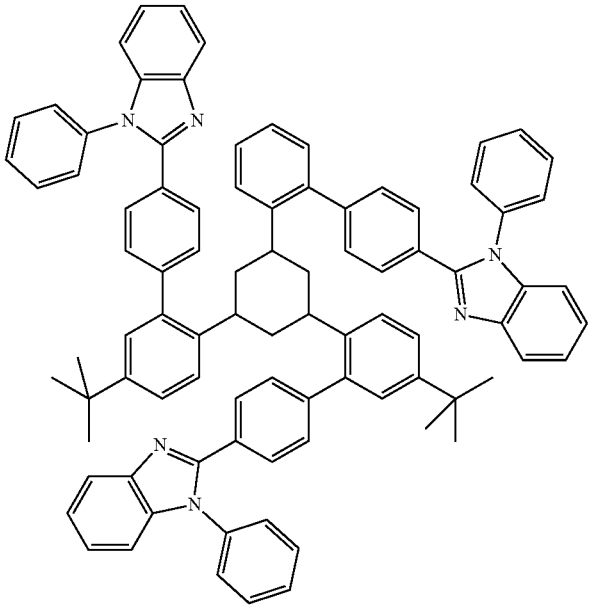 [SMILES: CC(C)(C)c1ccc(C2CC(c3ccccc3-c3ccc(-c4nc5ccccc5n4-c4ccccc4)cc3)CC(c3ccc(C(C)(C)C)cc3-c3ccc(-c4nc5ccccc5n4-c4ccccc4)cc3)C2)c(-c2ccc(-c3nc4ccccc4n3-c3ccccc3)cc2)c1] | 62% |

-continued
| Ex. | Bromide Boronic ester | Product | Yield |
|---|---|---|---|
| L11 | S3 1228267-13-7 | 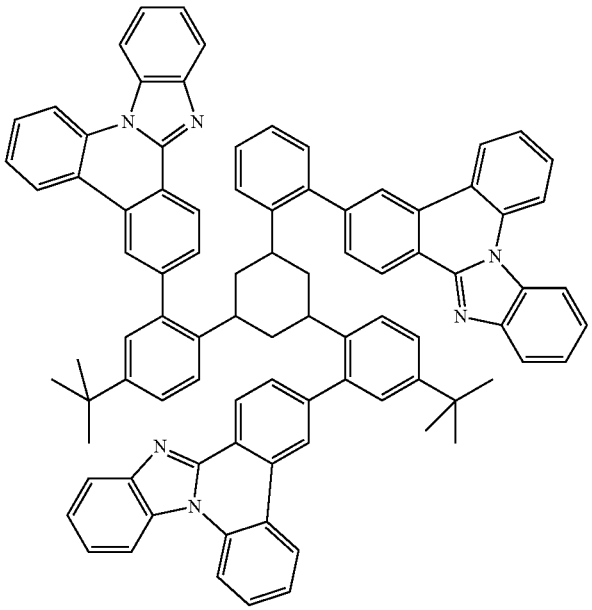 [SMILES: CC(C)(C)c1ccc(C2CC(c3ccccc3-c3ccc4c(c3)c3ccccc3n3c5ccccc5nc43)CC(c3ccc(C(C)(C)C)cc3-c3ccc4c(c3)c3ccccc3n3c5ccccc5nc43)C2)c(-c2ccc3c(c2)c2ccccc2n2c4ccccc4nc32)c1] | 65% |
| L12 | S3 S40 | 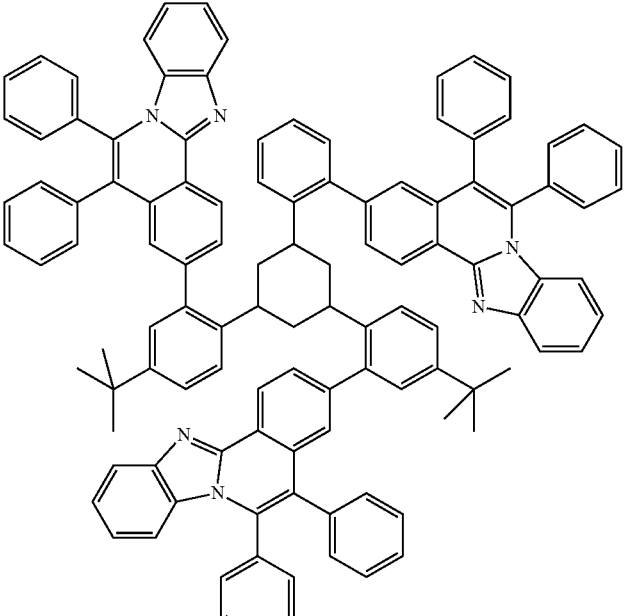 | 67% |

| Ex. | Bromide Boronic ester | Product | Yield |
|---|---|---|---|
| L13 | S3 1312478-63-9 | 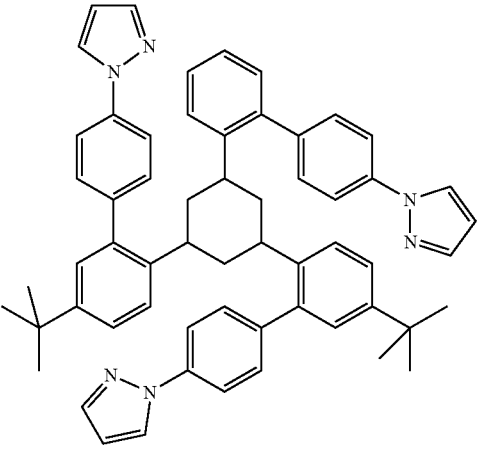 [SMILES: CC(C)(C)c1ccc(C2CC(c3ccccc3-c3ccc(-n4cccn4)cc3)CC(c3ccc(C(C)(C)C)cc3-c3ccc(-n4cccn4)cc3)C2)c(-c2ccc(-n3cccn3)cc2)c1] | 58% |
| L14 | S3 S39 | 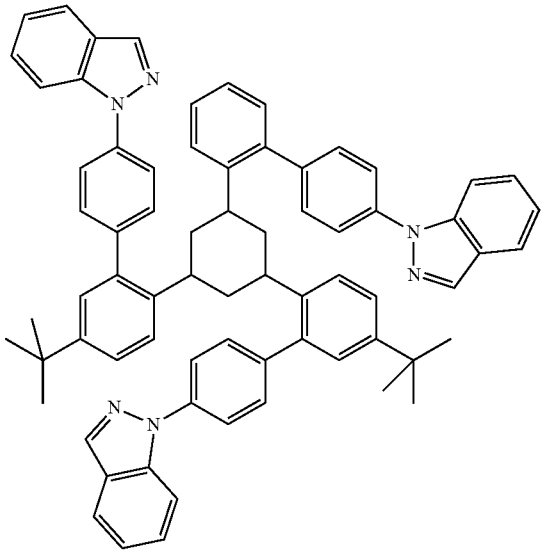 [SMILES: CC(C)(C)c1ccc(C2CC(c3ccccc3-c3ccc(-n4ncc5ccccc54)cc3)CC(c3ccc(C(C)(C)C)cc3-c3ccc(-n4ncc5ccccc54)cc3)C2)c(-c2ccc(-n3ncc4ccccc43)cc2)c1] | 61% |

| Ex. | Bromide Boronic ester | Product | Yield |
|---|---|---|---|
| L15 | S5<br>S31 | 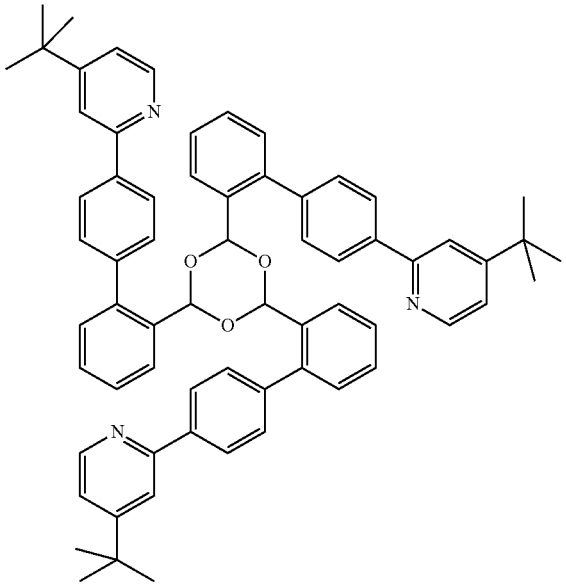 [SMILES: CC(C)(C)c1ccnc(-c2ccc(-c3ccccc3C3OC(c4ccccc4-c4ccc(-c5cc(C(C)(C)C)ccn5)cc4)OC(c4ccccc4-c4ccc(-c5cc(C(C)(C)C)ccn5)cc4)O3)cc2)c1] | 49% |
| L16 | S1<br>[562098-24-2] | 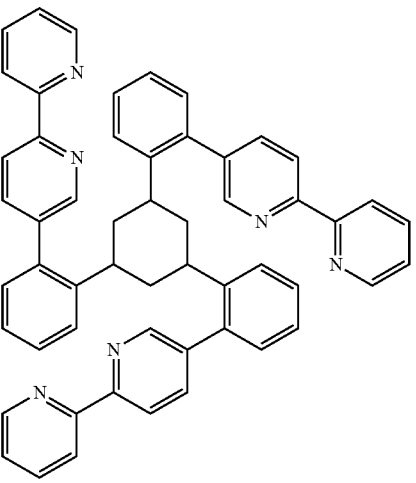 [SMILES: c1ccc(-c2ccc(-c3ccccc3C3CC(c4ccccc4-c4ccc(-c5ccccn5)nc4)CC(c4ccccc4-c4ccc(-c5ccccn5)nc4)C3)cn2)nc1] | 38% |
| L17 | S1<br>S41 | 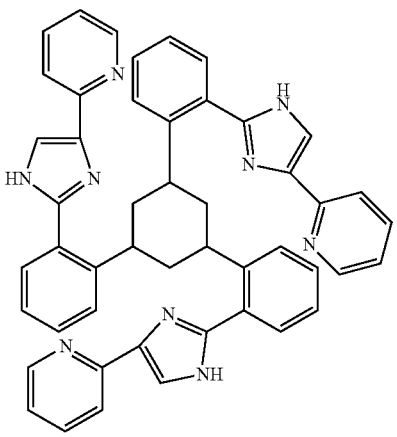<br>Before work-up, adjust to pH = 7 using glacial acetic acid | 33% |

-continued

| Ex. | Bromide Boronic ester | Product | Yield |
|---|---|---|---|
| L18 | S2 S42 | *(structure shown)* Before work-up, adjust to pH = 7 using glacial acetic acid | 41% |
| L19 | S3 S43 | *(structure shown)* Before work-up, adjust to pH = 7 using glacial acetic acid | 45% |

-continued

| Ex. | Bromide Boronic ester | Product | Yield |
|---|---|---|---|
| L20 | S3 [913836-11-0] | 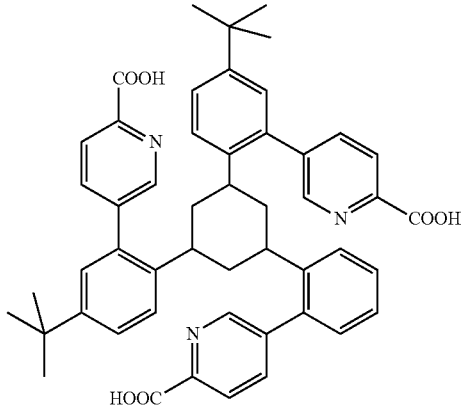<br>Before work-up, adjust to pH = 6 using glacial acetic acid | 29% |

Example L100

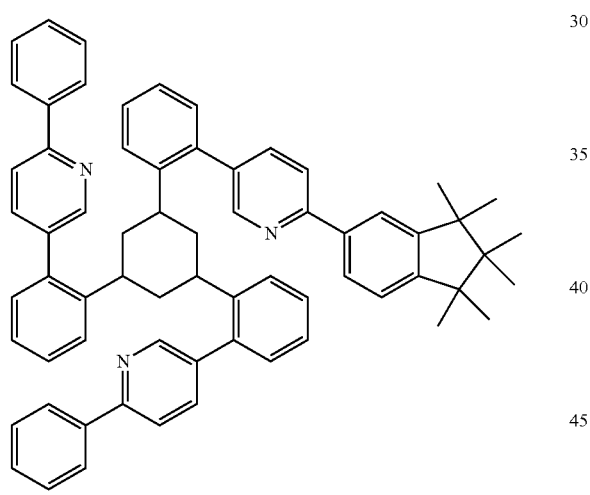

A mixture of 65.3 g (100 mmol) of S100, 42.5 g (105 mmol) of S30, 63.7 g (300 mmol) of tripotassium phosphate, 1.23 g (3 mmol) of S-Phos [657408-07-6], 449 mg (2 mmol) of palladium(II) acetate, 500 ml of toluene, 300 ml of dioxane and 300 ml of water is heated under reflux for 6 h.

After cooling, the org. phase is separated off, washed twice with 300 ml of water and once with 200 ml of sat. sodium chloride solution, dried over magnesium sulfate and then filtered through a Celite bed which has been pre-slurried with toluene, and the bed is rinsed with toluene. The filtrate is evaporated to dryness, and the residue is subsequently recrystallised twice from ethyl acetate/methanol. Yield: 56.5 g (63 mmol), 63%. Purity: about 97% according to $^1$H-NMR.

The following compounds can be synthesised analogously:
| Ex. | Boronic ester Bromide | Product | Yield |
|---|---|---|---|
| L101 | S100 S32 | 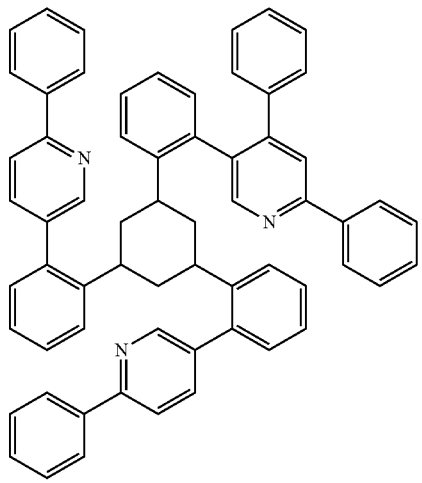 [SMILES: c1ccc(-c2ccc(-c3ccccc3C3CC(c4ccccc4-c4ccc(-c5ccccc5)nc4)CC(c4ccccc4-c4cnc(-c5ccccc5)cc4-c4ccccc4)C3)cn2)cc1] | 60% |
| L102 | S101 S31 | 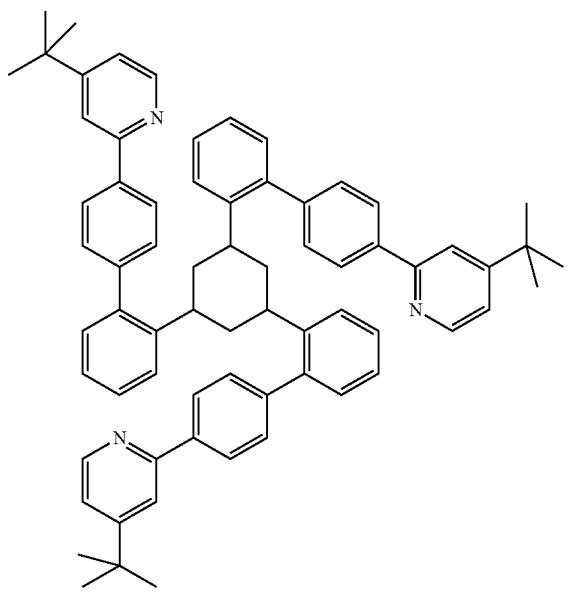 [SMILES: CC(C)(C)c1ccnc(-c2ccc(-c3ccccc3C3CC(c4ccccc4-c4ccc(-c5cc(C(C)(C)C)ccn5)cc4)CC(c4ccccc4-c4ccc(-c5cc(C(C)(C)C)ccn5)cc4)C3)cc2)c1] | 83% |

| Ex. | Boronic ester Bromide | Product | Yield |
|---|---|---|---|
| L103 | S101 S33 | 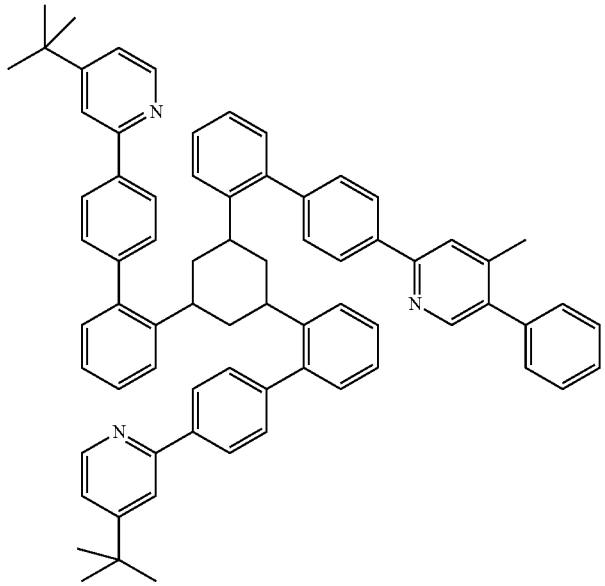 [SMILES: Cc1cc(-c2ccc(-c3ccccc3C3CC(c4ccccc4-c4ccc(-c5cc(C(C)(C)C)ccn5)cc4)CC(c4ccccc4-c4ccc(-c5cc(C(C)(C)C)ccn5)cc4)C3)cc2)ncc1-c1ccccc1] | 66% |
| L104 | S101 S34 | 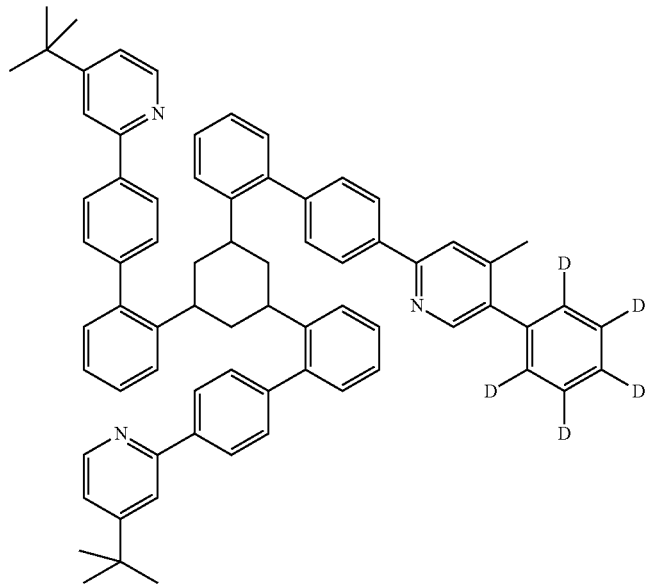 [SMILES: [2H]c1c([2H])c([2H])c(-c2cnc(-c3ccc(-c4ccccc4C4CC(c5ccccc5-c5ccc(-c6cc(C(C)(C)C)ccn6)cc5)CC(c5ccccc5-c5ccc(-c6cc(C(C)(C)C)ccn6)cc5)C4)cc3)cc2C)c([2H])c1[2H]] | 63% |

| Ex. | Boronic ester Bromide | Product | Yield |
|---|---|---|---|
| L105 | S101 S35 | 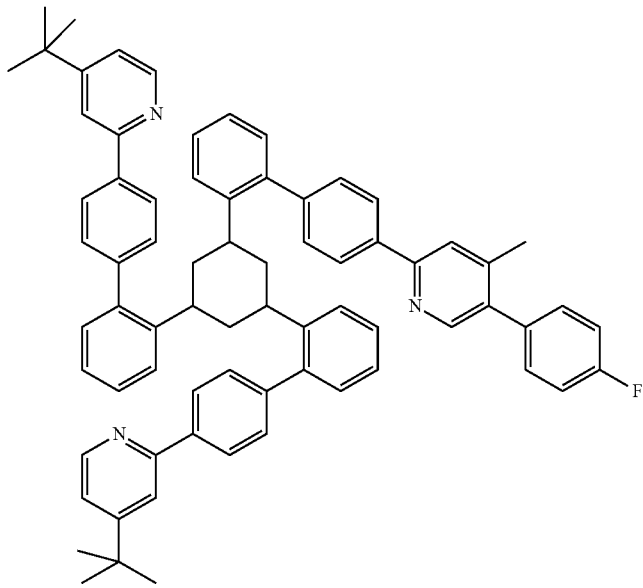 [SMILES: Cc1cc(-c2ccc(-c3ccccc3C3CC(c4ccccc4-c4ccc(-c5cc(C(C)(C)C)ccn5)cc4)CC(c4ccccc4-c4ccc(-c5cc(C(C)(C)C)ccn5)cc4)C3)cc2)ncc1-c1ccc(F)cc1] | 60% |
| L106 | S101 S36 | 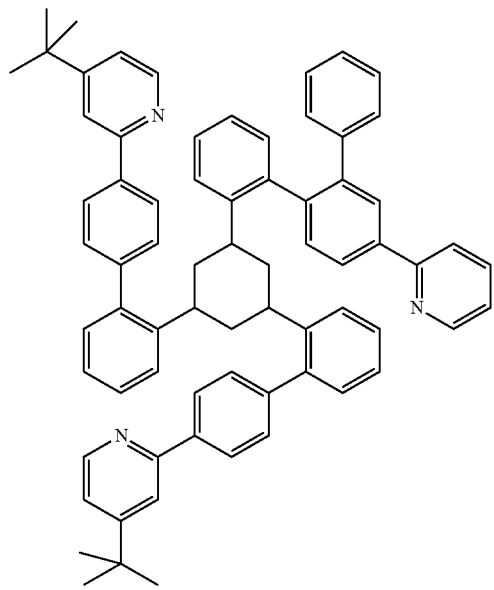 [SMILES: CC(C)(C)c1ccnc(-c2ccc(-c3ccccc3C3CC(c4ccccc4-c4ccc(-c5cc(C(C)(C)C)ccn5)cc4)CC(c4ccccc4-c4ccc(-c5ccccn5)cc4-c4ccccc4)C3)cc2)c1] | 67% |

| Ex. | Boronic ester Bromide | Product | Yield |
|---|---|---|---|
| L107 | S101 S37 | 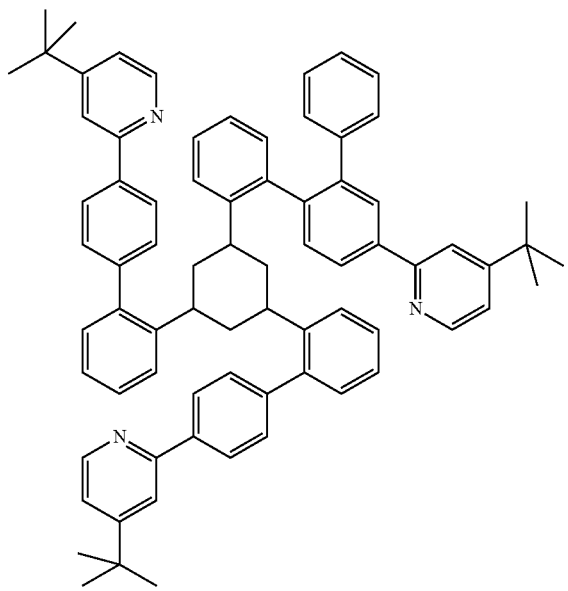 [SMILES: CC(C)(C)c1ccnc(-c2ccc(-c3ccccc3C3CC(c4ccccc4-c4ccc(-c5cc(C(C)(C)C)ccn5)cc4)CC(c4ccccc4-c4ccc(-c5cc(C(C)(C)C)ccn5)cc4-c4ccccc4)C3)cc2)c1] | 58% |
| L108 | S101 S38 | 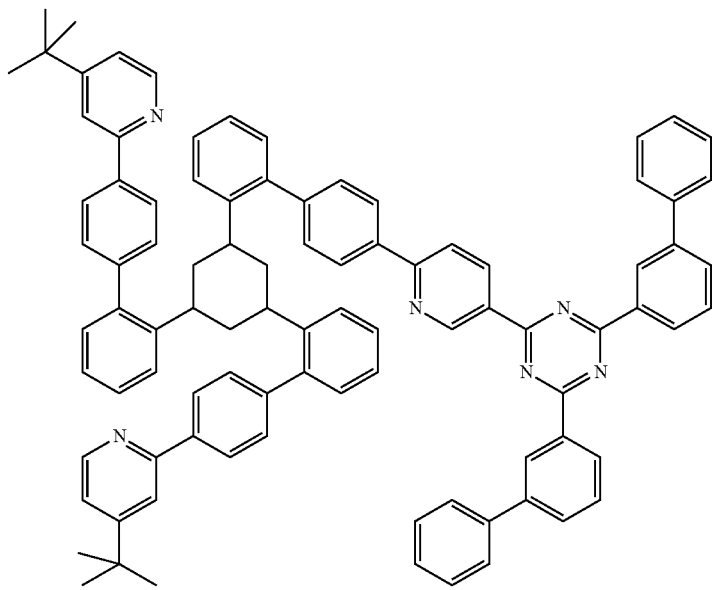 [SMILES: CC(C)(C)c1ccnc(-c2ccc(-c3ccccc3C3CC(c4ccccc4-c4ccc(-c5ccc(-c6nc(-c7cccc(-c8ccccc8)c7)nc(-c7cccc(-c8ccccc8)c7)n6)cn5)cc4)CC(c4ccccc4-c4ccc(-c5cc(C(C)(C)C)ccn5)cc4)C3)cc2)c1] | 70% |

-continued
| Ex. | Boronic ester Bromide | Product | Yield |
|---|---|---|---|
| L109 | S102 S33 | 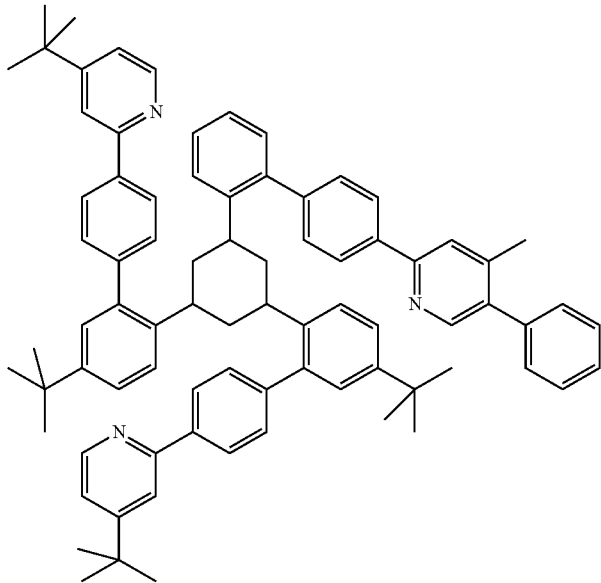 [SMILES: Cc1cc(-c2ccc(-c3ccccc3C3CC(c4ccc(C(C)(C)C)cc4-c4ccc(-c5cc(C(C)(C)C)ccn5)cc4)CC(c4ccc(C(C)(C)C)cc4-c4ccc(-c5cc(C(C)(C)C)ccn5)cc4)C3)cc2)ncc1-c1ccccc1] | 63% |
| L110 | S104 S31 | 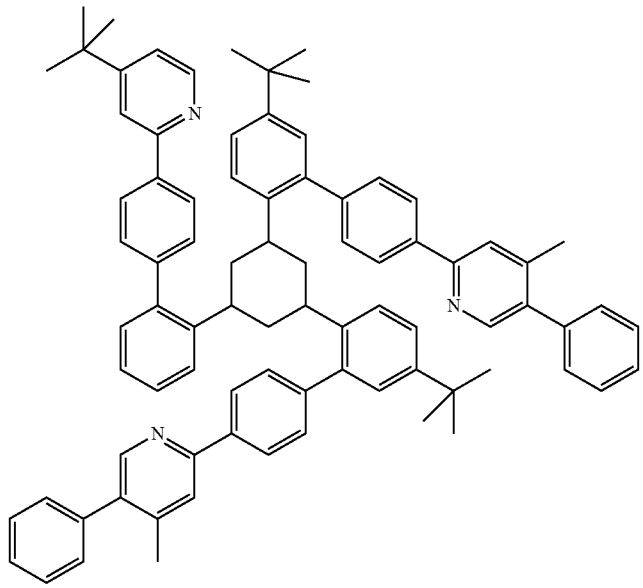 [SMILES: Cc1cc(-c2ccc(-c3cc(C(C)(C)C)ccc3C3CC(c4ccccc4-c4ccc(-c5cc(C(C)(C)C)ccn5)cc4)CC(c4ccc(C(C)(C)C)cc4-c4ccc(-c5cc(C)c(-c6ccccc6)cn5)cc4)C3)cc2)ncc1-c1ccccc1] | 65% |

| Ex. | Boronic ester Bromide | Product | Yield |
|---|---|---|---|
| L111 | S105 S31 | 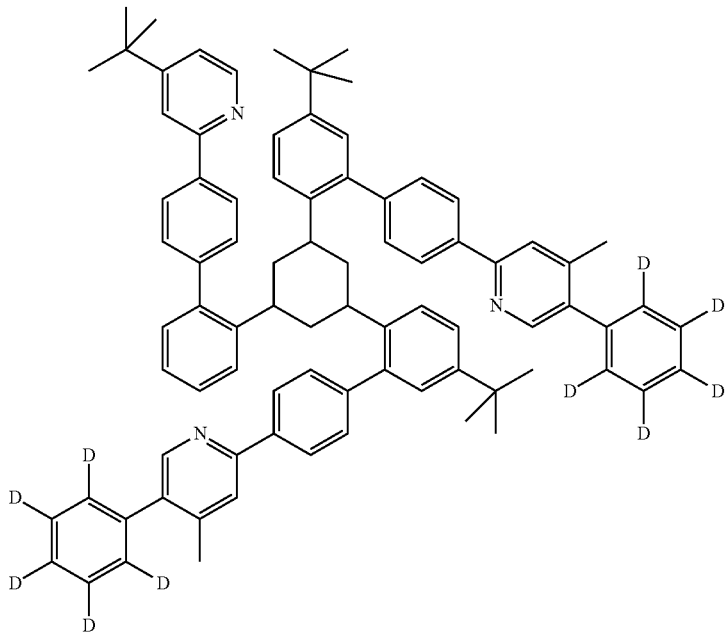 [SMILES: [2H]c1c([2H])c([2H])c(-c2cnc(-c3ccc(-c4cc(C(C)(C)C)ccc4C4CC(c5ccccc5-c5ccc(-c6cc(C(C)(C)C)ccn6)cc5)CC(c5ccc(C(C)(C)C)cc5-c5ccc(-c6cc(C)c(-c7c([2H])c([2H])c([2H])c([2H])c7[2H])cn6)cc5)C4)cc3)cc2C)c([2H])c1[2H]] | 68% |
| L112 | S106 S31 | 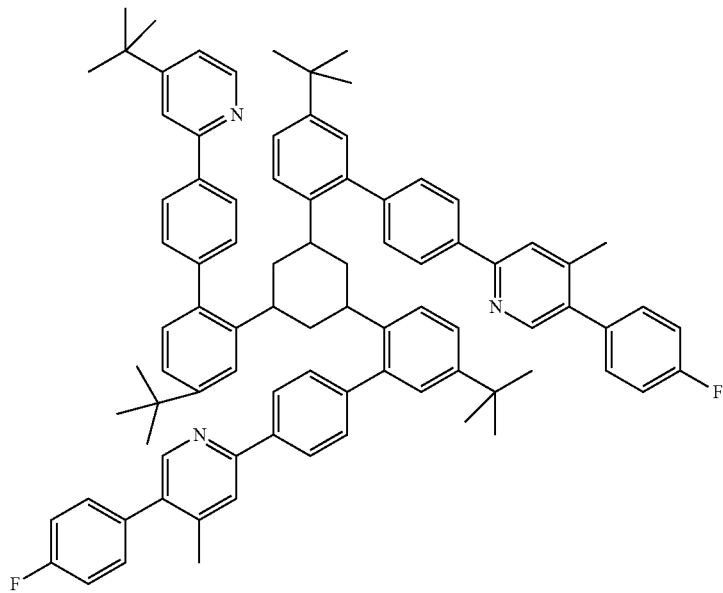 [SMILES: Cc1cc(-c2ccc(-c3cc(C(C)(C)C)ccc3C3CC(c4ccc(C(C)(C)C)cc4-c4ccc(-c5cc(C)c(-c6ccc(F)cc6)cn5)cc4)CC(c4cc(C(C)(C)C)ccc4-c4ccc(-c5cc(C(C)(C)C)ccn5)cc4)C3)cc2)ncc1-c1ccc(F)cc1] | 62% |

| Ex. | Boronic ester Bromide | Product | Yield |
|---|---|---|---|
| L113 | S107 S31 | 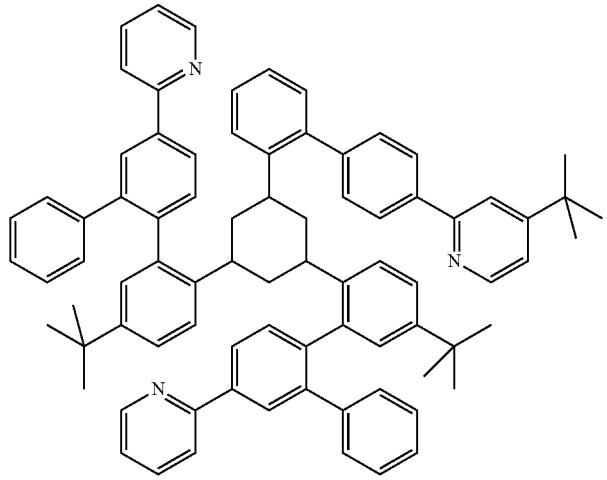 [SMILES: CC(C)(C)c1ccnc(-c2ccc(-c3ccccc3C3CC(c4ccc(C(C)(C)C)cc4-c4ccc(-c5ccccn5)cc4-c4ccccc4)CC(c4ccc(C(C)(C)C)cc4-c4ccc(-c5ccccn5)cc4-c4ccccc4)C3)cc2)c1] | 54% |
| L114 | S108 S31 | 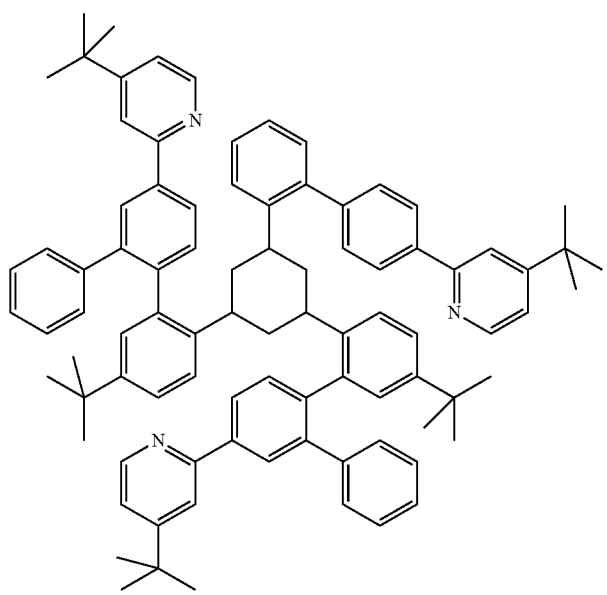 [SMILES: CC(C)(C)c1ccnc(-c2ccc(-c3ccccc3C3CC(c4ccc(C(C)(C)C)cc4-c4ccc(-c5cc(C(C)(C)C)ccn5)cc4-c4ccccc4)CC(c4ccc(C(C)(C)C)cc4-c4ccc(-c5cc(C(C)(C)C)ccn5)cc4-c4ccccc4)C3)cc2)c1] | 57% |

-continued
| Ex. | Boronic ester Bromide | Product | Yield |
|---|---|---|---|
| L115 | S109 S31 | 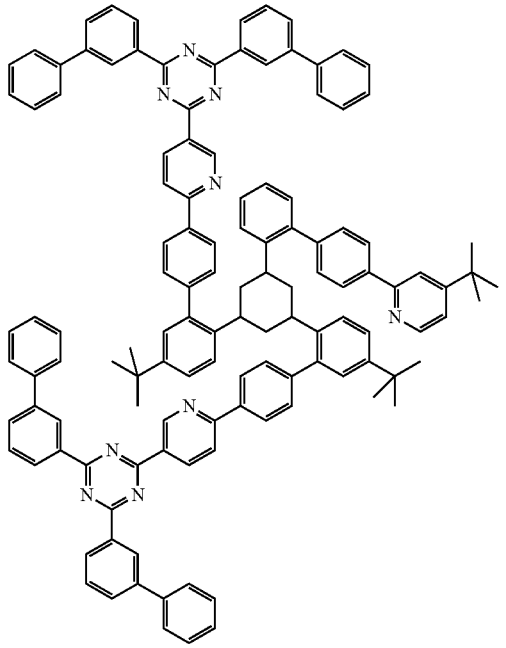 [SMILES: CC(C)(C)c1ccnc(-c2ccc(-c3ccccc3C3CC(c4ccc(C(C)(C)C)cc4-c4ccc(-c5ccc(-c6nc(-c7cccc(-c8ccccc8)c7)nc(-c7cccc(-c8ccccc8)c7)n6)cn5)cc4)CC(c4ccc(C(C)(C)C)cc4-c4ccc(-c5ccc(-c6nc(-c7cccc(-c8ccccc8)c7)nc(-c7cccc(-c8ccccc8)c7)n6)cn5)cc4)C3)cc2)c1] | 69% |
| L116 | S103 S30 | 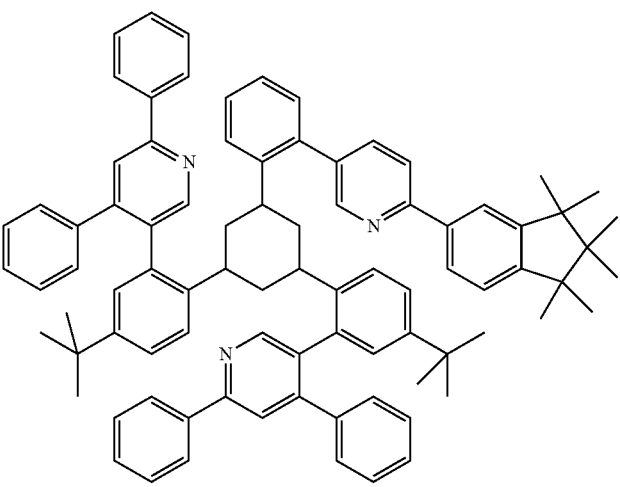 [SMILES: CC(C)(C)c1ccc(C2CC(c3ccccc3-c3ccc(-c4ccc5c(c4)C(C)(C)C(C)(C)C5(C)C)nc3)CC(c3ccc(C(C)(C)C)cc3-c3cnc(-c4ccccc4)cc3-c3ccccc3)C2)c(-c2cnc(-c3ccccc3)cc2-c2ccccc2)c1] | 70% |

-continued

| Ex. | Boronic ester Bromide | Product | Yield |
|---|---|---|---|
| L117 | S101 1383803-71-1 | | 60% |
| L118 | S101 1848992-66-4 | | 70% |

| Ex. | Boronic ester Bromide | Product | Yield |
|---|---|---|---|
| L119 | S101 1310383-27-7 | 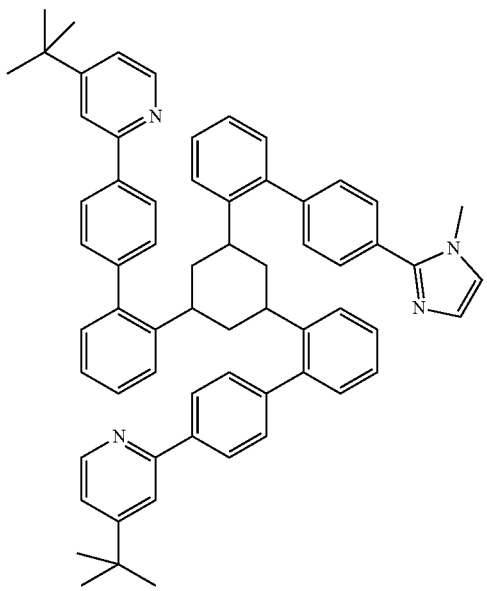 [SMILES: Cn1ccnc1-c1ccc(-c2ccccc2C2CC(c3ccccc3-c3ccc(-c4cc(C(C)(C)C)ccn4)cc3)CC(c3ccccc3-c3ccc(-c4cc(C(C)(C)C)ccn4)cc3)C2)cc1] | 65% |
| L120 | S102 1146340-38-6 | 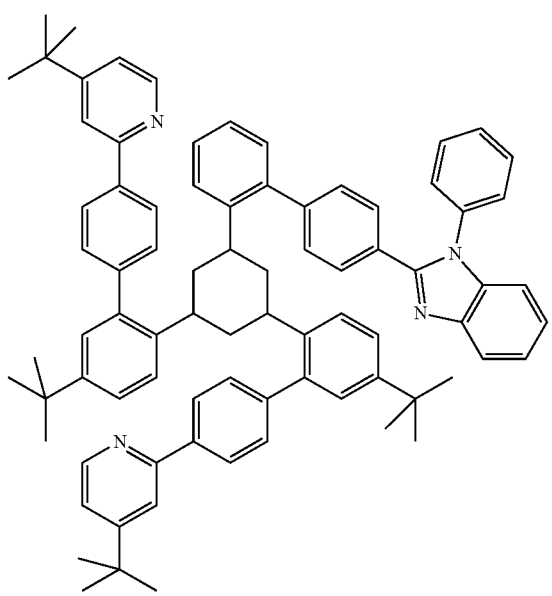 [SMILES: CC(C)(C)c1ccnc(-c2ccc(-c3cc(C(C)(C)C)ccc3C3CC(c4ccccc4-c4ccc(-c5nc6ccccc6n5-c5ccccc5)cc4)CC(c4ccc(C(C)(C)C)cc4-c4ccc(-c5cc(C(C)(C)C)ccn5)cc4)C3)cc2)c1] | 71% |

| Ex. | Boronic ester Bromide | Product | Yield |
|---|---|---|---|
| L121 | S102 1228267-13-7 | 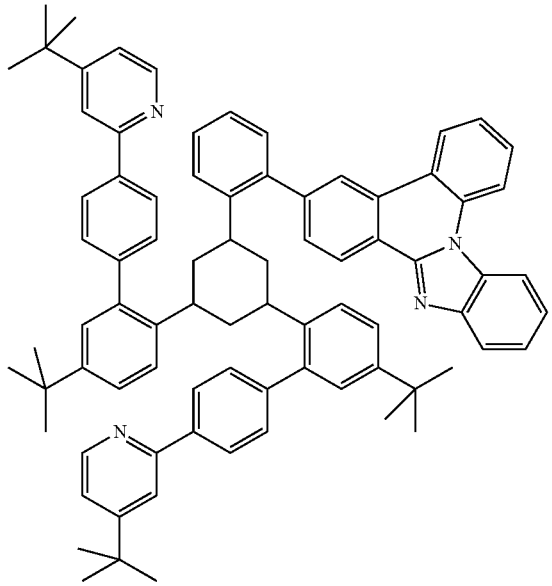 [SMILES: CC(C)(C)c1ccnc(-c2ccc(-c3cc(C(C)(C)C)ccc3C3CC(c4ccccc4-c4ccc5c(c4)c4ccccc4n4c6ccccc6nc54)CC(c4ccc(C(C)(C)C)cc4-c4ccc(-c5cc(C(C)(C)C)ccn5)cc4)C3)cc2)c1] | 73% |
| L122 | S101 S40 | 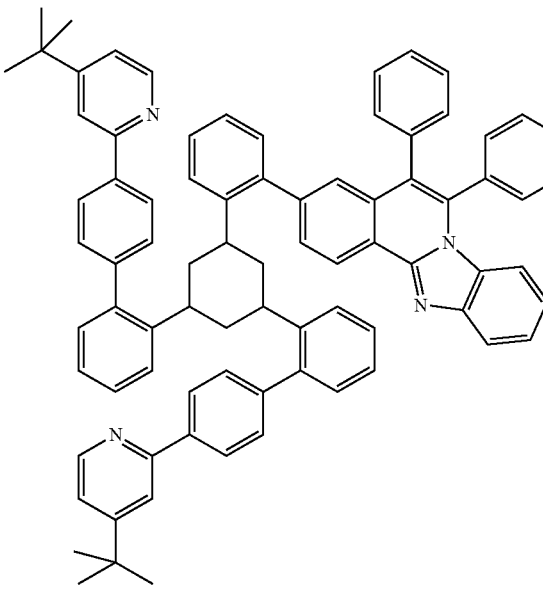 | 67% |

-continued

| Ex. | Boronic ester Bromide | Product | Yield |
|---|---|---|---|
| L123 | S101 1312478-63-9 | (structure) | 60% |
| L124 | S101 S39 | (structure) | 65% |

Example L200

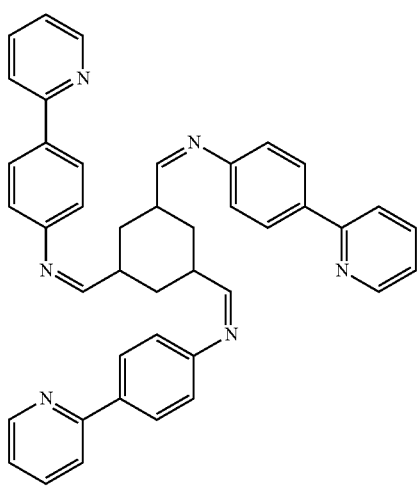 [SMILES: C(=N/c1ccc(-c2ccccn2)cc1)/C1CC(/C=N\c2ccc(-c3ccccn3)cc2)CC(/C=N\c2ccc(-c3ccccn3)cc2)C1]

Variant A, for Aldehydes:

Procedure analogous to J. G. Muntaner et al., Org. & Biomol. Chem., 2014, 12, 286. 97 ml of a 2 N sodium ethoxide solution in ethanol are added to a solution of 24.3 g (100 mmol) of 4-(2-pyridyl)anilinium dihydrochloride [856849-12-2] in 200 ml of ethanol. 5.1 g (30 mmol) of cis,cis-1,3,5-cyclohexanetricarboxaldehyde [107354-37-0] is then added, and the mixture is heated under reflux for 3 h. The ethanol is subsequently distilled off virtually to dryness, the oily residue is taken up in 300 ml of DCM, insoluble components are filtered off through a Celite bed which has been pre-slurried with DCM, the DCM is removed in vacuo, and the crude product is recrystallised from acetonitrile/cyclohexane. Yield: 14.4 g (23 mmol), 69%. Purity: about 97% according to $^1$H-NMR.

Example L201

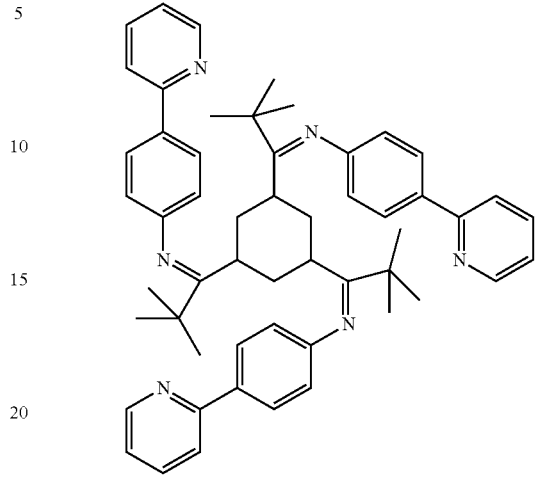

Variant B, for Ketones:

Procedure analogous to P. Sulmon et al., Synthesis 1985, 192. Three drops of methanol and then, in portions, 8.0 g (200 mmol) of sodium hydride, 60% by weight dispersion in mineral oil, are added to a suspension of 24.3 g (100 mmol) of 4-(2-pyridyl)anilinium dihydrochloride in 200 ml of diethyl ether (care: evolution of hydrogen!). After 3 h at room temperature, the evolution hydrogen is complete. 10.1 g (30 mmol) of cis,cis-1,1',1"-(1,3,5-cyclohexanetriyl)tris[2,2-dimethyl-1-propanone][98013-15-1] are added, and the reaction mixture is cooled to 0° C. in an ice/salt bath. 95 ml of 1 N titanium tetrachloride solution in DCM are then added dropwise, the mixture is allowed to warm to room temperature and is then heated under reflux for 18 h. After cooling, the solid which has precipitated out is filtered off with suction, rinsed three times with 100 ml of DCM, the filtrate is evaporated to dryness, the oily residue is taken up in 300 ml of DCM, washed three times with 100 ml of 2 N aqueous KOH solution each time and then dried over magnesium sulfate. The DCM is removed in vacuo, and the residue is chromatographed on silica gel (deactivated using triethylamine) with cyclohexane:ethyl acetate:triethylamine (90:9:1, vv). Yield: 5.6 g (7 mmol), 23%. Purity: about 97% according to $^1$H-NMR.

The following compounds can be synthesised analogously:
| Ex. | Carbonyl component Amine | Product Variant | Yield |
|---|---|---|---|
| L202 | 187805-79-4 S200 | 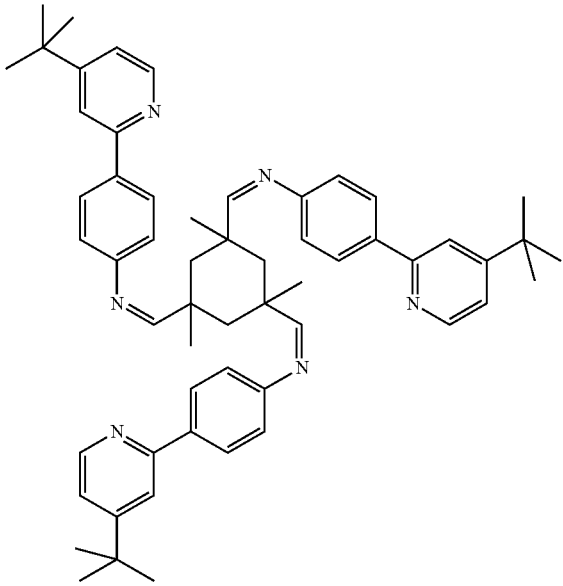 A | 54% |
| L203 | 187805-79-4 S201 | 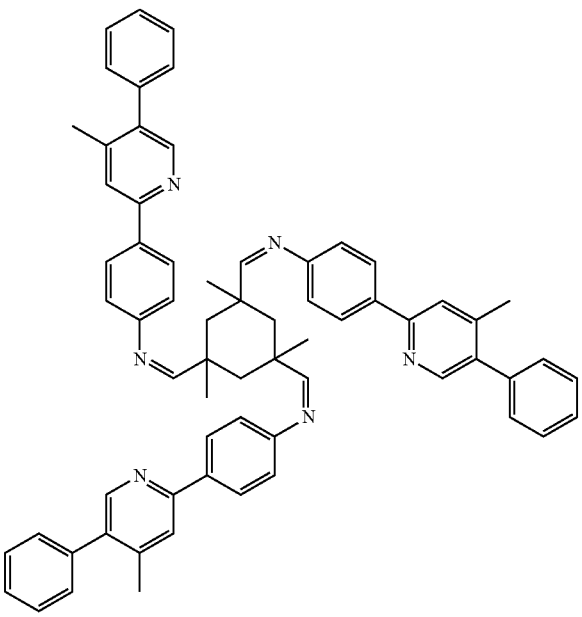 A | 57% |

-continued
| Ex. | Carbonyl component Amine | Product Variant | Yield |
|---|---|---|---|
| L204 | 107354-37-0 S202 | 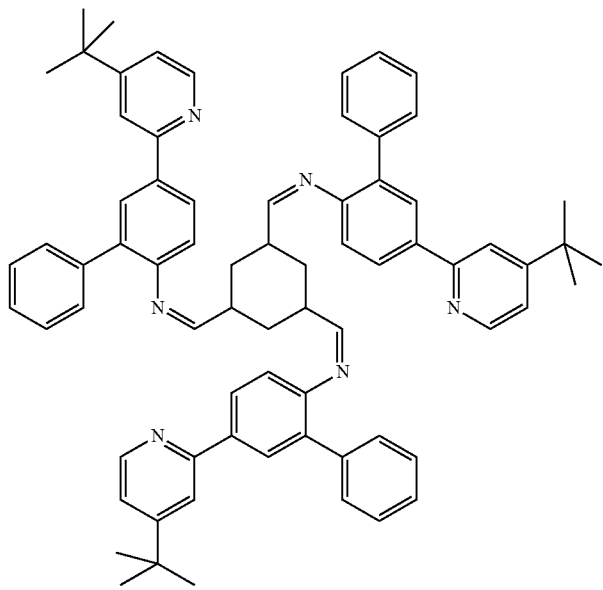  A | 69% |
| L205 | 98013-04-8 S203 | 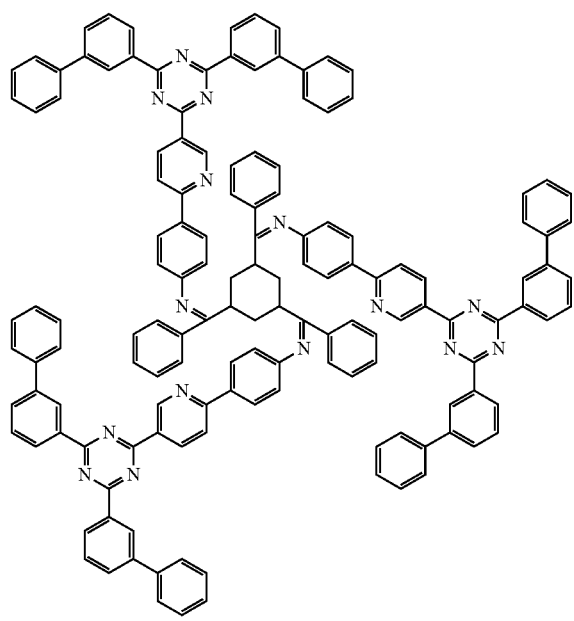  B | 38% |

-continued
| Ex. | Carbonyl component Amine | Product Variant | Yield |
|---|---|---|---|
| L206 | 98013-15-1 S204 | 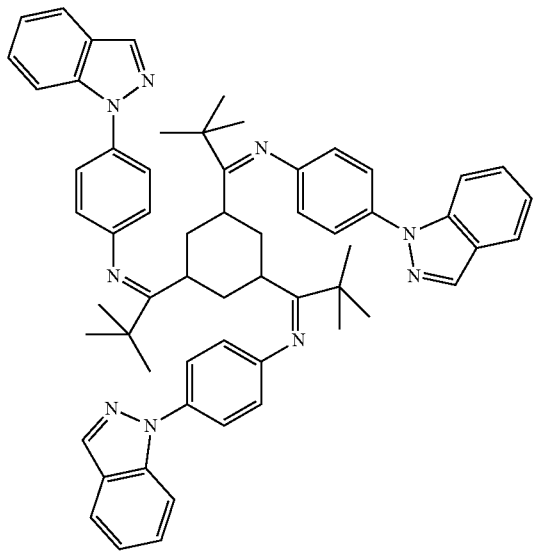<br>B | 25% |
| L207 | 187805-79-4 1246767-56-5 | 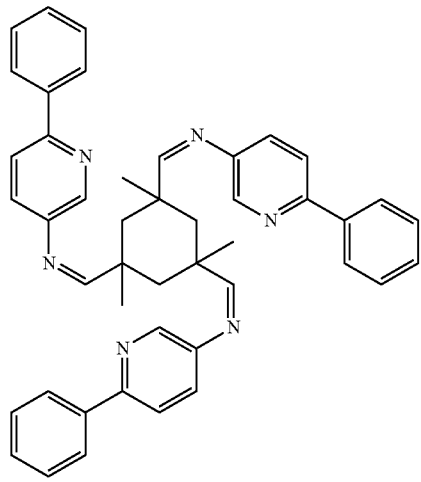<br>A | 54% |

| Ex. | Carbonyl component Amine | Product Variant | Yield |
|---|---|---|---|
| L208 | 187805-79-4 52090-60-5 | 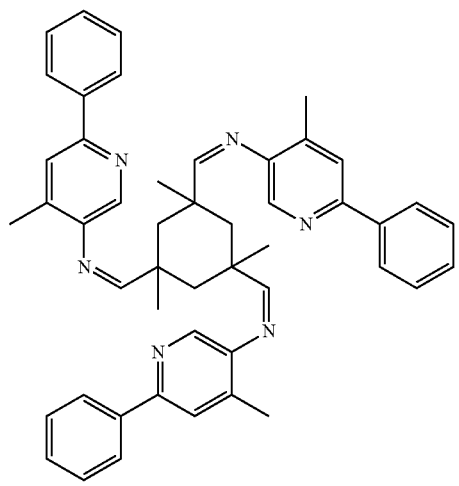<br>A | 49% |
| L209 | 98013-15-1 66728-99-2 | 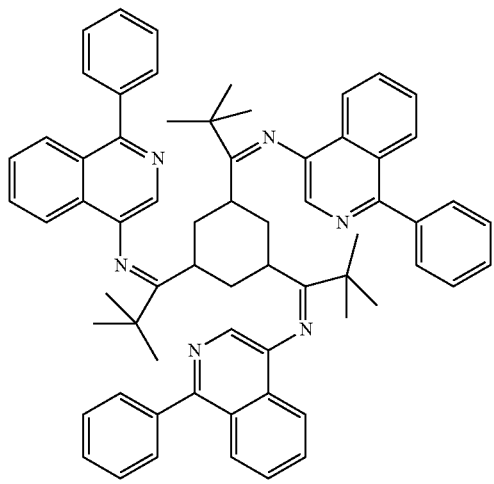<br>B | 27% |

| Ex. | Carbonyl component Amine | Product Variant | Yield |
|---|---|---|---|
| L210 | 98013-15-1<br>1110656-27-3 | 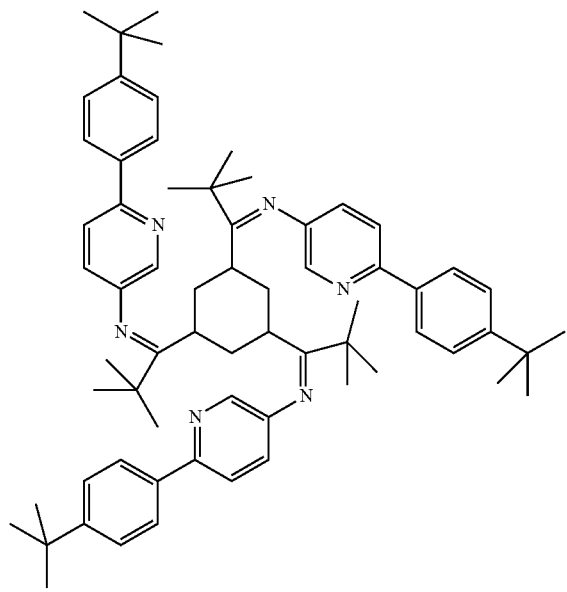<br>B | 24% |
| L211 | 107354-37-0<br>1357165-91-3 | 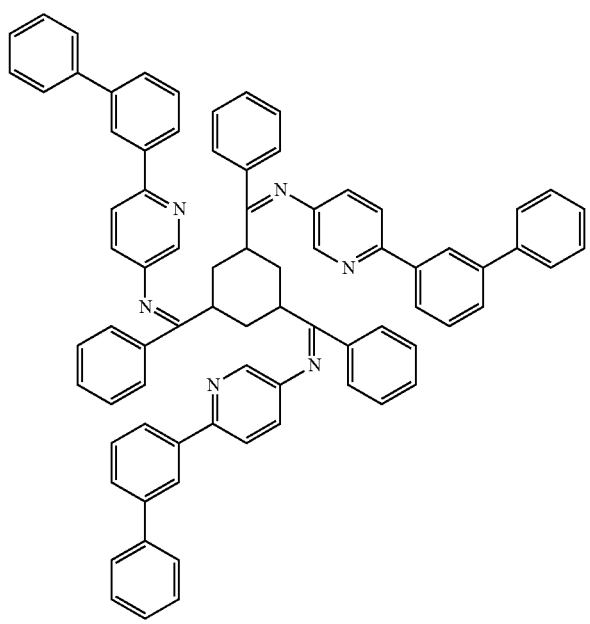<br>B | 71% |

Example L300

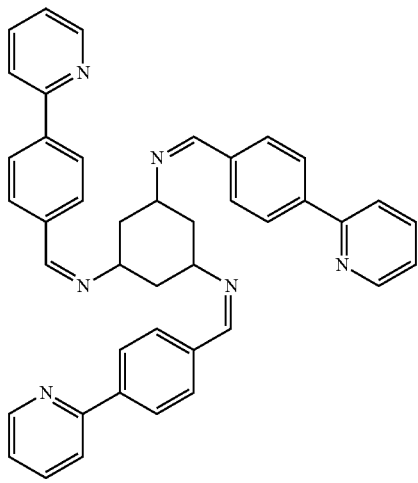 [SMILES: C(=N/C1CC(/N=C\c2ccc(-c3ccccn3)cc2)CC(/N=C\c2ccc(-c3ccccn3)cc2)C1)/c1ccc(-c2ccccn2)cc1]

A mixture of 3.9 g (30 mmol) of cis,cis-1,3,5-triamino-cyclohexane [26150-46-9], 18.3 g (100 mmol) of 4-(2-pyridinyl)benzaldehyde [127406-56-8], 951 mg (5 mmol) of 4-toluenesulfonic acid monohydrate [6192-52-5] and 300 ml of mesitylene is heated under reflux until the separation of water is complete. After cooling, the mesitylene is removed in vacuo, and the residue is chromatographed on silica gel (deactivated using triethylamine) with cyclohexane:ethyl acetate:triethylamine (90:9:1, vv). Yield: 15.0 g (24 mmol), 88%. Purity: about 97% according to $^1$H-NMR.

The following compounds can be synthesised analogously:

| Ex. | Carbonyl component<br>Amine | Product<br>Variant | Yield |
|---|---|---|---|
| L301 | 52199-29-8<br>478978-03-9 | | 64% |
| L302 | 221910-24-3<br>478978-03-9 | | 60% |

-continued
| Ex. | Carbonyl component Amine | Product Variant | Yield |
|---|---|---|---|
| L303 | 1138735-13-3 478978-03-9 | 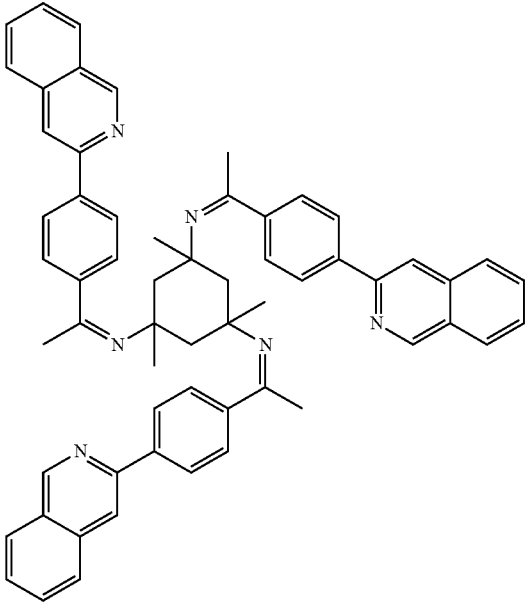 [SMILES: C/C(=N/C1(C)CC(C)(/N=C(/C)c2ccc(-c3cc4ccccc4cn3)cc2)CC(C)(/N=C(/C)c2ccc(-c3cc4ccccc4cn3)cc2)C1)c1ccc(-c2cc3ccccc3cn2)cc1] | 58% |
| L304 | 1107640-93-6 582312-14-9 | 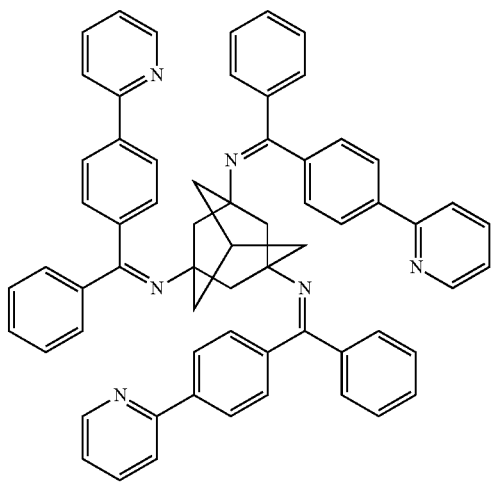 [SMILES: CC(CC(CC(C)/N=C(/c1ccccc1)c1ccc(-c2ccccn2)cc1)CC(C)/N=C(/c1ccccc1)c1ccc(-c2ccccn2)cc1)/N=C(/c1ccccc1)c1ccc(-c2ccccn2)cc1] | 53% |

| Ex. | Carbonyl component Amine | Product Variant | Yield |
|---|---|---|---|
| L305 | 1094356-84-9 478978-03-9 | 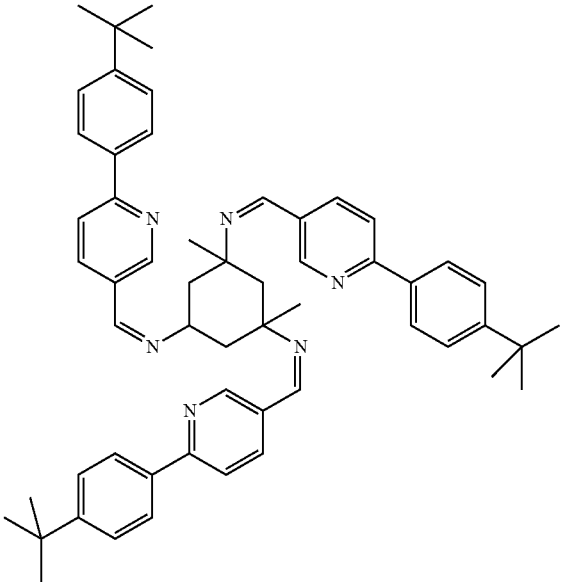 [SMILES: CC1(/N=C\c2ccc(-c3ccc(C(C)(C)C)cc3)nc2)CC(/N=C\c2ccc(-c3ccc(C(C)(C)C)cc3)nc2)CC(C)(/N=C\c2ccc(-c3ccc(C(C)(C)C)cc3)nc2)C1] | 55% |
| L306 | 1401797-64-5 582312-14-9 | 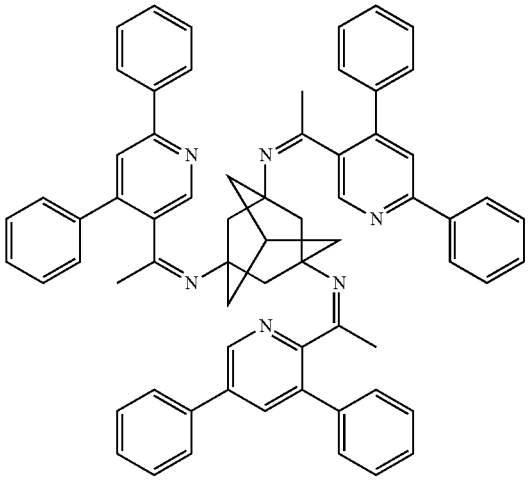 [SMILES: C/C(=N/C(C)CC(CC(C)/N=C(/C)c1cnc(-c2ccccc2)cc1-c1ccccc1)CC(C)/N=C(/C)c1ncc(-c2ccccc2)cc1-c1ccccc1)c1cnc(-c2ccccc2)cc1-c1ccccc1] | 57% |
| L307 | 64869-17-6 582312-14-9 | 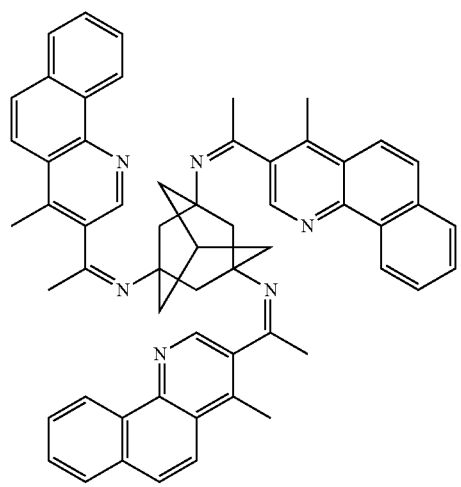 [SMILES: C/C(=N/C(C)CC(CC(C)/N=C(/C)c1cnc2c(ccc3ccccc32)c1C)CC(C)/N=C(/C)c1cnc2c(ccc3ccccc32)c1C)c1cnc2c(ccc3ccccc32)c1C] | 47% |

-continued
| Ex. | Carbonyl component Amine | Product Variant | Yield |
|---|---|---|---|
| L308 | 30091-51-1<br>478978-03-9 | 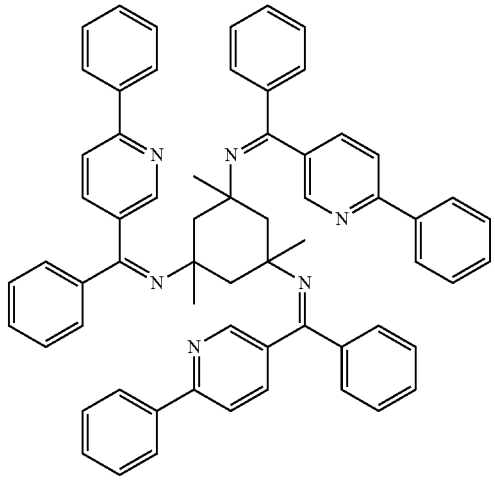 [SMILES: CC1(/N=C(/c2ccccc2)c2ccc(-c3ccccc3)nc2)CC(C)(/N=C(/c2ccccc2)c2ccc(-c3ccccc3)nc2)CC(C)(/N=C(/c2ccccc2)c2ccc(-c3ccccc3)nc2)C1] | 59% |
| L309 | 1252578-97-4<br>478978-03-9 | 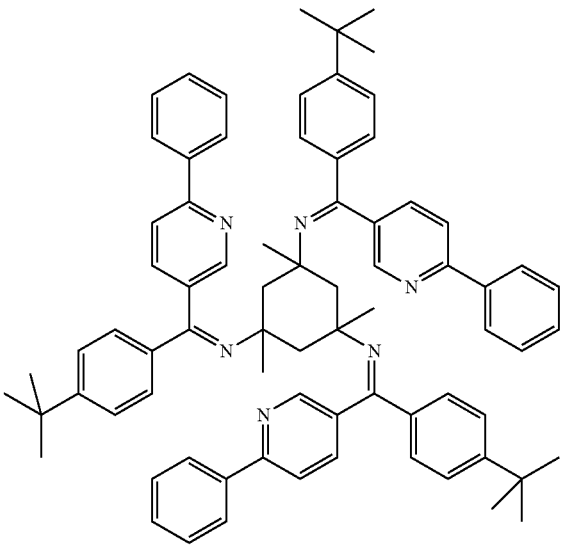 [SMILES: CC1(/N=C(/c2ccc(C(C)(C)C)cc2)c2ccc(-c3ccccc3)nc2)CC(C)(/N=C(/c2ccc(C(C)(C)C)cc2)c2ccc(-c3ccccc3)nc2)CC(C)(/N=C(/c2ccc(C(C)(C)C)cc2)c2ccc(-c3ccccc3)nc2)C1] | 56% |

Example L400

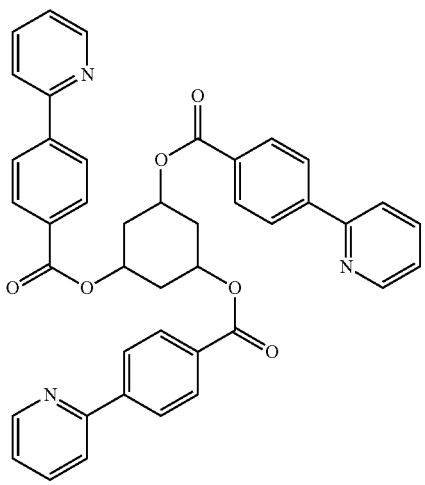 [SMILES: O=C(OC1CC(OC(=O)c2ccc(-c3ccccn3)cc2)CC(OC(=O)c2ccc(-c3ccccn3)cc2)C1)c1ccc(-c2ccccn2)cc1]

28 ml of triethylamine and then, dropwise, a solution of 21.8 g [100 mmol] of 4-(2-pyridinyl)benzoyl chloride [190850-37-4] in 100 ml of dichloromethane are added to a vigourously stirred solution of 4.0 g (30 mmol) of cis,cis-1,3,5-cyclohexanetriol [50409-12-6] in 100 ml of dichloromethane, and the mixture is stirred under reflux for 12 h. After cooling, the volatile constituents are removed in vacuo, the residue is washed by stirring with 300 ml of hot methanol, the product is filtered off with suction, washed three times with 50 ml of methanol each time and finally recrystallised from ethyl acetate/methanol. Yield: 14.0 g (21 mmol), 69%. Purity: about 97% according to $^1$H-NMR.

The following compounds can be prepared analogously, where the purification of the crude products can be carried out by bulb-tube distillation, recrystallisation or chromatography. If a mixture of alcohols, amines or acid chlorides is employed, ligands containing different bidentate part-ligands can also be obtained in addition to the symmetrical ligands by chromatographic separation (CombiFlash Torrent, Axel Semrau GmbH&Co KG).

| Ex. | Starting material | Product | Yield |
|---|---|---|---|
| L401 | 50409-12-6<br>257876-10-3 | | 75% |
| L402 | 26150-46-9<br>190850-37-4 | | 68% |

-continued
| Ex. | Starting material | Product | Yield |
|---|---|---|---|
| L403 | 26150-46-9 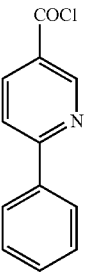 257876-10-3 | 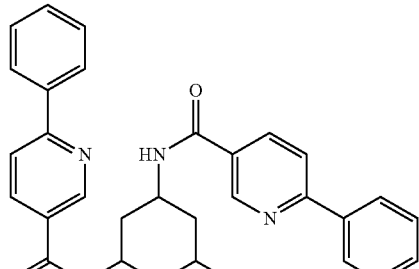 | 70% |
| L404 | 147365-19-3 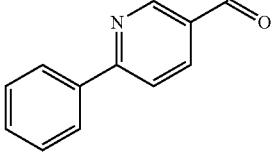 51035-40-6 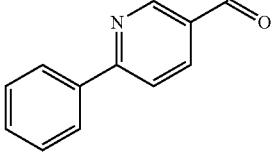 | 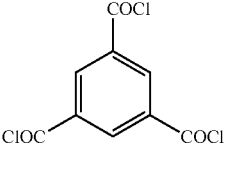 | 69% |
| L405 | 147365-19-3 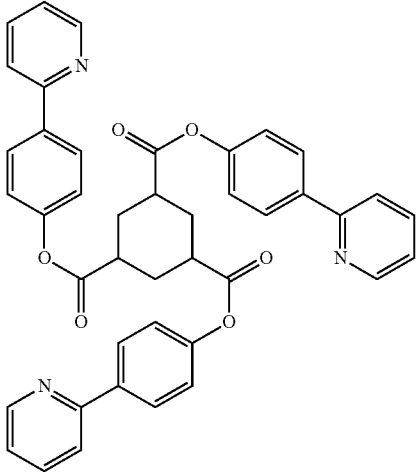 [SMILES: O=C(Oc1ccc(-c2ccccn2)cc1)C1CC(C(=O)Oc2ccc(-c3ccccn3)cc2)CC(C(=O)Oc2ccc(-c3ccccn3)cc2)C1] 66131-77-9 | 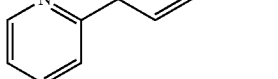 | 68% |

-continued

| Ex. | Starting material | Product | Yield |
|---|---|---|---|
| L406 | 147365-19-3<br>18471-73-3 | | 70% |
| L407 | 147365-19-3<br>126370-67-0 | | 77% |
| L408 | 50409-12-6<br>90828-20-2 | | 73% |

-continued
| Ex. | Starting material | Product | Yield |
|---|---|---|---|
| L409 | 26150-46-9<br>37041-29-5 | 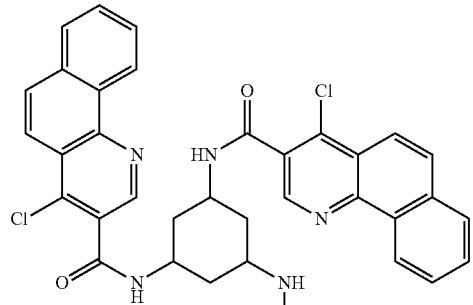 | 71% |
| L410 | 50409-12-6<br>854167-98-9 | 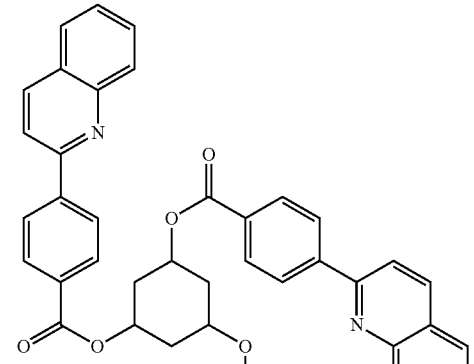 | 73% |
| L411 | 26150-46-9<br>111647-50-8 | 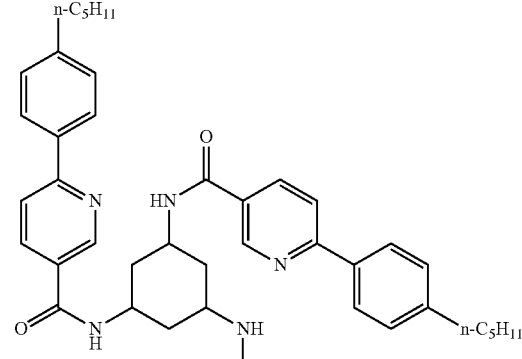 | 64% |

-continued
| Ex. | Starting material | Product | Yield |
|---|---|---|---|
| L412 | 147365-19-3 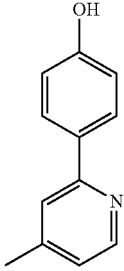 53164-95-7 | 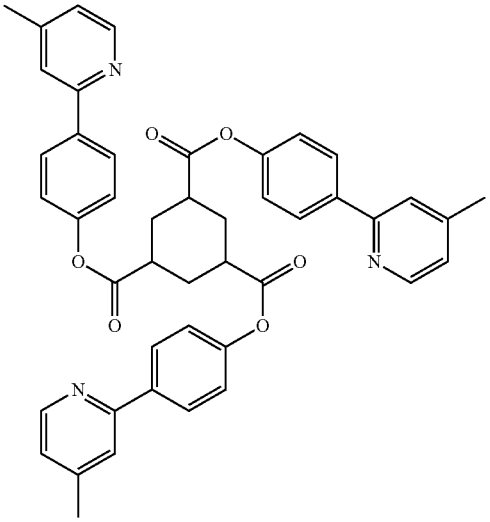 | 69% |
| L413 | 147365-19-3 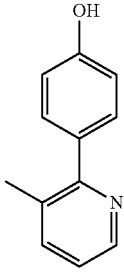 371201-06-8 | 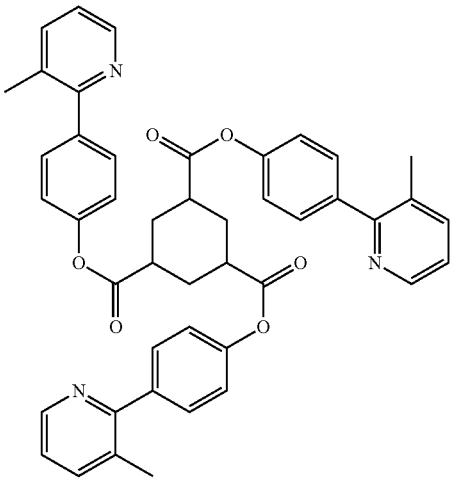 [SMILES: Cc1cccnc1-c1ccc(OC(=O)C2CC(C(=O)Oc3ccc(-c4ncccc4C)cc3)CC(C(=O)Oc3ccc(-c4ncccc4C)cc3)C2)cc1] | 66% |
| L414 | 147365-19-3 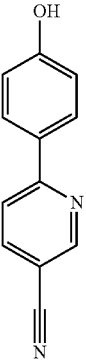 149353-76-4 | 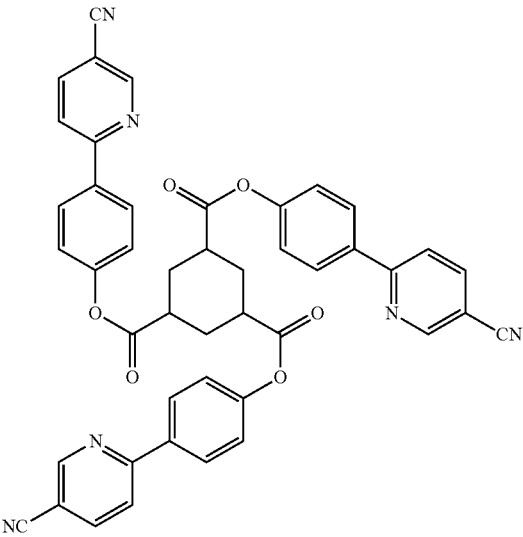 [SMILES: N#Cc1ccc(-c2ccc(OC(=O)C3CC(C(=O)Oc4ccc(-c5ccc(C#N)cn5)cc4)CC(C(=O)Oc4ccc(-c5ccc(C#N)cn5)cc4)C3)cc2)nc1] | 64% |

| Ex. | Starting material | Product | Yield |
|---|---|---|---|
| L415 | 147365-19-3 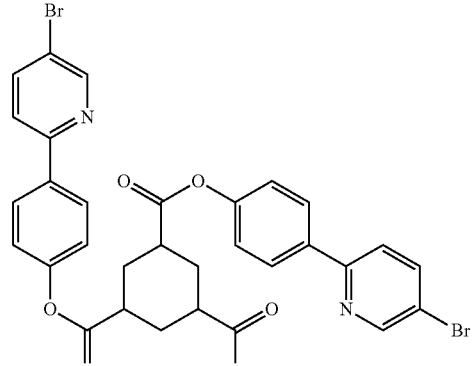 1032825-10-7 | 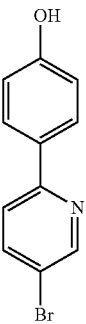 | 65% |
| L416 | 147365-19-3 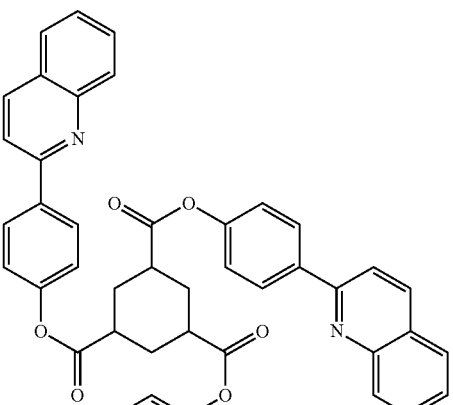 30696-03-8 | 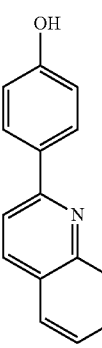 | 68% |

-continued
| Ex. | Starting material | Product | Yield |
|---|---|---|---|
| L417 | 147365-19-3<br><br>884500-88-3 | 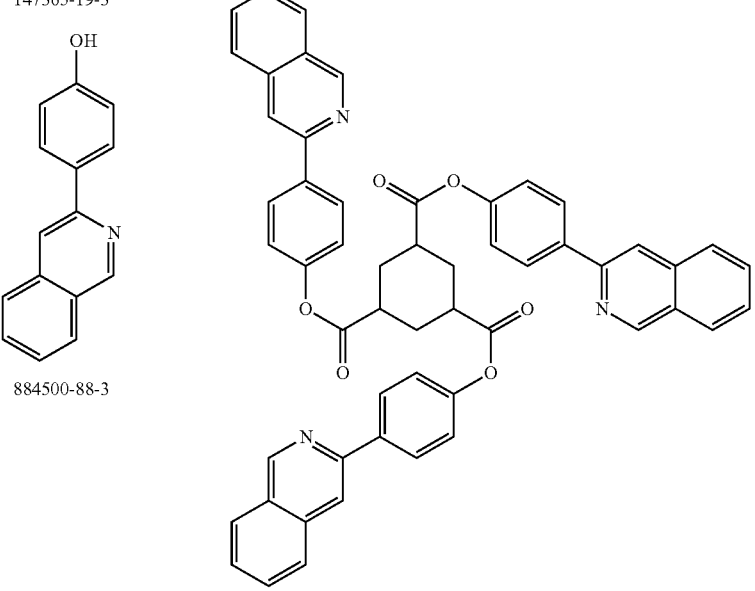 | 66% |
| L418 | 147365-19-3<br><br>855839-55-3 | 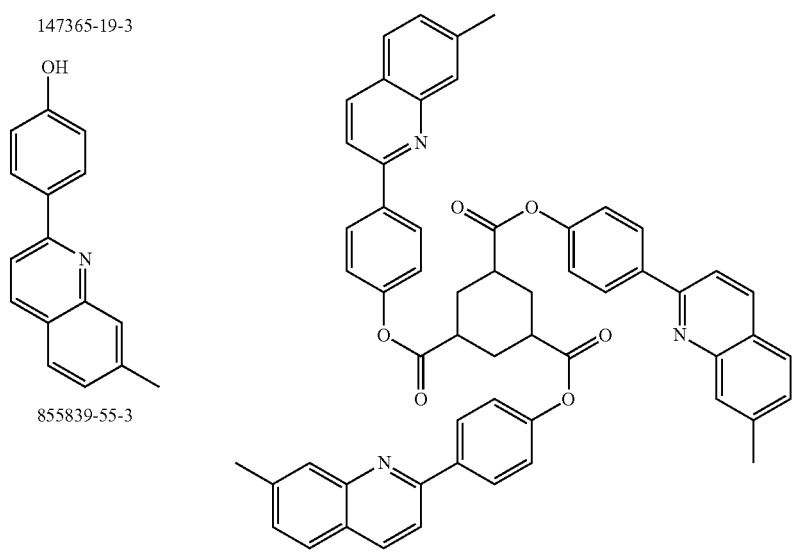 | 69% |

-continued

| Ex. | Starting material | Product | Yield |
|---|---|---|---|
| L419 | 147365-19-3<br>775344-00-8 | | 68% |
| L420 | 147365-19-3<br>54231-47-9 | | 70% |
| L421 | 147365-19-3<br>139218-75-0 | | 59% |

| Ex. | Starting material | Product | Yield |
|---|---|---|---|
| L422 | 147365-19-3 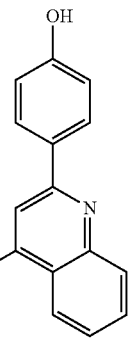 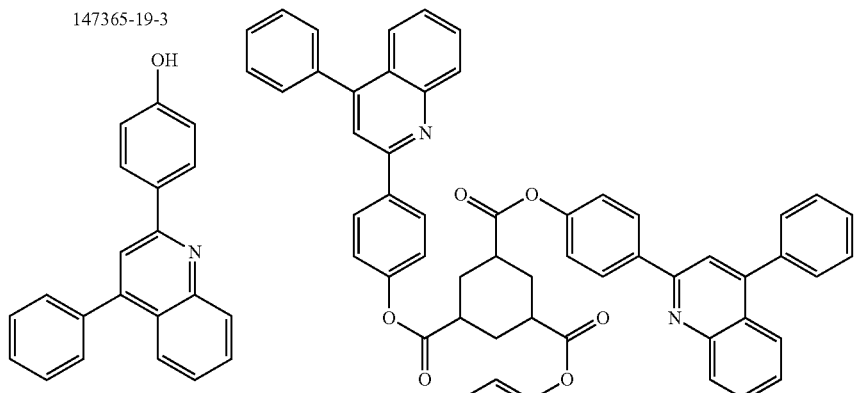 1087269-19-9 | 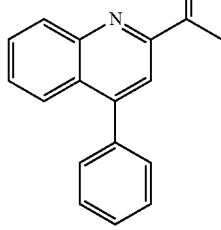 | 63% |
| L423 | 147365-19-3 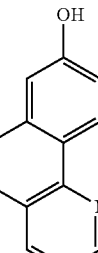 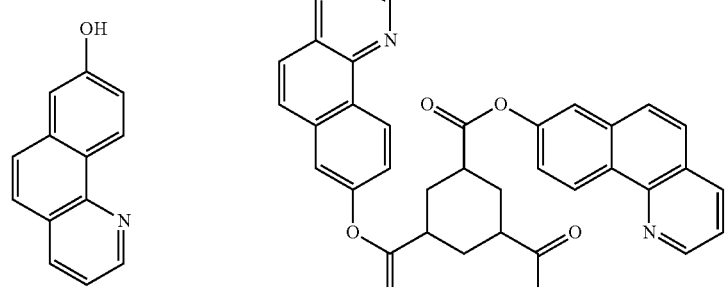 57442-05-4 | 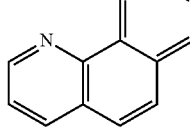 | 70% |

| Ex. | Starting material | Product | Yield |
|---|---|---|---|
| L424 | 147365-19-3 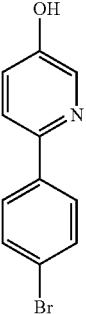 150595-78-1 | 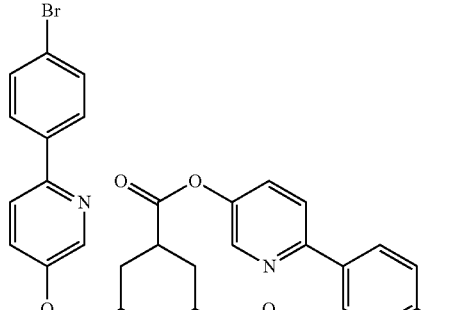 | 65% |
| L425 | 147365-19-3 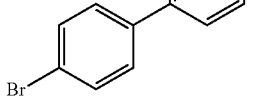 1261970-83-5 |  | 67% |
| L426 | 147365-19-3 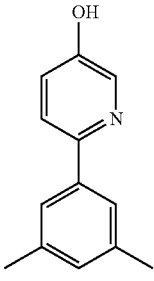 942134-44-3 | 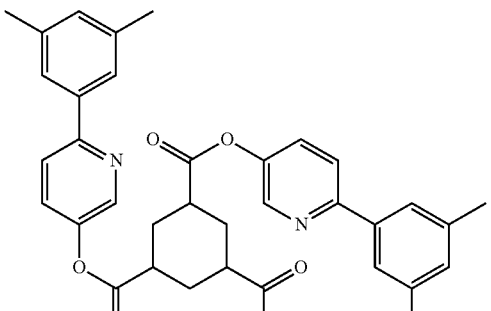 | 68% |

-continued

| Ex. | Starting material | Product | Yield |
|---|---|---|---|
| L427 | 147365-19-3 906101-30-2 | | 65% |
| L428 | 147365-19-3 1551357-67-5 | | 71% |

-continued

| Ex. | Starting material | Product | Yield |
|---|---|---|---|
| L429 | 147365-19-3<br>1876770-00-1 | | 53% |
| L430 | 147365-19-3<br>1903525-21-2 | | 68% |
| L431 | 147365-19-3<br>1698352-04-3 | | 69% |

-continued

| Ex. | Starting material | Product | Yield |
|---|---|---|---|
| L432 | 147365-19-3 / 76570-31-5 | | 70% |
| L433 | 147365-19-3 / 1894503-17-3 | | 58% |
| L434 | 147365-19-3 / 91804-13-6 | | 68% |

-continued

| Ex. | Starting material | Product | Yield |
|---|---|---|---|
| L435 | 147365-19-3  84731-41-9 | | 69% |
| L436 | 147365-19-3  1702400-65-4 | | 67% |
| L437 | 147365-19-3  66404-96-4 | | 65% |

-continued
| Ex. | Starting material | Product | Yield |
|---|---|---|---|
| L438 | 147365-19-3<br>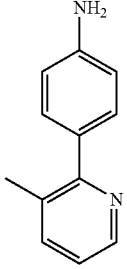<br>885955-74-8 | 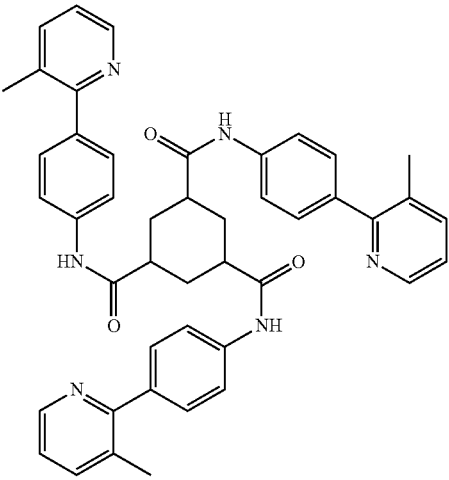 [SMILES: Cc1cccnc1-c1ccc(NC(=O)C2CC(C(=O)Nc3ccc(-c4ncccc4C)cc3)CC(C(=O)Nc3ccc(-c4ncccc4C)cc3)C2)cc1] | 73% |
| L439 | 147365-19-3<br>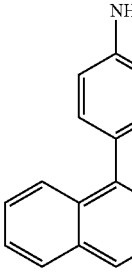<br>58992-84-0 | 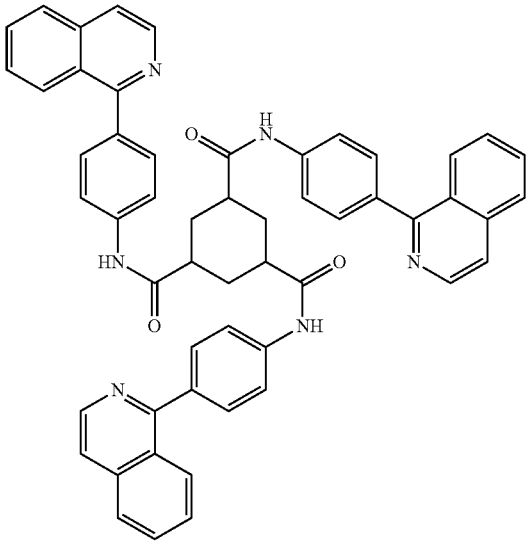 [SMILES: O=C(Nc1ccc(-c2nccc3ccccc23)cc1)C1CC(C(=O)Nc2ccc(-c3nccc4ccccc34)cc2)CC(C(=O)Nc2ccc(-c3nccc4ccccc34)cc2)C1] | 79% |
| L440 | 147365-19-3<br>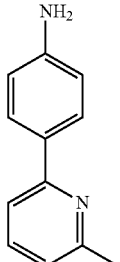<br>1224953-47-2 | 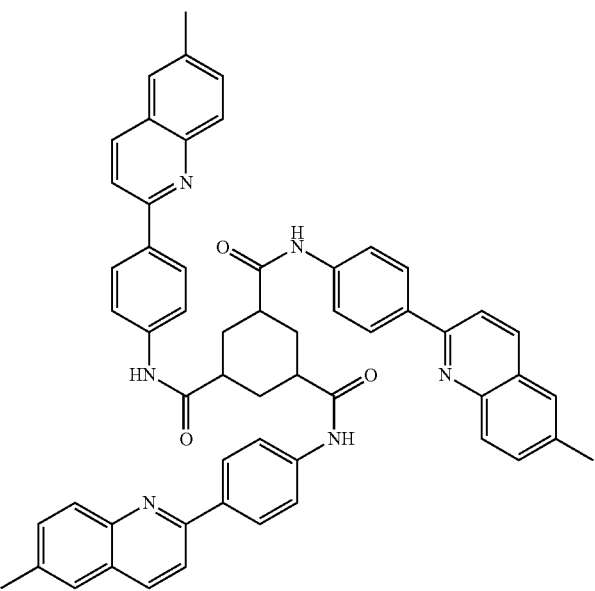 | 73% |

| Ex. | Starting material | Product | Yield |
|---|---|---|---|
| L441 | 147365-19-3 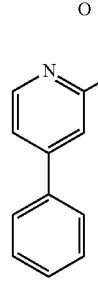 1351665-31-0 | 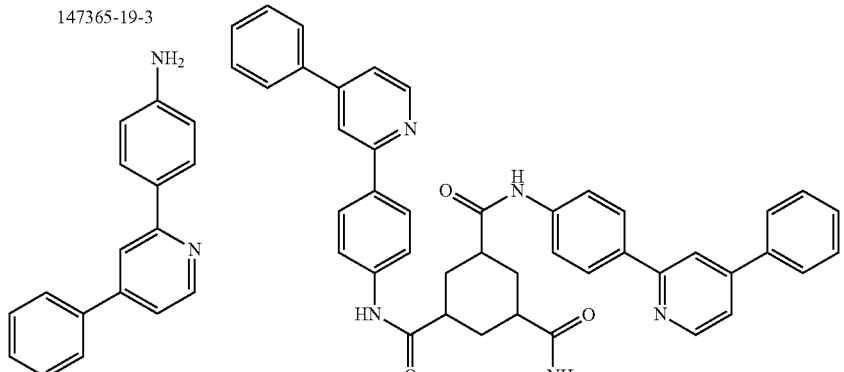 | 70% |
| L442 | 147365-19-3 580-38-1 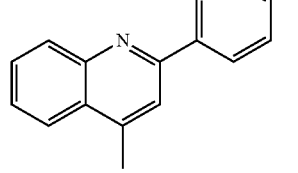 | 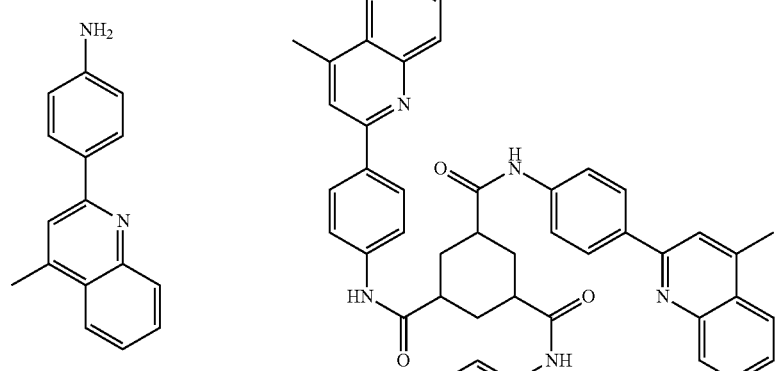 | 74% |

| Ex. | Starting material | Product | Yield |
|---|---|---|---|
| L443 | 147365-19-3<br>1798331-49-3 | 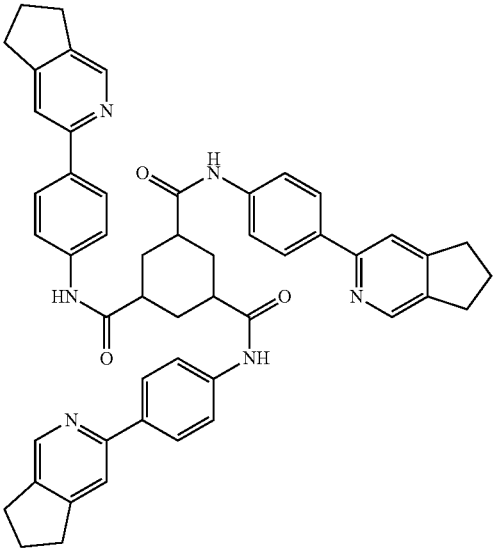 [SMILES: O=C(Nc1ccc(-c2cc3c(cn2)CCC3)cc1)C1CC(C(=O)Nc2ccc(-c3cc4c(cn3)CCC4)cc2)CC(C(=O)Nc2ccc(-c3cc4c(cn3)CCC4)cc2)C1] | 69% |
| L444 | 147365-19-3<br>94211-88-8 | 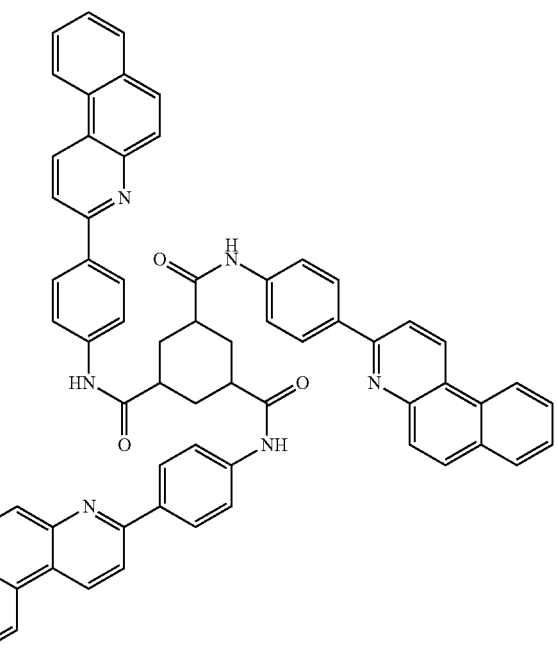 | 72% |

| Ex. | Starting material | Product | Yield |
|---|---|---|---|
| L445 | 147365-19-3<br>530086-92-1 | 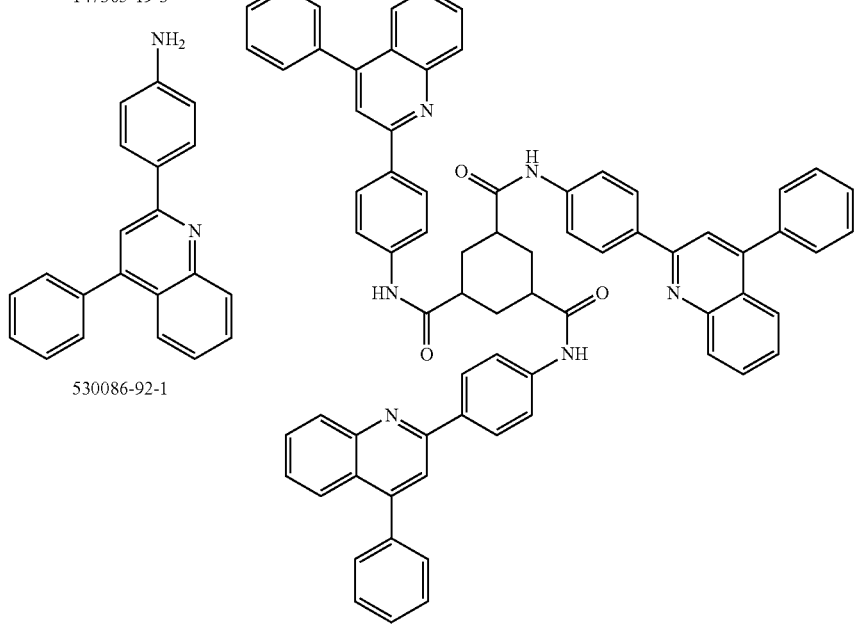 | 74% |
| L446 | 147365-19-3<br>344285-96-7 | 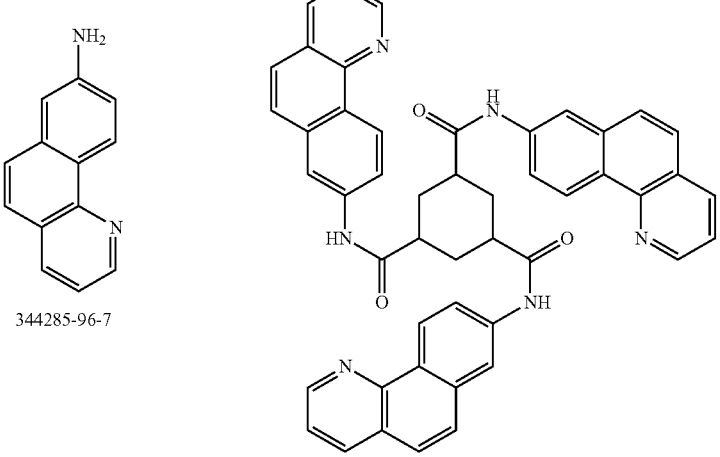 | 71% |

| Ex. | Starting material | Product | Yield |
|---|---|---|---|
| L447 | 147365-19-3 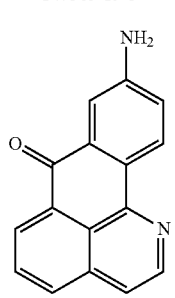 13102354-6 | 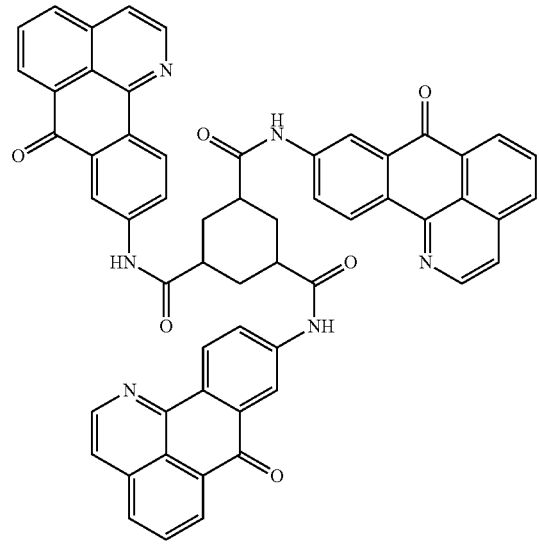 [SMILES: O=C1c2cc(NC(=O)C3CC(C(=O)Nc4ccc5c(c4)C(=O)c4cccc6ccnc-5c46)CC(C(=O)Nc4ccc5c(c4)C(=O)c4cccc6ccnc-5c46)C3)ccc2-c2nccc3cccc1c23] | 72% |
| L448 | 147365-19-3 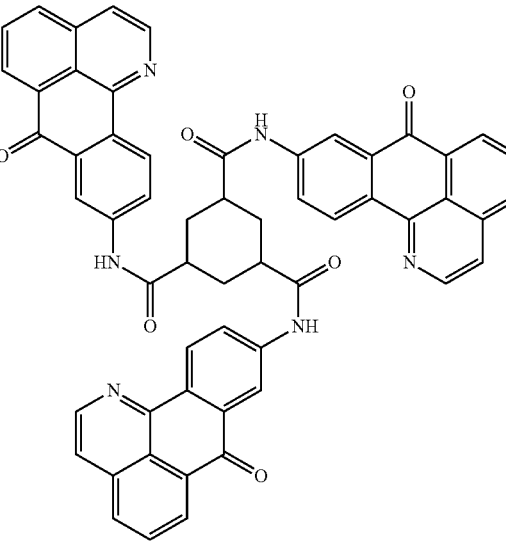 1159407-94-9 | 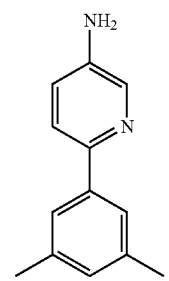 | 70% |
| L449 | 147365-19-3 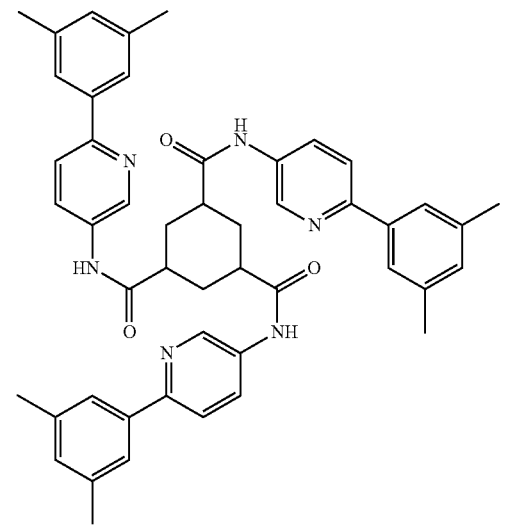 126370-67-0 | 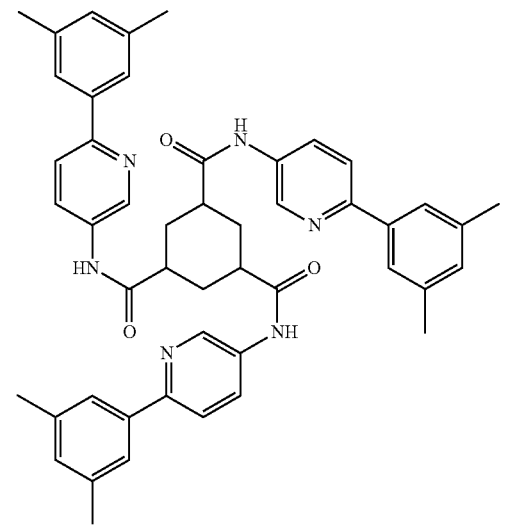 | 69% |

-continued
| Ex. | Starting material | Product | Yield |
|---|---|---|---|
| L450 | 147365-19-3<br>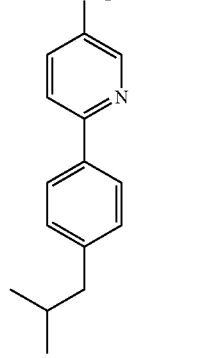<br>1554504-03-8 |  | 65% |
| L451 | 147365-19-3<br>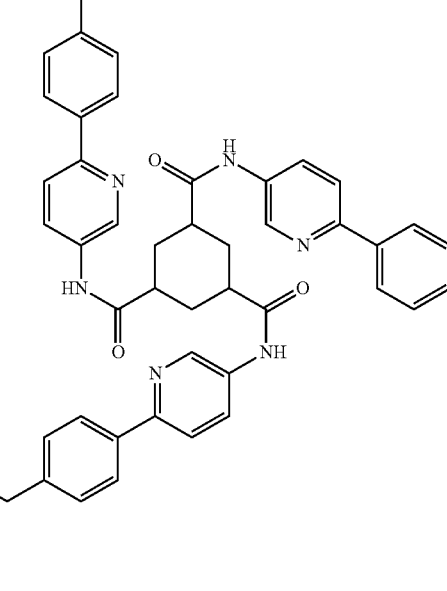<br>1551869-82-9 | 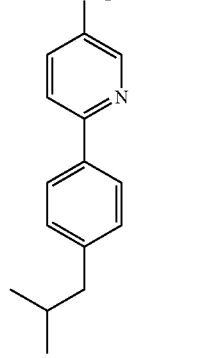 | 71% |

-continued

| Ex. | Starting material | Product | Yield |
|---|---|---|---|
| L452 | 147365-19-3<br>1192165-48-2 | | 67% |
| L453 | 147365-19-3<br>151585-47-6 | | 70% |
| L454 | 147365-19-3<br>66728-99-2 | | 67% |

-continued
| Ex. | Starting material | Product | Yield |
|---|---|---|---|
| L455 | 147365-19-3<br>1357166-67-6 | 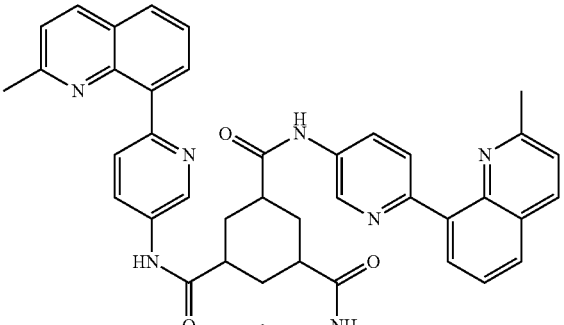 | 74% |
| L456 | 147365-19-3<br>151585-47-6 | 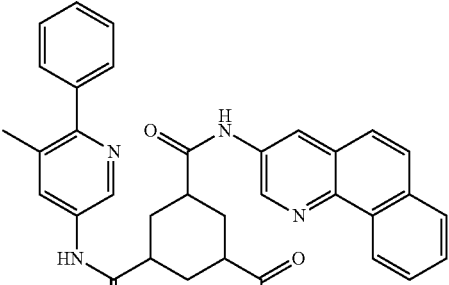 | 19% |
| L457 | 126370-67-0 | 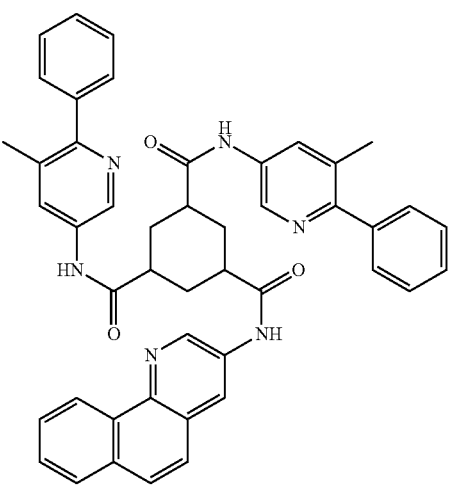 [SMILES: Cc1cc(NC(=O)C2CC(C(=O)Nc3cnc(-c4ccccc4)c(C)c3)CC(C(=O)Nc3cnc4c(ccc5ccccc54)c3)C2)cnc1-c1ccccc1] | 16% |

-continued
| Ex. | Starting material | Product | Yield |
|---|---|---|---|
| L458 | 147365-19-3 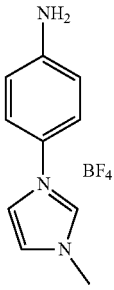 1870003-70-5 Addition as DMF solution | 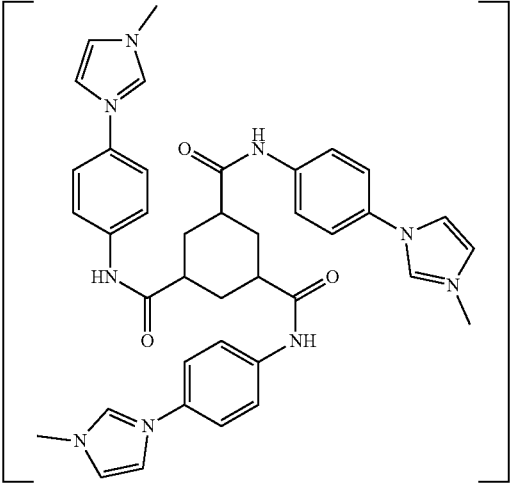 | 28% |
| L459 | 147365-19-3 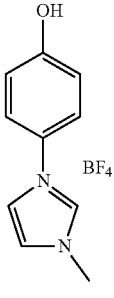 1870003-72-7 Addition as DMF solution | 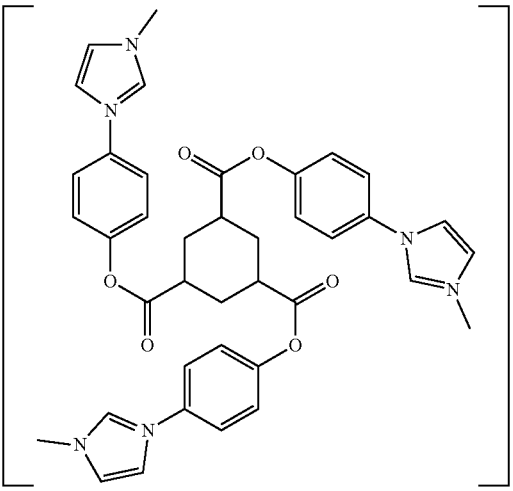 | 33% |
| L460 | 147365-19-3 1255636-82-8 | 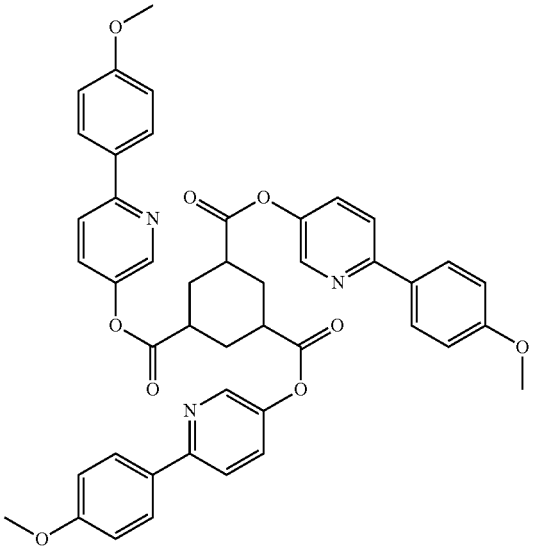 | 70% |

Example L500

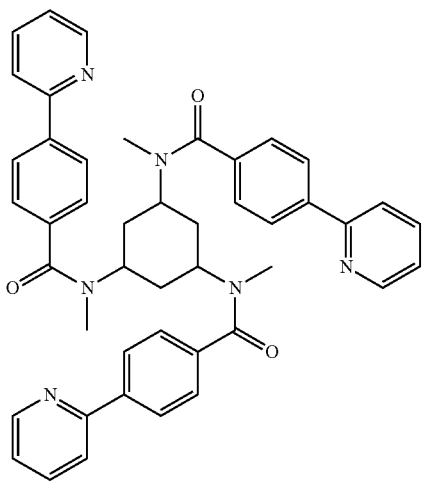 [SMILES: CN(C(=O)c1ccc(-c2ccccn2)cc1)C1CC(N(C)C(=O)c2ccc(-c3ccccn3)cc2)CC(N(C)C(=O)c2ccc(-c3ccccn3)cc2)C1]

1.2 g (50 mmol) of sodium hydride are added in portions to a suspension of 6.7 g (10 mmol) of L402 in 150 ml of dimethylacetamide, and the mixture is stirred at room temperature for 30 min. 2.1 ml (33 mmol) of methyl iodide [74-88-4] are then added, and the mixture is warmed at 60° C. for 16 h. 20 ml of conc. ammonia solution are added dropwise, the mixture is stirred for a further 30 min., the solvent is substantially removed in vacuo, the residue is taken up in 300 ml of dichloromethane, washed once with 200 ml of 5% by weight ammonia water, twice with 100 ml of water each time, once with 100 ml of sat. sodium chloride solution and then dried over magnesium sulfate. The dichloromethane is removed in vacuo, and the crude product is recrystallised from ethyl acetate/methanol. Yield: 5.0 g (7.0 mmol), 70%. Purity: about 97% according to $^1$H-NMR.

The following compounds can be prepared analogously, where methyl iodide is replaced by the electrophiles indicated. In the case of the use of secondary alkyl halides, 60 mmol of NaH and 60 mmol of the secondary alkylating agent are used. The crude products can be purified by bulb-tube distillation, recrystallisation or chromatography.

| Ex. | Starting materials | Product | Yield |
|---|---|---|---|
| L501 | L403 74-88-4 | | 72% |
| L502 | L406 74-88-4 | | 76% |

| Ex. | Starting materials | Product | Yield |
|---|---|---|---|
| L503 | L407 74-88-4 | 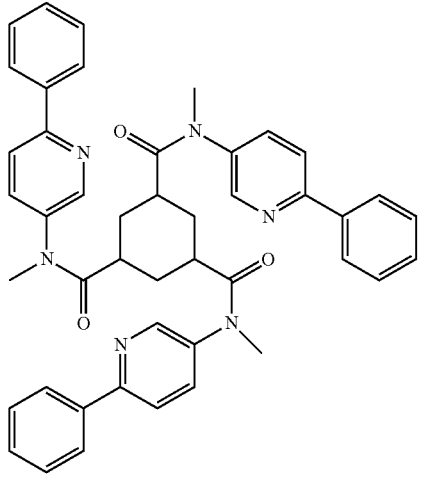 [SMILES: CN(C(=O)C1CC(C(=O)N(C)c2ccc(-c3ccccc3)nc2)CC(C(=O)N(C)c2ccc(-c3ccccc3)nc2)C1)c1ccc(-c2ccccc2)nc1] | 71% |
| L504 | L409 74-88-4 | 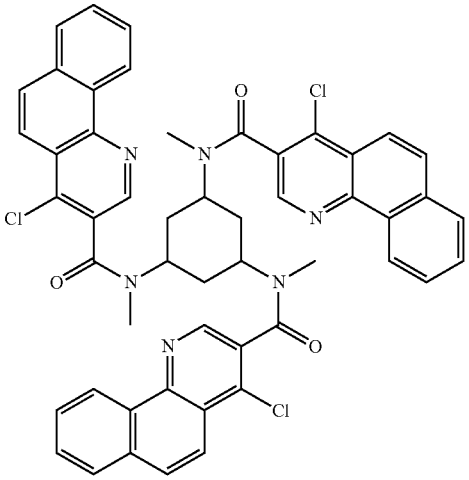 [SMILES: CN(C(=O)c1cnc2c(ccc3ccccc32)c1Cl)C1CC(N(C)C(=O)c2cnc3c(ccc4ccccc43)c2Cl)CC(N(C)C(=O)c2cnc3c(ccc4ccccc43)c2Cl)C1] | 68% |
| L505 | L411 865-50-9 | 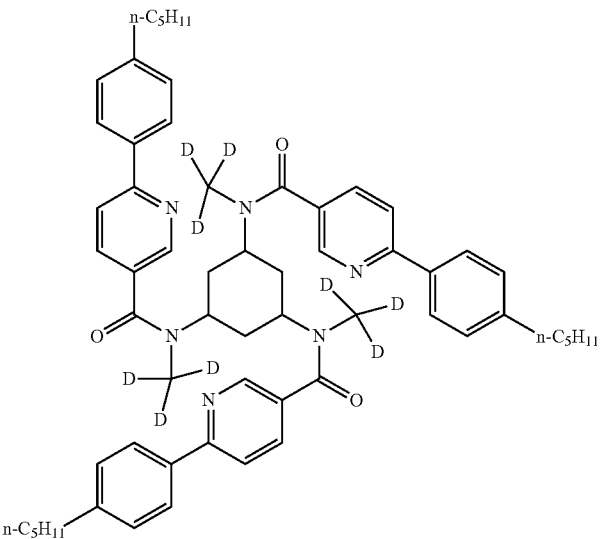 | 66% |

| Ex. | Starting materials | Product | Yield |
|---|---|---|---|
| L506 | L438 71162-19-1 | 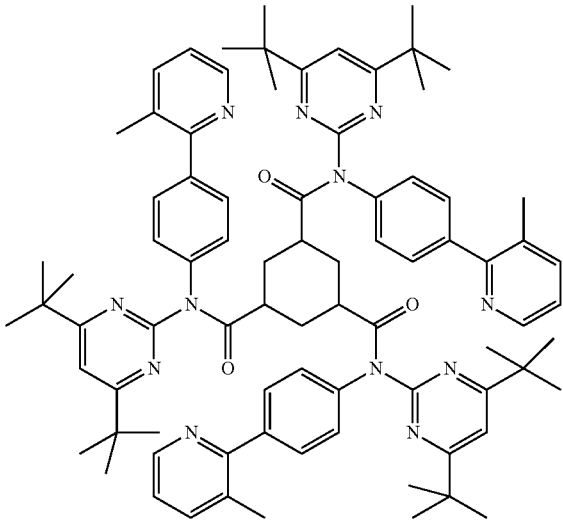 [SMILES: Cc1cccnc1-c1ccc(N(C(=O)C2CC(C(=O)N(c3ccc(-c4ncccc4C)cc3)c3nc(C(C)(C)C)cc(C(C)(C)C)n3)CC(C(=O)N(c3ccc(-c4ncccc4C)cc3)c3nc(C(C)(C)C)cc(C(C)(C)C)n3)C2)c2nc(C(C)(C)C)cc(C(C)(C)C)n2)cc1] | 39% |
| L507 | L439 29394-58-9 | 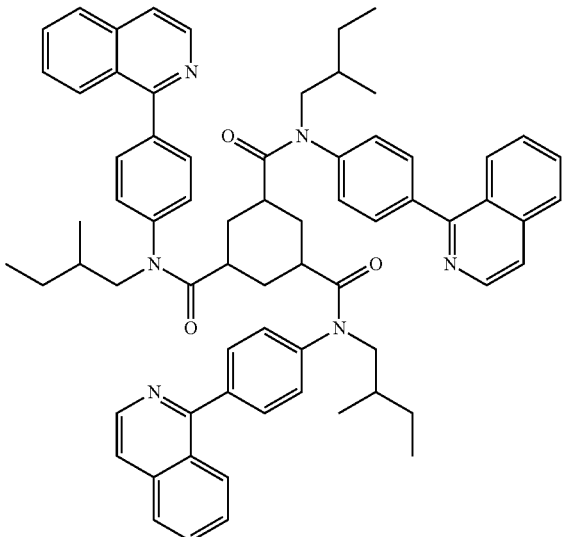 [SMILES: CCC(C)CN(C(=O)C1CC(C(=O)N(CC(C)CC)c2ccc(-c3nccc4ccccc34)cc2)CC(C(=O)N(CC(C)CC)c2ccc(-c3nccc4ccccc34)cc2)C1)c1ccc(-c2nccc3ccccc23)cc1] | 59% |

-continued
| Ex. | Starting materials | Product | Yield |
|---|---|---|---|
| L508 | L440 75-03-6 | 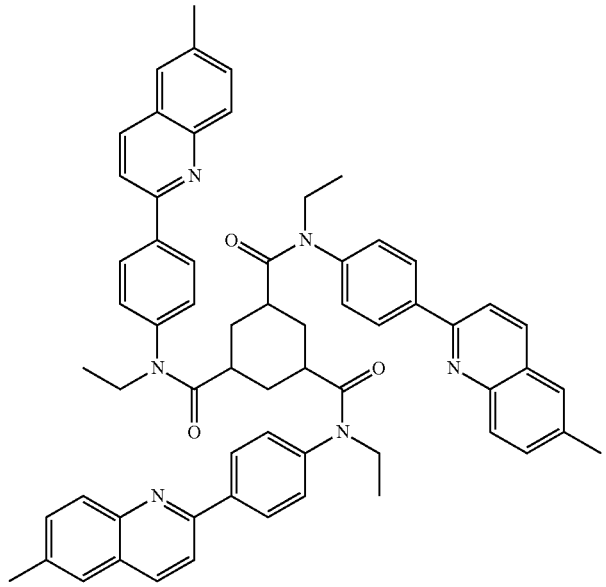 | 70% |
| L509 | L441 15501-33-4 | 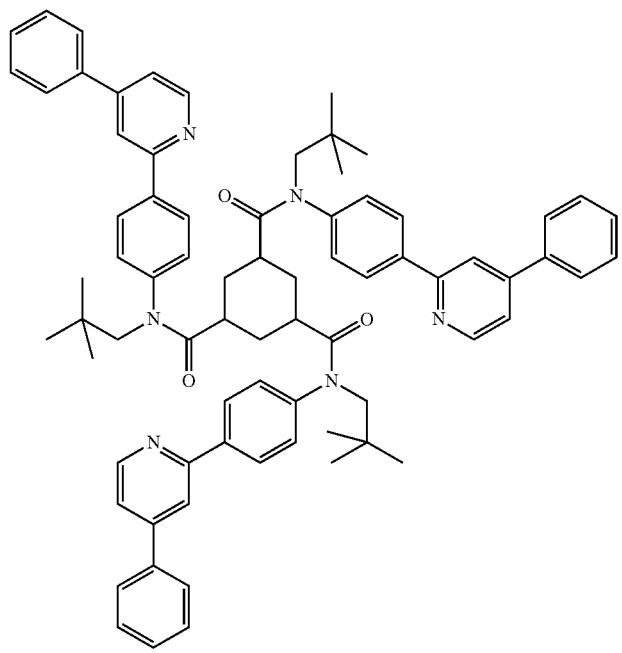 [SMILES: CC(C)(C)CN(C(=O)C1CC(C(=O)N(CC(C)(C)C)c2ccc(-c3cc(-c4ccccc4)ccn3)cc2)CC(C(=O)N(CC(C)(C)C)c2ccc(-c3cc(-c4ccccc4)ccn3)cc2)C1)c1ccc(-c2cc(-c3ccccc3)ccn2)cc1] | 71% |

| Ex. | Starting materials | Product | Yield |
|---|---|---|---|
| L510 | L442<br>74-88-4<br>24424-99-5 | | 73% |
| L511 | L443<br>24424-99-5 | | 69% |

| Ex. | Starting materials | Product | Yield |
|---|---|---|---|
| L512 | L444 865-50-9 | 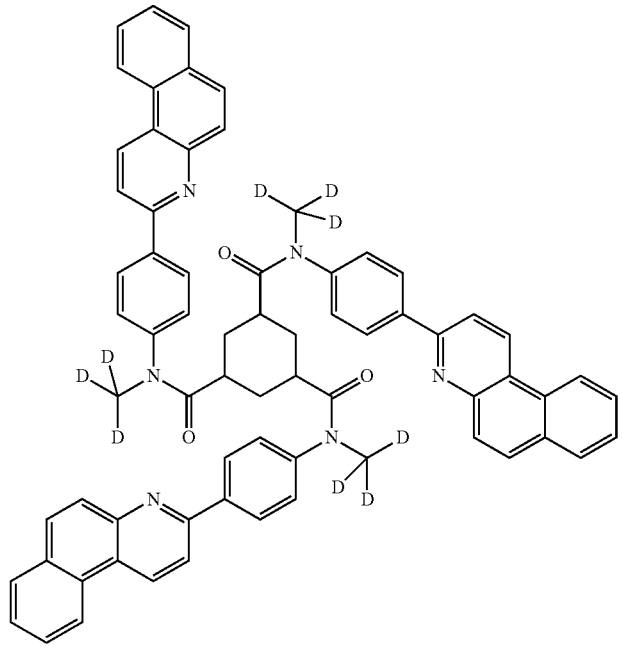 [SMILES: [2H]C([2H])([2H])N(C(=O)C1CC(C(=O)N(c2ccc(-c3ccc4c(ccc5ccccc54)n3)cc2)C([2H])([2H])[2H])CC(C(=O)N(c2ccc(-c3ccc4c(ccc5ccccc54)n3)cc2)C([2H])([2H])[2H])C1)c1ccc(-c2ccc3c(ccc4ccccc43)n2)cc1] | 68% |
| L513 | L445 75-26-3 | 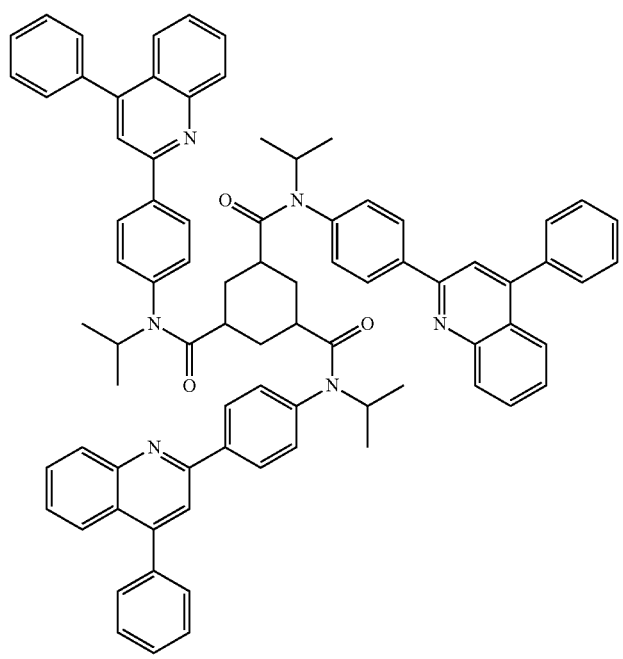 [SMILES: CC(C)N(C(=O)C1CC(C(=O)N(c2ccc(-c3cc(-c4ccccc4)c4ccccc4n3)cc2)C(C)C)CC(C(=O)N(c2ccc(-c3cc(-c4ccccc4)c4ccccc4n3)cc2)C(C)C)C1)c1ccc(-c2cc(-c3ccccc3)c3ccccc3n2)cc1] | 42% |

-continued
| Ex. | Starting materials | Product | Yield |
|---|---|---|---|
| L514 | L447 513-38-2 | 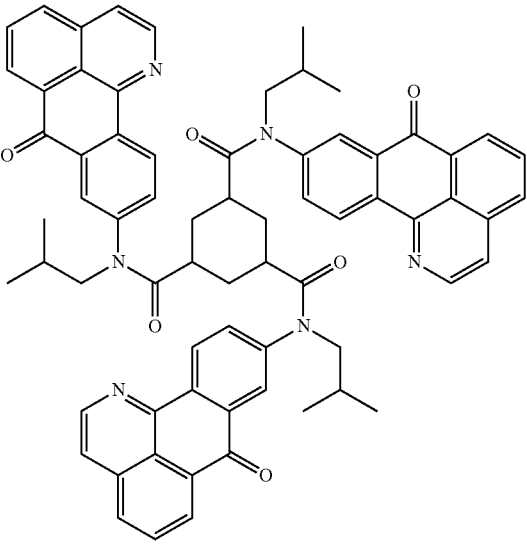 [SMILES: CC(C)CN(C(=O)C1CC(C(=O)N(CC(C)C)c2ccc3c(c2)C(=O)c2cccc4ccnc-3c24)CC(C(=O)N(CC(C)C)c2ccc3c(c2)C(=O)c2cccc4ccnc-3c24)C1)c1ccc2c(c1)C(=O)c1cccc3ccnc-2c13] | 65% |
| L515 | L450 15501-33-4 | 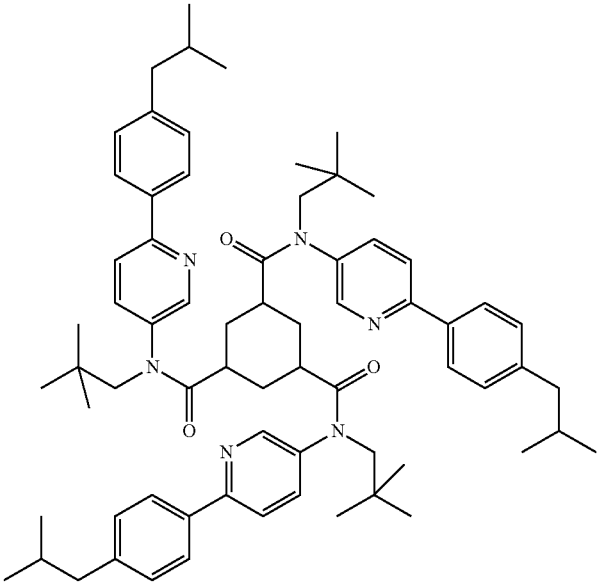 [SMILES: CC(C)Cc1ccc(-c2ccc(N(CC(C)(C)C)C(=O)C3CC(C(=O)N(CC(C)(C)C)c4ccc(-c5ccc(CC(C)C)cc5)nc4)CC(C(=O)N(CC(C)(C)C)c4ccc(-c5ccc(CC(C)C)cc5)nc4)C3)cn2)cc1] | 63% |

| Ex. | Starting materials | Product | Yield |
|---|---|---|---|
| L516 | L451 620-05-3 | | 70% |
| L517 | L453 15501-33-4 | | 61% |
| L518 | L454 15501-33-4 | | 68% |

| Ex. | Starting materials | Product | Yield |
|---|---|---|---|
| L519 | L455 74-88-4 | 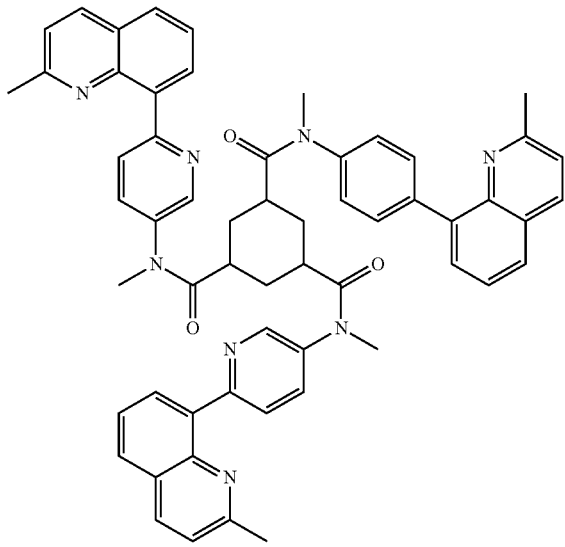 [SMILES: Cc1ccc2cccc(-c3ccc(N(C)C(=O)C4CC(C(=O)N(C)c5ccc(-c6cccc7ccc(C)nc67)nc5)CC(C(=O)N(C)c5ccc(-c6cccc7ccc(C)nc67)nc5)C4)cc3)c2n1] | 61% |
| L520 | L456 75-77-4 | 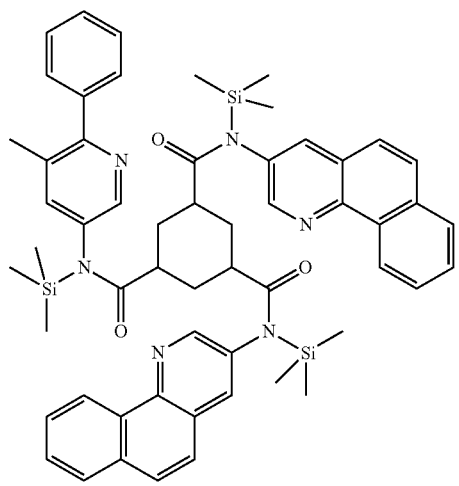 [SMILES: Cc1cc(N(C(=O)C2CC(C(=O)N(c3cnc4c(ccc5ccccc54)c3)[Si](C)(C)C)CC(C(=O)N(c3cnc4c(ccc5ccccc54)c3)[Si](C)(C)C)C2)[Si](C)(C)C)cnc1-c1ccccc1] | 41% |

-continued

| Ex. | Starting materials | Product | Yield |
|---|---|---|---|
| L521 | L457 15501-33-4 | 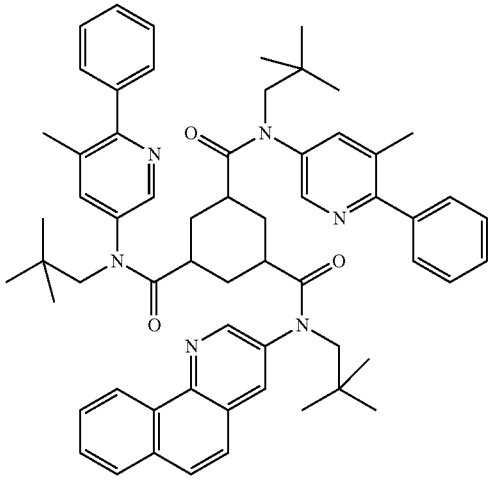 [SMILES: Cc1cc(N(CC(C)(C)C)C(=O)C2CC(C(=O)N(CC(C)(C)C)c3cnc(-c4ccccc4)c(C)c3)CC(C(=O)N(CC(C)(C)C)c3cnc4c(ccc5ccccc54)c3)C2)cnc1-c1ccccc1] | 72% |
| L522 | L458 74-88-4 base Cs$_2$CO$_3$ solvent acetone | 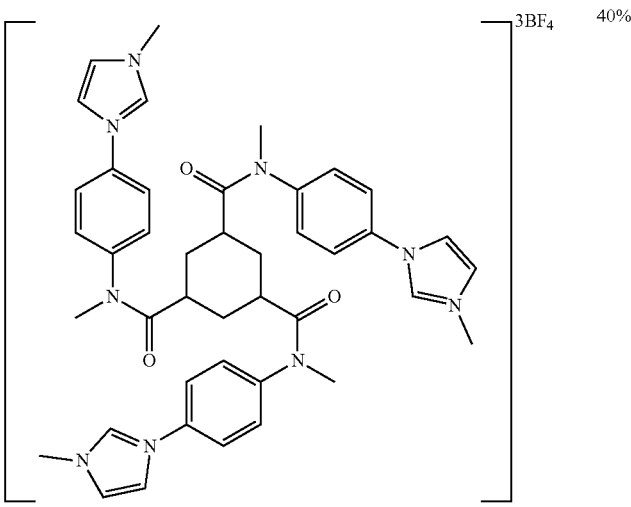 3BF$_4$ | 40% |

Example L600

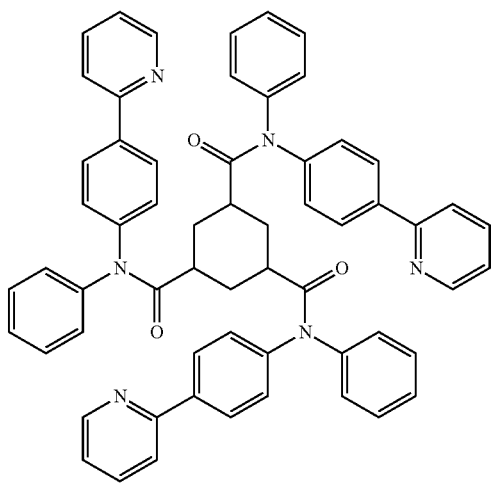 [SMILES: O=C(C1CC(C(=O)N(c2ccccc2)c2ccc(-c3ccccn3)cc2)CC(C(=O)N(c2ccccc2)c2ccc(-c3ccccn3)cc2)C1)N(c1ccccc1)c1ccc(-c2ccccn2)cc1]

A mixture of 6.7 g (10 mmol) of L406, 4.5 ml (40 mmol) of iodobenzene [591-50-4], 12.7 g (60 mmol) of tripotassium phosphate, 292 mg (1.5 mmol) of copper (I) iodide, 553 mg (3 mmol) of 2,2,6,6-tetramethyl-3,5-heptanedione [1118-71-4], 50 g of glass beads (diameter 3 mm) and 150 ml o-xylene is heated at 130° C. for 24 h. After cooling, the solvent is removed in vacuo, the residue is taken up in 500 ml of dichloromethane, the salts are filtered off via a pre-slurried Celite bed, the filtrate is washed three times with 100 ml of 5% by weight ammonia solution and once with 100 ml of water and then dried over magnesium sulfate. The crude product obtained after removal of the solvent is recrystallised from ethyl acetate/methanol. Yield: 6.5 g (7.2 mmol), 72%. Purity: about 97% according to $^1$H-NMR.

The following compounds can be prepared analogously. The crude products an be purified by bulb-tube distillation, recrystallisation or chromatography.

| Ex. | Starting materials | Product | Yield |
|---|---|---|---|
| L601 | L446 37055-53-1 | | 51% |
| L602 | L448 20442-79-9 | | 56% |
| L603 | L449 857784-97-5 | | 33% |

| Ex. | Starting materials | Product | Yield |
|---|---|---|---|
| L604 | L452 1643766-87-3 | | 61% |

Example L700

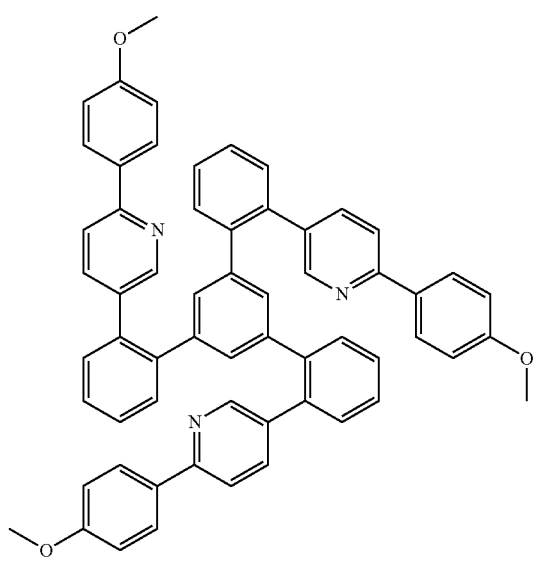

A vigourously stirred mixture of 16.3 g (30 mmol) of 1,3,5-tris(2-bromo-phenyl)benzene [380626-56-2], 31.1 g (100 mmol) of 2-(4-methoxy-phenyl)-5-(4,4,5,5-tetramethyl-1,3,2-dioxaborolan-2-yl)pyridine [1374263-53-2], 42.5 g (200 mol) of tripotassium phosphate, 534 mg (1.3 mmol) of S-Phos [657408-07-6], 224 mg (1.0 mmol) of palladium(II) acetate, 300 ml of toluene, 100 ml of dioxane and 300 ml of water is heated under reflux for 16 h. After cooling, the aqueous phase is separated off, and the organic phase is evaporated to dryness. The brown foam is taken up in 300 ml of ethyl acetate and filtered through a silica-gel bed (diameter 15 cm, length 20 cm) which has been a pre-slurried with ethyl acetate, in order to remove brown components. After evaporation to 100 ml, 300 ml of methanol are added dropwise to the warm solution with very vigourous stirring, during which a beige solid crystallises out. The solid is filtered off with suction, washed twice with 100 ml of methanol each time and dried in vacuo. Yield: 20.5 g (24 mmol), 80%. Purity: about 95% according to $^1$H-NMR.

The following compounds can be prepared analogously.
| Ex. | Starting materials | Product | Yield |
|---|---|---|---|
| L701 | S300 | 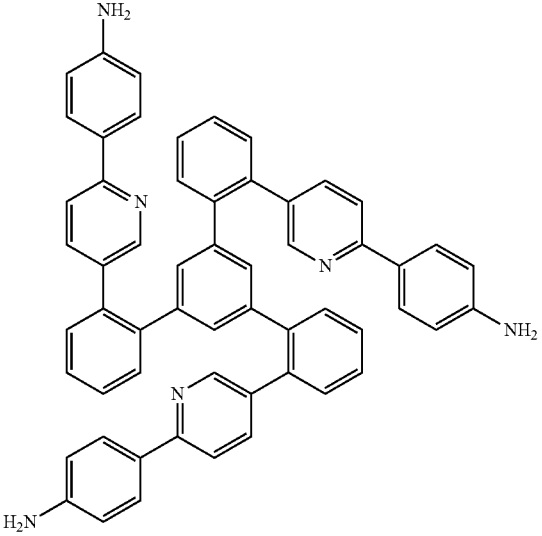 [SMILES: Nc1ccc(-c2ccc(-c3ccccc3-c3cc(-c4ccccc4-c4ccc(-c5ccc(N)cc5)nc4)cc(-c4ccccc4-c4ccc(-c5ccc(N)cc5)nc4)c3)cn2)cc1] | 54% |
| L702 | S301 | 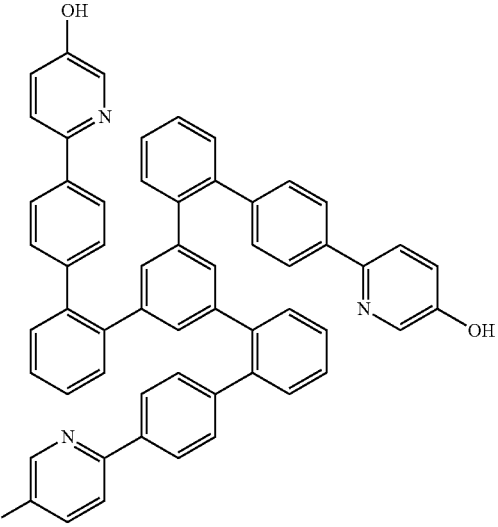 | 57% |

-continued

| Ex. | Starting materials | Product | Yield |
|---|---|---|---|
| L703 | S302 | 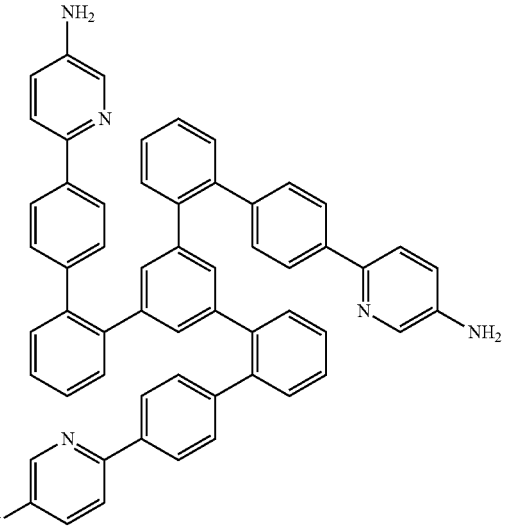 | 49% |

3. Preparation of the Metal Complexes:

Example Ir(L1)

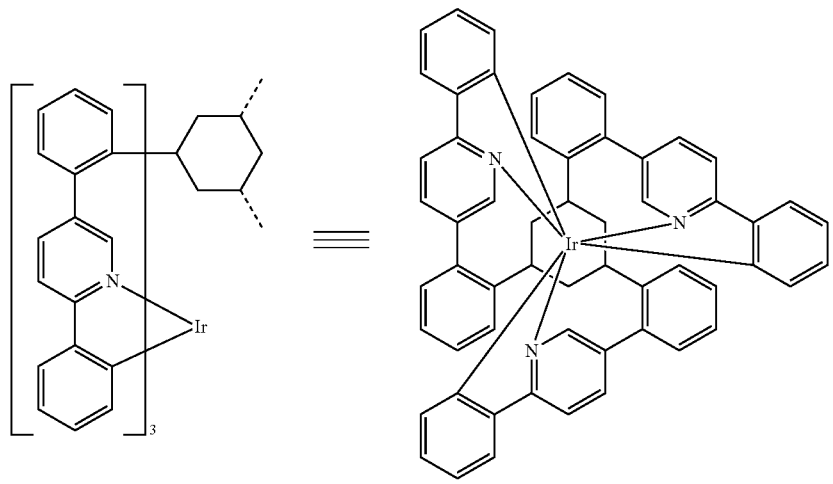

A mixture of 7.72 g (10 mmol) of ligand L1, 4.90 g (10 mmol) of tris(acetylacetonato)iridium(III) [15635-87-7] and 100 g of hydroquinone [123-31-9] is initially introduced in a 500 ml two-necked round-bottomed flask with a glass-clad magnetic stirrer bar. The flask is provided with a water separator (for media of lower density than water) and an air condenser with argon blanketing. The flask is placed in a metal heating dish. The apparatus is flushed with argon from above via the argon blanketing for 15 min., during which the argon is allowed to stream out of the side neck of the two-necked flask. A glass-clad Pt-100 thermocouple is introduced into the flask via the side neck of the two-necked flask and the end is positioned just above the magnetic stirrer bar. The apparatus is then thermally insulated by means of several loose coils of household aluminium foil, where the insulation is run as far as the centre of the riser tube of the water separator. The apparatus is then quickly heated to 250-260° C., measured at the Pt-100 temperature sensor, which dips into the molten, stirred reaction mixture, using a laboratory hotplate stirrer. During the next 1.5 h, the reaction mixture is held at 250-260° C., during which little condensate is distilled off and collects in the water separator. The reaction mixture is allowed to cool to 190° C., 50 ml of ethylene glycol are added dropwise, the mixture is allowed to cool to 70° C., and 250 ml of methanol are then added dropwise. After cooling, the beige suspension obtained in this way is filtered through a reverse frit, the beige solid is washed three times with 50 ml of methanol and then dried in vacuo. Crude yield: quantitative. The solid obtained in this way is dissolved in 1000 ml of dichloromethane and filtered through about 800 g of silica gel which has been pre-slurried with dichloromethane (column diameter about 18 cm) with exclusion of air and light, where dark components remain at the start. The core fraction is cut out and substantially evaporated in a rotary evaporator, with MeOH simultaneously being continuously added dropwise to crystallisation. The yellow product is filtered off with suction, washed with a little MeOH and dried in vacuo, then purified further by continuous hot extraction with DCM five times (initially introduced amount in each case about 150 ml, extraction thimble: standard cellulose Soxhlett thimbles from Whatman) with careful exclusion of air and light. Yield: 7.03 g (7.3 mmol), 73%. Purity: >99.9% according to HPLC.

The following compounds can be prepared analogously:

| Ex. | Ligand | Product<br>Reaction time*<br>Reaction temperature*<br>Extractant* | Yield |
|---|---|---|---|
| Rh(L1) | L1 | Rh(L1)<br>Use of Rh(acac)$_3$ [14284-92-5] | 36% |
| Ir(L2) | L2 | Ir(L2)<br>Acetonitrile | 57% |
| Ir(L3) | L3 | Ir(L3)<br>Ethyl acetate | 54% |
| Ir(L4) | L4 | Ir(L4)<br>Butyl acetate | 59% |
| Ir(L5) | L5 | Ir(L5)<br>Toluene | 60% |
| Ir(L6) | L6 | Ir(L6)<br>Toluene | 61% |

-continued

| Ex. | Ligand | Product<br>Reaction time*<br>Reaction temperature*<br>Extractant* | Yield |
|---|---|---|---|
| Ir(L7) | L7 | Ir(L7)<br>Toluene | 57% |
| Ir(L8) | L8 | Ir(L8)<br>Toluene | 27% |
| Ir(L9) | L9 | Ir(L9)<br>Butyl acetate | 63% |
| Ir(L10) | L10 | Ir(L10)<br>o-Xylene | 65% |
| Ir(L11) | L11 | Ir(L11)<br>265° C./2 h | 53% |
| Ir(L12) | L12 | Ir(L12)<br>265° C./2 h | 57% |
| Ir(L13) | L13 | Ir(L13)<br>Toluene | 51% |
| Ir(L14) | L14 | Ir(L14)<br>Toluene | 39% |

-continued
| Ex. | Ligand | Product<br>Reaction time*<br>Reaction temperature*<br>Extractant* | Yield |
|---|---|---|---|
| Ir(L15) | L15 | 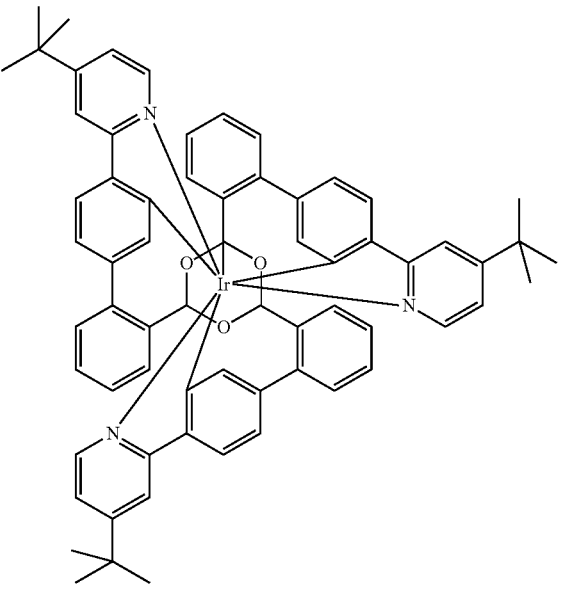<br>Ir(L15) | 24% |
| Ir(L100) | L100 | 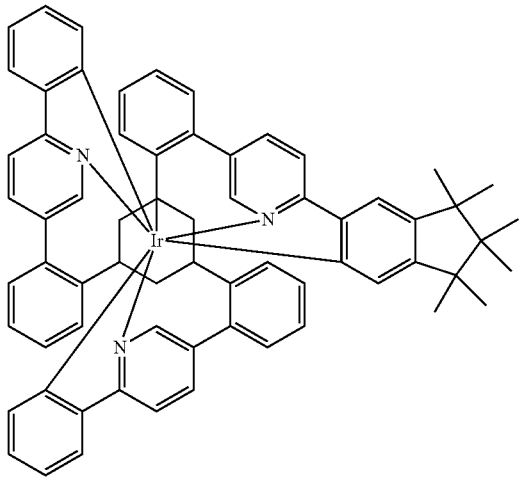<br>Ir(L100) | 57% |
| Ir(L101) | L101 | Ir(L101)<br>DCM | 62% |
| Ir(L102) | L102 | Ir(L102)<br>DCM | 65% |

-continued

| Ex. | Ligand | Product<br>Reaction time*<br>Reaction temperature*<br>Extractant* | Yield |
|---|---|---|---|
| Ir(L103) | L103 | Ir(L103) | 61% |
| Ir(L104) | L104 | Ir(L104) | 58% |
| Ir(L105) | L105 | Ir(L105) | 61% |
| Ir(L106) | L106 | Ir(L106) | 65% |
| Ir(L107) | L107 | Ir(L107) | 65% |
| Ir(L108) | L108 | Ir(L108)<br>o-Xylene | 57% |
| Ir(L109) | L109 | Ir(L109) | 70% |
| Ir(L110) | L110 | Ir(L110) | 63% |
| Ir(L111) | L111 | Ir(L111) | 60% |
| Ir(L112) | L112 | Ir(L112) | 62% |
| Ir(L113) | L113 | Ir(L113) | 66% |
| Ir(L114) | L114 | Ir(L114) | 58% |
| Ir(L115) | L115 | Ir(L115)<br>o-Xylene | 55% |
| Ir(L116) | L116 | Ir(L116) | 60% |
| Ir(L117) | L117 | Ir(L117) | 69% |
| Ir(L118) | L118 | Ir(L118)<br>o-Xylene | 55% |
| Ir(L119) | L119 | Ir(L119) | |
| Ir(L120) | L120 | Ir(L120) | 61% |
| Ir(L121) | L121 | Ir(L121)<br>DCM | 54% |
| Ir(L122) | L122 | Ir(L122)<br>DCM | 56% |
| Ir(L123) | L123 | Ir(L123) | 70% |
| Ir(L124) | L124 | Ir(L124) | 67% |

-continued

| Ex. | Ligand | Product<br>Reaction time*<br>Reaction temperature*<br>Extractant* | Yield |
|---|---|---|---|
| Ir(L200) | L200 | Ir(L200)<br>DCM | 23% |
| Ir(L201) | L201 | Ir(L201) | 34% |
| Ir(L202) | L202 | Ir(L202) | 37% |
| Ir(L203) | L203 | Ir(L203) | 35% |
| Ir(L204) | L204 | Ir(L204) | 28% |
| Ir(L205) | L205 | Ir(L205) | 40% |

-continued

| Ex. | Ligand | Product<br>Reaction time*<br>Reaction temperature*<br>Extractant* | Yield |
|---|---|---|---|
| Ir(L206) | L206 | Ir(L206) | 29% |
| Ir(L207) | L207 | Ir(L207) | 33% |
| Ir(L208) | L208 | Ir(L208) | 36% |
| Ir(L209) | L209 | Ir(L209) | 29% |
| Ir(L210) | L210 | Ir(L210) | 32% |
| Ir(L211) | L211 | Ir(L211) | 39% |
| Ir(L300) | L300 | Ir(L300) | 27% |
| Ir(L301) | L301 | Ir(L301) | 35% |
| Ir(L302) | L302 | Ir(L302) | 14% |
| Ir(L303) | L303 | Ir(L303) | 28% |
| Ir(L304) | L304 | Ir(L304) | 38% |
| Ir(L305) | L305 | Ir(L305) | 35% |

-continued

| Ex. | Ligand | Product Reaction time* Reaction temperature* Extractant* | Yield |
|---|---|---|---|
| Ir(L306) | L306 | Ir(L306) | 38% |
| Ir(L307) | L307 | Ir(L307) 265° C./2 h | 24% |
| Ir(L308) | L308 | Ir(L308) | 33% |
| Ir(L309) | L309 | Ir(L309) | 31% |
| Ir(L400) | L400 | Ir(L400) | 33% |
| Ir(L401) | IrL401 | Ir(L401) | 29% |

-continued

| Ex. | Ligand | Product<br>Reaction time*<br>Reaction temperature*<br>Extractant* | Yield |
|---|---|---|---|
| Ir(L404) | IrL404 | Ir(L404) 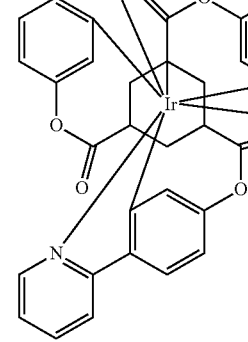 | 31% |
| Ir(L405) | IrL405 | Ir(L405) | 30% |
| Ir(L408) | IrL408 | Ir(L408) | 28% |
| Ir(L410) | IrL410 | Ir(L410) | 23% |
| Ir(L411) | IrL411 | Ir(L411)<br>Methyl benzoate 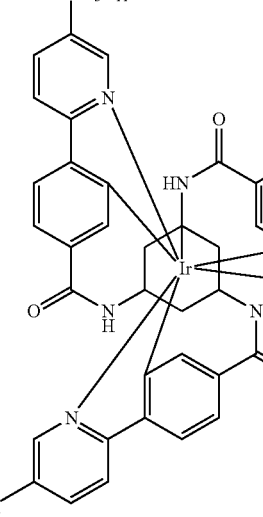 | 13% |
| Ir(L412) | IrL412 | Ir(L412) | 35% |
| Ir(L413) | IrL413 | Ir(L413) | 34% |
| Ir(L414) | IrL414 | Ir(L414) | 24% |
| Ir(L415) | IrL415 | Ir(L415) | 29% |
| Ir(L416) | IrL416 | Ir(L416) | 21% |
| Ir(L417) | IrL417 | Ir(L417) | 33% |
| Ir(L418) | IrL418 | Ir(L418) | 24% |
| Ir(L419) | IrL419 | Ir(L419) | 30% |
| Ir(L420) | IrL420 | Ir(L420) | 24% |
| Ir(L421) | IrL421 | Ir(L421) | 19% |
| Ir(L422) | IrL422 | Ir(L422) | 23% |
| Ir(L423) | IrL423 | Ir(L423)<br>2.5 h | 25% |
| Ir(L424) | IrL424 | Ir(L424) | 29% |
| Ir(L425) | IrL425 | Ir(L425) | 18% |
| Ir(L426) | IrL426 | Ir(L426) | 23% |

-continued

| Ex. | Ligand | Product<br>Reaction time*<br>Reaction temperature*<br>Extractant* | Yield |
|---|---|---|---|
| Ir(L427) | IrL427 | Ir(L427) | 31% |
| Ir(L428) | IrL428 | Ir(L428) | 36% |
| Ir(L429) | IrL429 | Ir(L429) | 22% |
| Ir(L430) | IrL430 | Ir(L430) | 21% |
| Ir(L431) | IrL431 | Ir(L431) | 31% |
| Ir(L432) | IrL432 | Ir(L432) | 33% |
| Ir(L433) | IrL433 | Ir(L433) | 23% |
| Ir(L434) | IrL434 | Ir(L434)<br>2.5 h | 24% |
| Ir(L435) | IrL435 | Ir(L435) | 30% |
| Ir(L436) | IrL436 | Ir(L436) | 21% |
| Ir(L437) | IrL437 | Ir(L437) | 19% |
| Ir(L459) | IrL459 | Ir(L459)<br>Addition of 33 mmol of NaO-t-Bu<br>250° C.<br>2 h<br>Toluene | 17% |
| Ir(L460) | IrL460 | Ir(L460) | 51% |
| Ir(L500) | L500 | 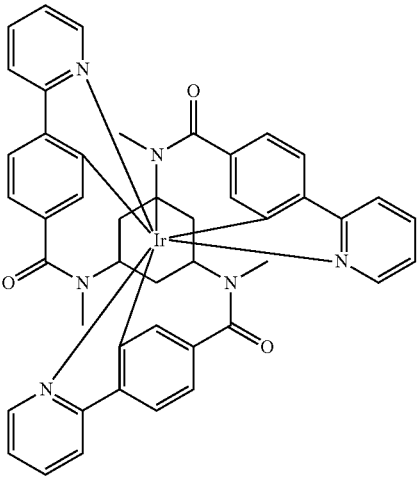<br>Ir(L500) | 54% |
| Ir(L501) | L501 | Ir(L501) | 49% |
| Ir(L502) | L502 | Ir(L502) | 55% |
| Ir(L503) | L503 | Ir(L503) | 50% |
| Ir(L504) | L504 | Ir(L504) | 36% |
| Ir(L505) | L505 | Ir(L505) | 48% |
| Ir(L506) | L506 | Ir(L506) | 50% |
| Ir(L507) | L507 | Ir(L507) | 52% |
| Ir(L508) | L508 | Ir(L508) | 33% |
| Ir(L509) | L59 | Ir(L509) | 46% |
| Ir(L510) | L510 | Ir(L510) | 30% |
| Ir(L511) | L511 | Ir(L511) | 53% |
| Ir(L512) | L512 | Ir(L512) | 26% |
| Ir(L513) | L513 | Ir(L513) | 32% |
| Ir(L514) | L514 | Ir(L514) | 50% |
| Ir(L515) | L515 | Ir(L515) | 51% |
| Ir(L516) | L516 | Ir(L516) | 56% |
| Ir(L517) | L517 | Ir(L517) | 38% |
| Ir(L518) | L518 | Ir(L518) | 50% |
| Ir(L519) | L519 | Ir(L519) | 54% |
| Ir(L520) | L520 | Ir(L520) | 19% |
| Ir(L521) | L521 | Ir(L521) | 49% |
| Ir(L522) | L522 | Ir(L522) | 17% |

-continued

| Ex. | Ligand | Product<br>Reaction time*<br>Reaction temperature*<br>Extractant* | Yield |
|---|---|---|---|
| Ir(L600) | L600 | Ir(L600) | 54% |
| Ir(L601) | L601 | Ir(L601) | 23% |
| Ir(L602) | L602 | Ir(L602) | 19% |
| Ir(L603) | L603 | Ir(L603) | 56% |
| Ir(L700) | L(700) | Ir(L700)<br>250° C.<br>1.5 h<br>1 × hot extraction of the crude product with DCM | 85% |
| Ir(L701) | L(701) | Ir(L701)<br>as for Ir(L700) | 56% |
| Ir(L702) | L(702) | Ir(L702)<br>as for Ir(L700) | 49% |
| Ir(L703) | L(703) | Ir(L703)<br>as for Ir(L700) | 46% |

*Stated if different from general procedure

Metal Complexes of Ligand L16:

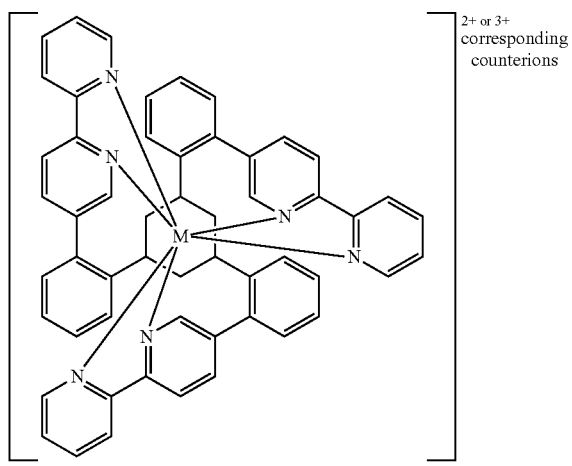

Metal Complexes of Ligand L17:

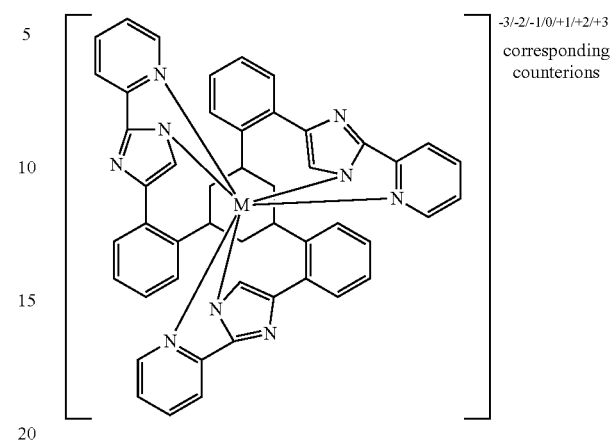

A solution, held at a temperature of 75° C., of 1 mmol of the corresponding metal salt in 15 ml of EtOH or EtOH/water (1:1 vv) is added dropwise to a solution of 769 mg (1 mmol) of L16 in 10 ml of DMSO at 75° C., and the mixture is stirred for a further 10 h. An anion exchange is optionally carried out with addition of 6 mmol of the corresponding salt ($KPF_6$, $(NH_4)PF_6$, $KBF_4$, etc.) in 10 ml of EtOH or EtOH/water (1:1, vv). After cooling, the microcrystalline precipitate is filtered off with suction, washed with cold MeOH and dried in vacuo. The purification can be carried out by recrystallisation from acetonitrile/methanol.

The following compounds can be prepared analogously:

| Ex. | Ligand Metal salt | Product | Yield |
|---|---|---|---|
| M1 | L16<br>$Fe(ClO_4)_2$ | $[Fe(L16)](ClO_4)_2$ | 56% |
| M2 | L16<br>$Fe(ClO_4)_3$ | $[Fe(L16)](ClO_4)_3$ | 64% |
| M3 | L16<br>$Ru(ClO_4)_3$ | $[Ru(L16)](ClO_4)_3$ | 71% |
| M4 | L16<br>$Os(ClO_4)_2$ | $[Os(L16)](ClO_4)_2$ | 52% |
| M5 | L16<br>$Co(ClO_4)_3$ | $[Co(L16)](ClO_4)_3$ | 43% |
| M6 | L16<br>$RhCl_3 \times H_2O$<br>$KPF_6$ | $[Rh(L16)](PF_6)_3$ | 50% |
| M7 | L16<br>$IrCl_3 \times H_2O$<br>$KPF_6$ | $[Ir(L16)](PF_6)_3$ | 55% |
| M8 | L16<br>$ZnCl_2$<br>$KPF_6$ | $[Zn(L16)](PF_6)_2$ | 68% |

A solution, held at a temperature of 75° C., of 1 mmol of the corresponding metal salt in 15 ml of EtOH or EtOH/water (1:1 vv) is added dropwise to a solution of 736 mg (1 mmol) of L17 and 643 mg (6 mmol) of 2,6-dimethylpyridine in 10 ml of DMSO at 75° C., and the mixture is stirred for a further 10 h. An anion exchange is optionally carried out with addition of 6 mmol of the corresponding salt ($KPF_6$, $(NH_4)PF_6$, $KBF_4$, etc.) in 10 ml of EtOH or EtOH/water (1:1, vv). After cooling, the microcrystalline precipitate is filtered off with suction, washed with cold MeOH and dried in vacuo. The purification can be carried out by recrystallisation from acetonitrile/methanol.

The following compounds can be prepared analogously:

| Ex. | Ligand Metal salt | Product | Yield |
|---|---|---|---|
| M100 | L17<br>$FeBr_3$ hydrate | Fe(L17) | 70% |
| M101 | L17<br>$[Ru(NH_3)_6]Cl_2$<br>No 2,6-dimethylpyridine | $NH_4[Ru(L17)]$ | 54% |
| M102 | L17<br>$RuCl_3$ hydrate | Ru(L17) | 66% |
| M103 | L17<br>$OsCl_3$ hydrate | Os(L17) | 58% |
| M104 | L17<br>$RhCl_3$ hydrate | Rh(L17) | 41% |
| M105 | L17<br>$IrCl_3$ hydrate | Ir(L17) | 67% |
| M106 | L17<br>$(NH_4)_2[PtCl_6]$<br>added as solid<br>$NH_4PF_6$ | $[Pt(L17)](PF_6)$ | 71% |

Metal Complexes of Ligand L18:

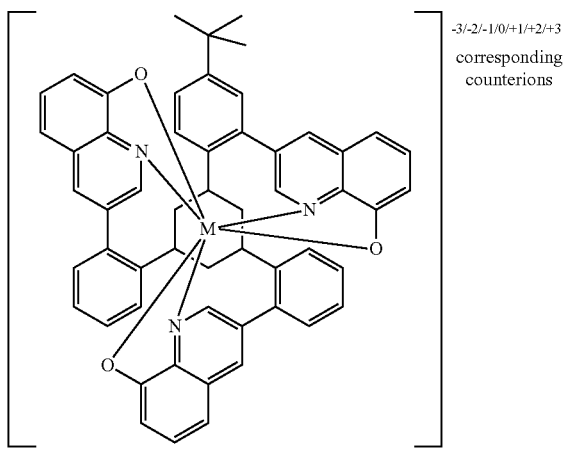

A solution, held at a temperature of 75° C., of 1 mmol of the corresponding metal salt in 20 ml of EtOH or EtOH/water (1:1 vv) is added dropwise to a solution of 736 mg (1 mmol) of L18 and 643 mg (6 mmol) of 2,6-dimethylpyridine in 10 ml of DMSO at 75° C., and the mixture is stirred for a further 10 h. An anion exchange is optionally carried out with addition of 6 mmol of the corresponding salt (KPF$_6$, (NH$_4$)PF$_6$, KBF$_4$, etc.) in 10 ml of EtOH or EtOH/water (1:1, vv). After cooling, the microcrystalline precipitate is filtered off with suction, washed with cold MeOH and dried in vacuo. The purification can be carried out by recrystallisation from acetonitrile/methanol.

The following compounds can be prepared analogously:

| Ex. | Ligand Metal salt | Product | Yield |
|---|---|---|---|
| M200 | L18 AlCl$_3$ | Al(L18) | 74% |
| M201 | L18 GaCl$_3$ | Ga(L18) | 77% |
| M202 | L18 InCl$_3$ | In(L18) | 80% |
| M203 | L18 LaCl$_3$ | La(L18) | 46% |
| M204 | L18 CeCl$_3$ | Ce(L18) | 40% |
| M205 | L18 FeCl$_3$ | Fe(L18) | 88% |
| M206 | L18 RuCl$_3$ | Ru(L18) | 90% |

Metal Complexes of Ligand L19:

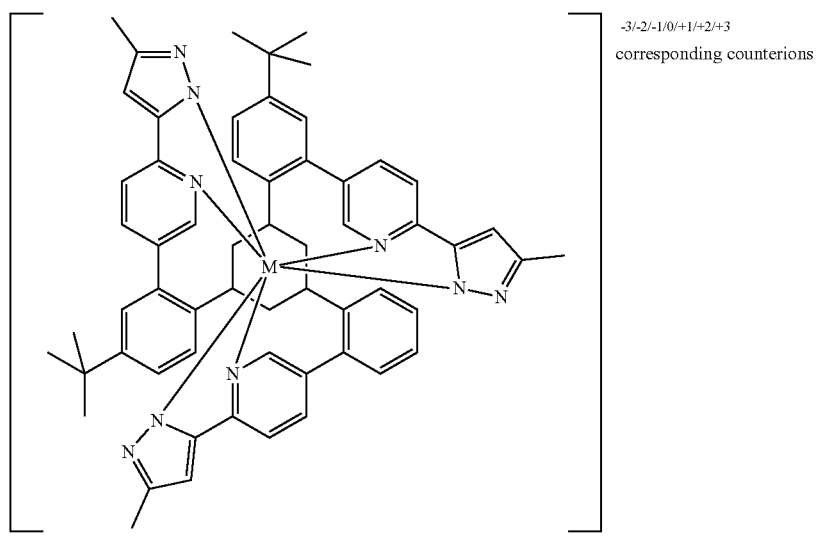

A solution, held at a temperature of 75° C., of 1 mmol of the corresponding metal salt in 20 ml of EtOH or EtOH/water (1:1 vv) is added dropwise to a solution of 778 mg (1 mmol) of L19 and 643 mg (6 mmol) of 2,6-dimethylpyridine in 10 ml of DMSO at 80° C., and the mixture is stirred for a further 12 h. An anion exchange is optionally carried out with addition of 6 mmol of the corresponding salt (KPF$_6$, (NH$_4$)PF$_6$, KBF$_4$, etc.) in 10 ml of EtOH or EtOH/water (1:1, vv). After cooling, the microcrystalline precipitate is filtered off with suction, washed with cold MeOH and dried in vacuo. The purification can be carried out by recrystallisation from acetonitrile/methanol or by hot extraction and subsequent fractional sublimation.

The following compounds can be prepared analogously:

| Ex. | Ligand Metal salt | Product | Yield |
|---|---|---|---|
| M300 | L19 GaCl$_3$ | Ga(L19) | 67% |

| Ex. | Ligand Metal salt | Product | Yield |
|---|---|---|---|
| M301 | L19 InCl$_3$ | In(L19) | 63% |
| M302 | L19 IrCl$_3$ hydrate | Ir(L19) | 66% |
| M303 | L19 LaCl$_3$ | La(L19) | 48% |
| M304 | L19 FeCl$_3$ | Fe(L19) | 83% |
| M305 | L19 IrCl$_3$ hydrate | Ir(L19) | 79% |
| M306 | L19 RuCl$_3$ | Ru(L19) | 80% |

Metal Complexes of Ligand L20:

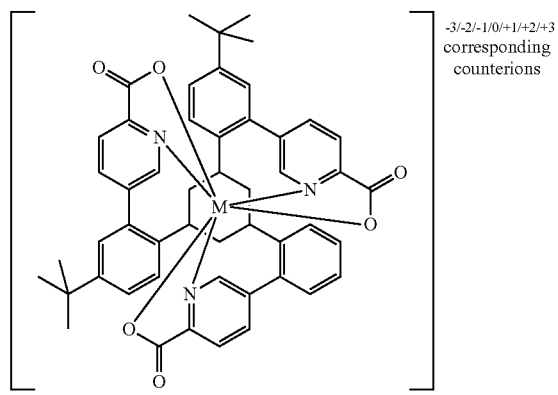

-3/-2/-1/0/+1/+2/+3 corresponding counterions

A solution, held at a temperature of 75° C., of 1 mmol of the corresponding metal salt in 15 ml of EtOH or EtOH/water (1:1 vv) is added dropwise to a solution of 736 mg (1 mmol) of L20 and 643 mg (6 mmol) of 2,6-dimethylpyridine in 10 ml of DMSO at 75° C., and the mixture is stirred for a further 12 h. An anion exchange is optionally carried out with addition of 6 mmol of the corresponding salt (KPF$_6$, (NH$_4$)PF$_6$, KBF$_4$, etc.) in 10 ml of EtOH or EtOH/water (1:1, vv). After cooling, the microcrystalline precipitate is filtered off with suction, washed with cold MeOH and dried in vacuo. The purification can be carried out by recrystallisation from acetonitrile/methanol.

The following compounds can be prepared analogously:

| Ex. | Ligand Metal salt | Product | Yield |
|---|---|---|---|
| M400 | L20 AlCl$_3$ | Al(L20) | 72% |
| M401 | L20 GaCl$_3$ | Ga(L20) | 68% |
| M402 | L20 LaCl$_3$ | La(L20) | 55% |
| M403 | L20 CeCl$_3$ | Ce(L20) | 51% |
| M404 | L20 FeCl$_3$ | Fe(L20) | 78% |
| M405 | L20 RuCl$_3$ | Ru(L20) | 83% |
| M406 | L20 IrCl$_3$ hydrate | Ir(L20) | 77% |

4: Functionalisation of the Metal Complexes 4.1 Halogenation of the Iridium Complexes:

A solution or suspension of 10 mmol of a complex which carries A×C—H groups (where A=1, 2, 3) in the para position to the iridium in 500 ml to 2000 ml of dichloromethane, depending on the solubility of the metal complexes, is mixed with A×10.5 mmol of N-halosuccinimide (halogen: Cl, Br, I) at −30 to +30° C. with exclusion of light and air, and the mixture is stirred for 20 h. Complexes which have low solubility in DCM can also be reacted in other solvents (TCE, THF, DMF, chlorobenzene, etc.) and at elevated temperature. The solvent is subsequently substantially removed in vacuo. 100 ml of methanol and 1 ml of hydrazine hydrate are added to the residue, the mixture is stirred briefly, the solid is filtered off with suction, washed three times with 30 ml of methanol and then dried in vacuo, giving the iridium complexes which are brominated in the para position to the iridium. Complexes having an HOMO (CV) of about −5.1 to −5.0 eV or lower tend towards oxidation (Ir(III)→Ir(IV)), where the oxidant is bromine, liberated from NBS. This oxidation reaction is evident from a clear green coloration of the otherwise yellow to red solutions/suspensions of the emitters. In such cases, a further equivalent of NBS is added. For work-up, 100-500 ml of methanol and 2 ml of hydrazine hydrate as reducing agent are added, causing the green solutions/suspension to change colour to yellow (reduction Ir(IV)>Ir(III)). The solvent is then substantially stripped off in vacuo, 300 ml of methanol are added, the solid is filtered off with suction, washed three times with 100 ml of methanol each time and dried in vacuo.

Sub-stoichiometric brominations, for example mono- and dibrominations, of complexes having 3 C—H groups in the para position to the iridium usually proceed less selectively than the stoichiometric brominations. The crude products of these brominations can be separated by chromatography (CombiFlash Torrent from A. Semrau).

Example Ir(L1-3Br)

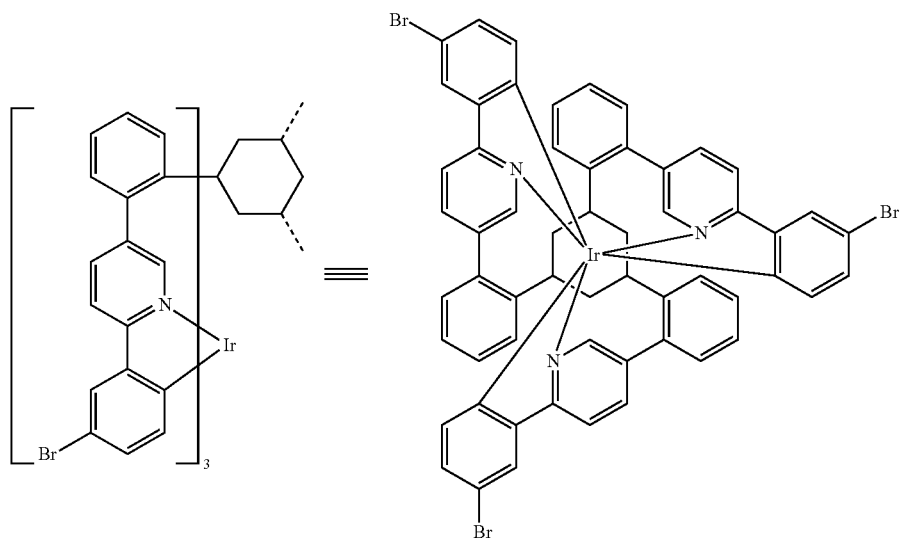

5.6 g (31.5 mmol) of N-bromosuccinimide are added in one portion to a suspension, stirred at 0° C., of 9.6 g (10 mmol) of Ir(L1) in 500 ml of dichloromethane (DCM), and the mixture is then stirred at room temperature for a further 6 h. After removal of about 400 ml of the DCM in vacuo, a mixture of 100 ml of methanol and 1 ml of hydrazine hydrate is added to the yellow suspension, the solid is filtered off with suction, washed three times with about 30 ml of methanol and then dried in vacuo. Yield: 11.2 g (9.5 mmol), 93%; purity: >99.0% according to NMR.

The following complexes can be prepared analogously:

| Ex. | Starting material > brominated complex Conditions | Yield |
|---|---|---|
| | Tribromination | |
| Ir(L3-3Br) | 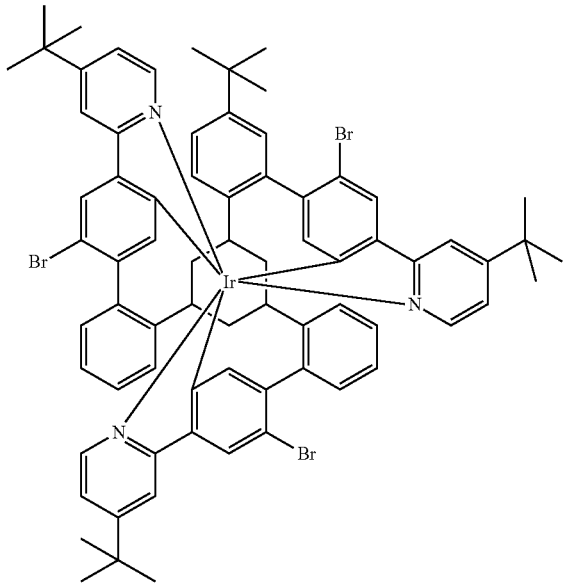<br>Ir(L3) > Ir(L3-3Br) | 93% |

| Ex. | Starting material > brominated complex Conditions | Yield |
|---|---|---|
| Ir(L5-3Br) | 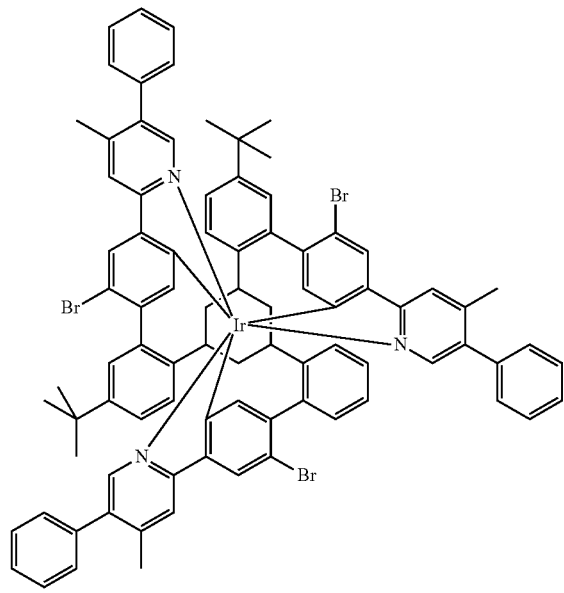<br>Ir(L5) > Ir(L5-3Br) | 95% |
| Ir(L7-3Br) | 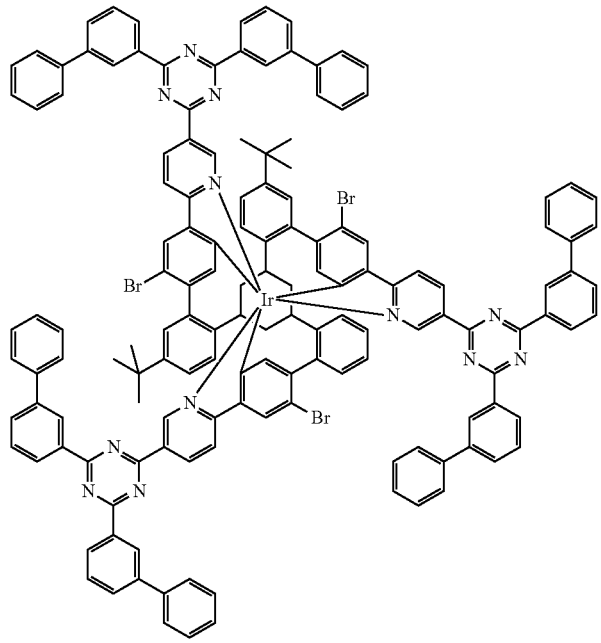<br>Ir(L7) > Ir(L7-3Br) | 87% |

| Ex. | Starting material > brominated complex Conditions | Yield |
|---|---|---|
| Ir(L9-3Br) | 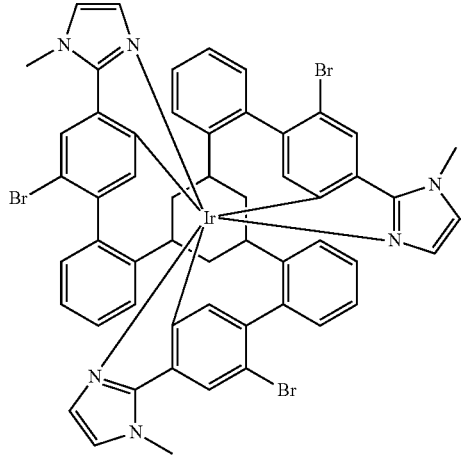<br>Ir(L9) > Ir(L9-3Br) | 84% |
| Ir(L101-3Br) | 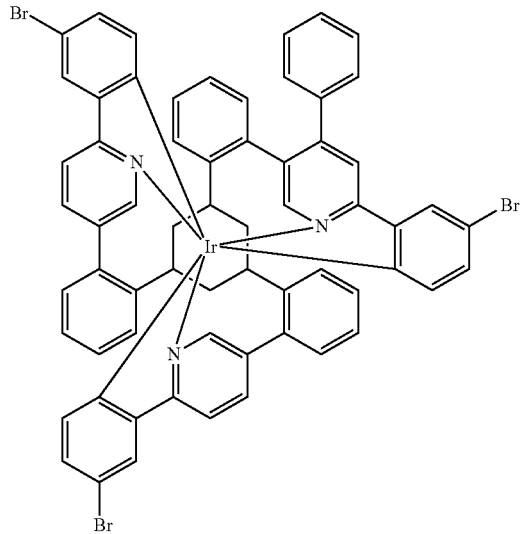<br>Ir(L101) > Ir(L101-3Br) | 93% |

| Ex. | Starting material > brominated complex Conditions | Yield |
|---|---|---|
| Ir(L102-3Br) | 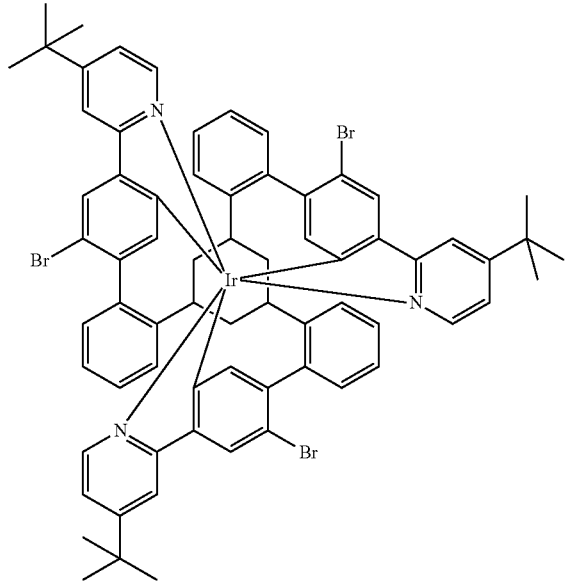<br>Ir(L102) > Ir(L102-3Br) | 95% |
| Ir(L103-3Br) | 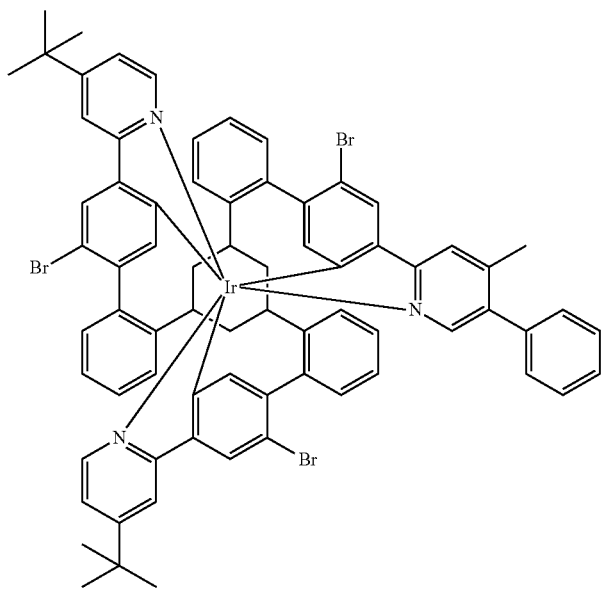<br>Ir(L103) > Ir(L103-3Br) | 90% |

-continued
| Ex. | Starting material > brominated complex Conditions | Yield |
|---|---|---|
| Ir(L108-3Br) | | 88% |
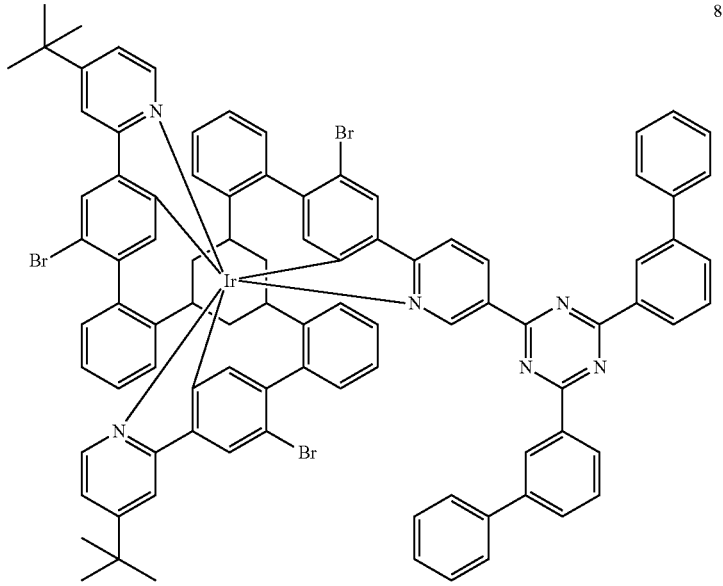
Ir(L108) > Ir(L108-3Br)
| Ir(L109-3Br) | | 89% |
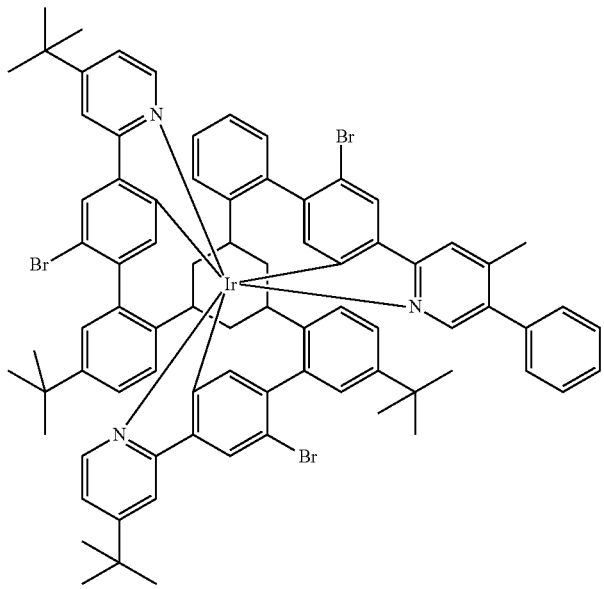
Ir(L109) > Ir(L109-3Br)

| Ex. | Starting material > brominated complex Conditions | Yield |
|---|---|---|
| Ir(L110-3Br) | 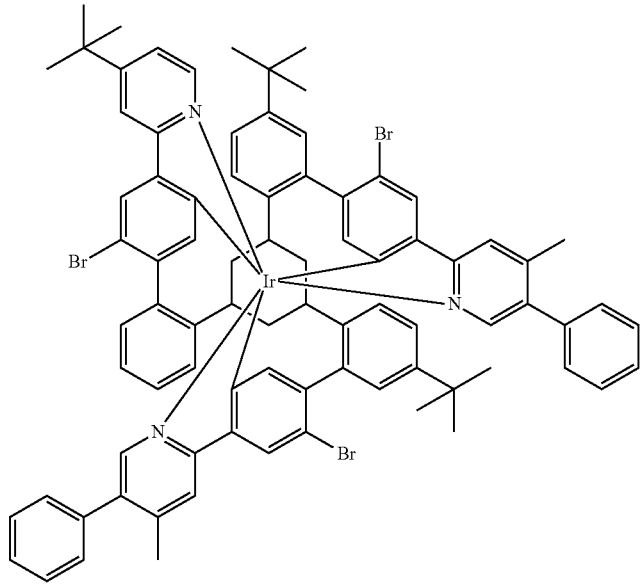  Ir(L110) > Ir(L110-3Br) | 90% |
| Ir(L111-3Br) | 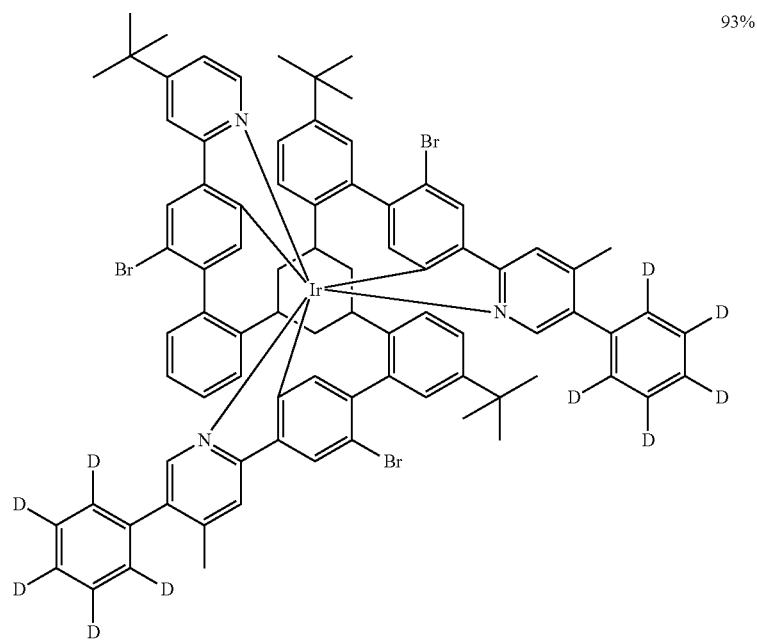  Ir(L111) > Ir(L111-3Br) | 93% |

| Ex. | Starting material > brominated complex Conditions | Yield |
|---|---|---|
| Ir(L112-3Br) | 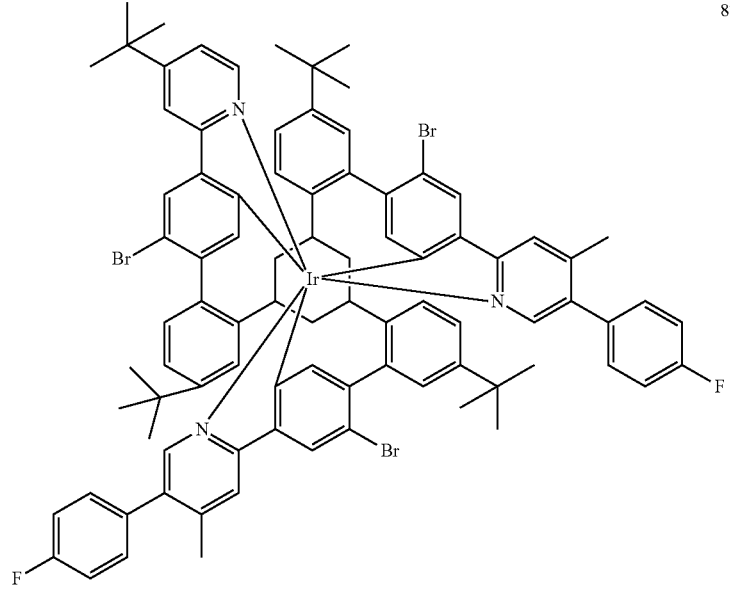  Ir(L112) > Ir(L112-3Br) | 87% |
| Ir(L115-3Br) | 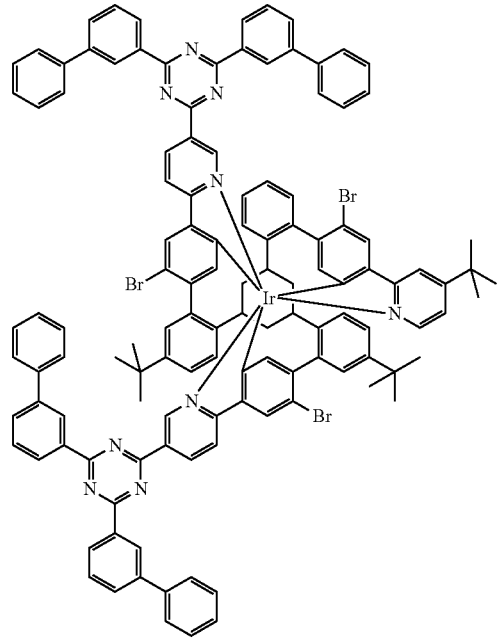  Ir(L115) > Ir(L115-3Br) | 84% |

| Ex. | Starting material > brominated complex Conditions | Yield |
|---|---|---|
| Ir(L117-3Br) | 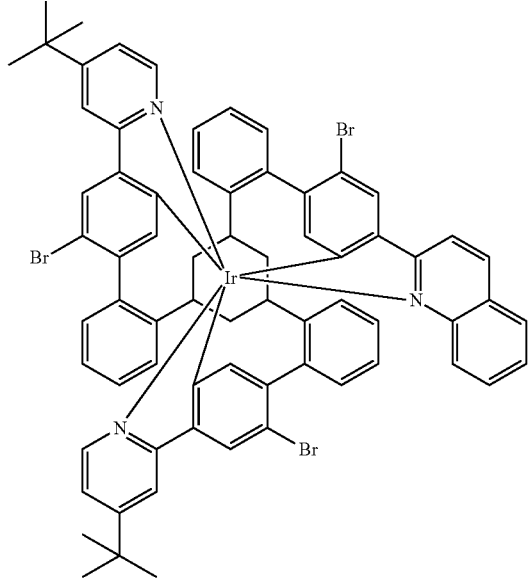 Ir(L117) > Ir(L117-3Br) | 91% |
| Ir(L120-3Br) | 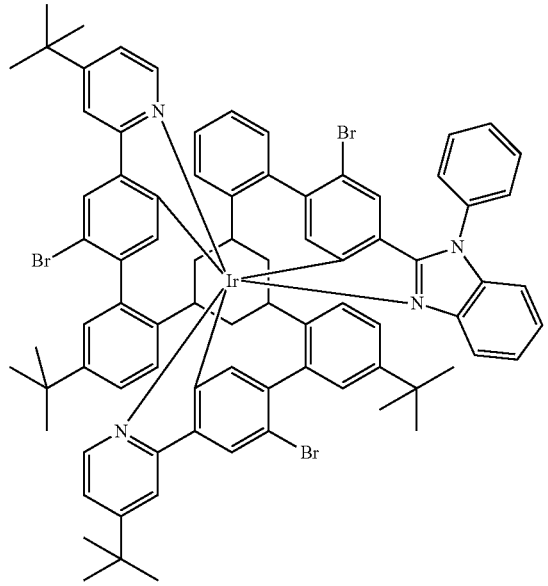 Ir(L120) > Ir(L120-3Br) | 85% |

| Ex. | Starting material > brominated complex Conditions | Yield |
|---|---|---|
| Ir(L123-3Br) | 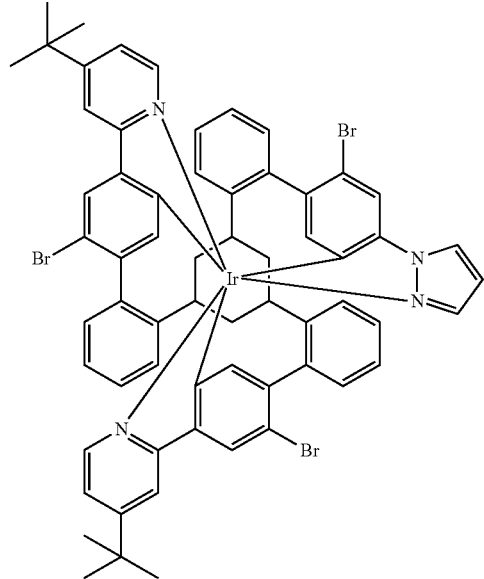Ir(L123) > Ir(L123-3Br) | 83% |
| Ir(L201-3Br) | 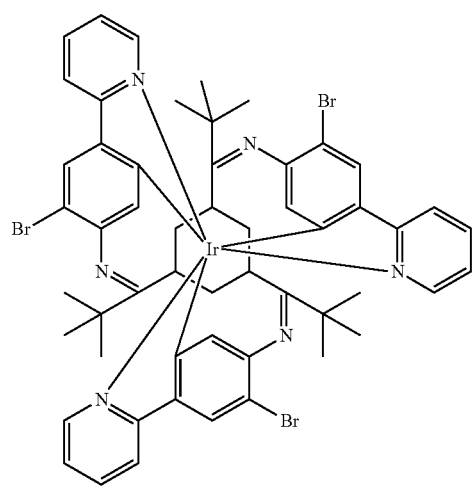Ir(L201) > Ir(L201-3Br) | 92% |

| Ex. | Starting material > brominated complex Conditions | Yield |
|---|---|---|
| Ir(L203-3Br) | 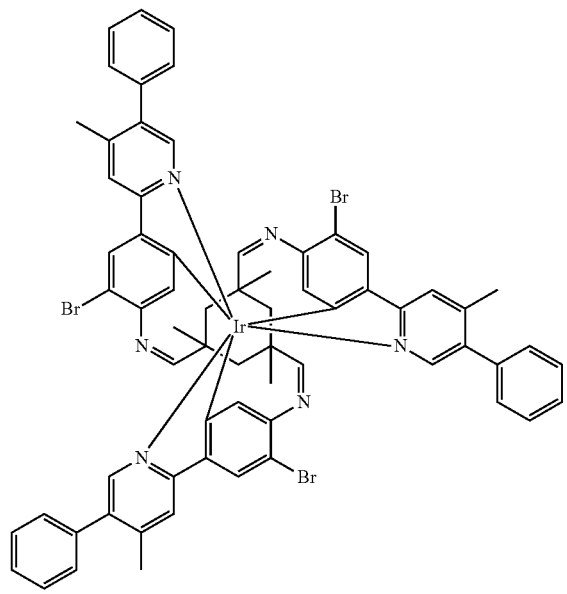<br>Ir(L203) > Ir(L203-3Br) | 90% |
| Ir(L208-3Br) | 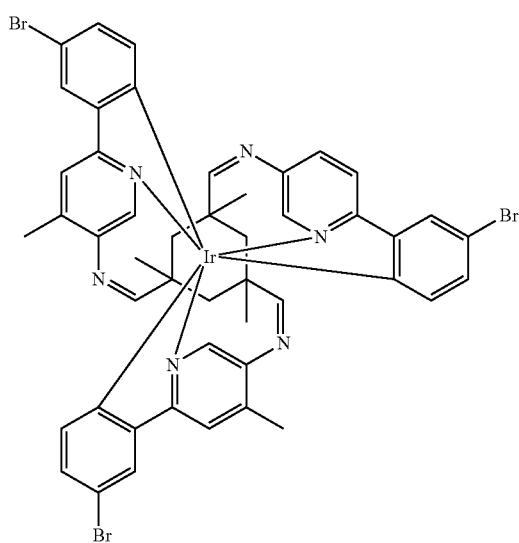<br>Ir(L208) > Ir(L208-3Br) | 88% |

-continued
| Ex. | Starting material > brominated complex Conditions | Yield |
|---|---|---|
| Ir(L301-3Br) | 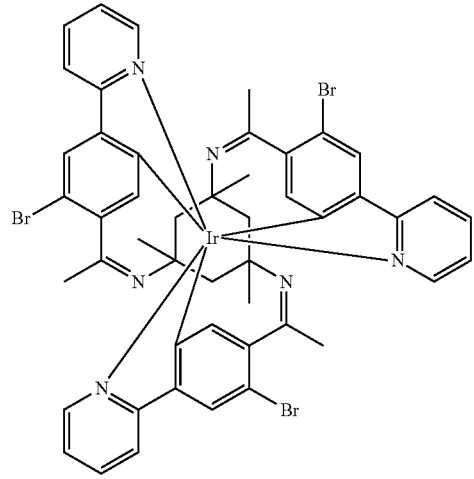<br>Ir(L301) > Ir(L301-3Br) | 85% |
| Ir(L306-3Br) | 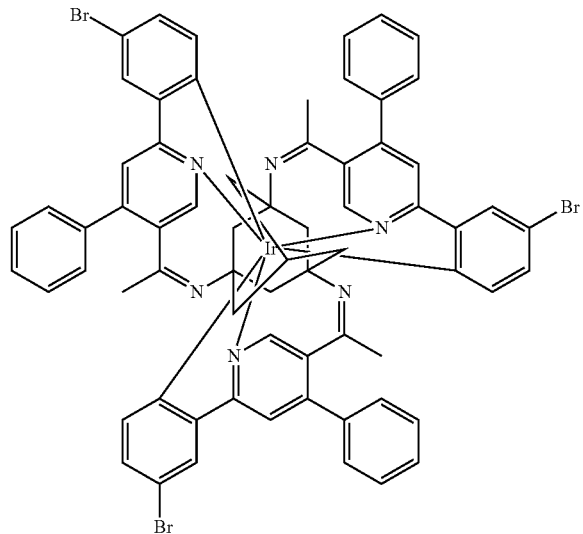<br>Ir(L306) > Ir(L306-3Br) | 86% |

-continued
| Ex. | Starting material > brominated complex Conditions | Yield |
|---|---|---|
| Ir(L400-3Br) | 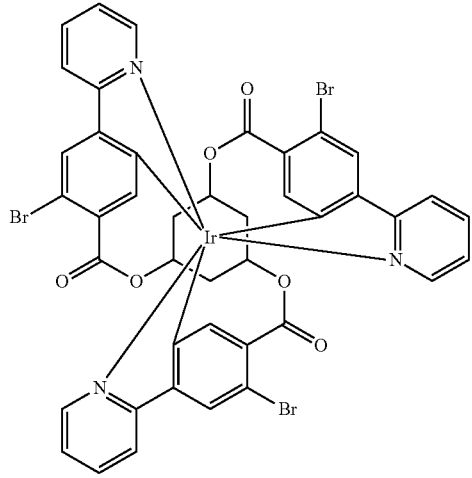 Ir(L400) > Ir(L400-3Br) | 76% |
| Ir(L404-3Br) | 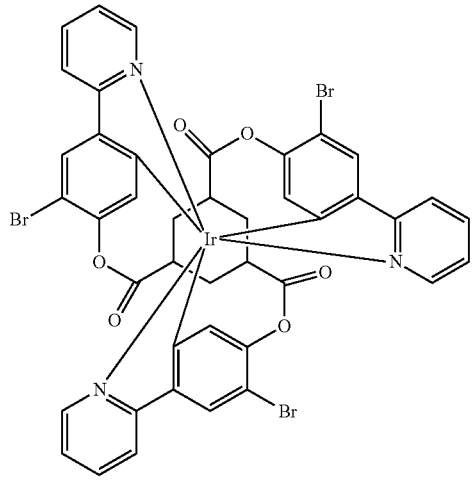 Ir(L404) > Ir(L404-3Br) | 90% |

| Ex. | Starting material > brominated complex Conditions | Yield |
|---|---|---|
| Ir(L405-3Br) | 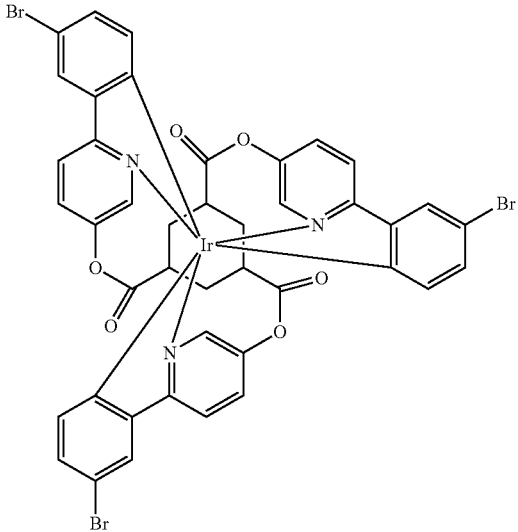<br>Ir(L405) > Ir(L405-3Br) | 90% |
| Ir(L500-3Br) | 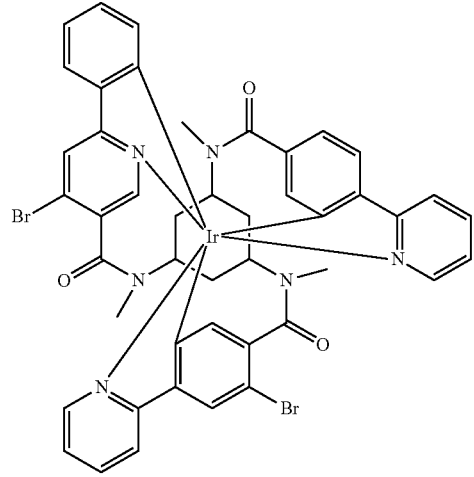<br>Ir(L500) > Ir(L500-3Br) | 86% |

| Ex. | Starting material > brominated complex Conditions | Yield |
|---|---|---|
| Ir(L503-3Br) | 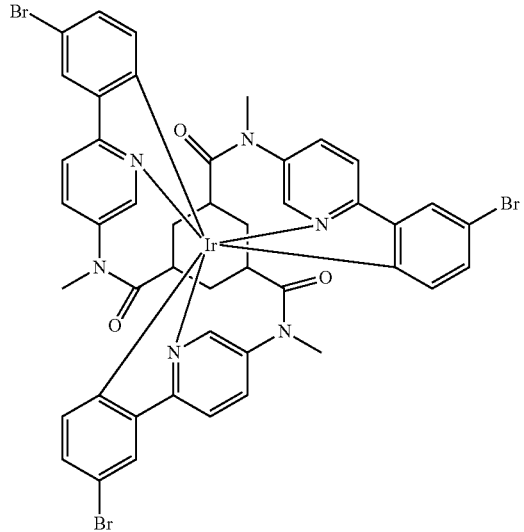<br>Ir(L503) > Ir(L503-3Br) | 93% |
| Dibromination | | |
| Ir(L100-2Br) | 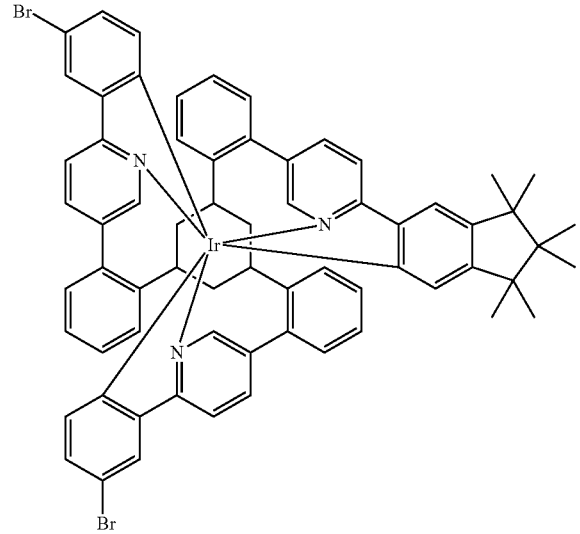<br>Ir(L100) > Ir(L100-2Br) | 95% |

-continued
| Ex. | Starting material > brominated complex Conditions | Yield |
|---|---|---|
| Ir(L102-2Br) | 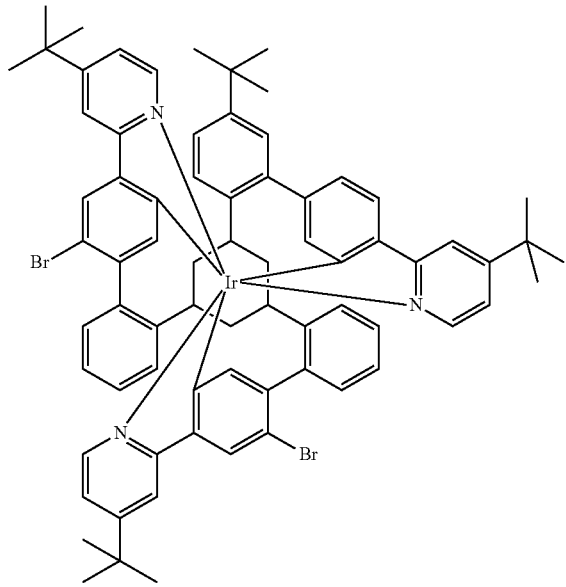\nChromatographic purification\nIr(L102) > Ir(L102-2Br) | 26% |
| Ir(L106-2Br) | 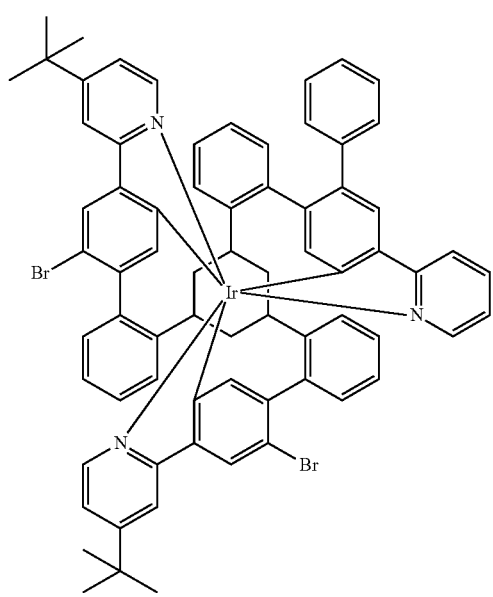\nIr(L106) > Ir(L106-2Br) | 94% |

| Ex. | Starting material > brominated complex Conditions | Yield |
|---|---|---|
| Ir(L107-2Br) | 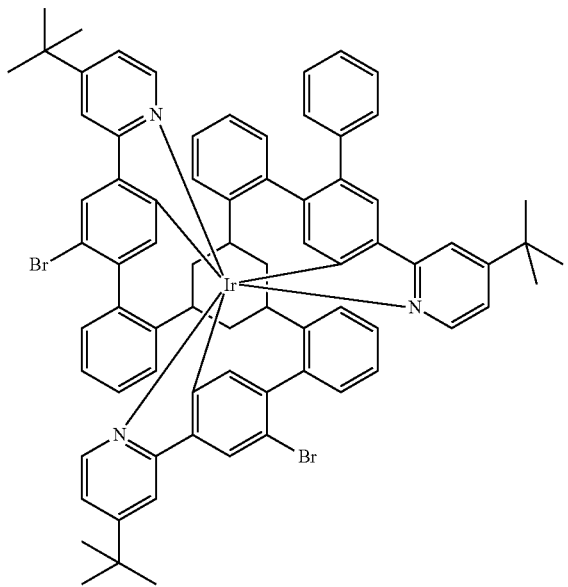 Ir(L107) > Ir(L107-2Br) | 96% |
| Ir(L116-2Br) | 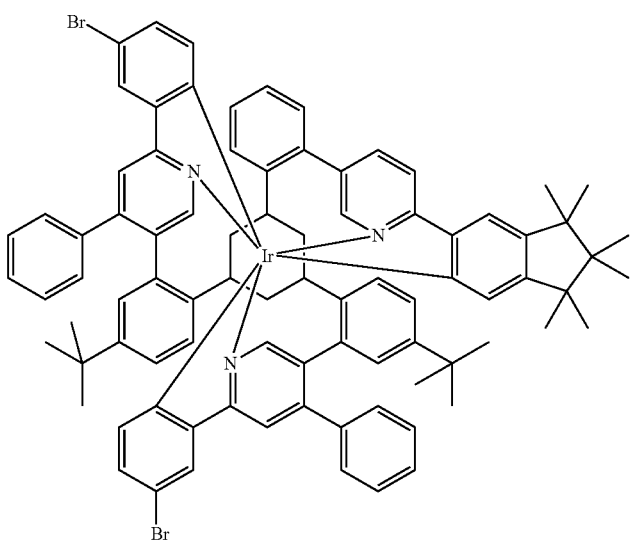 Ir(L116) > Ir(L116-2Br) | 96% |

-continued
| Ex. | Starting material > brominated complex Conditions | Yield |
|---|---|---|
| Ir(L121-2Br) | 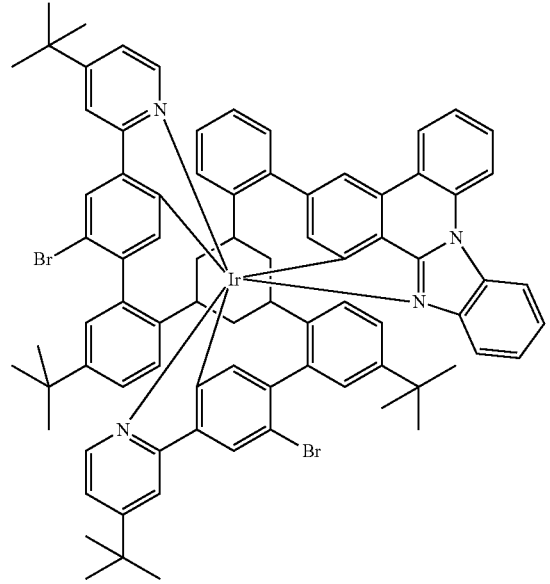<br>Ir(L121) > Ir(L121-2Br) | 89% |
| | Monobromination | |
| Ir(L102-1Br) | 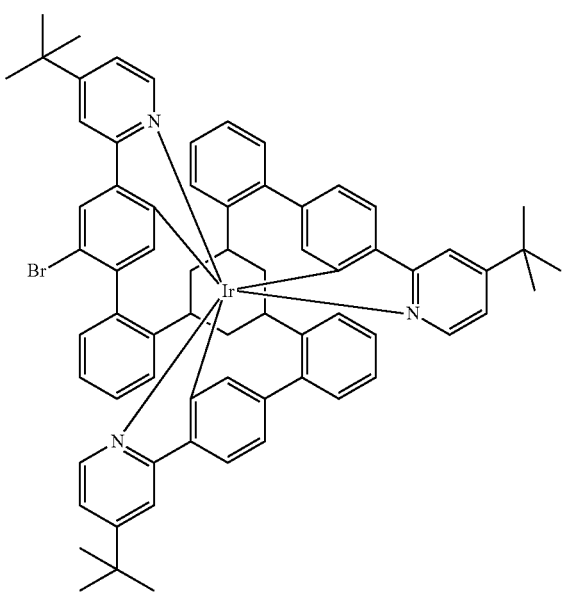<br>Ir(L102) > Ir(L102-1Br)<br>Chromatographic purification | 57% |

| Ex. | Starting material > brominated complex Conditions | Yield |
|---|---|---|
| Ir(L113-Br) | 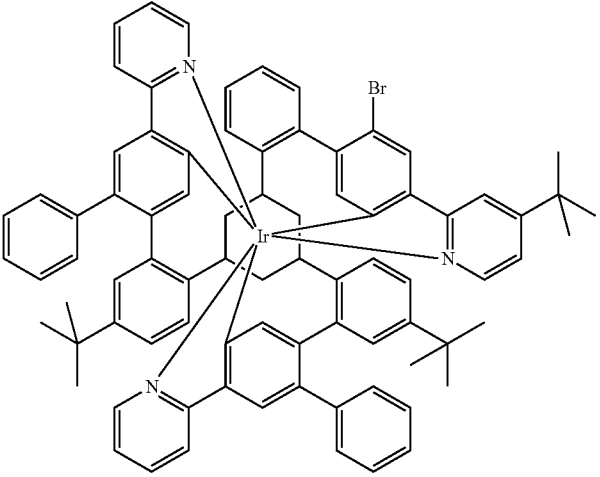  Ir(L113) > Ir(L113-1Br) | 92% |
| Ir(L114-Br) | 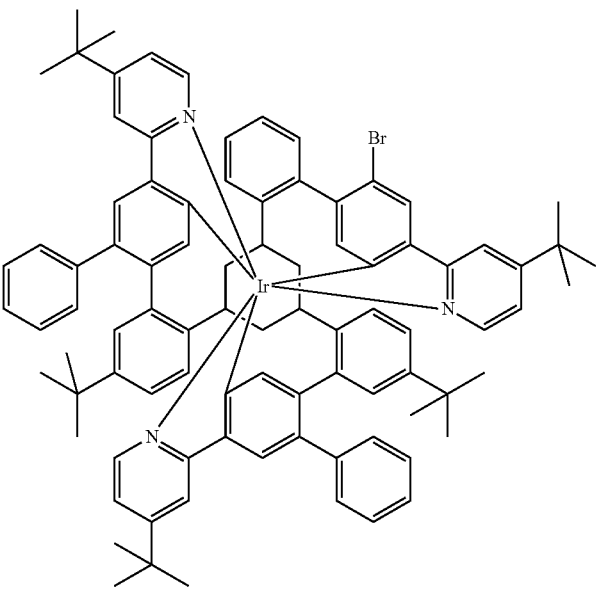  Ir(L114) > Ir(L114-1Br) | 94% |

4.2 Borylation of the Metal Complexes Containing a Bromine Function:

A mixture of 10 mmol of the brominated complex, 12 mmol of bis(pinacolato)diborane [73183-34-3] per bromine function, 30 mmol of potassium acetate, anhydrous, per bromine function, 0.2 mmol of tricyclohexylphosphine, 0.1 mmol of palladium(II) acetate (Variant A) or 0.2 mmol of dppfPdCl$_2$*CH$_2$Cl$_2$ [95464-05-4] (Variant B) and 300 ml of solvent (dioxane, DMSO, NMP, toluene, etc.) is stirred at 80-160° C. for 4-16 h. After removal of the solvent in vacuo, the residue is taken up in 300 ml of dichloromethane, THF or ethyl acetate, filtered through a Celite bed, the filtrate is evaporated in vacuo to incipient crystallisation, and finally about 100 ml of methanol are added dropwise in order to complete the crystallisation. The compounds can be recrystallised from dichloromethane, ethyl acetate or THF with addition of methanol or chromatographed on silica gel.

Synthesis of Ir(L1-3BE)-Variant B:

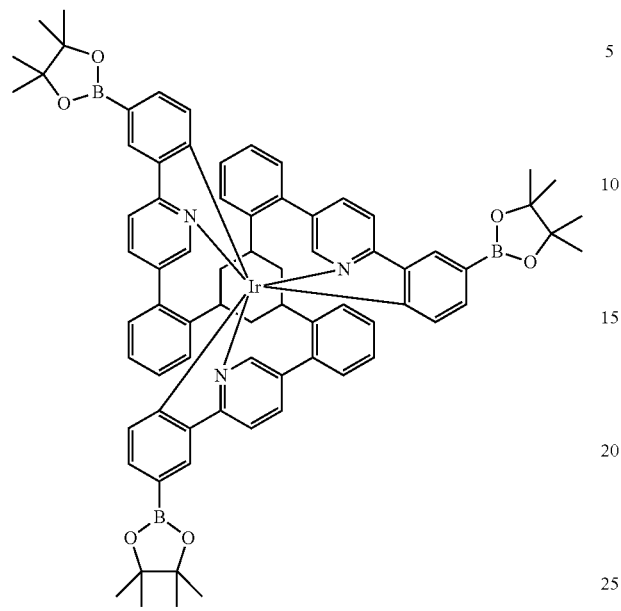

Use of 12.0 g (10 mmol) of Ir(L1-3Br) and 9.1 g (36 mmol) of bis(pinacolato)diborane [73183-34-3], dioxane/toluene 1:1 vv, 1200, 16 h, take up and Celite filtration in THF, recrystallisation from THF:methanol. Yield: 7.9 g (5.9 mmol), 59%; purity: about 99.8% according to HPLC.

The following compounds can be prepared analogously:

| Ex. | Product Starting material/Variant | Yield |
|---|---|---|
| | Triborylation | |
| Ir(L3-3BE) | 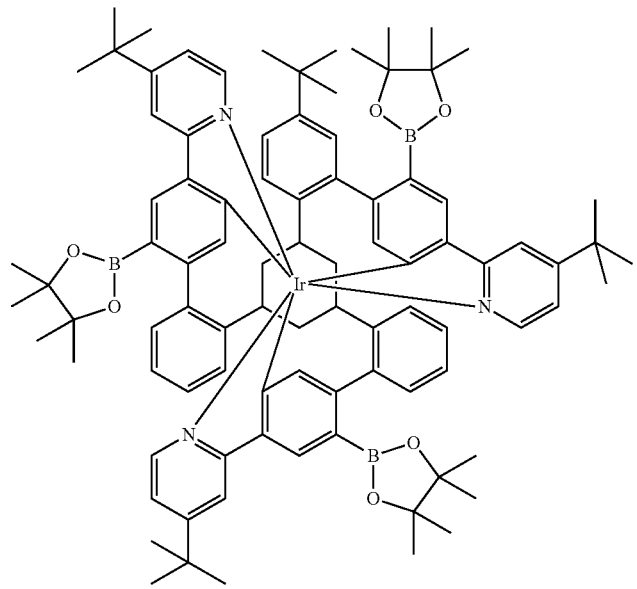 Ir(L3-3Br) > Ir(L3-3BE)/B | 55% |

-continued

| Ex. | Product Starting material/Variant | Yield |
|---|---|---|
| Ir(L5-3BE) | [structure: Ir(L3-3Br) > Ir(L3-3BE)/B] | 52% |

Diborylation

| | | |
|---|---|---|
| Ir(L107-2BE) | [structure: Ir(L107-2Br) > Ir(L107-2BE)/B] | 66% |

| Ex. | Product Starting material/Variant | Yield |
|---|---|---|
| | Monoborylation | |
| Ir(L114-BE) | 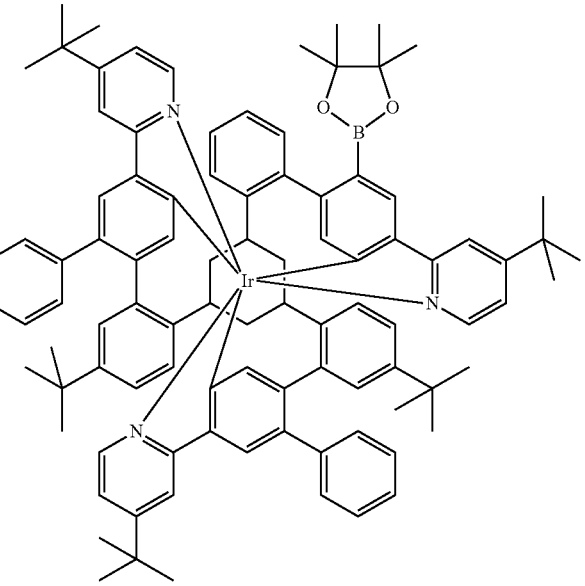<br>Ir(L114-1Br) > Ir(L114-1BE)/B | 81% |

4.3 Suzuki Coupling to the Halogenated Metal Complexes

Variant A, Two-Phase Reaction Mixture:

0.6 mmol of tri-o-tolylphosphine and then 0.1 mmol of palladium(II) acetate are added to a suspension of 10 mmol of a brominated complex, 12-20 mmol of boronic acid or boronic acid ester per Br function and 40-80 mmol of tripotassium phosphate in a mixture of 300 ml of toluene, 100 ml of dioxane and 300 ml of water, and the mixture is heated under reflux for 16 h. After cooling, 500 ml of water and 200 ml of toluene are added, the aqueous phase is separated off, the organic phase is washed three times with 200 ml of water and once with 200 ml of saturated sodium chloride solution and dried over magnesium sulfate. The mixture is filtered through a Celite bed, the latter is rinsed with toluene, the toluene is removed virtually completely in vacuo, 300 ml of methanol are added, the crude product which has precipitated out is filtered off with suction, washed three times with 50 ml of methanol each time and dried in vacuo. The crude product is passed through a silica-gel column. The further purification can be carried by chromatography, recrystallisation or hot extraction. Finally, the metal complex can optionally be heat treated or sublimed. The heat treatment is carried out in a high vacuum (p about $10^{-6}$ mbar) in the temperature range from about 200-300° C. The sublimation is carried out in the case of suitable sublimable complexes in a high vacuum (p about $10^{-6}$ mbar) in the temperature range from about 300-400° C., where the sublimation is preferably carried out in the form of a fractional sublimation.

Variant B, Single-Phase Reaction Mixture:

0.6 mmol of tri-o-tolylphosphine and then 0.1 mmol of palladium(II) acetate or 0.3 mmol of tetrakis(triphenylphosphine)palladium(0) are added to a suspension of 10 mmol of a brominated complex, 12-20 mmol of boronic acid or boronic acid ester per Br function and 60-100 mmol of the base (potassium fluoride, tripotassium phosphate (anhydrous or monohydrate or trihydrate), potassium carbonate, caesium carbonate, etc.) and 100 g of glass beads (diameter 3 mm) in 100 ml-500 ml of an aprotic solvent (THF, dioxane, xylene, mesitylene, dimethylacetamide, NMP, DMSO, etc.), and the mixture is stirred with warming (80-130° C.) for 1-24 h. Alternatively, other phosphines, such as triphenylphosphine, tri-tert-butylphosphine, S-Phos, X-Phos, RuPhos, XanthPhos, etc., can be employed, where, in the case of these phosphines, the preferred phosphine: palladium ratio is 3:1 to 1.2:1. The solvent is removed in vacuo, the product is taken up in a suitable solvent (toluene, dichloromethane, ethyl acetate, etc.) and purified as described under Variant A.

Synthesis of Ir100:

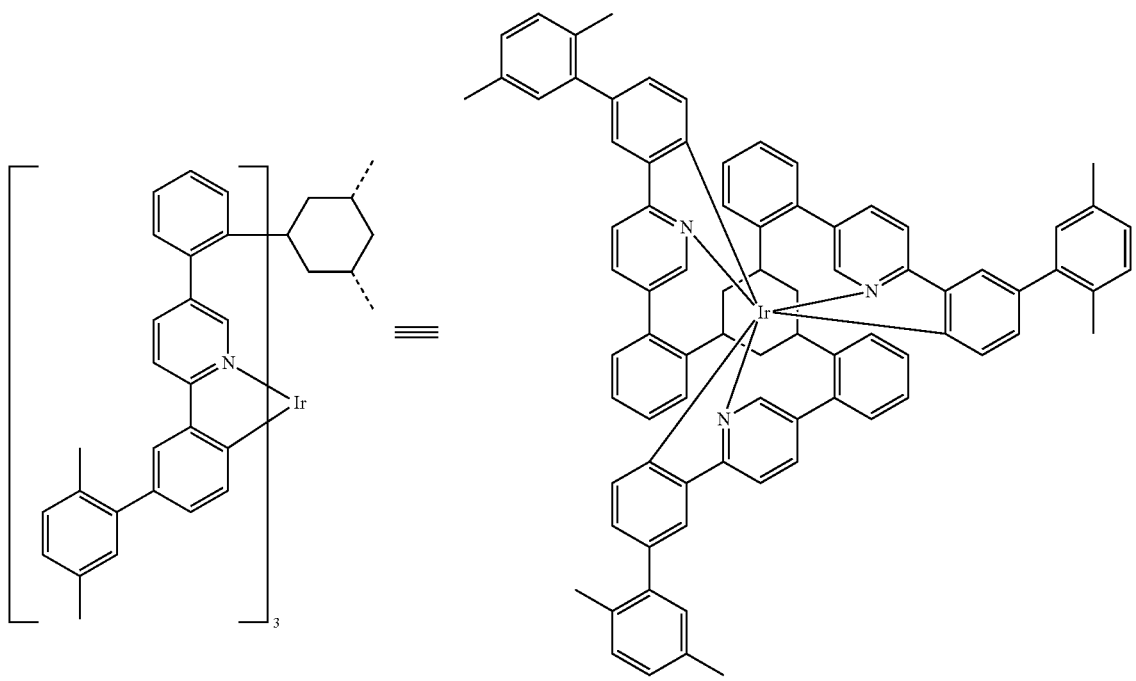

Variant A:

Use of 12.0 g (10.0 mmol) of Ir(L1-3Br) and 9.0 g (60.0 mmol) of 2,5-dimethylphenylboronic acid [85199-06-0], 17.7 g (60 mmol) of tripotassium phosphate (anhydrous), 183 mg (0.6 mmol) of tri-o-tolylphosphine [6163-58-2], 23 mg (0.1 mmol) of palladium(II) acetate, 300 ml of toluene, 100 ml of dioxane and 300 ml of water, reflux, 16 h. Chromatographic separation twice on silica gel with toluene/ ethyl acetate (9:1, vv), subsequently hot extraction twice with toluene with addition of 0.5 ml of hydrazine hydrate, then hot extraction five times with butyl acetate. Yield: 6.9 g (5.4 mmol), 54%; purity: about 99.9% according to HPLC.

Variant B:

Use of 12.0 g (10.0 mmol) of Ir(L1-3Br) and 9.0 g (60.0 mmol) of 2,5-dimethylphenylboronic acid pinacolyl ester [356570-53-1], 17.7 g (60 mmol) of tripotassium phosphate monohydrate, 347 mg (0.3 mmol) of tetrakis(triphenylphosphino)palladium(0), 300 ml of DMSO, 90° C., 24 h. Purification as described under Variant A. Yield: 7.3 g (5.7 mmol), 57%; purity: about 99.8% according to HPLC.

The following compounds can be prepared analogously:
| Ex. | Bromide/Boronic acid/Variant Product Hot extractant | Yield |
|---|---|---|
| Ir101 | Ir(L1-3Br)/5122-95-2/A 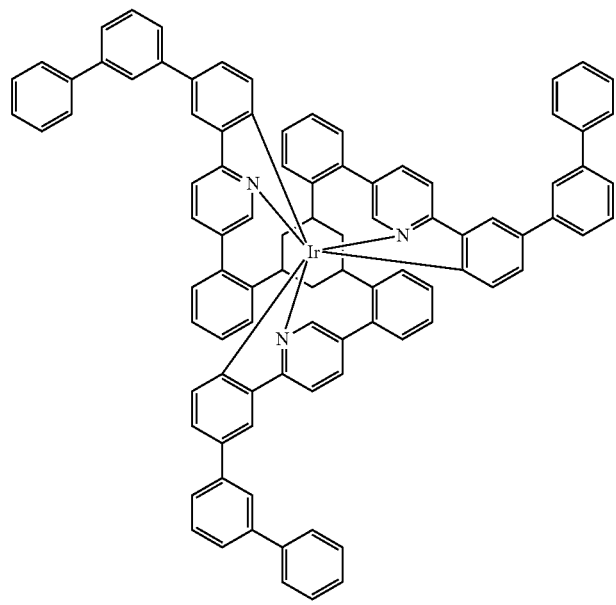 Butyl acetate, then toluene | 57% |
| Ir102 | Ir(L1-3Br)/1233200-59-3/A 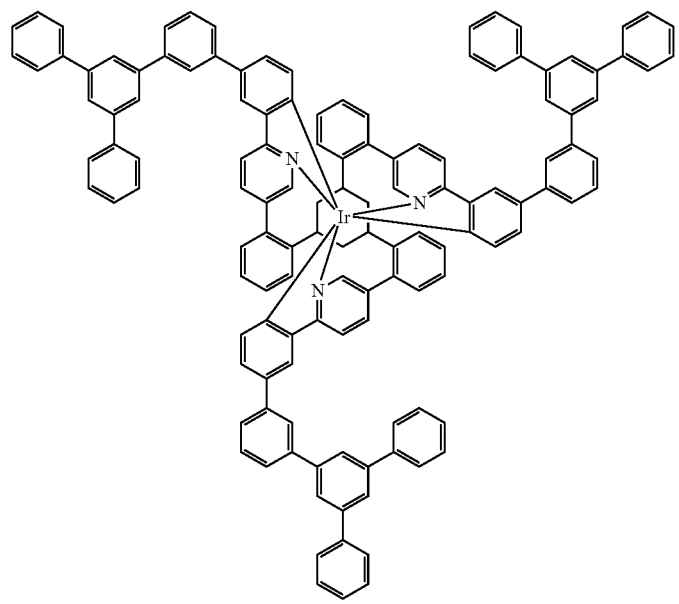 Butyl acetate | 59% |

| Ex. | Bromide/Boronic acid/Variant Product Hot extractant | Yield |
|---|---|---|
| Ir103 | Ir(L3-3Br)/98-80-6/B | 64% |
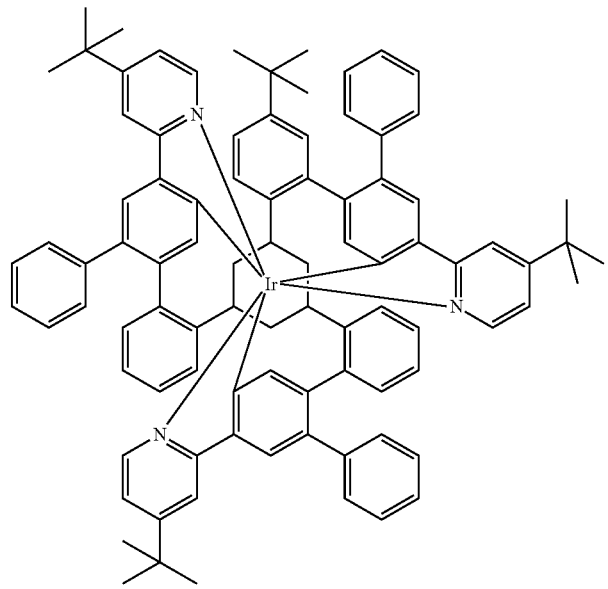
Toluene
| Ir104 | Ir(L3-3Br)/560132-24-3/B | 51% |
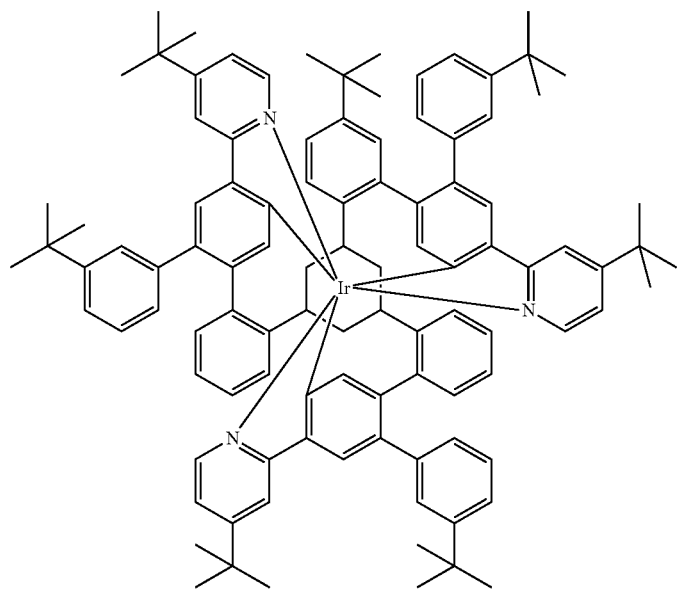
Ethyl acetate/acetonitrile

| Ex. | Bromide/Boronic acid/Variant Product Hot extractant | Yield |
|---|---|---|
| Ir105 | Ir(L3-3Br)/197223-39-5/B 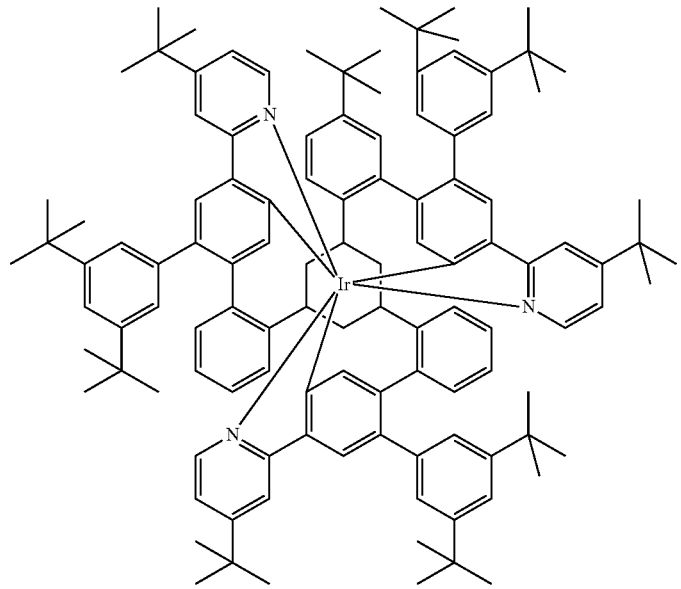 Ethyl acetate/acetonitrile | 55% |
| Ir106 | Ir(L3-3Br)/177171-16-3/B 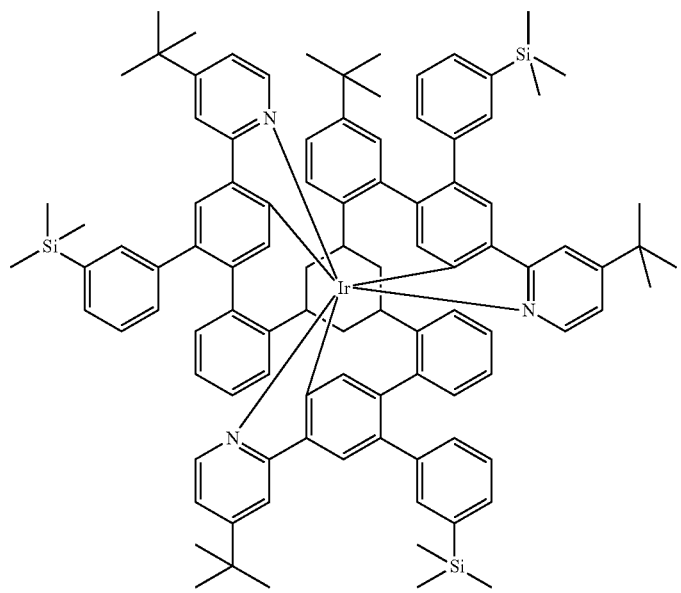 Ethyl acetate | 58% |

| Ex. | Bromide/Boronic acid/Variant Product Hot extractant | Yield |
|---|---|---|
| Ir107 | Ir(L3-3Br)/915230-75-0/B | 63% |
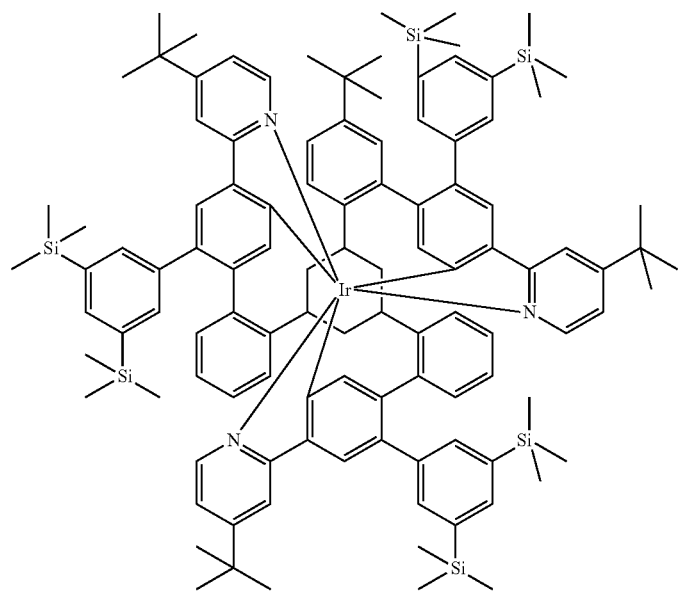
Cyclohexane
| Ir108 | Ir(L5-3Br)/162607-19-4/A | 67% |
|---|---|---|
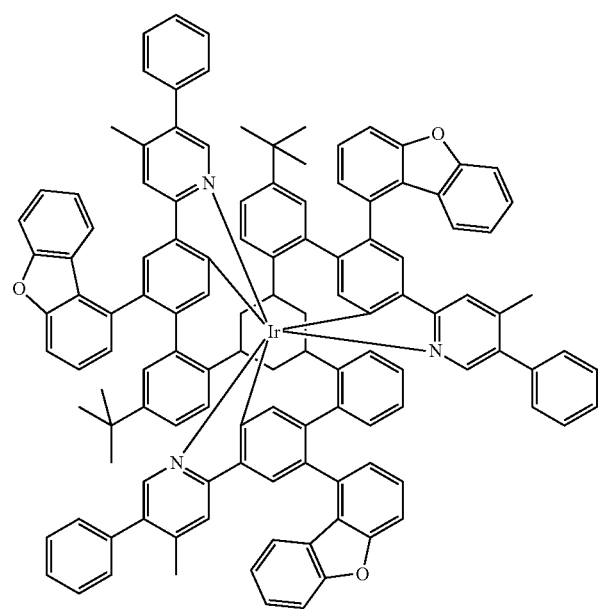
Toluene

| Ex. | Bromide/Boronic acid/Variant Product Hot extractant | Yield |
|---|---|---|
| Ir109 | Ir(L7-3Br)/100124-06-9/A | 60% |
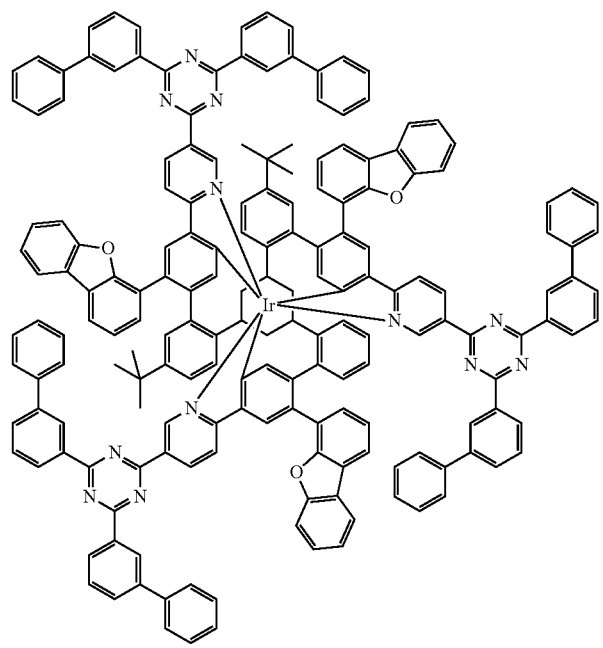
Toluene
| Ir110 | Ir(L9-3Br)/1392146-23-4/B | 59% |
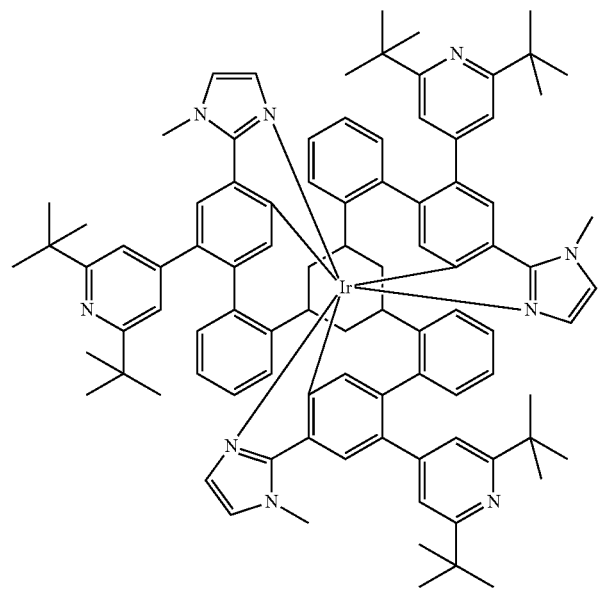
Ethyl acetate/acetonitrile -continued
| Ex. | Bromide/Boronic acid/Variant Product Hot extractant | Yield |
|---|---|---|
| Ir111 | Ir(L101-3Br)/854952-58-2/B | 65% |
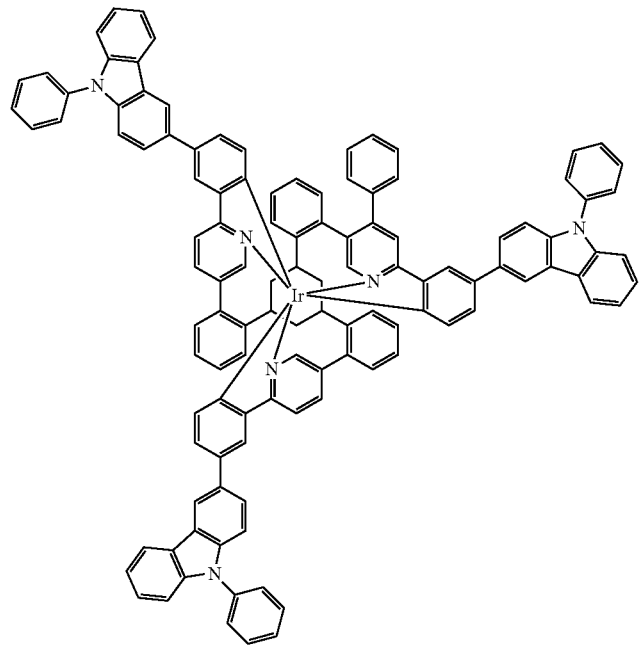
Toluene
| Ir112 | Ir(L102-3Br)/1392146-23-4/B | 60% |
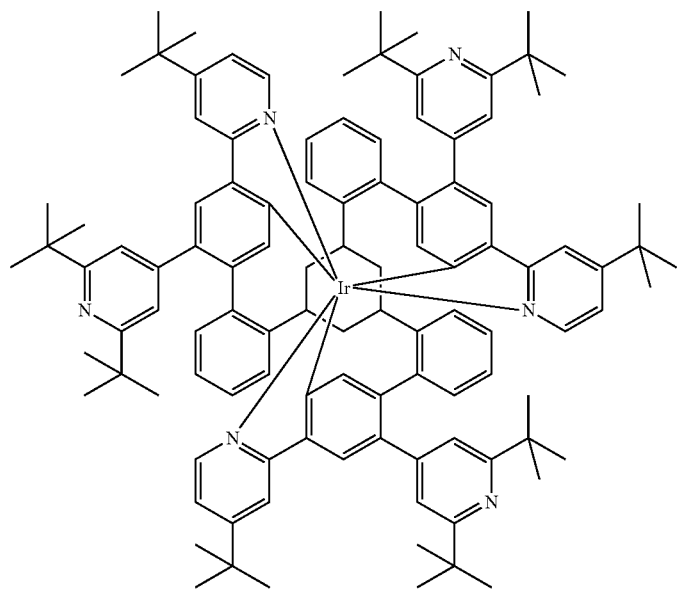
Toluene -continued
| Ex. | Bromide/Boronic acid/Variant<br>Product<br>Hot extractant | Yield |
|---|---|---|
| Ir113 | Ir(L102-3Br)/1313018-07-3/B | 67% |
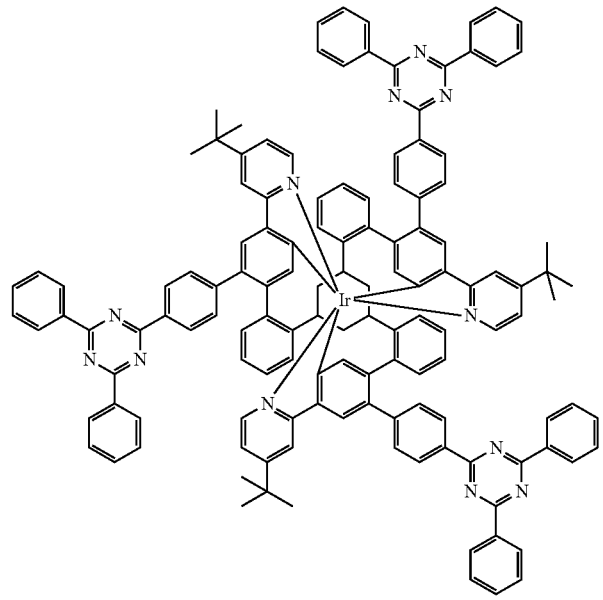
Toluene
| Ir114 | Ir(L103-3Br)/1809075-56-6/B | 58% |
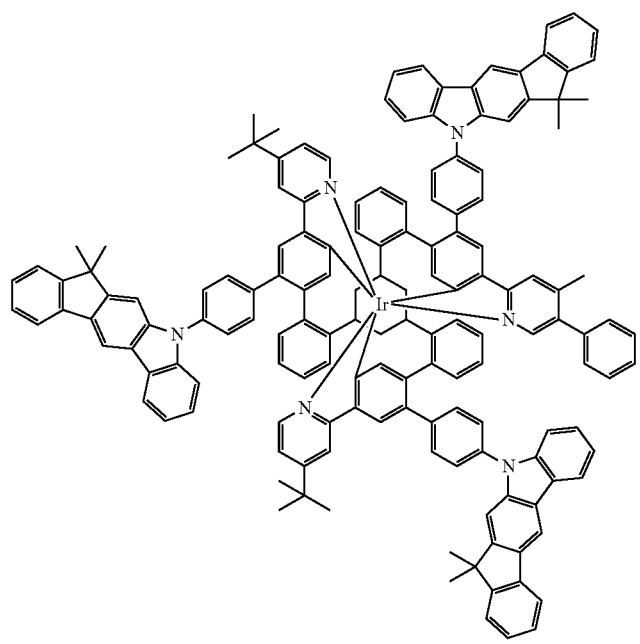
o-Xylene -continued
| Ex. | Bromide/Boronic acid/Variant<br>Product<br>Hot extractant | Yield |
|---|---|---|
| Ir115 | Ir(L108-3Br)/1562418-16-9/A | 49% |
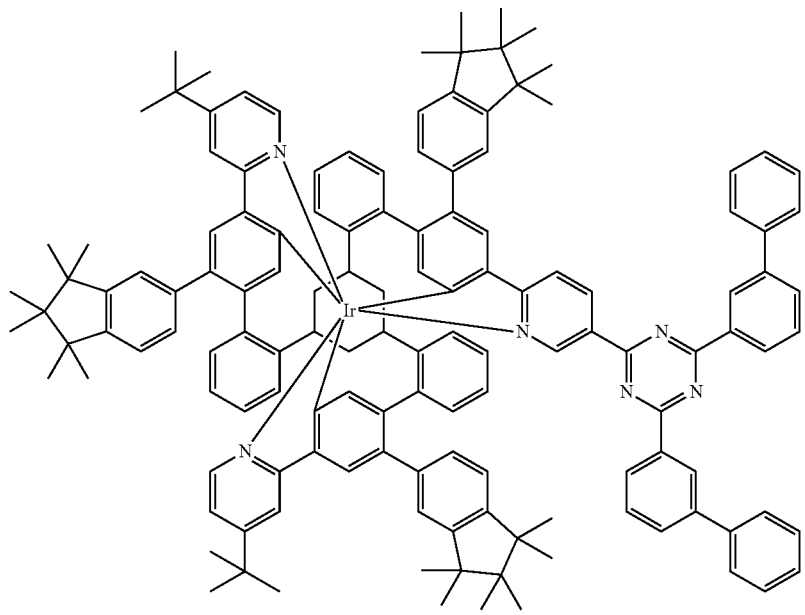
Ethyl acetate/acetonitrile
| Ir116 | Ir(L109-3Br)/1680179-22-9/B | 66% |
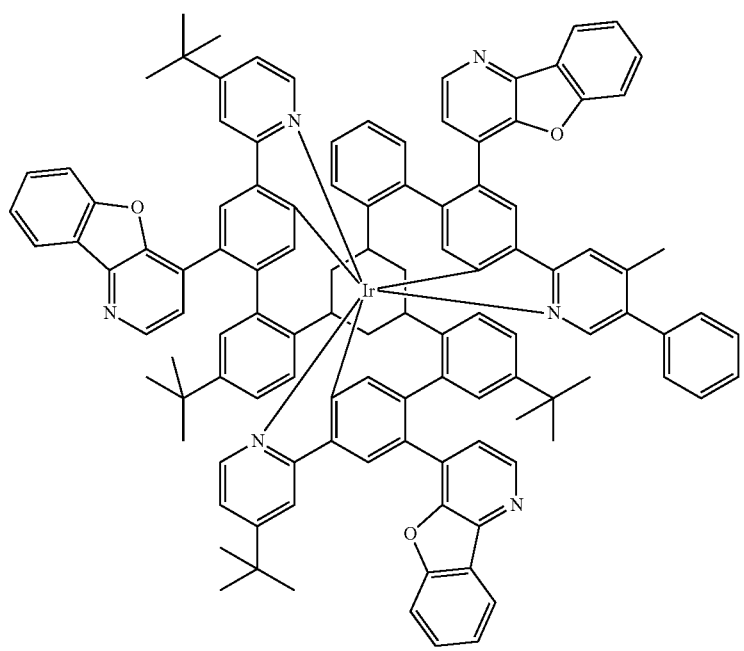
Toluene -continued
| Ex. | Bromide/Boronic acid/Variant<br>Product<br>Hot extractant | Yield |
|---|---|---|
| Ir117 | Ir(L110-3Br)/1345508-82-8/B | 60% |
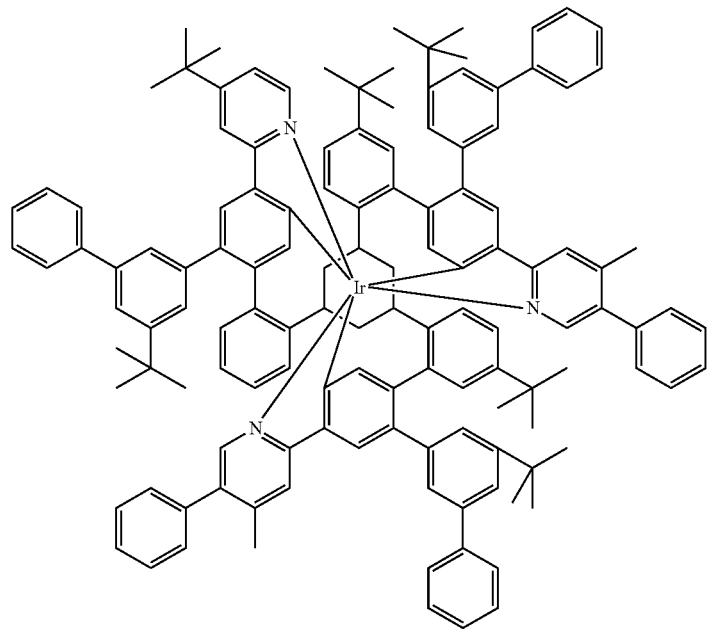
Toluene
| Ir118 | Ir(L111-3Br)/5122-95-2/B | 63% |
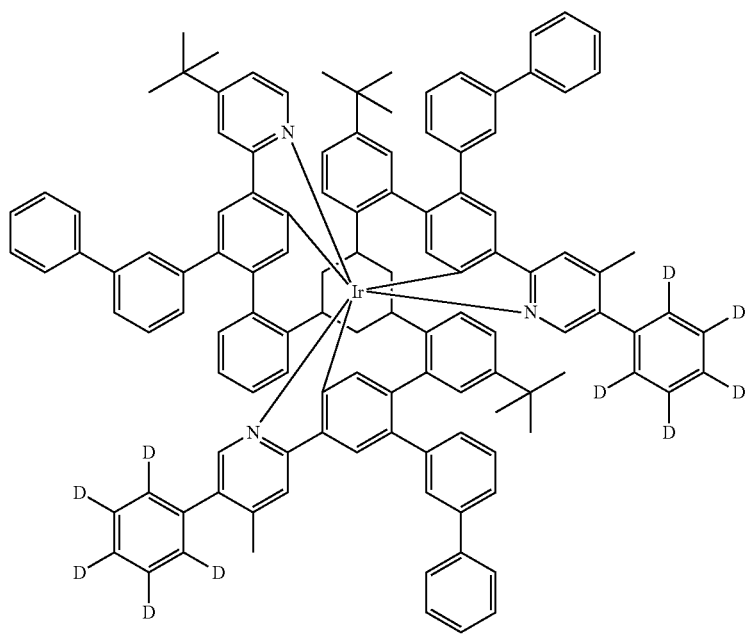
Toluene -continued
| Ex. | Bromide/Boronic acid/Variant<br>Product<br>Hot extractant | Yield |
|---|---|---|
| Ir119 | Ir(L112-3Br)/123324-71-0/B | 61% |
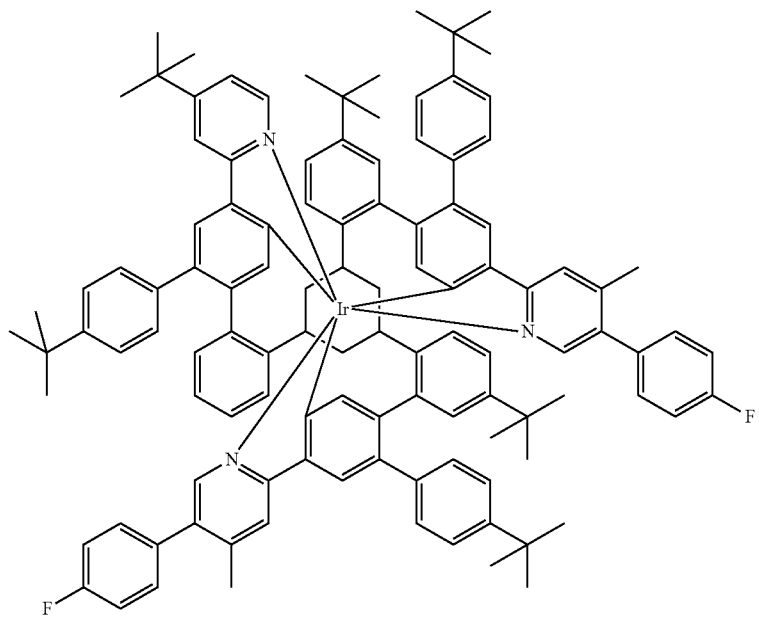
Butyl acetate then toluene
| Ir120 | Ir(L115-3Br)/701261-35-0/B | 65% |
|---|---|---|
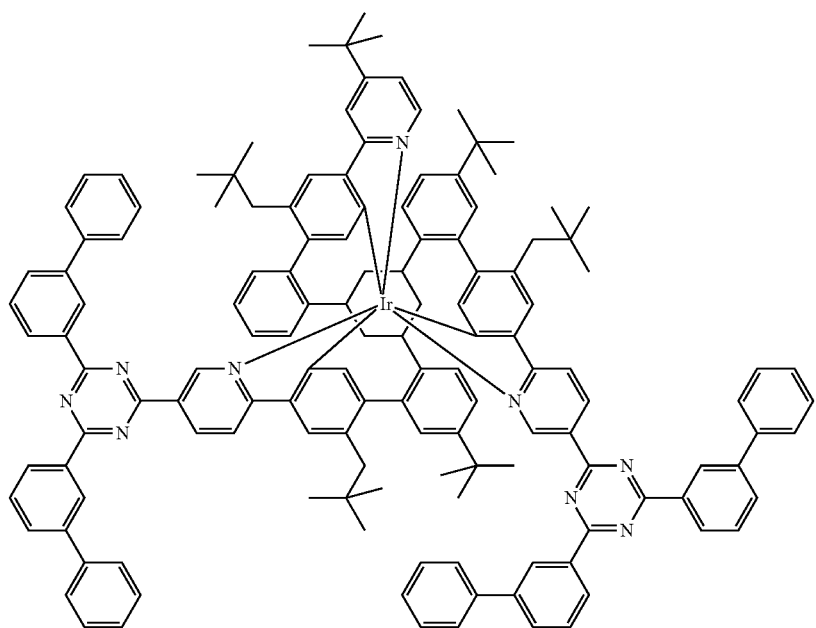
Toluene

| Ex. | Bromide/Boronic acid/Variant Product Hot extractant | Yield |
|---|---|---|
| Ir121 | Ir(L117-3Br)/84110-40-7/B | 47% |
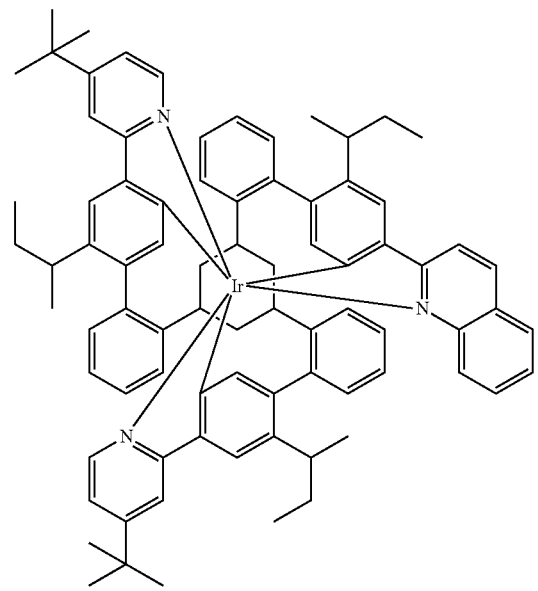
Ethyl acetate
| Ir122 | Ir(L120-3Br)/1269508-31-7/B | 54% |
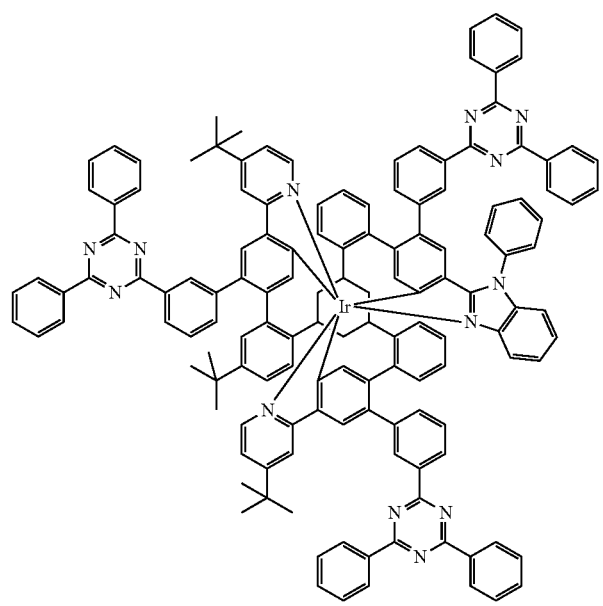
Toluene

| Ex. | Bromide/Boronic acid/Variant Product Hot extractant | Yield |
|---|---|---|
| Ir123 | Ir(L123-3Br)/98-80-6/B | 59% |
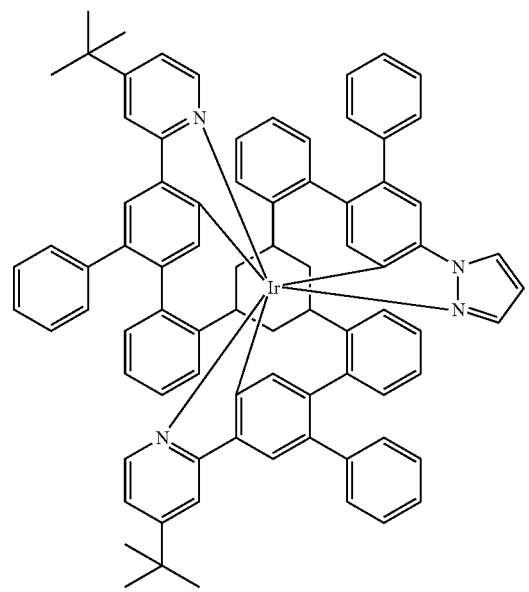
o-Xylene
| Ir124 | Ir(L201-3Br)/51067-38-0/A | 47% |
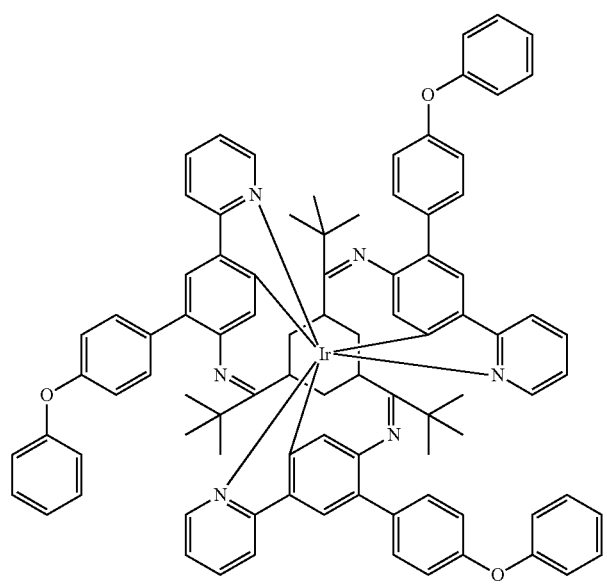
Toluene -continued
| Ex. | Bromide/Boronic acid/Variant<br>Product<br>Hot extractant | Yield |
|---|---|---|
| Ir125 | Ir(L203-3Br)/4688-76-0/B | 57% |
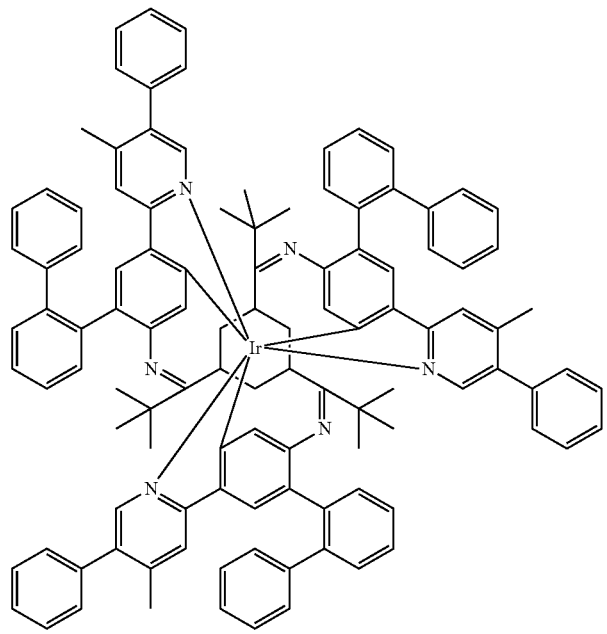
Toluene
| Ir126 | Ir(L208-3Br)/1245943-60-5/B | 50% |
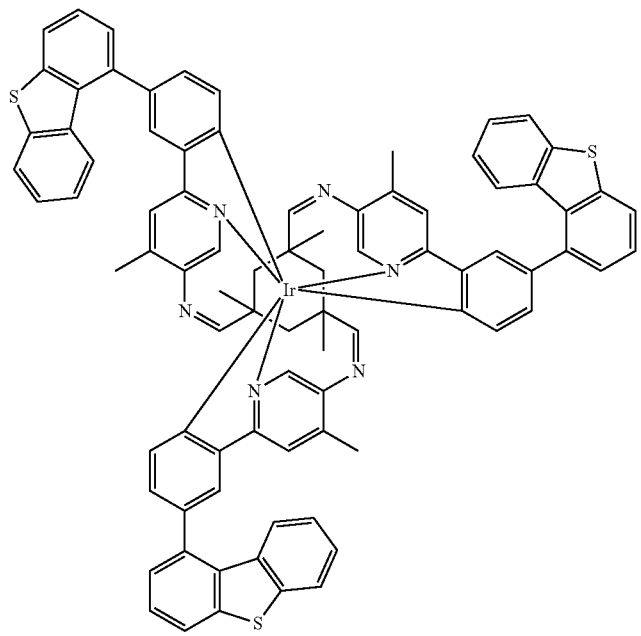
p-Xylene -continued
| Ex. | Bromide/Boronic acid/Variant<br>Product<br>Hot extractant | Yield |
|---|---|---|
| Ir127 | Ir(301-3Br)/400607-32-1/B | 62% |
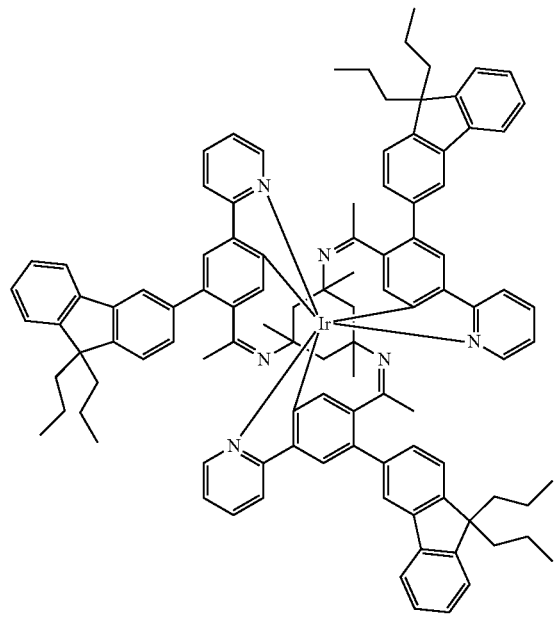
Toluene
| Ir128 | Ir(L306-3Br)/1421789-05-0/B | 60% |
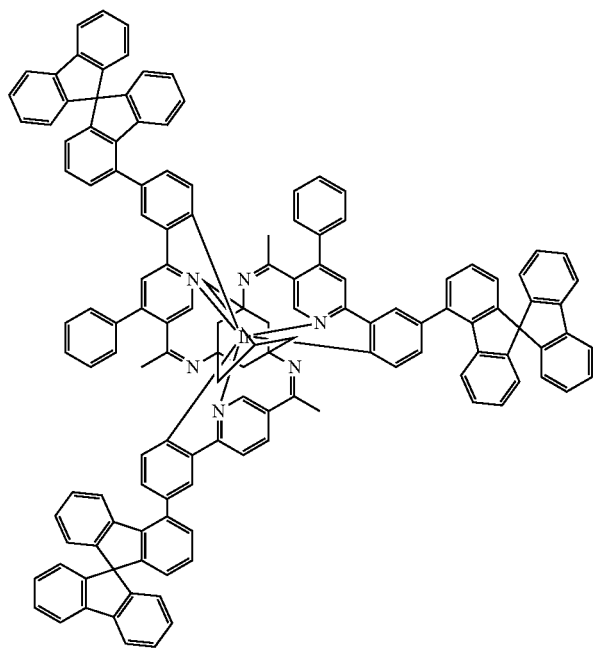
o-Xylene -continued
| Ex. | Bromide/Boronic acid/Variant Product Hot extractant | Yield |
|---|---|---|
| Ir129 | Ir(L100-2Br)/1233200-59-3/B | 65% |
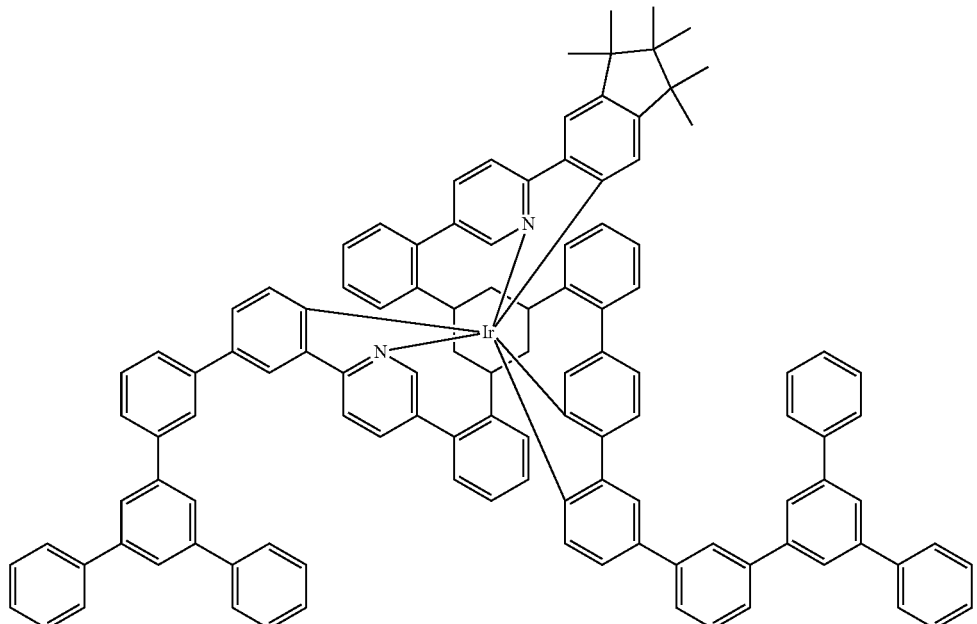
Toluene
| Ir130 | Ir(L102-2Br)/197223-39-5/B | 66% |
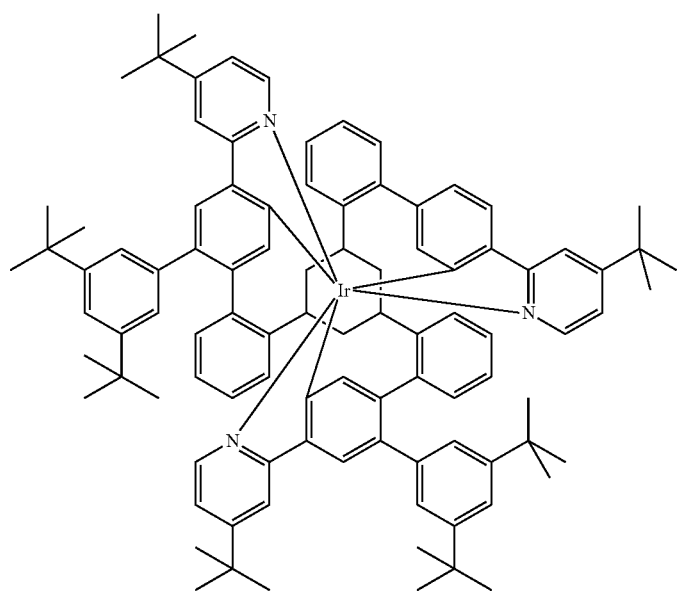
Butyl acetate

| Ex. | Bromide/Boronic acid/Variant Product Hot extractant | Yield |
|---|---|---|
| Ir131 | Ir(L106-2Br)/5122-95-2/B | 70% |
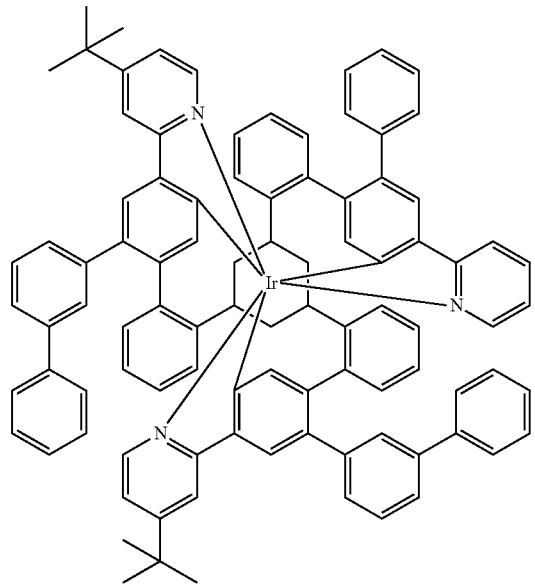
Toluene
| Ir132 | Ir(L107-2Br)/786071-96-0 | 68% |
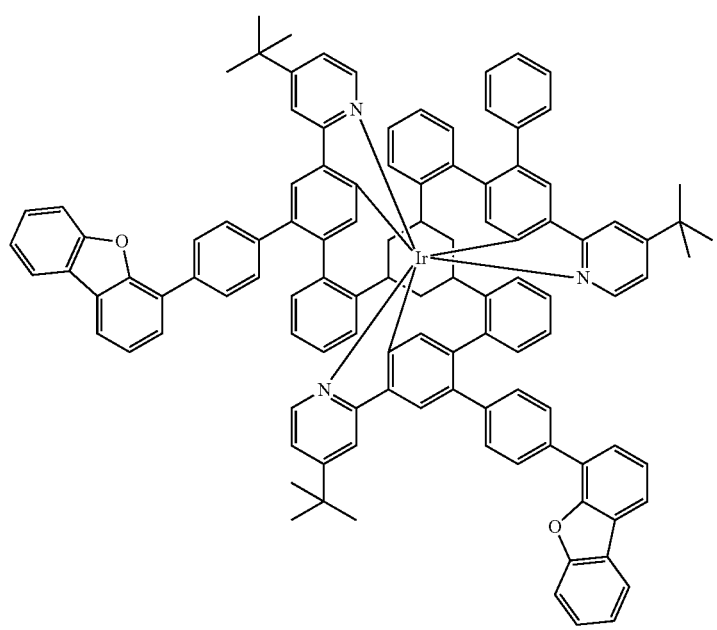
Toluene

| Ex. | Bromide/Boronic acid/Variant<br>Product<br>Hot extractant | Yield |
|---|---|---|
| Ir133 | Ir(L116-2Br)/1416814-68-0/B | 67% |
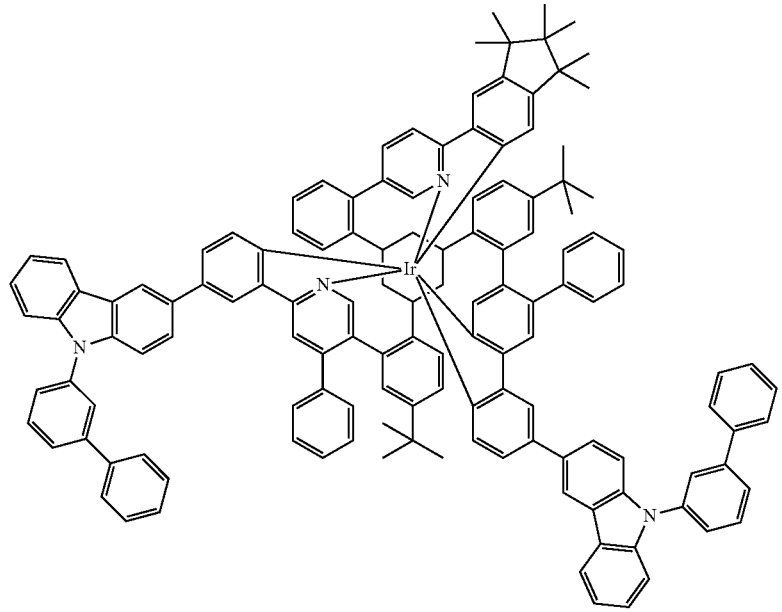
Butyl acetate
| Ir134 | Ir(L121-2Br)/1423-26-3/B | 63% |
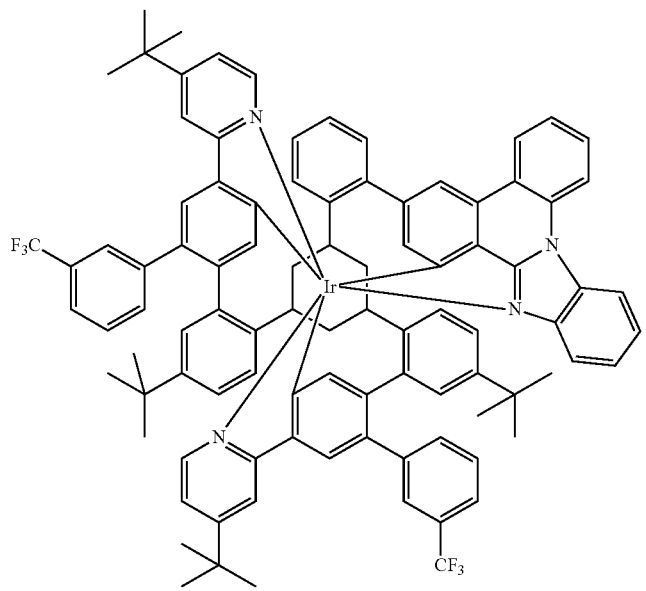
Butyl acetate

| Ex. | Bromide/Boronic acid/Variant<br>Product<br>Hot extractant | Yield |
|---|---|---|
| Ir135 | Ir(L102-1Br)/1565126-29-5/B | 65% |sn
| | 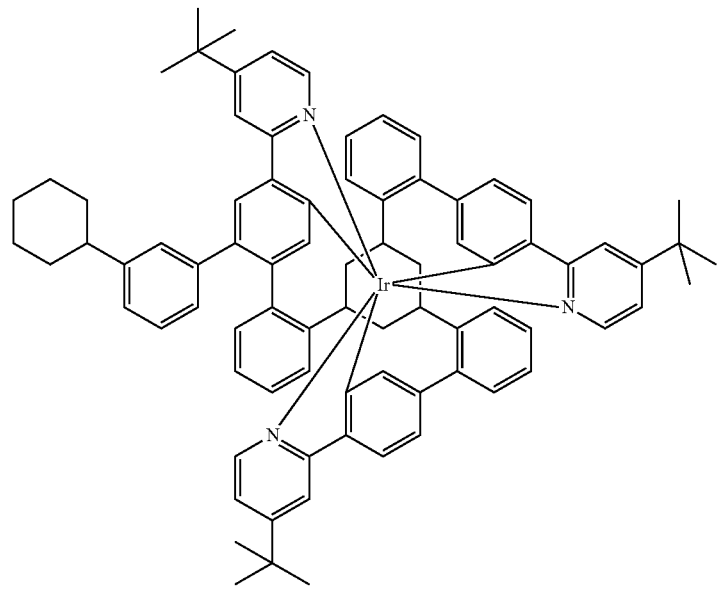<br>Toluene | |
| Ir136 | Ir(L113-Br)/1801624-63-4/B | 62% |
| | 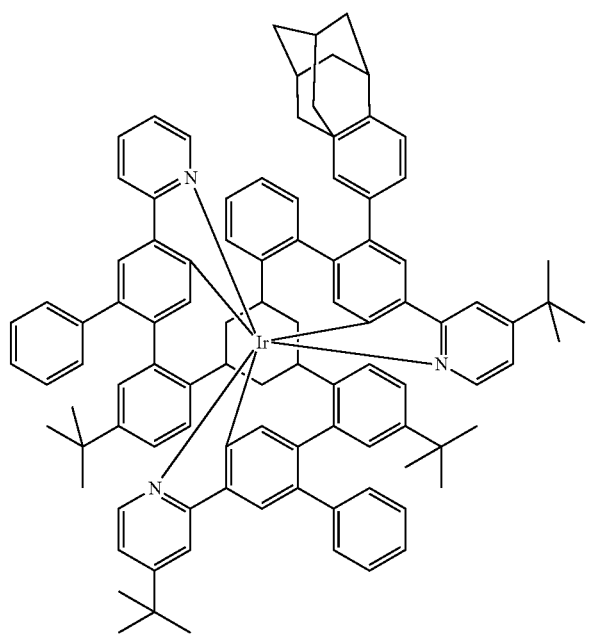<br>Butyl acetate | |

-continued
| Ex. | Bromide/Boronic acid/Variant<br>Product<br>Hot extractant | Yield |
|---|---|---|
| Ir137 | Ir(L114-Br)/1000869-26-0/B | 71% |
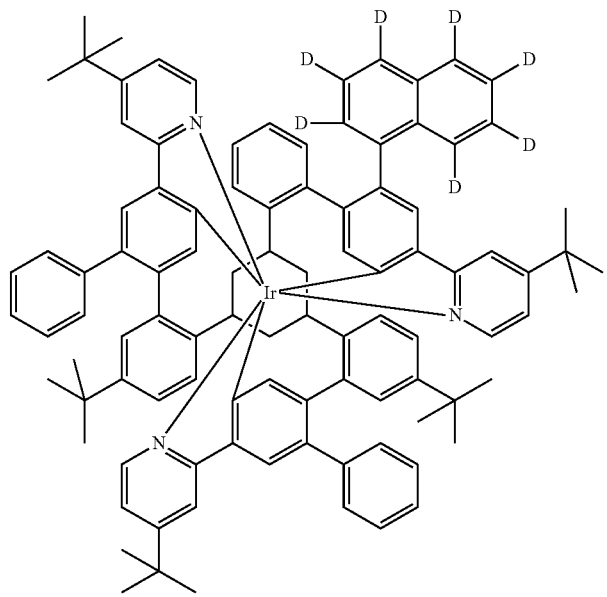
Toluene
| Ir138 | Ir(L400-3Br)/5122-95-2/B | 58% |
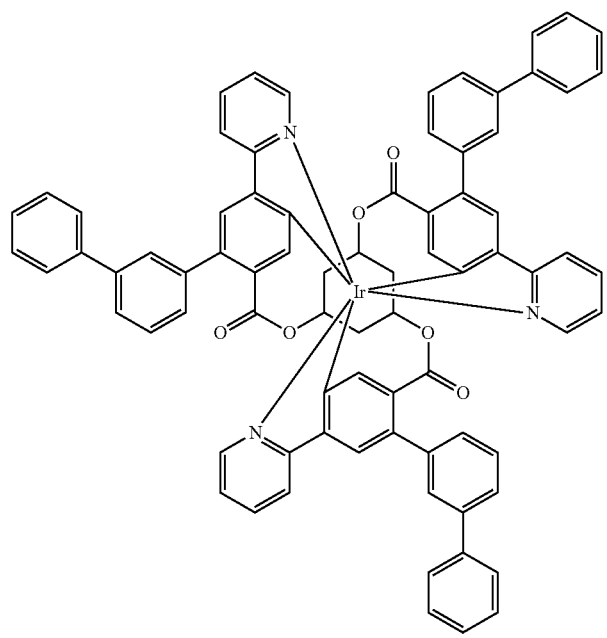
Toluene -continued
| Ex. | Bromide/Boronic acid/Variant Product Hot extractant | Yield |
|---|---|---|
| Ir139 | Ir(L404-3Br)/84110-40-7/B | 47% |
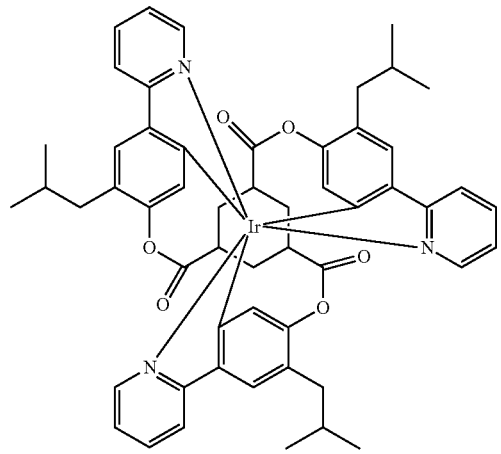
| Ir140 | Ir(L405-3Br)/1056113-44-0/B | 54% |
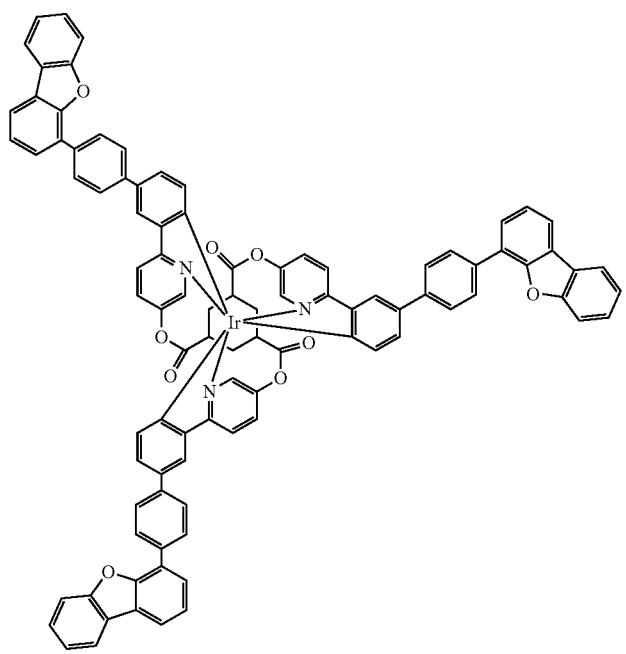
Toluene -continued
| Ex. | Bromide/Boronic acid/Variant Product Hot extractant | Yield |
|---|---|---|
| Ir141 | Ir(L500-3Br)/1801285-73-3/B | 49% |
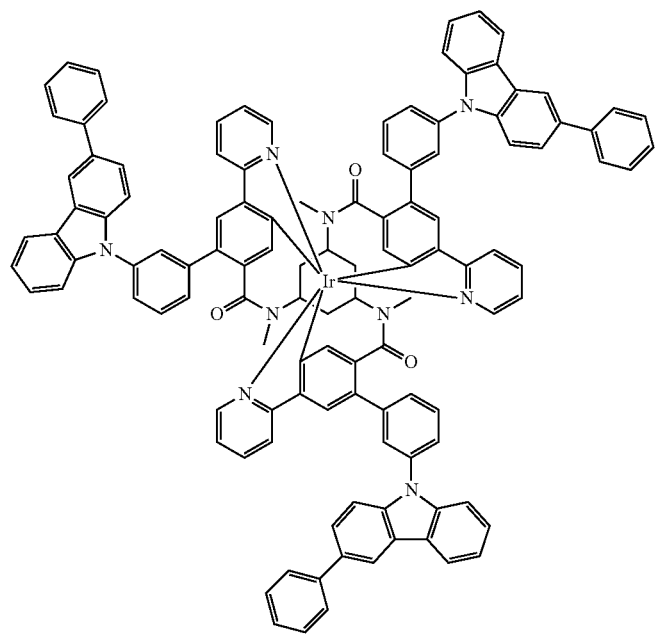
| Ir142 | Ir(L503-3Br)/1345508-82-8/B | 52% |
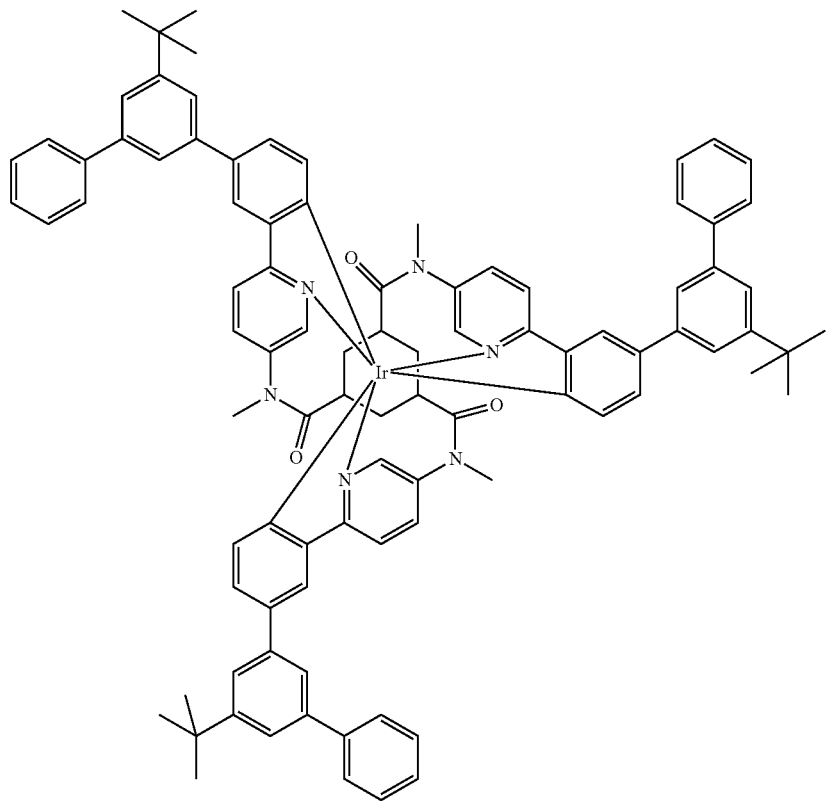

4.4 Buchwald Coupling to the Ir Complexes
Variant A:

0.4 mmol of tri-tert-butylphosphine and then 0.3 mmol of palladium(II) acetate are added to a mixture of 10 mmol of the brominated complex, 12-20 mmol of the diarylamine or carbazole per bromine function, 1.1 molar amount of sodium tert-butoxide per amine employed or 80 mmol of tripotassium phosphate (anhydrous) in the case of carbazoles, 100 g of glass beads (diameter 3 mm) and 300-500 ml of toluene or o-xylene in the case of carbazoles, and the mixture is heated under reflux with vigourous stirring for 16-30 h. After cooling, 500 ml of water are added, the aqueous phase is separated off, the organic phase is washed twice with 200 ml of water, once with 200 ml of saturated sodium chloride solution and dried over magnesium sulfate. The mixture is filtered through a Celite bed, the latter is rinsed with toluene or o-xylene, almost all the solvent is removed in vacuo, 300 ml of ethanol are added, the crude product which has precipitated out is filtered off with suction, washed three times with 50 ml of EtOH each time and dried in vacuo. The crude product is purified by chromatography on silica gel and/or by hot extraction. Finally, the metal complex is heat-treated or sublimed. The heat treatment is carried out in a high vacuum (p about $10^{-6}$ mbar) in the temperature range from about 200-300° C. The sublimation is carried out in a high vacuum (p about $10^{-6}$ mbar) in the temperature range from about 300-400° C., where the sublimation is preferably carried out in the form of a fractional sublimation.

Variant B:

A mixture of 10 mmol of the brominated complex, 12-20 mmol of the diarylamine or carbazole per bromine function, 30 mmol of potassium carbonate and 30 mmol of sodium sulfate per bromine function, 10 mmol of copper iodide per bromine function, 50 g of glass beads (diameter 3 mm) and 150 ml of nitrobenzene is heated at 200° C. with vigourous stirring for 16-30 h. After cooling to 100° C., the nitrobenzene is substantially removed in vacuo, 300 ml of MeOH are added, the product which has precipitated out and the salts are filtered off, the latter are rinsed with 50 ml of methanol and dried in vacuo. The residue is taken up in 300 ml of dichloromethane, the salts are filtered off via a silica-gel bed which has been pre-slurried with dichloromethane, the dichloromethane is removed in vacuo, and the product is re-chromatographed on silica gel.

Synthese von Ir200:

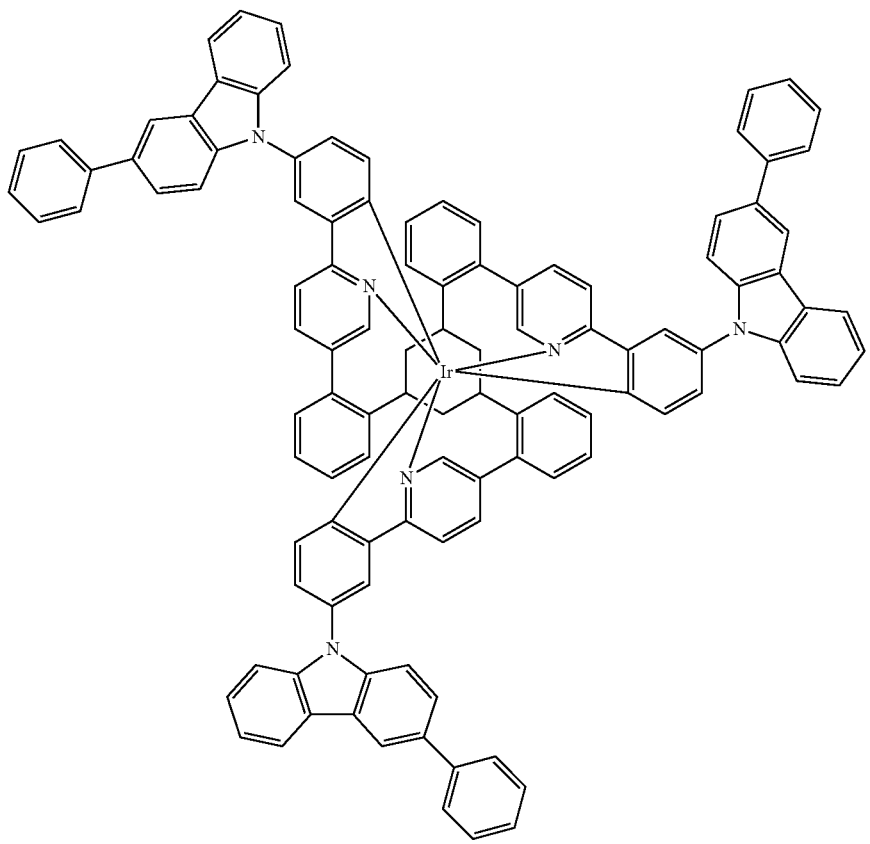

Variant A:

Use of 12.0 g (10 mmol) of Ir(L1-3Br) and 9.7 g (40 mmol) of 3-phenylcarbazole [103012-26-6]. Chromatography three times on silica gel with DCM, heat treatment. Yield: 6.3 g (3.7 mmol), 37%; purity: about 99.8% according to HPLC.

Variant B:

Use of 12.0 g (10 mmol) of Ir(L1-3Br) and 9.7 g (40 mmol) of 3-phenylcarbazole [103012-26-6]. Chromatography three times on silica gel with DCM, heat treatment. Yield: 7.5 g (4.4 mmol), 44%; purity: about 99.7% according to HPLC.

The following compounds can be prepared analogously:
| Ex. | Starting material/amine or carbazole<br>Product<br>Hot extractant | Yield |
|---|---|---|
| Ir201 | Ir(L102-3Br)/1257220-47-5 | 30% |
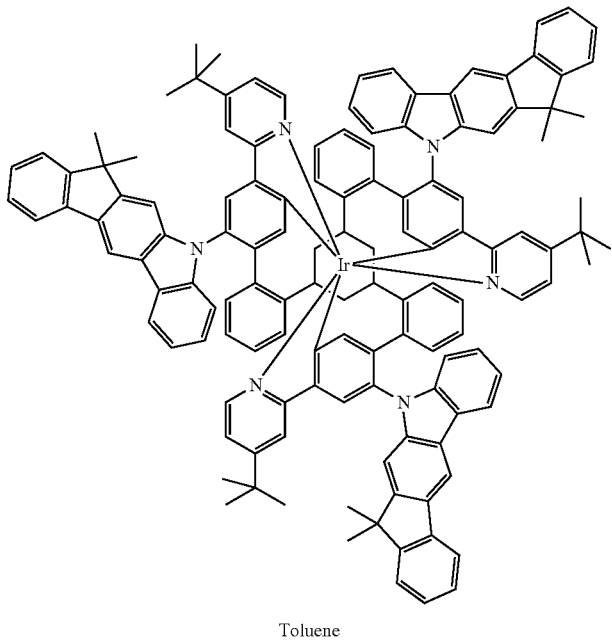
Toluene
| Ir202 | Ir(L301-3Br)/1421789-16-3 | 38% |
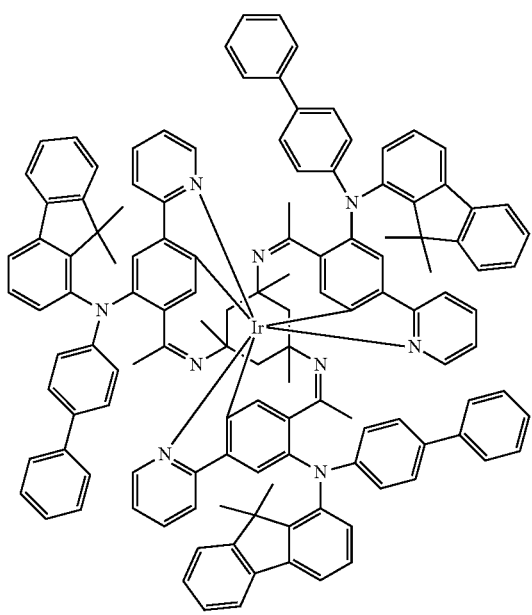
Toluene

| Ex. | Starting material/amine or carbazole<br>Product<br>Hot extractant | Yield |
|---|---|---|
| Ir203 | Ir(L114-Br)/103012-26-6 | 69% |

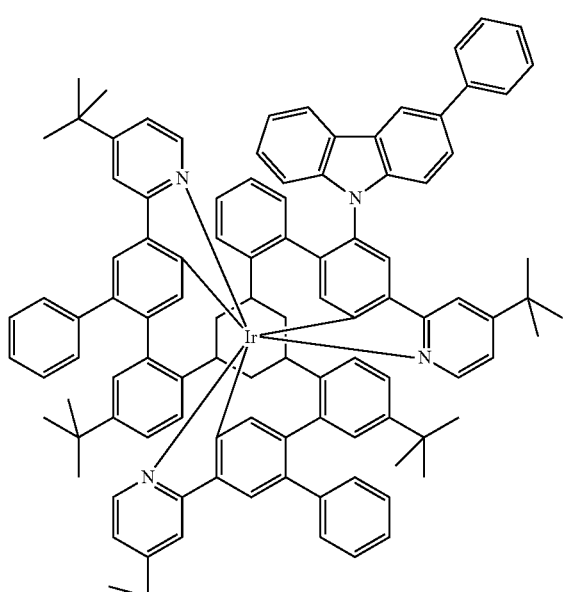

Toluene

4.5 Cyanation of the Iridium Complexes:

A mixture of 10 mmol of the brominated complex, 13 mmol of copper(I) cyanide per bromine function and 300 ml of NMP is stirred at 180° C. for 20 h. After cooling, the solvent is removed in vacuo, the residue is taken up in 500 ml of dichloromethane, the copper salts are filtered off via Celite, the dichloromethane is evaporated virtually to dryness in vacuo, 100 ml of ethanol are added, the solid which has precipitated out is filtered off with suction, washed twice with 50 ml of ethanol each time and dried in vacuo. The crude product is purified by chromatography and/or hot extraction.

The heat treatment is carried out in a high vacuum (p about $10^{-6}$ mbar) in the temperature range from about 200-300° C. The sublimation is carried out in a high vacuum (p about $10^{-6}$ mbar) in the temperature range from about 300-400° C., where the sublimation is preferably carried out in the form of a fractional sublimation.

Synthesis of Ir300:

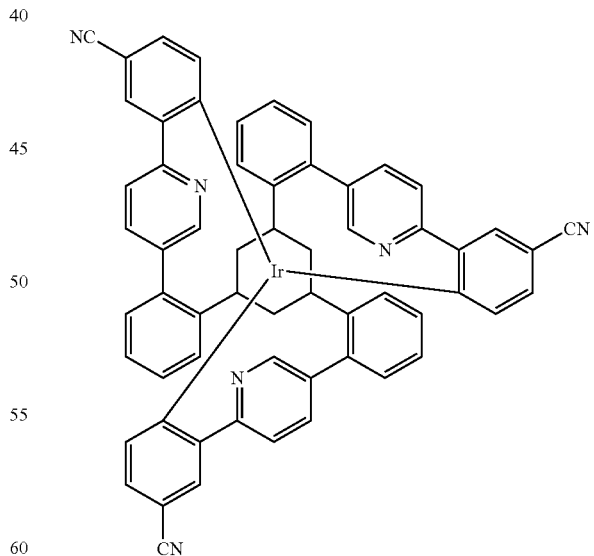

Use of 12.0 g (10 mmol) of Ir(L1-3Br) and 3.5 g (39 mmol) of copper(I) cyanide. Chromatography twice on silica gel with dichloromethane, hot extraction with DCM, sublimation. Yield: 4.9 g (4.7 mmol), 47%; purity: about 99.9% according to HPLC.

The following compounds can be prepared analogously:

| Ex. | Starting material Cyanation product | |
|---|---|---|
| Ir301 | Ir(L123-3Br) | 51% |

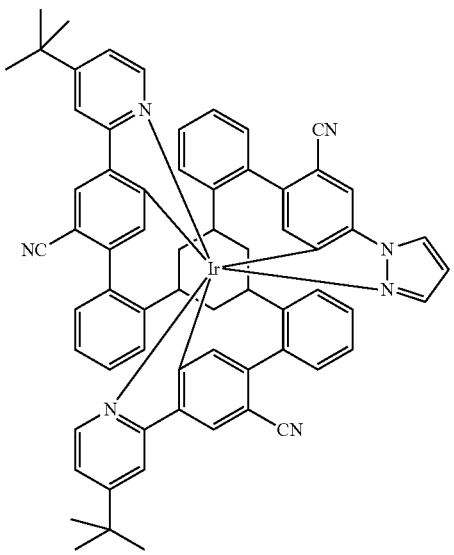

| Ir302 | Ir(L121-2Br) | 64% |

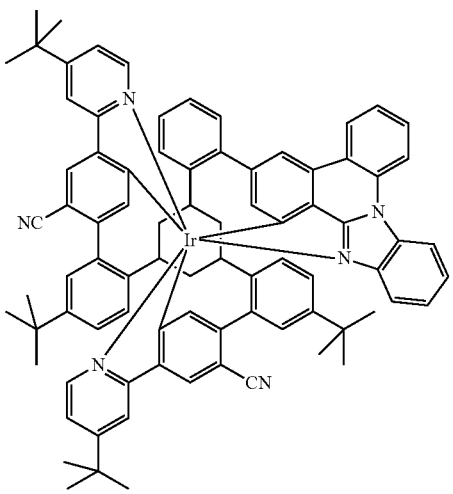

| Ex. | Starting material Cyanation product | |
|---|---|---|
| Ir303 | Ir(L208-3Br) | 47% |

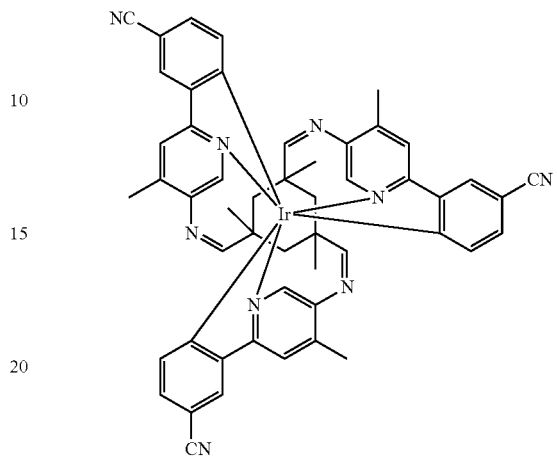

4.6 Suzuki Coupling to the Borylated Iridium Complexes:

Variant A, Two-Phase Reaction Mixture:

0.6 mmol of tri-o-tolylphosphine and then 0.1 mmol of palladium(II) acetate are added to a suspension of 10 mmol of a borylated complex, 12-20 mmol of aryl bromide per $(RO)_2B$ function and 80 mmol of tripotassium phosphate in a mixture of 300 ml of toluene, 100 ml of dioxane and 300 ml of water, and the mixture is heated under reflux for 16 h. After cooling, 500 ml of water and 200 ml of toluene are added, the aqueous phase is separated off, the organic phase is washed three times with 200 ml of water, once with 200 ml of saturated sodium chloride solution and dried over magnesium sulfate. The mixture is filtered through a Celite bed, the latter is rinsed with toluene, almost all the toluene is removed in vacuo, 300 ml of methanol are added, the crude product which has precipitated out is filtered off with suction, washed three times with 50 ml of methanol each time and dried in vacuo. The crude product is passed through a silica-gel column twice and/or purified by hot extraction. Finally, the metal complex is heat-treated or sublimed. The heat treatment is carried out in a high vacuum (p about $10^{-6}$ mbar) in the temperature range from about 200-300° C. The sublimation is carried out in a high vacuum (p about $10^{-6}$ mbar) in the temperature range from about 300-400° C., where the sublimation is preferably carried out in the form of a fractional sublimation.

Variant B, Single-Phase Reaction Mixture:

0.6 mmol of tri-o-tolylphosphine and then 0.1 mmol of palladium(II) acetate or 0.3 mmol of tetrakis(triphenylphosphino)palladium(0) are added to a suspension of 10 mmol of a borylated complex, 12-20 mmol of aryl bromide per $(RO)_2B$ function and 60-100 mmol of the base (potassium fluoride, tripotassium phosphate (anhydrous, monohydrate or trihydrate), potassium carbonate, caesium carbonate, etc.) and 100 g of glass beads (diameter 3 mm) in 100 ml-500 ml of an aprotic solvent (THF, dioxane, xylene, mesitylene, dimethylacetamide, NMP, DMSO, etc.), and the mixture is heated under reflux for 1-24 h. Alternatively, other phosphines, such as triphenylphosphine, tri-tert-butylphosphine, S-Phos, X-Phos, Ru-Phos, XanthPhos, etc. can be employed, where, in the case of these phosphines, the preferred phosphine:palladium ratio is 3:1 to 1.2:1. The solvent is removed in vacuo, the product is taken up in a suitable solvent (toluene, dichloromethane, ethyl acetate, etc.) and purified as described under Variant A.

Synthesis of Ir400:

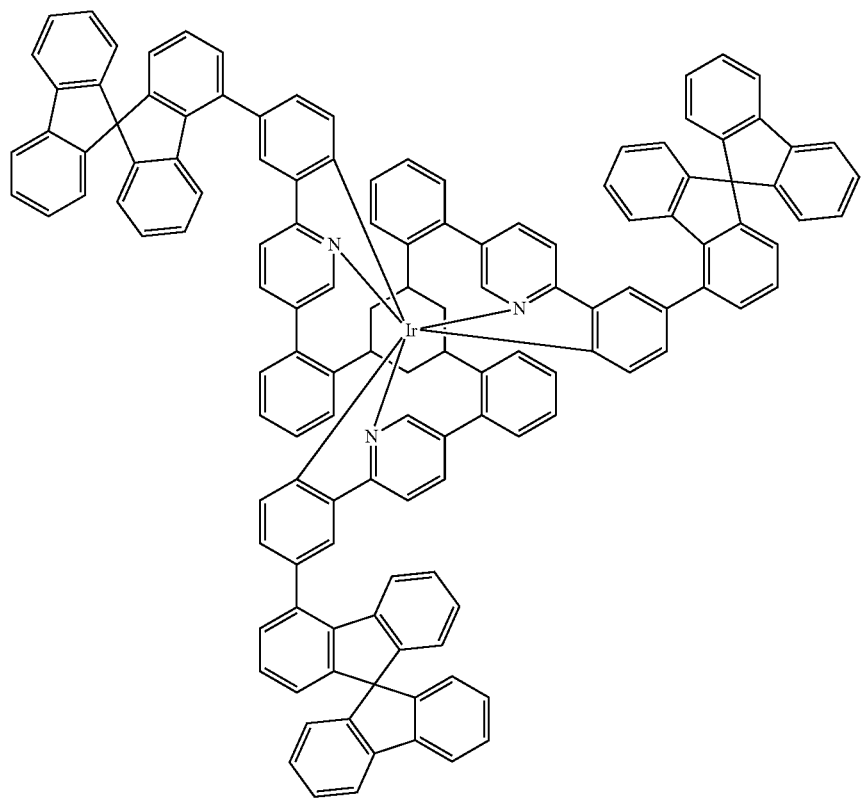

Variant A:

Use of 13.4 g (10.0 mmol) of Ir(L1-3BE) and 7.4 g (40.0 mmol) of 9,9'-spirobifluorene-4-boronic acid pinacolyl ester [1161009-88-6], 17.7 g (60 mmol) of tripotassium phosphate (anhydrous), 183 mg (0.6 mmol) of tri-o-tolylphosphine [6163-58-2], 23 mg (0.1 mmol) of palladium(II) acetate, 300 ml of toluene, 100 ml of dioxane and 300 ml of water, 100° C., 16 h. Chromatographic separation twice on silica gel with toluene/ethyl acetate (9:1, vv), hot extraction three times with o-xylene. Yield: 10.9 g (5.7 mmol), 57%; purity: about 99.9% according to HPLC.

The following compounds can be prepared analogously:
| Ex. | Starting materials/Variant Product Hot extractant | Yield |
|---|---|---|
| Ir401 | Ir(L3-3BE)/1613576-58-1/A | 48% |
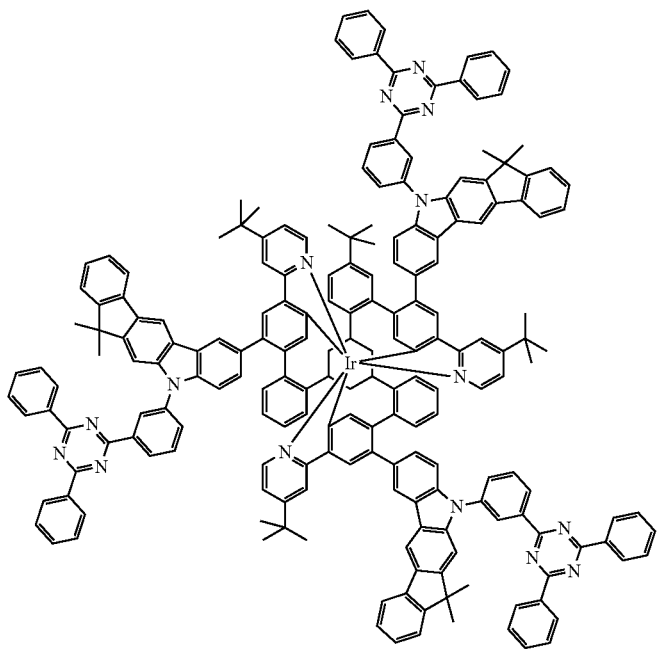
Toluene
| Ir402 | Ir(L5-3BE)/3842-55-5/B | 37% |
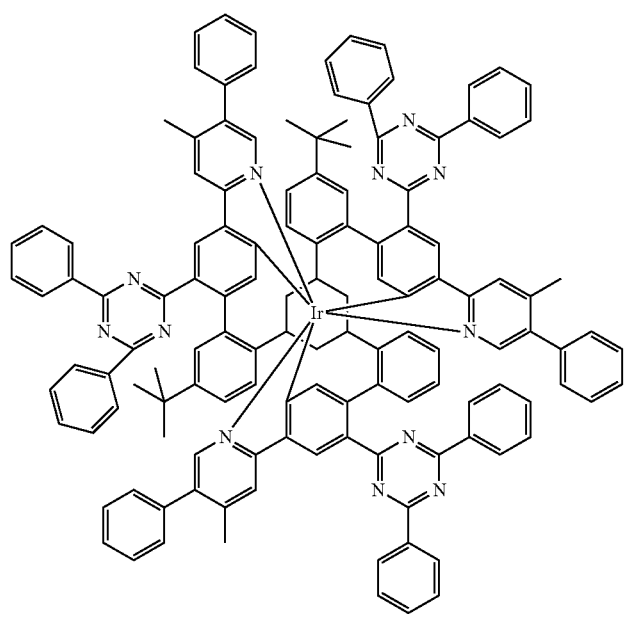
Toluene -continued

| Ex. | Starting materials/Variant<br>Product<br>Hot extractant | Yield |
|---|---|---|
| Ir403 | Ir(L107-2BE)/50548-45-3/B/PPh$_3$:Pd(ac)$_2$ 3:1/<br>K$_3$PO$_4$ * H$_2$O/DMSO/90° C./18 h | 41% |

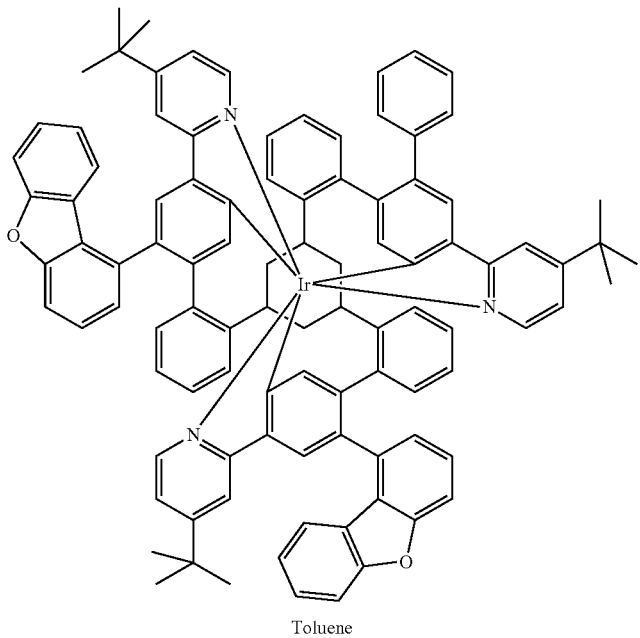

Toluene

4.7 Alkylation on Iridium Complexes:

50 ml of a freshly prepared LDA solution, 1 molar in THF, are added to a suspension of 10 mmol of the complex in 1500 ml of THF, and the mixture is stirred at 25° C. for a further 24 h. 200 mmol of the alkylating agent are then added in one portion with vigourous stirring, where liquid alkylating agents are added without dilution, solid ones are added as a solution in THF. The mixture is stirred at room temperature for a further 60 min., the THF is removed in vacuo, and the residue is chromatographed on silica gel. The further purification can be carried out by hot extraction—as described above. Finally, the metal complex is heat-treated or sublimed. The heat treatment is carried out in a high vacuum (p about $10^{-6}$ mbar) in the temperature range from about 200-300° C. The sublimation is carried out in a high vacuum (p about $10^{-6}$ mbar) in the temperature range from about 300-400° C., where the sublimation is preferably carried out in the form of a fractional sublimation.

Synthesis of Ir500:

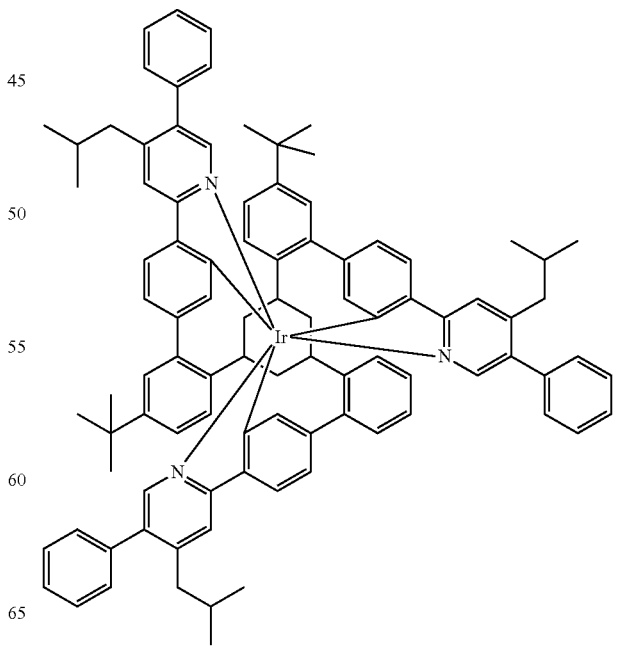

Use of 13.4 g (10.0 mmol) of Ir(L5) and 21.7 ml (200 mmol) of 1-bromo-2-methylpropane [78-77-3]. Chromatographic separation twice on silica gel with toluene, subsequent hot extraction five times with ethyl acetate/acetonitrile. Yield: 4.6 g (3.1 mmol), 31%; purity: about 99.7% according to HPLC.

The following compounds can be prepared analogously:

| Ex. | Starting material/alkylating agent Product | Yield |
|---|---|---|
| Ir501 | Ir(L103)/1.5 eq of LDA/6 eq of 78-77-3 | 42% |

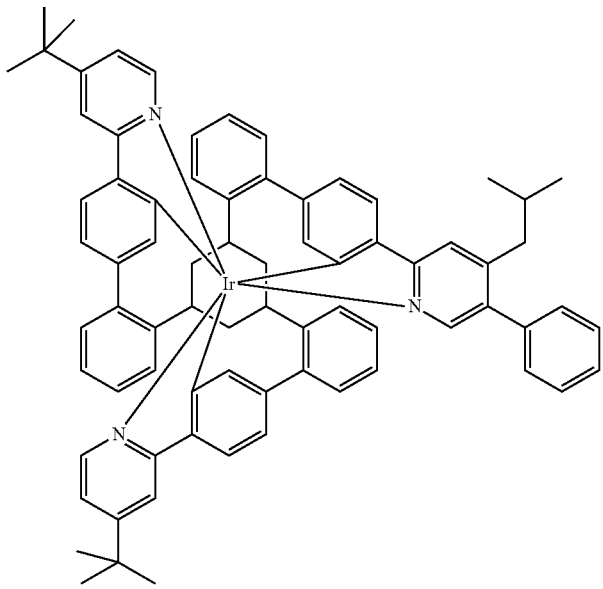

| Ir502 | Ir(L104)/1.5 eq of LDA/6 eq of 108-85-0 | 29% |

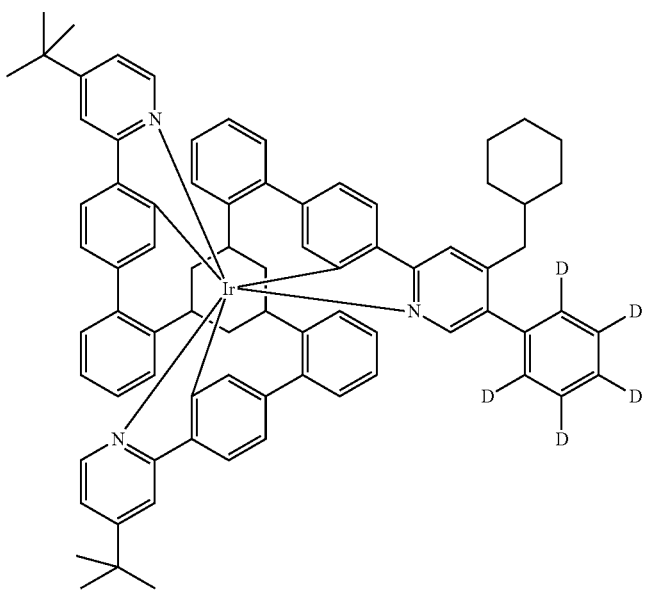

-continued
| Ex. | Starting material/alkylating agent Product | Yield |
|---|---|---|
| Ir503 | Ir(L105)/1.5 eq of LDA/6 eq of 630-17-1 | 35% |
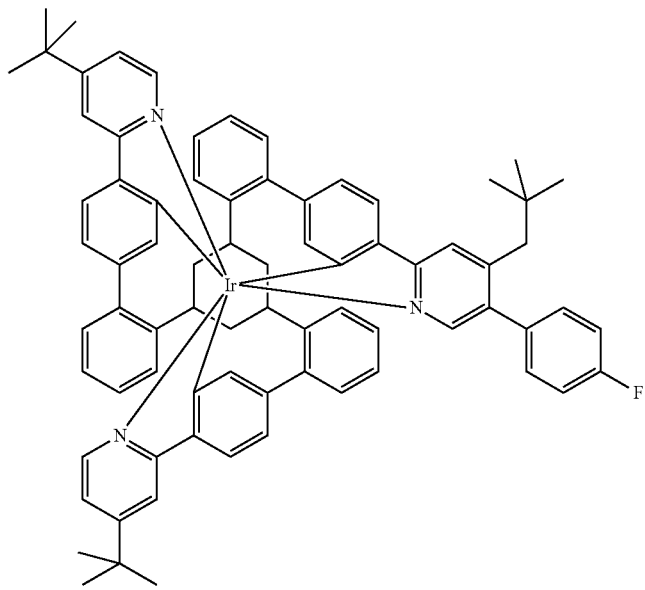
| Ir504 | Ir(L110)/3 eq of LDA/9 eq of 74-83-9 | 32% |
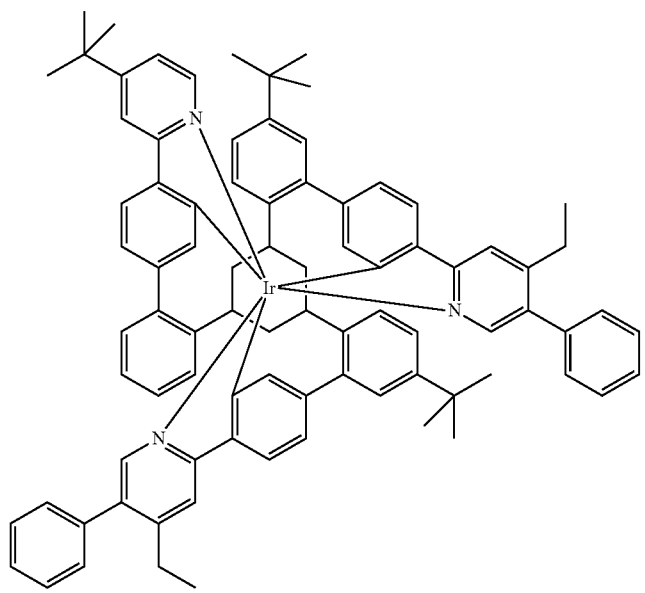

| Ex. | Starting material/alkylating agent<br>Product | Yield |
|---|---|---|
| Ir505 | Ir(L203)/5 eq of LDA/20 eq of 78-77-3 | 27% |

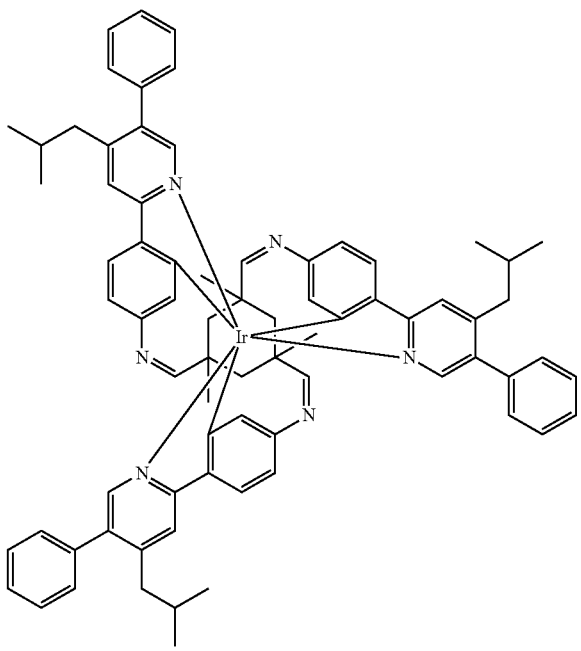

4.8 Deuteration of Ir Complexes:

Example: Ir(L5-D9)

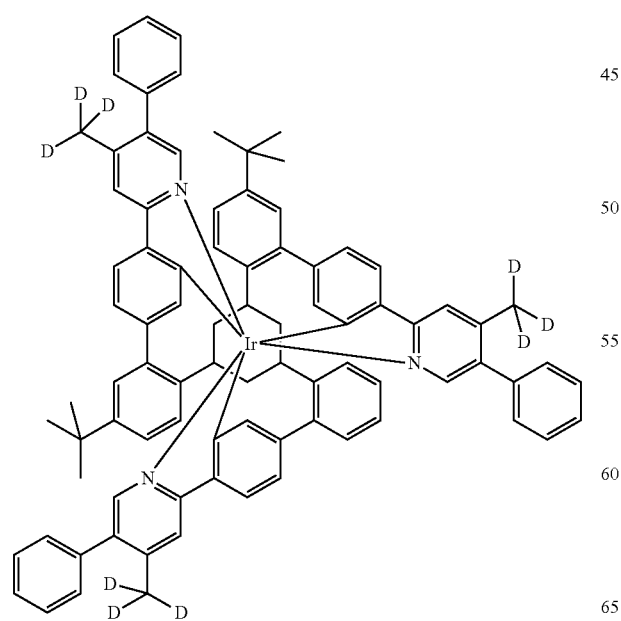

A mixture of 1.34 g (1.0 mmol) of Ir(L5), 24 mg (1.0 mmol) of sodium hydride, 3 ml of methanol-D4 and 30 ml of DMSO-D6 is heated at 80° C. for 18 h. After cooling, 1.0 ml of 5 M DCl in $D_2O$ is added, the mixture is stirred briefly, and 80 ml of methanol are then added dropwise. The solid which has precipitated out is filtered off with suction, washed three times with 10 ml of methanol each time, dried in vacuo, and the residue is chromatographed on silica gel with DCM. Yield: 1.14 g (0.84 mmol), 84%, degree of deuteration>90%.

The following compounds can be prepared analogously:
| Ex. | Starting material/product | Yield |
|---|---|---|
| Ir(L103-D3) | Ir(L103)/0.3 mmol of NaH<br>2 ml of methanol-D4/10 ml of DMSO-D6 | 90% |
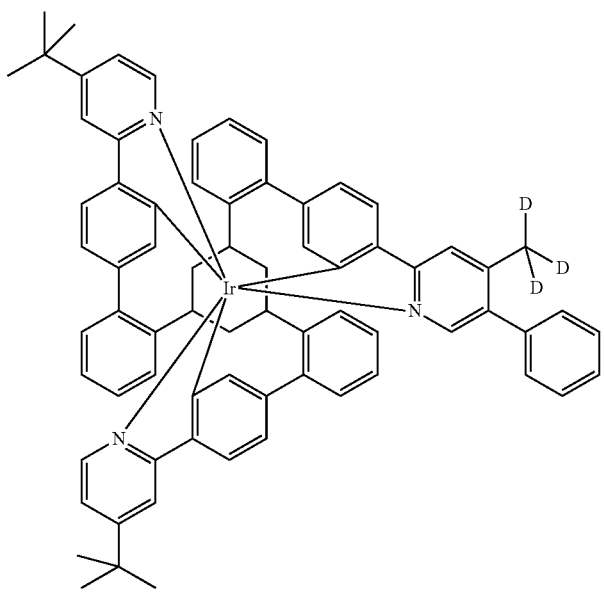
| Ir(L104-D3) | Ir(L104)/0.3 mmol of NaH<br>2 ml of methanol-D4/10 ml of DMSO-D6 | 87% |
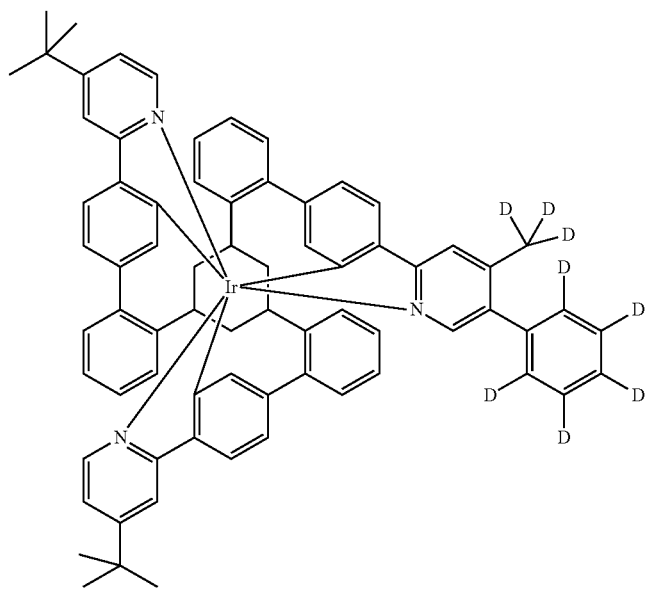

-continued
| Ex. | Starting material/product | Yield |
|---|---|---|
| Ir(L105-D3) | Ir(L105)/0.3 mmol of NaH<br>2 ml of methanol-D4/10 ml of DMSO-D6 | 92% |
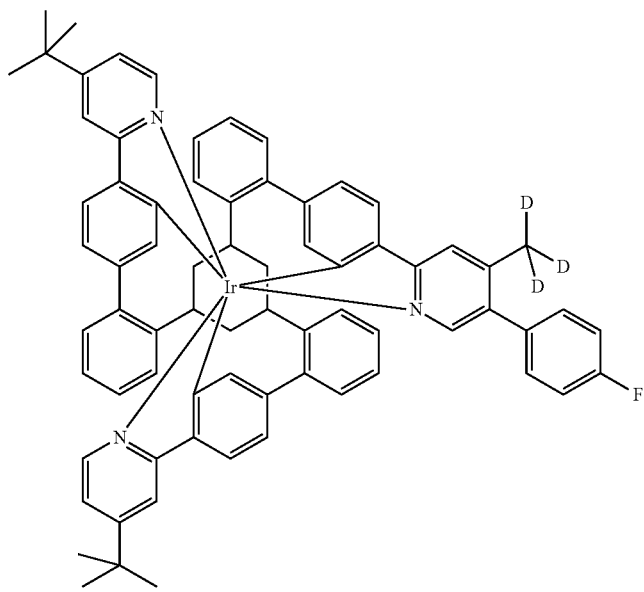
| Ir(110-D6) | Ir(L110)/0.6 mmol of NaH<br>2 ml of methanol-D4/20 ml of DMSO-D6 | 90% |
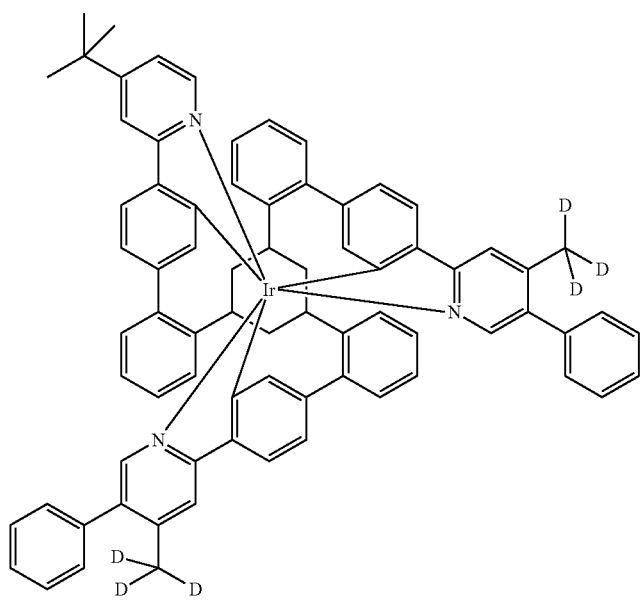

-continued

| Ex. | Starting material/product | Yield |
|---|---|---|
| Ir(L203-D9) | Ir(L203)/1.0 mmol of NaH<br>4 ml Methanol-D4/30 ml of DMSO-D6 | 93% |

4.9 Separation of the Δ and Λ Enantiomers of the Metal Complexes by Means of Chromatography on Chiral Columns:

The Δ and Λ enantiomers of the complexes can be separated by means of analytical and/or preparative chromatography on chiral columns by standard laboratory methods, for example separation of Ir105 on ChiralPak AZ-H (Chiral Technologies Inc.) with n-hexane/ethanol (90:10), retention times 13.4 min. and 16.8 min. respectively.

5. Polymers Containing the Metal Complexes:

General Polymerisation Procedure for the Bromides or Boronic Acid

Derivatives as Polymerisable Group, Suzuki Polymerisation

Variant A—Two-Phase Reaction Mixture:

The monomers (bromides and boronic acids or boronic acid esters, purity according to HPLC>99.8%) in the composition indicated in the table are dissolved or suspended in a mixture of 2 parts by volume of toluene:6 parts by volume of dioxane:1 part by volume of water in a total concentration of about 100 mmol/l. 2 mol equivalents of tripotassium phosphate per Br functionality employed are then added, the mixture is stirred for a further 5 min., 0.03 to 0.003 mol equivalent of tri-ortho-tolylphosphine and then 0.005 to 0.0005 mol equivalent of palladium(II) acetate (phosphine to Pd ratio preferably 6:1) per Br functionality employed are then added, and the mixture is heated under reflux with very vigourous stirring for 2-3 h. If the viscosity of the mixture increases excessively, it can diluted with a mixture of 2 parts by volume of toluene:3 parts by volume of dioxane. After a total reaction time of 4-6 h, 0.05 mol equivalent of a monobromoaromatic compound per boronic acid functionality employed and then, 30 min. later, 0.05 mol equivalent of a monoboronic acid or monoboronic acid ester per Br functionality employed are added for end capping, and the mixture is boiled for a further 1 h. After cooling, the mixture is diluted with 300 ml of toluene, the aqueous phase is separated off, the organic phase is washed twice with 300 ml of water each time, dried over magnesium sulfate, filtered through a Celite bed in order to remove palladium and then evaporated to dryness. The crude polymer is dissolved in THF (concentration about 10-30 g/l) and the solution is allowed to run slowly into twice the volume of methanol with very vigourous stirring. The polymer is filtered off with suction and washed three times with methanol. The reprecipitation process is repeated five times, and the polymer is then dried to constant weight in vacuo at 30-50° C.

Variant B—Single-Phase Reaction Mixture:

The monomers (bromides and boronic acids or boronic acid esters, purity according to HPLC>99.8%) in the composition indicated in the table are dissolved or suspended in a solvent (THF, dioxane, xylene, mesitylene, dimethylacetamide, NMP, DMSO, etc.) in a total concentration of about 100 mmol/l. 3 mol equivalents of base (potassium fluoride, tripotassium phosphate (anhydrous, monohydrate or trihydrate), potassium carbonate, caesium carbonate, etc., in each case anhydrous) per Br functionality and the weight equivalent of glass beads (diameter 3 mm) are added, the mixture is stirred for a further 5 min., 0.03 to 0.003 mol equivalent of tri-ortho-tolylphosphine and then 0.005 to 0.0005 mol equivalent of palladium(II) acetate (phosphine to Pd ratio preferably 6:1) per Br functionality are then added, and the mixture is heated under reflux with very vigourous stirring for 2-3 h. Alternatively, other phosphines, such as tri-tert-butylphosphine, S-Phos, X-Phos, Ru-Phos, XanthPhos, etc., can be employed, where, in the case of these phosphines, the preferred phosphine:palladium ratio is 2:1 to 1.3:1. After a total reaction time of 4-12 h, 0.05 mol equivalent of a monobromoaromatic compound and then, 30 min. later, 0.05 mol equivalent of a monoboronic acid or monoboronic acid ester are added for end capping, and the mixture is boiled for a further 1 h. The solvent is substantially removed in vacuo, the residue is taken up in toluene, and the polymer is purified as described under Variant A.

Monomers M/End Cappers E:

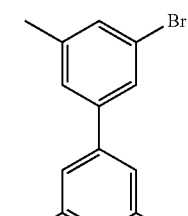

M1

13974-84-0

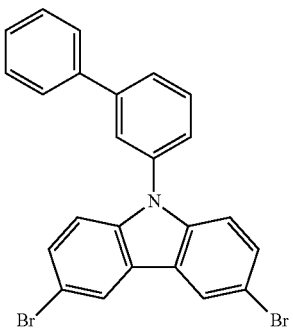

M2

57103-20-5

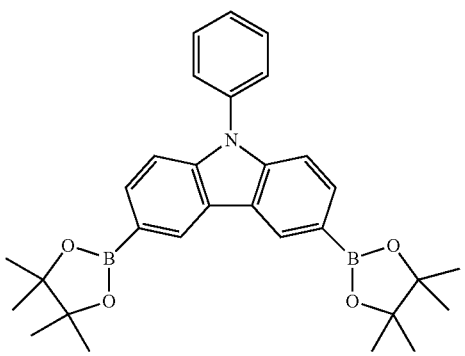

M3

618442-57-2

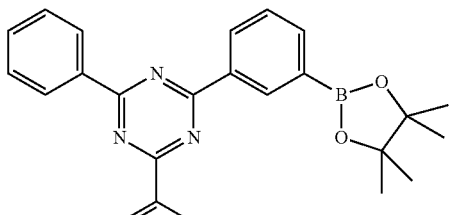

M4

1238752-26-5

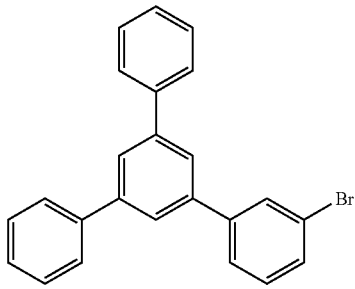

E1

1233200-57-1

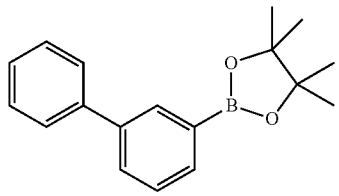

E2

912844-88-3

Polymers:

| Composition of the polymers, mmol: | | | | | |
|---|---|---|---|---|---|
| Polymer | M1 | M2 | M3 | M4 | Ir complex |
| P1 | — | 30 | — | 45 | Ir(L102-3Br)/10 |
| P2 | 5 | 25 | — | 40 | Ir(L107-2Br)/10 |
| P3 | 10 | 40 | 25 | 20 | Ir(L107-2BE)/5 |

| Molecular weights and yield of the polymers according to the invention: | | | |
|---|---|---|---|
| Polymer | Mn [gmol$^{-1}$] | Polydispersity | Yield |
| P1 | 200,000 | 5.3 | 70% |
| P2 | 350,000 | 2.4 | 53% |
| P3 | 240,000 | 2.2 | 57% |

6. Thermal and Photophysical Properties and Oxidation and Reduction Potentials

Table 1 summarises the thermal and photochemical properties and oxidation and reduction potentials of the comparative materials IrPPy, Ir1 to Ir3 (structures see Table 5)

and the selected materials according to the invention. The compounds according to the invention have improved thermal stability and photostability compared with the materials in accordance with the prior art. While materials in accordance with the prior art exhibit brown colorations and ashing after thermal storage at 380° C. for seven days and secondary components in the range >2 mol % can be detected in the 1H-NMR, the complexes according to the invention are inert under these conditions. This thermal robustness is crucial, in particular, for the processing of the materials in a high vacuum (vapour small-molecule devices). In addition, the compounds according to invention have very good photostability in anhydrous $C_6D_6$ solution on irradiation with light having a wavelength of about 455 nm. In particular, in contrast to complexes in accordance with the prior art which contain bidentate ligands, facial-meridional isomerisation is not evident in the $^1$H-NMR. As is evident from Table 1, the compounds according to the invention are all distinguished by very high PL quantum efficiencies in solution.

TABLE 1

| Complex | Therm. stab. Photo. stab. | PL-max. FWHM | PLQE | HOMO LUMO |
|---|---|---|---|---|
| Comparative examples, structures see Table 5 |
| IrPPy | Decomposition | 509 | 0.97 | — |
|  | Decomposition | 67 | Toluene | — |
| Ir1 | — | 513 | 0.97 | −5.09 |
|  | — | 60 | Toluene | −1.99 |
| Ir2 | Decomposition | 516 | 0.97 | −5.05 |
|  | Decomposition | 69 | Toluene | −1.71 |
| Ir3 | Decomposition | 510* | 0.76* | — |
|  | Decomposition | — | BuCN | — |
| Examples according to the invention |
| Ir(L1) | No decomp. | 523 | 0.99 | −5.09 |
|  | No decomp. | 63 | Toluene | −2.01 |
|  |  |  | 0.91 |  |
|  |  |  | MeCN |  |
| Ir(L6) | No decomp. | 520 | 0.96 | −5.02 |
|  | No decomp. | 56 | Toluene | −1.96 |
| Ir(L103) | No decomp. | 528 | 0.95 | −5.04 |
|  | No decomp. | 67 | Toluene | −1.97 |
| Ir(L400) | No decomp. | 495 | 0.97 | −5.02 |
|  | No decomp. | 57 | Toluene | −2.00 |
| Ir(L404) | No decomp. | 552 | 0.94 | −5.26 |
|  | No decomp. | 62 | Toluene | −2.21 |
| Ir(L500) | No decomp. | 512 | 0.96 | −5.03 |
|  | No decomp. | 61 | Toluene | −1.99 |

*Data from G. St-Pierre et al., Dalton Trans, 2011, 40, 11726.

Legend

Therm. Stab. (Thermal Stability):

Storage in ampules sealed in vacuo, 7 days at 380° C. Visual assessment for colour change/brown coloration/ashing and analysis by means of $^1$H-NMR spectroscopy.

Photo. Stab. (Photochemical Stability):

Irradiation of approx. 1 mmolar solutions in anhydrous $C_6D_6$ (degassed and sealed NMR tubes) with blue light (about 455 nm, 1.2 W Lumispot from Dialight Corporation, USA) at RT.

PL-Max.:

Maximum of the PL spectrum in [nm] of a degassed, approx. $10^{-5}$ molar solution at RT, excitation wavelength 370 nm, solvent: see PLQE column.

FWHM:

Full width at half maximum of the PL spectrum in [nm] at RT.

PLQE:

Abs. photoluminescence quantum efficiency of a degassed, approx. $10^{-5}$ molar solution in the solvent indicated at RT.

HOMO, LUMO:

in [eV] vs. vacuum, determined in dichloromethane solution (oxidation) or THF (reduction) with internal ref. ferrocene (−4.8 eV vs. vacuum).

7. Solubility of Selected Complexes at 25° C.

For the processing of the complexes according to the invention from solution (spin coating, ink-jet printing, nozzle printing, knife coating, etc.), long-term-stable solutions having solids contents of about 5 mg/ml or more are required.

TABLE 2

Solubilities of selected complexes

| Complex | Solvent | Solubility |
|---|---|---|
| Ir(L4) | Toluene | >10 mg/ml |
| Ir(L4) | 3-Phenoxytoluene | >30 mg/ml |
| Ir(L5) | Toluene | >5 mg/ml |
| Ir(L7) | Toluene | >10 mg/ml |
| Ir(L107) | Toluene | >10 mg/ml |
| Ir(L109) | Toluene | >15 mg/ml |
| Ir(L115) | Toluene | >15 mg/ml |
| Ir(L115) | Anisole | >20 mg/ml |
| Ir(L115) | 3-Phenoxytoluene | >25 mg/ml |
| Ir(L120) | Toluene | >10 mg/ml |
| Ir(L120) | 3-Phenoxytoluene | >20 mg/ml |
| Ir(138) | 3-Phenoxytoluene | >25 mg/ml |
| Ir(141) | 3-Phenoxytolueene | >35 mg/ml |
| Ir(142) | 3-Phenoxytoluol | >30 mg/ml |

Production of OLEDs

1) Vacuum-Processed Devices:

OLEDs according to the invention and OLEDs in accordance with the prior art are produced by a general process in accordance with WO 2004/058911, which is adapted to the circumstances described here (layer-thickness variation, materials used).

In the following examples, the results for various OLEDs are presented. Glass plates with structured ITO (50 nm, indium tin oxide) form the substrates to which the OLEDs are applied. The OLEDs have in principle the following layer structure: substrate/hole-transport layer 1 (HTL1) consisting of HTM doped with 5% of NDP-9 (commercially available from Novaled), 20 nm/hole-transport layer 2 (HTL2)/optional electron-blocking layer (EBL)/emission layer (EML)/optional hole-blocking layer (HBL)/electron-transport layer (ETL)/optional electron-injection layer (EIL) and finally a cathode. The cathode is formed by an aluminium layer with a thickness of 100 nm.

Firstly, vacuum-processed OLEDs are described. For this purpose, all materials are applied by thermal vapour deposition in a vacuum chamber. The emission layer here always consists of at least one matrix material (host material) and an emitting dopant (emitter), with which the matrix material or matrix materials is (are) admixed in a certain proportion by volume by co-evaporation. An expression such as M3:M2: Ir(L1) (55%:35%:10%) here means that material M3 is present in the layer in a proportion by volume of 55%, M2 is present in the layer in a proportion of 35% and Ir(L1) is present in the layer in a proportion of 10%. Analogously, the electron-transport layer may also consist of a mixture of two materials. The precise structure of the OLEDs is shown in Table 1. The materials used for the production of the OLEDs are shown in Table 5.

The OLEDs are characterised by standard methods. For this purpose, the electroluminescence spectra, the current efficiency (measured in cd/A) and the voltage (measured at 1000 cd/m² in V), determined from current/voltage/brightness characteristic lines (IUL characteristic lines), are determined. For selected experiments, the lifetime is determined. The lifetime is defined as the time after which the luminous density has dropped to a certain proportion from a particular initial luminous density. The expression LT50 means that the said lifetime is the time at which the luminous density has dropped to 50% of the initial luminous density, i.e. from, for example, 1000 cd/m² to 500 cd/m². Depending on the emission colour, different initial brightnesses were selected. The values for the lifetime can be converted into a value for other initial luminous densities with the aid of conversion formulae known to the person skilled in the art. The lifetime for an initial luminous density of 1000 cd/m² is a usual expression here.

Use of Compounds According to the Invention as Emitter Materials in Phosphorescent OLEDs The compounds according to the invention can be employed, inter alia, as phosphorescent emitter materials (dopants) in the emission layer in OLEDs and as electron-transport material. As comparison in accordance with the prior art, the iridium compounds shown in Table 5 are used. The results for the OLEDs are summarised in Table 2.

TABLE 1

Structure of the OLEDs

| Ex. | HTL2 Thickness | EBL Thickness | EML Thickness | HBL Thickness | ETL Thickness |
|---|---|---|---|---|---|
| | | Green - yellow devices | | | |
| Ref.-D1 | HTM 40 nm | — | M1:IrPPy (85%:15%) 30 nm | ETM1 10 nm | ETM1:ETM2 (50%:50%) 30 nm |
| Ref.-D2 | HTM 40 nm | — | M1:Ir2 (85%:15%) 30 nm | ETM1 10 nm | ETM1:ETM2 (50%:50%) 30 nm |
| Ref.-D3 | HTM 40 nm | — | M1:M3:Ir2 (60%:30%:10%) 30 nm | ETM1 10 nm | ETM1:ETM2 (50%:50%) 30 nm |
| Ref.-D4 | HTM 40 nm | — | M1:Ir3 (85%:15%) 30 nm | ETM1 10 nm | ETM1:ETM2 (50%:50%) 30 nm |
| Ref.-D5 | HTM 40 nm | — | M1:M3:Ir3 (60%:30%:10%) 30 nm | ETM1 10 nm | ETM1:ETM2 (50%:50%) 30 nm |
| D1 | HTM 40 nm | — | M1:Ir(L1) (85%:15%) 30 nm | ETM1 10 nm | ETM1:ETM2 (50%:50%) 30 nm |
| D2 | HTM 40 nm | — | M1:Ir(L3) (85%:15%) 30 nm | ETM1 10 nm | ETM1:ETM2 (50%:50%) 30 nm |
| D3 | HTM 40 nm | — | M1:Ir(L102) (85%:15%) 30 nm | ETM1 10 nm | ETM1:ETM2 (50%:50%) 30 nm |
| D4 | HTM 40 nm | — | M1:M3:Ir(L1) (60%:30%:10%) 30 nm | ETM1 10 nm | ETM1:ETM2 (50%:50%) 30 nm |
| D5 | HTM 40 nm | — | M1:M3:Ir(L102) (60%:30%:10%) 30 nm | ETM1 10 nm | ETM1:ETM2 (50%:50%) 30 nm |
| D6 | HTM 40 nm | — | M1:M3:Ir(L103) (60%:30%:10%) 30 nm | ETM1 10 nm | ETM1:ETM2 (50%:50%) 30 nm |
| D7 | HTM 40 nm | — | M1:M3:Ir(L102) (60%:30%:10%) 30 nm | ETM1 10 nm | M200 30 nm |
| D8 | HTM 40 nm | — | M1:M3:Ir(L400) (60%:30%:10%) 30 nm | ETM1 10 nm | ETM1:ETM2 (50%:50%) 30 nm |
| D9 | HTM 40 nm | — | M1:M3:Ir(L500) (60%:30%:10%) 30 nm | ETM1 10 nm | M200 30 nm |
| | | Orange - red devices | | | |
| D100 | HTM 40 nm | — | M1:Ir(L8) (90%:10%) 30 nm | ETM1 10 nm | ETM1:ETM2 (50%:50%) 30 nm |
| D100 | HTM 40 nm | — | M2:M3:Ir(L8) (50%:40%:10%) 30 nm | ETM1 10 nm | ETM1:ETM2 (50%:50%) 30 nm |
| D102 | HTM 40 nm | — | M2:M3:Ir(L404) (60%:30%:10%) 30 nm | ETM1 10 nm | ETM1:ETM2 (50%:50%) 30 nm |

TABLE 2

Results for the vacuum-processed OLEDs

| Ex. | EQE (%) 1000 cd/m$^2$ | Voltage (V) 1000 cd/m$^2$ | CIE x/y 1000 cd/m$^2$ | LT50 (h) 1000 cd/m$^2$ |
|---|---|---|---|---|
| *Green - yellow devices* | | | | |
| Ref.-D1 | 15.7 | 2.8 | 0.33/0.62 | 60000 |
| Ref.-D2 | 18.6 | 2.9 | 0.35/0.61 | 200000 |
| Ref.-D3 | 18.8 | 2.9 | 0.35/0.61 | 330000 |
| Ref.-D4 | 18.7 | 3.0 | 0.34/0.62 | 180000 |
| Ref.-D5 | 18.6 | 3.0 | 0.34/0.62 | 270000 |
| D1 | 19.7 | 2.9 | 0.35/0.61 | 280000 |
| D2 | 19.3 | 2.9 | 0.34/0.62 | 260000 |
| D3 | 20.4 | 2.9 | 0.34/0.63 | 270000 |
| D4 | 19.5 | 2.9 | 0.35/0.61 | 370000 |
| D5 | 21.0 | 3.1 | 0.34/0.62 | 360000 |
| D6 | 20.2 | 3.0 | 0.37/0.61 | 390000 |
| D7 | 20.9 | 3.0 | 0.34/0.62 | 350000 |
| D8 | 19.8 | 2.9 | 0.22/0.61 | 260000 |
| D9 | 20.7 | 3.1 | 0.34/0.62 | 410000 |
| *Orange - red devices* | | | | |
| D100 | 19.4 | 2.9 | 0.45/0.55 | 270000 |
| D101 | 19.7 | 2.9 | 0.46/0.54 | 380000 |
| D102 | 20.1 | 3.2 | 0.40/0.58 | 360000 |

Solution-Processed Devices:

A: From Soluble Functional Materials

The iridium complexes according to the invention can also be processed from solution, where they result in OLEDs which are significantly simpler from a process engineering point of view compared with vacuum-processed OLEDs, but nevertheless have good properties. The production of such components is based on the production of polymeric light-emitting diodes (PLEDs), which has already been described many times in the literature (for example in WO 2004/037887). The structure is composed of substrate/ITO/hole-injection layer (60 nm)/interlayer (20 nm)/emission layer (60 nm)/hole-blocking layer (10 nm)/electron-transport layer (40 nm)/cathode. To this end, use is made of substrates from Techno-print (soda-lime glass), to which the ITO structure (indium tin oxide, a transparent, conductive anode) is applied. The substrates are cleaned with deionised water and a detergent (Deconex 15 PF) in a clean room and then activated by UV/ozone plasma treatment. A 60 nm hole-injection layer is then applied by spin coating, likewise in a clean room. The spin rate required depends on the degree of dilution and the specific spin-coater geometry. In order to remove residual water from the layer, the substrates are dried by heating at 200° C. on a hotplate for 30 minutes. The interlayer used serves for hole transport, in this case an HL-X from Merck is used. The interlayer may alternatively also be replaced by one or more layers which merely have to satisfy the condition of not being detached again by the subsequent processing step of EML deposition from solution. For the production of the emission layer, the triplet emitters according to the invention are dissolved in toluene or chlorobenzene together with the matrix materials. The typical solids content of such solutions is between 16 and 25 g/l if, as here, the typical layer thickness of 60 nm for a device is to be achieved by means of spin coating. The solution-processed devices of type 1 contain an emission layer comprising M4:M5:IrL (25%:55%:20%), those of type 2 contain an emission layer comprising M4:M5:IrLa:IrLb (30%:34%:30%:6%), i.e. they contain two different Ir complexes. The emission layer is applied by spin coating in an inert-gas atmosphere, in the present case argon, and dried by heating at 160° C. for 10 min. The hole-blocking layer (10 nm of ETM1) and the electron-transport layer (40 nm of ETM1 (50%)/ETM2 (50%)) are applied on top by vapour deposition (vapour-deposition units from Lesker or others, typical vapour-deposition pressure 5×10$^{-6}$ mbar). Finally, an aluminium cathode (100 nm) (high-purity metal from Aldrich) is applied by vapour deposition. In order to protect the device against air and atmospheric moisture, the device is finally encapsulated and then characterised. The OLED examples given have not yet been optimised, Table 3 summarises the data obtained.

TABLE 3

Results with materials processed from solution

| Ex. | Emitter Device | EQE (%) 1000 cd/m$^2$ | Voltage (V) 1000 cd/m$^2$ | CIE x/y | LT50 (h) 1000 cd/m$^2$ |
|---|---|---|---|---|---|
| *Green and yellow OLEDs* | | | | | |
| Sol-Ref.-D1 | Ir1 Typ1 | 19.8 | 5.1 | 0.34/0.62 | 200000 |
| Sol-D1 | Ir(L4) Typ1 | 20.6 | 5.0 | 0.36/0.61 | 240000 |
| Sol-D2 | Ir(L107) Typ1 | 21.2 | 5.0 | 0.34/0.62 | 270000 |
| Sol-D3 | Ir(L109) Typ1 | 20.7 | 5.1 | 0.37/0.60 | 280000 |
| Sol-D4 | Ir(L120) Typ1 | 20.7 | 5.2 | 0.35/0.61 | 260000 |
| Sol-D5 | Ir139 Typ1 | 18.8 | 5.3 | 0.24/0.62 | 180000 |
| Sol-D6 | Ir142 Typ1 | 19.9 | 5.1 | 0.33/0.63 | 260000 |
| *Orange and red OLEDs* | | | | | |
| Sol-D100 | Ir(L7) Typ1 | 16.2 | 6.1 | 0.64/0.36 | 45000 |
| Sol-D101 | Ir1 Ir(L7) Typ2 | 17.6 | 6.0 | 0.64/0.36 | 135000 |
| Sol-D102 | Ir(L5) Ir(L7) Typ2 | 18.0 | 6.1 | 0.64/0.36 | 190000 |
| Sol-D103 | Ir(L107) Ir(L115) Typ2 | 17.4 | 6.1 | 0.66/0.34 | 270000 |

B: From Polymeric Functional Materials:

Production of the OLEDs as described under A. For the production of the emission layer, the polymers according to the invention are dissolved in toluene. The typical solids content of such solutions is between 10 and 15 g/l if, as here, the typical layer thickness of 40 nm for a device is to be achieved by means of spin coating. The OLED examples given have not yet been optimised, Table 4 summarises the data obtained.

TABLE 4

Results with materials processed from solution

| Ex. | Polymer | EQE (%) 1000 cd/m$^2$ | Voltage (V) 1000 cd/m$^2$ | CIE x/y 1000 cd/m$^2$ |
|---|---|---|---|---|
| *Green OLEDs* | | | | |
| D-P1 | P1 | 19.8 | 4.1 | 0.35/0.61 |
| D-P2 | P2 | 20.3 | 4.4 | 0.36/0.60 |
| D-P3 | P3 | 20.1 | 4.3 | 0.36/0.60 |

TABLE 5
Structural formulae of the materials used
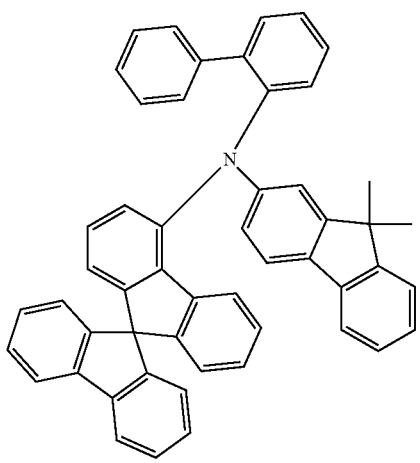 [SMILES: CC1(C)c2ccccc2-c2ccc(N(c3ccccc3-c3ccccc3)c3cccc4c3-c3ccccc3C43c4ccccc4-c4ccccc43)cc21]
HTM
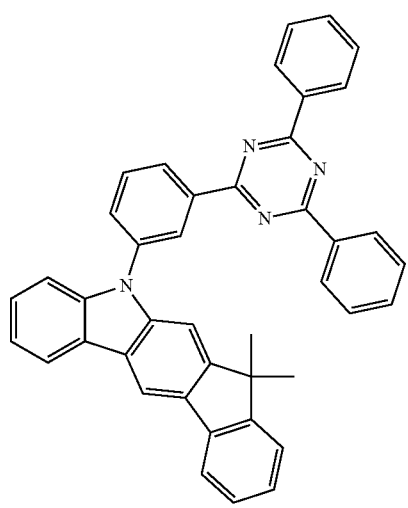 [SMILES: CC1(C)c2ccccc2-c2cc3c4ccccc4n(-c4cccc(-c5nc(-c6ccccc6)nc(-c6ccccc6)n5)c4)c3cc21]
M1
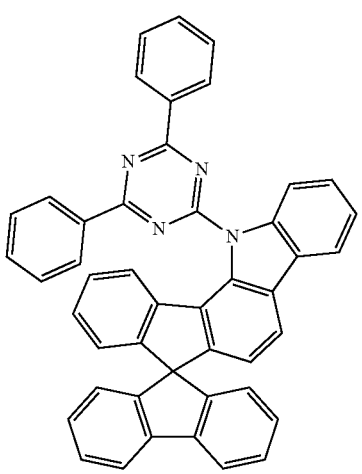 [SMILES: c1ccc(-c2nc(-c3ccccc3)nc(-n3c4ccccc4c4ccc5c(c43)-c3ccccc3C53c4ccccc4-c4ccccc43)n2)cc1]
M2

TABLE 5-continued
Structural formulae of the materials used
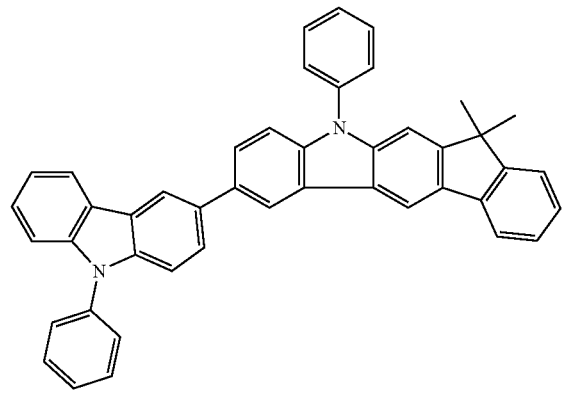 [SMILES: CC1(C)c2ccccc2-c2cc3c4cc(-c5ccc6c(c5)c5ccccc5n6-c5ccccc5)ccc4n(-c4ccccc4)c3cc21]
M3
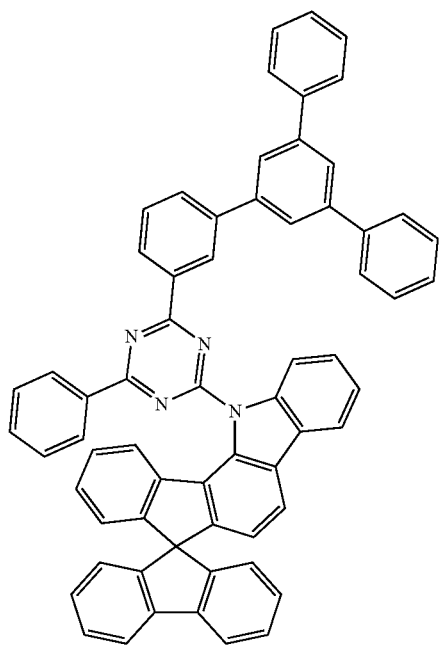 [SMILES: c1ccc(-c2cc(-c3ccccc3)cc(-c3cccc(-c4nc(-c5ccccc5)nc(-n5c6ccccc6c6ccc7c(c65)-c5ccccc5C75c6ccccc6-c6ccccc65)n4)c3)c2)cc1]
M4
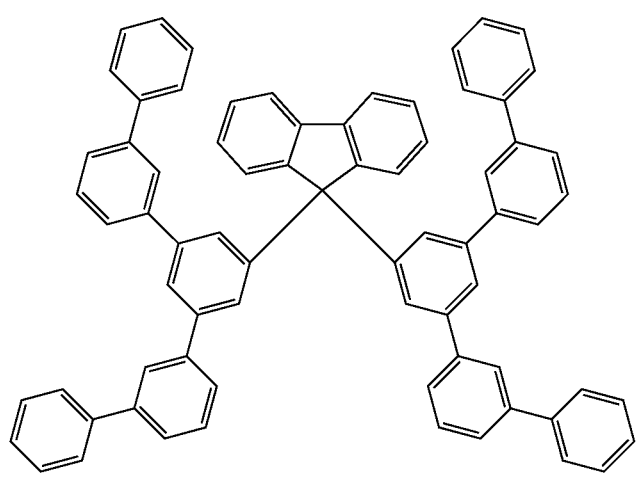
M5

TABLE 5-continued
Structural formulae of the materials used
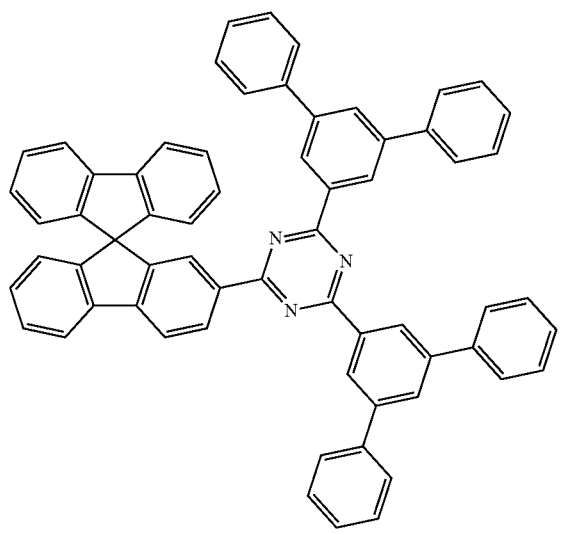
ETM1
1233200-52-6
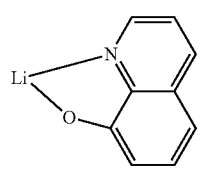
ETM2
25387-93-3
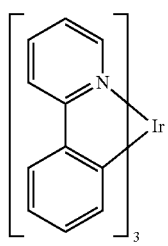
IrPPy
693794-98-8
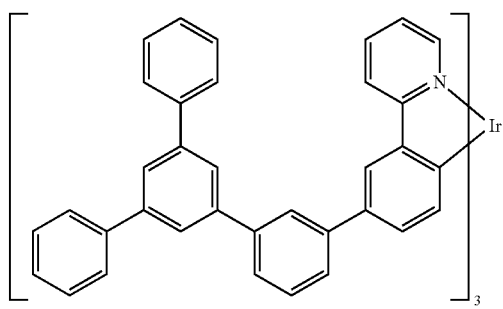
Ir1
1269508-30-6

TABLE 5-continued

Structural formulae of the materials used

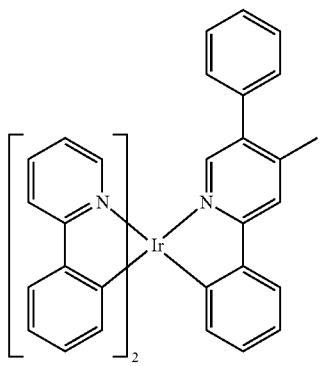

Ir2

1215692-34-4

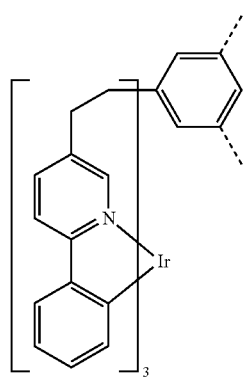

Ir3*

861806-70-4

*G. St-Pierre et al., Dalton Trans, 2011, 40, 11726.

The invention claimed is:

1. A monometallic compound comprising a hexadentate tripodal ligand wherein three bidentate part-ligands, which may be identical or different, are coordinated to a metal selected from the group consisting of ruthenium, osmium, rhodium and iridium, and the three bidentate part-ligands are linked to one another via a bridge of formula (1):

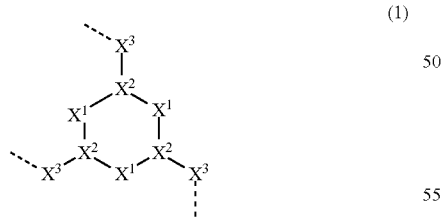

(1)

wherein the dashed bonds are the direct bonds from the bidentate part-ligands to the structure of formula (1);

$X^1$ is on each occurrence, identically or differently, $CR_2$ or O;

$X^2$ is on each occurrence, identically or differently, CR, P=O, B, or Si, which is optionally substituted, with the proviso that, when $X^2$ is P=O, B, or Si, which is optionally substituted, $X^1$ is O; and wherein substituents optionally present on $X^1$ and $X^2$ optionally define an aliphatic or heteroaliphatic ring system with themselves or with one another;

$X^3$ is on each occurrence, identically or differently, —CR=CR—, —CR=N—, —CR—NR''—, —C(=O)—O—, —C(=O)—NR''—, —C(=O)—S—, —C(=S)—O—, —C(=S)—S—;

R is on each occurrence, identically or differently, H, D, F, Cl, Br, I, $N(R^1)_2$, CN, $NO_2$, $OR^1$, $SR^1$, COOH, $C(=O)N(R^1)_2$, $Si(R^1)_3$, $B(OR^1)_2$, $C(=O)R^1$, $P(=O)(R^1)_2$, $S(=O)R^1$, $S(=O)_2R^1$, $OSO_2R^1$, a straight-chain alkyl group having 1 to 20 C atoms or an alkenyl or alkynyl group having 2 to 20 C atoms or a branched or cyclic alkyl group having 3 to 20 C atoms, wherein the alkyl, alkenyl, or alkynyl group in each case is optionally substituted by one or more radicals $R^1$, wherein one or more non-adjacent $CH_2$ groups are optionally replaced by $R^1C=CR^1$, C≡C, $Si(R^1)_2$, C=O, $NR^1$, O, S, or $CONR^1$, or an aromatic or heteroaromatic ring system having 5 to 40 aromatic ring atoms, which in each case is optionally substituted by one or more radicals $R^1$; and wherein two or more radicals R which are bonded to $X^1$ and/or $X^2$ optionally define an aliphatic or heteroaliphatic ring system with one another; and wherein two radicals R when $X^3$ is —CR=CR— optionally define an aliphatic, heteroaliphatic, aromatic, or heteroaromatic ring system with one another; and wherein radicals R and R'' when $X^3$ is —CR—NR''— define a heteroaromatic ring system with one another;

R" is on each occurrence, identically or differently, H, D, a straight-chain alkyl group having 1 to 20 C atoms or a branched or cyclic alkyl group having 3 to 20 C atoms or an alkenyl group having 2 to 20 C atoms, wherein the alkyl or alkenyl group in each case is optionally substituted by one or more radicals $R^1$ and wherein one or more non-adjacent $CH_2$ groups are optionally replaced by $Si(R^1)_2$, or an aromatic or heteroaromatic ring system having 5 to 40 aromatic ring atoms, which in each case is optionally substituted by one or more radicals R';

$R^1$ is on each occurrence, identically or differently, H, D, F, Cl, Br, I, $N(R^2)_2$, CN, $NO_2$, $OR^2$, $SR^2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl group having 1 to 20 C atoms or an alkenyl or alkynyl group having 2 to 20 C atoms or a branched or cyclic alkyl group having 3 to 20 C atoms, wherein the alkyl, alkenyl, or alkynyl group in each case is optionally substituted by one or more radicals $R^2$, wherein one or more non-adjacent $CH_2$ groups are optionally replaced by $R^2C=CR^2$, $C\equiv C$, $Si(R^2)_2$, C=O, $NR^2$, O, S, or $CONR^2$, or an aromatic or heteroaromatic ring system having 5 to 40 aromatic ring atoms, which in each case is optionally substituted by one or more radicals $R^2$; wherein a plurality of substituents $R^1$ optionally define an aliphatic, heteroaliphatic, aromatic, or heteroaromatic ring system with one another;

furthermore, the groups R or R substituted with $R^1$ optionally form a ring system, and groups R and $R^1$ optionally form a ring system with one another;

$R^2$ is on each occurrence, identically or differently, H, D, F, or an aliphatic, aromatic, and/or heteroaromatic organic radical having 1 to 20 C atoms, wherein one or more H atoms are optionally replaced by F; and wherein the bidentate part-ligands are selected, identically or differently on each occurrence, from the group consisting of structures of formulae (L-1), (L-2), (L-3), and (L-4):

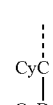

(L-1)

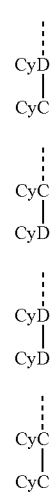

(L-2)

(L-3)

(L-4)

wherein the dashed bond is the direct bond from the part-ligand to the bridge of formula (1);

CyC is, identically or differently on each occurrence, an optionally substituted aryl or heteroaryl group having 5 to 14 aromatic ring atoms, which is coordinated to the metal via a carbon atom and which is connected to CyD via a covalent bond;

CyD is, identically or differently on each occurrence, an optionally substituted heteroaryl group having 5 to 14 aromatic ring atoms, which is coordinated to the metal via a nitrogen atom or via a carbene carbon atom and which is connected to CyC via a covalent bond; and wherein a plurality of the optional substituents optionally defines a ring system with one another; and the three bidentate ligands are optionally cyclised by a further bridge, in addition to the bridge of formula (1), to define a cryptate.

2. The monometallic compound of claim 1, wherein the bridge of formula (1) is selected from the group consisting of structures of formulae (2) through (6):

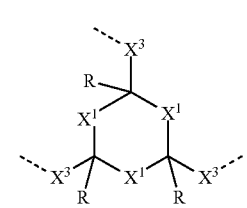

(2)

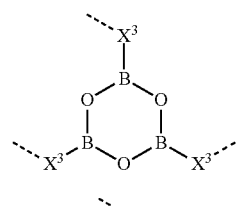

(3)

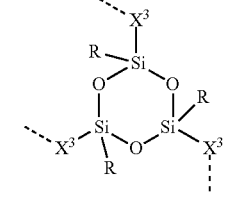

(4)

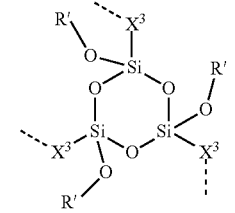

(5)

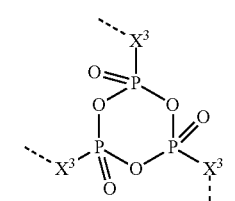

(6)

wherein

R' is on each occurrence, identically or differently, H, D, F, Cl, Br, I, $N(R^1)_2$, CN, $NO_2$, OR', SR', COOH, $C(=O)N(R^1)_2$, $C(=O)R^1$, $P(=O)(R^1)_2$, $S(=O)R^1$, $S(=O)_2R^1$, $OSO_2R^1$, a straight-chain alkyl group having 1 to 20 C atoms or an alkenyl or alkynyl group having 2 to 20 C atoms or a branched or cyclic alkyl group having 3 to 20 C atoms, where the alkyl, alkenyl, or alkynyl group in each case is optionally substituted by one or more radicals R', wherein one or more non-adjacent CH$_2$ groups are optionally replaced by R$^1$C=CR$^1$, C≡C, C=O, NR$^1$, O, S, or CONR$^1$, or an aromatic or heteroaromatic ring system having 5 to 40 aromatic ring atoms, which in each case are optionally substituted by one or more radicals R$^1$.

3. The monometallic compound of claim 1, wherein the bridge of formula (1) is selected from the structures of the formulae (2a) and (2b)

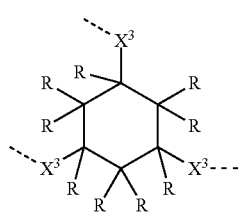

(2a)

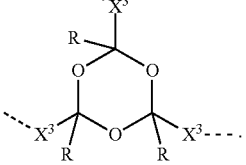

(2b)

4. The monometallic compound of claim 1, wherein the bidentate part-ligands are each monoanionic and wherein the three bidentate part-ligands are either selected identically or two bidentate part-ligands are selected identically and the third bidentate part-ligand is selected differently from the first two bidentate part-ligands and wherein the coordinating atoms of the bidentate part-ligands are selected, identically or differently on each occurrence, from C, and/or N.

5. The monometallic compound of claim 1, wherein the metal is Ir(III) and two of the bidentate part-ligands are coordinated to the iridium in each case via one carbon atom and one nitrogen atom or via two carbon atoms and the third of the bidentate part-ligands is coordinated to the iridium via one carbon atom and one nitrogen atom or via two carbon atoms or via two nitrogen atoms.

6. The monometallic compound of claim 1 wherein CyC is selected from the group consisting of structures of formulae (CyC-1) through (CyC-20):

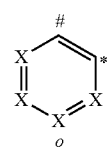

(CyC-1)

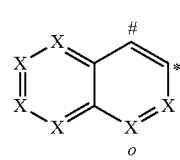

(CyC-2)

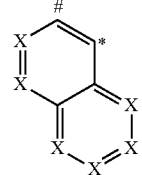

(CyC-3)

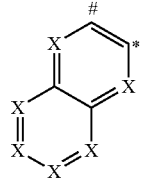

(CyC-4)

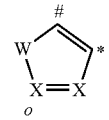

(CyC-5)

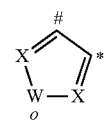

(CyC-6)

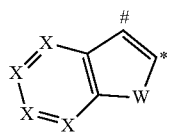

(CyC-7)

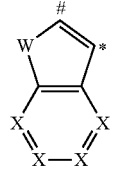

(CyC-8)

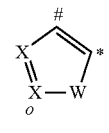

(CyC-9)

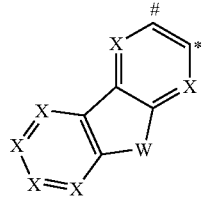

(CyC-10)

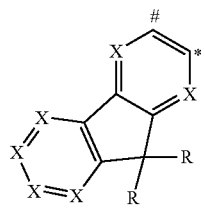

(CyC-11)

(CyC-12)
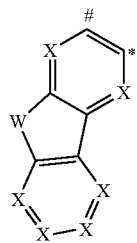
(CyC-13)
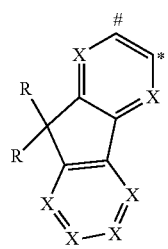
(CyC-14)
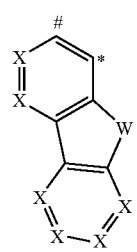
(CyC-15)
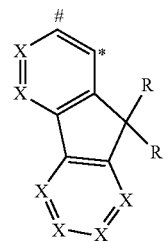
(CyC-16)
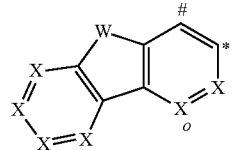
(CyC-17)
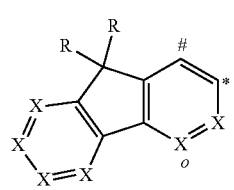
(CyC-18)
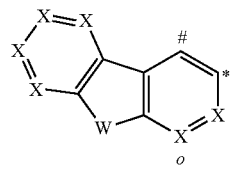
(CyC-19)
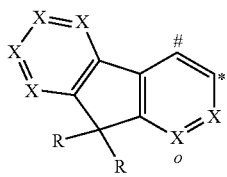
(CyC-20)
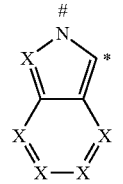
wherein
the group is in each case bonded to CyD in (L-1) or (L-2) or to CyC in (L-4) at the position denoted by # and is coordinated to the metal at the position denoted by *; and
CyD is selected from the group consisting of structures of formulae (CyD-1) through (CyD-14):
(CyD-1)
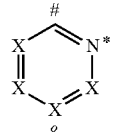
(CyD-2)
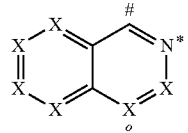
(CyD-3)
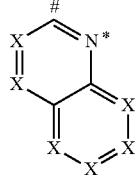
(CyD-4)
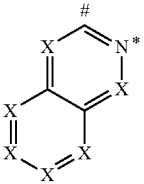
(CyD-5)

-continued (CyD-6)
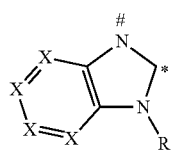

(CyD-7)
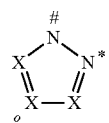

(CyD-8)
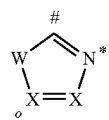

(CyD-9)
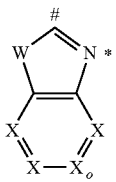

(CyD-10)
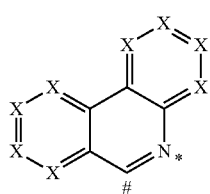

(CyD-11)
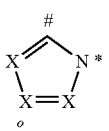

(CyD-12)
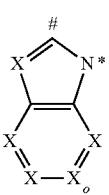

(CyD-13)
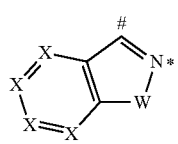

(CyD-14)
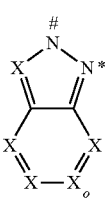

wherein the group is in each case bonded to CyC in (L-1) or (L-2) or to CyD in (L-3) at the position denoted by # and is coordinated to the metal at the position denoted by *; and wherein R is on each occurrence, identically or differently, H, D, F, Cl, Br, I, N(R$^1$)$_2$, CN, NO$_2$, OR$^1$, SR$^1$, COOH, C(=O)N(R$^1$)$_2$, Si(R$^1$)$_3$, B(OR$^1$)$_2$, C(=O)R$^1$, P(=O)(R$^1$)$_2$, S(=O)R$^1$, S(=O)$_2$R$^1$, OSO$_2$R$^1$, a straight-chain alkyl group having 1 to 20 C atoms or an alkenyl or alkynyl group having 2 to 20 C atoms or a branched or cyclic alkyl group having 3 to 20 C atoms, wherein the alkyl, alkenyl, or alkynyl group in each case is optionally substituted by one or more radicals R$^1$, wherein one or more non-adjacent CH$_2$ groups are optionally replaced by R$^1$C=CR$^1$, C≡C, Si(R$^1$)$_2$, C=O, NR$^1$, O, S, or CONR$^1$, or an aromatic or heteroaromatic ring system having 5 to 40 aromatic ring atoms, which in each case is optionally substituted by one or more radicals R$^1$; and wherein two or more radicals R which are bonded to X$^1$ and/or X$^2$ optionally define an aliphatic or heteroaliphatic ring system with one another; and wherein two radicals R when X$^3$ is —CR=CR— optionally define an aliphatic, heteroaliphatic, aromatic, or heteroaromatic ring system with one another; and wherein radicals R and R" when X$^3$ is —CR—NR"— define a heteroaromatic ring system with one another; and wherein two radicals R optionally define an aliphatic, heteroaliphatic, aromatic, or heteroaromatic ring system with one another:

X is on each occurrence, identically or differently, CR or N, with the proviso that a maximum of two X per ring are N;

W is on each occurrence, identically or differently, NR, O, or S; and wherein the bonding of these groups to the bridge of formula (1) is via the position denoted by "o" and the corresponding X is C.

7. The monometallic compound of claim 1, wherein the bidentate part-ligands are selected from the group consisting of structure of formulae (L-1-1), (L-1-2), (L-2-1), (L-2-2), (L-2-3), and (L-5) through (L-34):

(L-1-1)
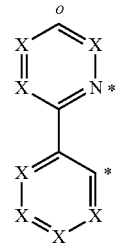

(L-1-2)
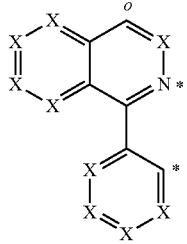

(L-2-1) 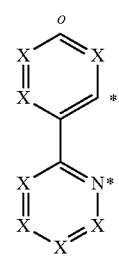
(L-2-2) 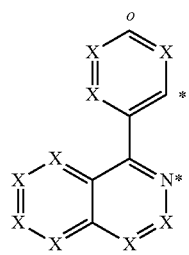
(L-2-3) 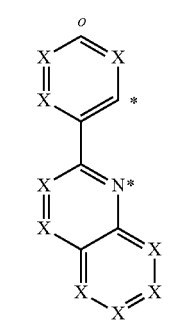
(L-5) 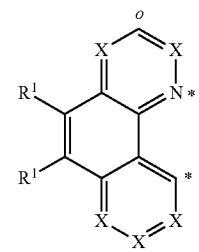
(L-6) 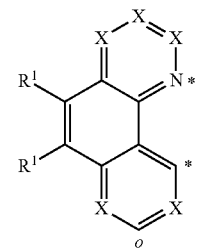
(L-7) 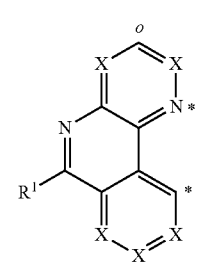
(L-8) 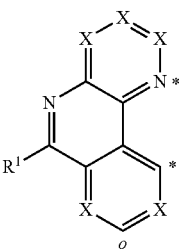
(L-9) 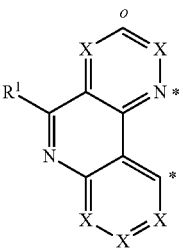
(L-10) 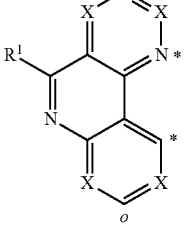
(L-11) 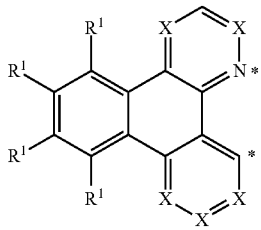
(L-12) 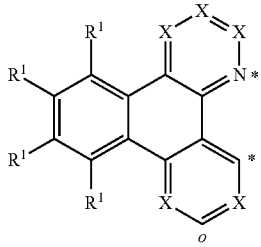
(L-13) 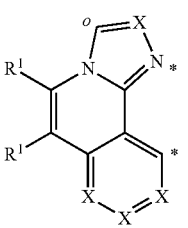

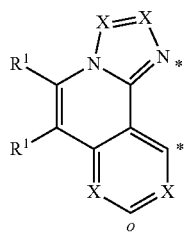
(L-14)
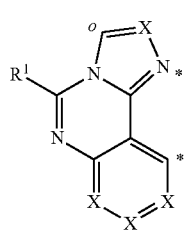
(L-15)
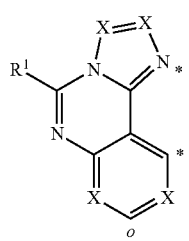
(L-16)
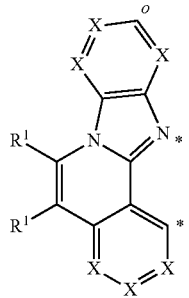
(L-17)
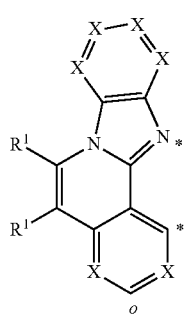
(L-18)
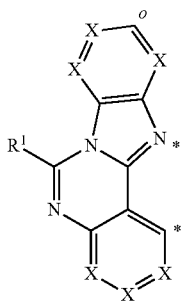
(L-19)
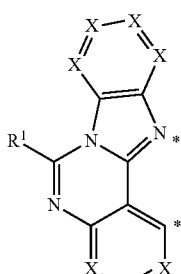
(L-20)
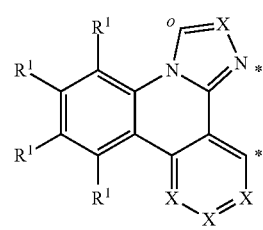
(L-21)
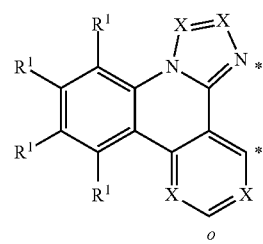
(L-22)
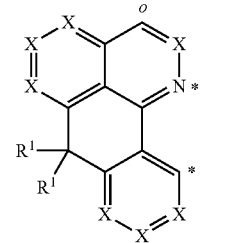
(L-23)
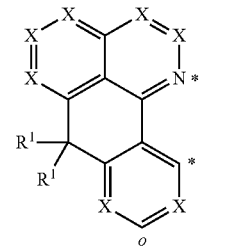
(L-24)

(L-25) 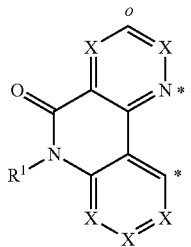
(L-26) 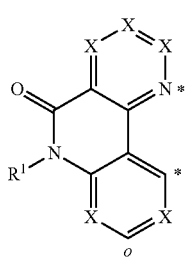
(L-27) 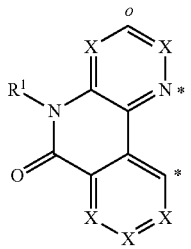
(L-28) 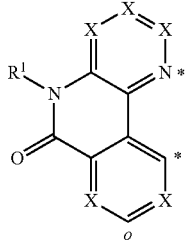
(L-29) 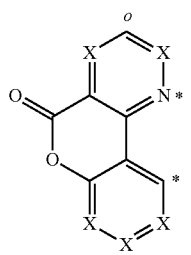
(L-30) 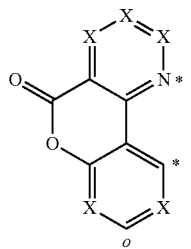
(L-31) 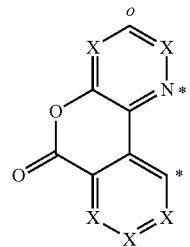
(L-32) 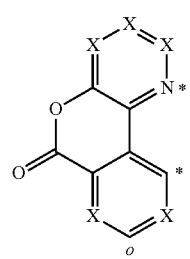
(L-33) 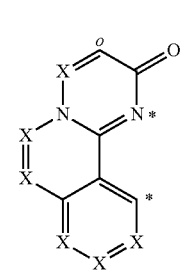
(L-34) 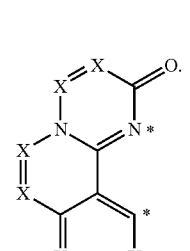
8. The monometallic compound of claim 1, wherein the monometallic compound comprises two substituents R, which are bonded to adjacent carbon atoms and which define a ring of one of formulae (43) through (49) with one another:
(43) 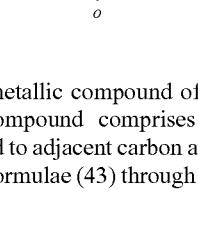
(44) 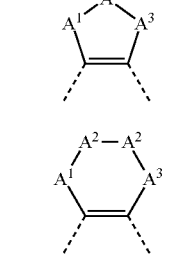

-continued

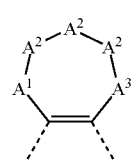
(45)

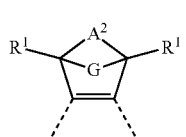
(46)

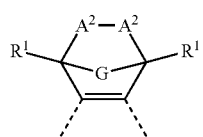
(47)

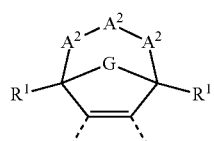
(48)

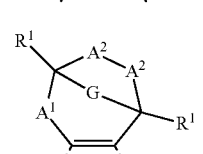
(49)

wherein
the dashed bonds indicate the linking of the two carbon atoms in the ligand;
$A^1$ and $A^3$ are, identically or differently on each occurrence, $C(R^3)_2$, O, S, $NR^3$, or C(=O);
$A^2$ is $C(R^1)_2$, O, S, $NR^3$, or C(=O);
G is an alkylene group having 1, 2, or 3 C atoms, which is optionally substituted by one or more radicals $R^2$, or is —$CR^2$=$CR^2$— or an ortho-linked arylene or heteroarylene group having 5 to 14 aromatic ring atoms, which is optionally substituted by one or more radicals $R^2$;
$R^3$ is, identically or differently on each occurrence, H, D, F, a straight-chain alkyl or alkoxy group having 1 to 10 C atoms, a branched or cyclic alkyl or alkoxy group having 3 to 10 C atoms, wherein the alkyl or alkoxy group in each case is optionally substituted by one or more radicals $R^2$, wherein one or more non-adjacent $CH_2$ groups are optionally replaced by $R^2C$=$CR^2$, C≡C, $Si(R^2)_2$, C=O, $NR^2$, O, S, or $CONR^2$, or an aromatic or heteroaromatic ring system having 5 to 24 aromatic ring atoms, which in each case is optionally substituted by one or more radicals $R^2$, or an aryloxy or heteroaryloxy group having 5 to 24 aromatic ring atoms, which is optionally substituted by one or more radicals $R^2$; and wherein two radicals $R^3$ bonded to the same carbon atom optionally define an aliphatic or aromatic ring system with one another to form a spiro system; and wherein $R^3$ optionally defines an aliphatic ring system with an adjacent radical R or $R^1$, with the proviso that no two heteroatoms are bonded directly to one another and no two groups C=O are bonded directly to one another in these groups.

9. A process for preparing the monometallic compound of claim 1, comprising reacting a free ligand with a metal alkoxides of formula (50), a metal ketoketonate of formula (51), a metal halide of formula (52), or a metal carboxylate of formula (53), or with a metal compound which carries both alkoxide and/or halide and/or hydroxyl and also ketoketonate radicals:

$$M(OR)_n \quad (50)$$

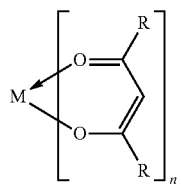
(51)

$$MHal_n \quad (52)$$

$$M(OOCR)_n \quad (53)$$

wherein
M is the metal of the monometallic compound being prepared;
n is the valency of the metal M; and
Hal is F, Cl, Br, or I; and
wherein the metal starting materials are optionally in the form of a corresponding hydrate.

10. An oligomer, polymer, or dendrimer comprising one or more monometallic compounds of claim 1, wherein one or more bonds from the monometallic compound to the polymer, oligomer, or dendrimer are present instead of one or more hydrogen atoms and/or substituents.

11. A formulation comprising at least one monometallic compound of claim 1 and at least one solvent.

12. A formulation comprising at least one oligomer, polymer, or dendrimer of claim 10 and at least one solvent.

13. An electronic device comprising at least one monometallic compound of claim 1.

14. An electronic device comprising at least one oligomer, polymer, or dendrimer of claim 10.

15. The electronic device of claim 13, wherein the electronic device is an organic electroluminescent device and the at least one monometallic compound is employed as an emitting compound in one or more emitting layers or as a hole-blocking material in a hole blocking layer or as an electron-transport material in an electron-transport layer.

* * * * *